(12) United States Patent
Okada et al.

(10) Patent No.: US 6,599,917 B1
(45) Date of Patent: Jul. 29, 2003

(54) QUINUCLIDINE COMPOUNDS AND DRUGS CONTAINING THE SAME AS THE ACTIVE INGREDIENT

(75) Inventors: Toshimi Okada, Ibaraki (JP); Nobuyuki Kurusu, Ibaraki (JP); Keigo Tanaka, Ibaraki (JP); Kazuki Miyazaki, Ibaraki (JP); Daisuke Shinmyo, Ibaraki (JP); Hiroyuki Sugumi, Ibaraki (JP); Hironori Ikuta, Ibaraki (JP); Hironobu Hiyoshi, Ibaraki (JP); Takao Saeki, Ibaraki (JP); Mamoru Yanagimachi, Ibaraki (JP); Masashi Ito, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/088,554

(22) PCT Filed: Sep. 27, 2000

(86) PCT No.: PCT/JP00/06665

§ 371 (c)(1), (2), (4) Date: Mar. 19, 2002

(87) PCT Pub. No.: WO01/23383

PCT Pub. Date: Apr. 5, 2001

(30) Foreign Application Priority Data

Sep. 28, 1999 (JP) ............................... 11-273905
Jun. 15, 2000 (JP) ......................... 2000-179352

(51) Int. Cl.[7] ..................... A61K 31/439; C07D 453/02
(52) U.S. Cl. .................. 514/305; 546/133; 546/137; 544/61; 544/333; 544/405; 514/228.2; 514/253; 514/256
(58) Field of Search ............................... 514/305, 228.2, 514/253, 256; 546/133, 137; 544/61, 333, 405

(56) References Cited

U.S. PATENT DOCUMENTS

| | | |
|---|---|---|
| 5,135,935 A | 8/1992 | Alberts et al. |
| 5,654,315 A | 8/1997 | Brown et al. |
| 5,712,270 A * | 1/1998 | Sabb .......................... 514/212 |
| 5,714,496 A | 2/1998 | Brown et al. |
| 5,731,323 A | 3/1998 | Whittamore |

FOREIGN PATENT DOCUMENTS

| | | |
|---|---|---|
| EP | 0 560 604 A1 | 9/1993 |
| JP | 7-502283 A | 3/1995 |
| JP | 8-502731 A | 3/1996 |
| JP | 8-134067 A | 5/1996 |
| JP | 8-504803 A | 5/1996 |
| JP | 8-269056 A | 10/1996 |
| JP | 8-509488 A | 10/1996 |
| WO | 92/15579 A1 | 9/1992 |
| WO | WO 93/13096 A1 | 7/1993 |
| WO | 93/21183 A1 | 10/1993 |
| WO | WO 94/05660 A1 | 3/1994 |
| WO | WO 94/14805 A1 | 7/1994 |
| WO | 94/14805 | 7/1994 |
| WO | WO 94/25459 A1 | 11/1994 |
| WO | 95/31458 A1 | 11/1995 |
| WO | 95/35295 A1 | 12/1995 |
| WO | 97/44339 A1 | 11/1997 |

OTHER PUBLICATIONS

Brown et al., Bioorganic & Medicinal Chemistry Letters, vol. 7, No. 5, pp. 597–600, 1997.
Orjales et al., Eur. J. Med. Chem, 34 (1999) 415–422.

* cited by examiner

*Primary Examiner*—Charanjit S. Aulakh
(74) *Attorney, Agent, or Firm*—Birch, Stewart, Kolasch & Birch, LLP

(57) ABSTRACT

The present invention provides an excellent squalene synthesizing enzyme inhibitor. Specifically, it provides a compound (I) represented by the following formula, a salt thereof or a hydrate of them.

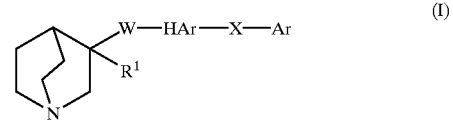

In which $R^1$ represents (1) hydrogen atom or (2) hydroxyl group; HAr represents an aromatic heterocycle which may be substituted with 1 to 3 groups; Ar represents an optionally substituted aromatic ring; W represents a chain represented by (1) —$CH_2$—$CH_2$— which may be substituted, (2) —CH═CH— which may be substituted, (3) —C≡C—, (4) —NH—CO—, (5) —CO—NH—, (6) —NH—$CH_2$—, (7) —$CH_2$—NH—, (8) —$CH_2$—CO—, (9) —CO—$CH_2$—, (10) —NH—S(O)$_l$—, (11) —S(O)$_l$—NH—, (12) —$CH_2$—S(O)— or (13) —S(O)$_l$—$CH_2$— (l denotes 0, 1 or 2); and X represents a chain represented by (1) a single bond, (2) an optionally substituted $C_{1-6}$ alkylene chain, (3) an optionally substituted $C_{2-6}$ alkenylene chain, (4) an optionally substituted $C_{2-6}$ alkynylene chain, (5) a formula —Q— (wherein Q represents oxygen atom, sulfur atom, CO or N($R^2$) (wherein $R^2$ represents a $C_{1-6}$ alkyl group or a $C_{1-6}$ alkoxy group)), (6) —NH—CO—, (7) —CO—NH—, (8) —NH—$CH_2$—, (9) —$CH_2$—NH—, (10) —$CH_2$—CO—, (11) —CO—$CH_2$—, (12) —NH—S(O)$_m$—, (13) —S(O)$_m$—NH—, (14) —$CH_2$—S(O)$_m$—, (15) —S(O)$_m$—$CH_2$— (wherein m denotes 0, 1 or 2) or (16) —(CH_2)$_n$—O— (wherein n denotes an integer from 1 to 6).

30 Claims, No Drawings

QUINUCLIDINE COMPOUNDS AND DRUGS CONTAINING THE SAME AS THE ACTIVE INGREDIENT

This application is the national phase under 35 U.S.C. § 371 of PCT International Application No. PCT/JP00/06665 which has an International filing date of Sep. 27, 2000, which designated the United States of America.

TECHNICAL FIELD

The present invention relates to a novel compound, a method for producing the novel compound, a squalene-synthesizing enzyme inhibitor, a cholesterol biosynthesis inhibitor and a triglyceride biosynthesis inhibitor containing such a novel compound and also to a medicinal composition containing them. More specifically, the present invention relates to preventive and curative agents for hyper lipidemia including arterial sclerosis diseases and ischemic heart diseases.

PRIOR ART

Cholesterol is a sterol which is biosynthesized in all animal cells except for a red blood cell and is a factor essential for maintaining a plasma membrane and for the creation of a steroid hormone. Cholesterol is liposoluble and exists as hypobaric lipoprotein (LDL), hyperbaric lipoprotein (HDL) and the like in blood. LDL in blood is incorporated into cells through an acceptor on the surface of the cells and regenerates free cholesterol after decomposed. This is a major route for incorporating cholesterol from the outside of cells. Also, it has been known that a major enzyme which participates in the biosynthesis of LDL acceptor protein and cholesterol undergoes feedback of the concentration of cholesterol which is the harvested product. In this manner, the level of cholesterol in cells is maintained and controlled exquisitely by the feedback control mechanism of the LDL acceptor and biosynthetic type enzyme on the basis of a balance between the biosynthesis of a cell itself and the incorporation of LDL from the outside of a cell.

In recent years, cholesterol has been recognized as the main culprit of hyper lipidemia and also as the most dangerous factor causing arterial sclerosis diseases (e.g., coronary diseases, cerebrovascular diseases, aortic diseases and peripheral arterial diseases) and ischemic heart diseases (e.g., angina pectoris and cardiac infarction), giving rise to a serious problem. Hyper lipidemia is defined as one showing any one or two or more of the followings: cholesterol in blood is 220 mg/dl or more, neutral lipid is 150 mg/dl or more and hyperbaric lipoprotein (HDL)-cholesterol is less than 35 mg/dl (Guideline of Japan Society of Arterial Sclerosis) and is catastrophic diseases causing arterial sclerosis and the like. One of the major reasons is a rise in the level of LDL-cholesterol in blood (high cholesteremia) and the deposition of cholesterol on the inner wall of a blood vessel. At present, treatment performed to reduce serum cholesterol has come to be thought effective to prevent the development and progress of arterial sclerosis and the like. A cholesterol biosynthesis inhibitor, especially, an inhibitor of 3-hydroxy-3-methyl glutaryl-CoA (HMG-CoA) reducing enzyme such as pravastatin has obtained good results as a medicine for reducing serum cholesterol in recent years instead of conventional fibrate type drugs and nicotinic acid preparations. The HMG-CoA reducing enzyme inhibitor competitively inhibits the HMG-CoA reducing enzyme which is an enzyme limiting the rate of biosynthesis of cholesterol in the liver to decrease the rate of biosynthesis of cholesterol, whereby the liver is increased in the ability to synthesize LDL acceptors, with the result that the serum LDL is decreased. However, the inhibition of the production of mevalonic acid based on the inhibition of the HMG-CoA reducing enzyme affects the production of isoprene including farnecyl diphosphoric acid (FPP). Therefore, there is a fear as to an influence on, for example, other metabolic substances, such as ubiquinone, dolichol, heme A, isopentenyl tRNA and prenyl protein, produced through isoprene as a synthetic intermediate. Further, risks of side effects such as cataract and myopathy have been pointed out.

The squalene synthesizing enzyme is a membrane-bound enzyme of 47-kDa and reducibly catalyzes the head-to-head condensation of two molecules of FPP to synthesize squalene which is an intermediate for the synthesis of cholesterol. In a cholesterol-biosynthesizing system, the squalene synthesizing enzyme is positioned downstream of a system generating the HMG-CoA reducing enzyme and isoprene and therefore the squalene synthesizing enzyme inhibitor is considered to have almost no effect on metabolic systems other than cholesterol and is therefore expected to work as a new cholesterol depressor which will solve the problems concerning the HMG-CoA reducing enzyme inhibitor. A squalene synthesizing enzyme inhibitor which was reported first is analogous compounds of FPP and squalene. However, these analogous compounds has an activity inhibiting the formation of prenyl protein and the like in addition to squalene synthesizing enzyme inhibitive action and it is difficult to put these analogous compounds to practical use. In the meantime, it has been disclosed recently that a certain type substituted phenylethynylquinuclidine compound and substituted pyridinylethynylquinuclidine compound are useful as a squalene synthesizing enzyme inhibitor in JP-A 7-502283, 8-502731, 8-504803 (U.S. Pat. No. 5,731,323) and 8-509488. However, no squalene synthesizing enzyme inhibitor which can produce an effect as a medicine for hyper lipidemia has been created so far.

That is, an object of the present invention is to search and to find a compound which has stronger squalene synthesizing enzyme inhibitive activities and cholesterol depressing action over those currently in use and is useful as a remedy for hyper lipidemia.

DISCLOSURE OF THE INVENTION

In view of the above situation, the inventors of the present invention have made earnest studies and as a result, found that a specific quinuclidine compound and its salt have unprecedented strong squalene synthesizing inhibitive activities. The inventors have also found that these compounds and their salts have strong cholesterol biosynthesizing inhibitive activities, triglyceride biosynthesizing inhibitive activities and serum cholesterol depressing action and serum triglyceride depressing action based on the squalene synthesizing inhibitive activities. The present invention has been thus completed. A compound according to the present invention is useful as a remedy for hyper lipidemia.

Accordingly, the present invention relates to:
(1) a compound (I) represented by the following formula:

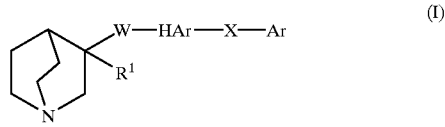

(in which $R^1$ represents (1) hydrogen atom or (2) hydroxyl group; HAr represents an aromatic heterocycle which may be substituted with 1 to 3 groups; Ar represents an optionally substituted aromatic ring; W represents a chain represented by (1) —CH$_2$—CH$_2$— which may be substituted, (2) —CH=CH— which may be substituted, (3) —C≡C—, (4) —NH—CO—, (5) —CO—NH—, (6) —NH—CH$_2$—, (7) —CH$_2$—NH—, (8) —CH$_2$—CO—, (9) —CO—CH$_2$—, (10) —NH—S(O)$_l$—, (11) —S(O)$_l$—NH—, (12) —CH$_2$—S(O)$_l$— or (13) —S(O)$_l$—CH$_2$— (l denotes 0, 1 or 2); and X represents a chain represented by (1) a single bond, (2) an optionally substituted C$_{1-6}$ alkylene chain, (3) an optionally substituted C$_{2-6}$ alkenylene chain, (4) an optionally substituted C$_{2-6}$ alkynylene chain, (5) a formula —Q— (wherein Q represents oxygen atom, sulfur atom, CO or N(R$^2$) (wherein R$^2$ represents a C$_{1-6}$ alkyl group or a C$_{1-6}$ alkoxy group)), (6) —NH—CO—, (7) —CO—NH—, (8) —NH—CH$_2$—, (9) —CH$_2$—NH—, (10) —CH$_2$—CO—, (11) —CO—CH$_2$—, (12) —NH—S(O)$_m$—, (13) —S(O)$_m$—NH—, (14) —CH$_2$—S(O)$_m$—, (15) —S(O)$_m$—CH$_2$— (wherein m denotes 0, 1 or 2) or (16) —(CH$_2$)$_n$—O— (wherein n denotes an integer from 1 to 6)), a salt thereof or a hydrate of them, (2) the compound described in (1), a salt thereof or a hydrate of them, wherein R$^1$ represents (1) hydrogen atom or (2) hydroxyl group; HAr is a 5- to 14-membered aromatic heterocycle which contains 1 to 4 atoms selected from nitrogen atom, sulfur atom and oxygen atom and may be substituted with 1 to 3 groups selected from (1) a halogen atom, (2) hydroxyl group, (3) thiol group, (4) nitro group, (5) nitrile group, (6) a C$_{1-6}$ chain hydrocarbon group which may be substituted, (7) a C$_{3-8}$ cyclic hydrocarbon group which may be substituted, (8) a C$_{6-14}$ aromatic cyclic hydrocarbon group which may be substituted, (9) a 5- to 14-membered aromatic heterocyclic group which may be substituted, (10) a 4- to 10-membered non-aromatic heterocyclic group which may be substituted, (11) a C$_{1-6}$ alkoxy group which may be substituted, (12) a C$_{3-8}$ cycloalkyloxy group which may be substituted, (13) a C$_{1-6}$ chain hydrocarbon-thio group which may be substituted, (14) a C$_{3-8}$ cyclic hydrocarbon-thio group which may be substituted, (15) a C$_{6-14}$ aromatic hydrocarbonoxy group which may be substituted, (16) a 5- to 14-membered heterocycle-oxy group which may be substituted, (17) a C$_{6-14}$ aromatic hydrocarbon-thio group which may be substituted, (18) a 5- to 14-membered heterocycle-thio group which may be substituted, (19) an amino group which may be substituted, (20) azide group, (21) guanidino group, (22) carbamide group, (23) formyl group, (24) a C$_{1-6}$ imidoyl group which may be substituted, (25) a substituted carbonyl group, (26) a substituted carbonyl-oxy group, (27) a carboxyl group which may form a salt, (28) a carbamoyl group which may be substituted, (29) a C$_{1-4}$ alkylenedioxy group which may be substituted, (30) a sulfinyl group which may be substituted and (31) a sulfonyl group which may be substituted; Ar is a C$_{6-14}$ aromatic hydrocarbon ring or a 5- to 14-membered aromatic heterocycle which may be substituted with one or more groups selected from (1) hydroxyl group, (2) a halogen atom, (3) a C$_{1-6}$ chain hydrocarbon group which may be substituted, (4) a C$_{3-8}$ cyclic hydrocarbon group which may be substituted, (5) a C$_{1-6}$ alkoxy group which may be substituted, (6) a C$_{3-8}$ cycloalkyloxy group which may be substituted, (7) a C$_{1-6}$ chain hydrocarbon-thio group which may be substituted, (8) a C$_{3-8}$ cyclic hydrocarbon-thio group, (9) a C$_{6-14}$ aromatic hydrocarbon cyclic group which may be substituted, (10) a 5- to 14-membered heterocyclic group which may be substituted, (11) an amino group which may be substituted with a C$_{1-6}$ alkyl group and (12) a C$_{1-4}$ alkylenedioxy group; W is a chain represented by (1) —CH$_2$—CH$_2$— which may be substituted, (2) —CH=CH— which may be substituted, (3) —C≡C—, (4) —NH—CO—, (5) —CO—NH—, (6) —NH—CH$_2$—, (7) —CH$_2$—NH—, (8) —CH$_2$—CO—, (9) —CO—CH$_2$—, (10) —NH—S(O)$_l$—, (11) —S(O)$_l$—NH—, (12) —CH$_2$—S(O)$_l$— or (13) —S(O)$_l$—CH$_2$— (l denotes 0, 1 or 2); and X represents a chain represented by (1) a single bond, (2) a C$_{1-6}$ alkylene chain which may be substituted, (3) a C$_{2-6}$ alkenylene chain which may be substituted, (4) a C$_{2-6}$ alkynylene chain which may be substituted, (5) the formula —Q— (wherein Q represents oxygen atom, sulfur atom, CO or N(R$^2$) (wherein R$^2$ represents a C$_{1-6}$ alkyl group or a C$_{1-6}$ alkoxy group)), (6) —NH—CO—, (7) —CO—NH—, (8) —NH—CH$_2$—, (9) —CH$_2$—NH—, (10) —CH$_2$—CO—, (11) —CO—CH$_2$—, (12) —NH—S(O)$_m$—, (13) —S(O)$_m$—NH—, (14) —CH$_2$—S(O)$_m$—, (15) —S(O)$_m$—CH$_2$— (wherein m denotes 0, 1 or 2) or (16) —(CH$_2$)$_n$—O— (wherein n represents an integer from 1 to 6), (3) the compound described in (1) or (2), a salt thereof or a hydrate of them, in which R$^1$ is hydroxyl group, (4) the compound described in (1) or (2), a salt thereof or a hydrate of them, in which W is —CH$_2$—CH$_2$—, —CH=CH— or —C≡C—, (5) the compound described in 1) or 2), a salt thereof or a hydrate of them, in which X is a single bond, —CH$_2$—, —CH$_2$—CH$_2$—, —CH=CH— or —CO—, (6) the compound described in (1) or (2), a salt thereof or a hydrate of them, wherein HAr is a 5- to 14-membered aromatic heterocycle containing 1 to 4 atoms selected from nitrogen atom, sulfur atom and oxygen atom and may be substituted with 1 to 3 groups selected from (1) hydroxyl group, (2) a halogen atom, (3) thiol group, (4) nitro group, (5) nitrile group, (6) a C$_{1-6}$ alkyl group, C$_{2-6}$ alkenyl group or C$_{2-6}$ alkynyl group, which may be substituted with one or two groups selected from (a) a hydroxyl group which may be protected, (b) a halogen atom, (c) nitrile group, (d) carboxyl group, (e) a C$_{3-8}$ cycloalkyl group, C$_{3-8}$ cycloalkenyl group or C$_{3-8}$ cycloalkynyl group, which may be hydroxylated or halogenated, (f) a C$_{1-6}$ alkoxy group which may be substituted with a group selected from a halogen atom, hydroxyl group, a C$_{6-14}$ aryl group, a 5- to 14-membered heteroaryl group and a C$_{6-14}$ aryl-C$_{1-6}$ alkoxy group, (g) a C$_{3-8}$ cycloalkyloxy group which may be halogenated or hydroxylated, (h) a C$_{3-8}$ cycloalkenyloxy group which may be halogenated or hydroxylated, (i) a 5- to 14-membered aryl-oxy group which may be halogenated or hydroxylated, (j) a 5- to 14 membered non-aromatic cycle-oxy group which may be halogenated or hydroxylated, (k) a C$_{1-6}$ alkoxy-carbonyl group, (l) a C$_{1-4}$ alkylenedioxy group which may be halogenated, (m) a C$_{1-6}$ alkanoyl group which may be substituted with a group selected from hydroxyl group, a C$_{1-6}$ alkoxy group and a C$_{1-6}$ alkanoyloxy group, (n) a C$_{6-14}$ aryl group which may be substituted with a group selected from a halogen atom, a C$_{1-6}$ alkyl group and a C$_{1-6}$ alkoxy group, (o) a 5- to 14-membered aromatic heterocyclic group which may be substituted with a group selected from a halogen atom, a C$_{1-6}$ alkyl group, a C$_{3-8}$ alkenyl group, a C$_{3-8}$ alkynyl group and a C$_{1-6}$ alkoxy group, (p) a 5- to 10-membered non-aromatic heterocyclic group which may be substituted with a group selected from a halogen atom, a C$_{1-6}$ alkyl group, a C$_{3-8}$ alkenyl group, a C$_{3-8}$ alkynyl group and a C$_{1-6}$ alkoxy group, (q) a group (EtO)$_2$PO—, (r) acetyl group, (s) a sulfonyl group which may be substituted with a group selected from a C$_{1-6}$ hydrocarbon group, a mono-(C$_{1-6}$ hydrocarbon)-amino group and a di-(C$_{1-6}$ hydrocarbon)-amino group, (t) an amino group which may be substituted with a C$_{1-6}$ hydrocarbon group, (u) a C$_{1-6}$ hydrocarbon group-thio group which may be hydroxylated or halogenated and (v) a carbamoyl group which may be substituted with a C$_{1-6}$ hydrocarbon group, (7) a C$_{3-8}$ cycloalkyl group or C$_{3-8}$ cycloalkenyl group which may be substituted with one or two groups selected from (a) hydroxyl group, (b) a halogen atom, (c) nitrile group, (d) carboxyl group, (e) a C$_{1-6}$ alkyl group which may be substituted with a group selected from a C$_{1-6}$ alkoxy group which may be hydroxylated or halogenated, a C$_{1-6}$ hydrocarbon-thio group which may be halogenated, an amino group which may be substituted with a C$_{1-6}$ hydrocarbon group and a C$_{1-6}$ alkanoyl group, (f) a C$_{1-6}$ alkenyl group which may be substituted with a group selected from a C$_{1-6}$ alkoxy group which may be hydroxylated or halogenated, a C$_{1-6}$ hydrocarbon-thio group which maybe halogenated, an amino group which may be substituted with a C$_{1-6}$ hydrocarbon group and a C$_{1-6}$ alkanoyl group, (g) a C$_{1-6}$ alkynyl group which may be substituted with a group selected from a C$_{1-6}$ alkoxy group which may be hydroxylated or halogenated, a C$_{1-6}$ hydrocarbon-thio group which may be halogenated, an amino group which may be substituted with a C$_{1-6}$ hydrocarbon group and a C$_{1-6}$ alkanoyl group, (h) an amino group which may be substituted with a group selected from a C$_{1-6}$ alkoxy group which may be hydroxylated or halogenated, a C$_{1-6}$ hydrocarbon-thio group which may be halogenated, a C$_{1-6}$ alkanoyl group and a C$_{1-6}$ hydrocarbon group, (i) a C$_{1-6}$ alkoxy group which may be substituted with a group selected from a C$_{1-6}$ alkyl group which may be hydroxylated or halogenated, a C$_{1-6}$ alkoxy group which may be hydroxylated or halogenated, a C$_{1-6}$ hydrocarbon-thio group which may be halogenated, an amino group which may be substituted with a C$_{1-6}$ hydrocarbon group and a C$_{1-6}$ alkanoyl group, (j) a C$_{1-6}$ hydrocarbon-thio group which may be substituted with a group selected from a C$_{1-6}$ alkyl group which may be hydroxylated or halogenated, a C$_{1-6}$ alkenyl group which may be halogenated, a C$_{1-6}$ alkynyl group which may be halogenated, a C$_{1-6}$ alkoxy group which may be hydroxylated or halogenated, a C$_{1-6}$ hydrocarbon-thio group which may be halogenated, an amino group which may be substituted with a C$_{1-6}$ hydrocarbon group and a C$_{1-6}$ alkanoyl group, (k) a C$_{1-6}$ alkanoyl group which may be substituted with a group selected from hydroxyl group, a C$_{1-6}$ alkoxy group and a C$_{1-6}$ alkanoyloxy group, (l) a C$_{6-14}$ aryl group which may be substituted with a group selected from a halogen atom, a C$_{1-6}$ alkyl group and a C$_{1-6}$ alkoxy group, (m) a 5- to 14-membered aromatic heterocyclic group which may be substituted with a group selected from a halogen atom, a C$_{1-6}$ alkyl group, a C$_{3-8}$ alkenyl group, a C$_{3-8}$ alkynyl group and a C$_{1-6}$ alkoxy group, (n) a non-aromatic heterocyclic group which may be substituted with a group selected from a halogen atom, a C$_{1-6}$ alkyl group, a C$_{3-8}$ alkenyl group, a C$_{3-8}$ alkynyl group and a C$_{1-6}$ alkoxy group, (o) a C$_{1-6}$ alkoxy-carbonyl group, (p) a C$_{1-4}$ alkylenedioxy group which may be halogenated, (q) a group (EtO)$_2$PO— and (r) acetyl group, (8) a C$_{6-14}$ aromatic hydrocarbon group which may be substituted with one or more groups selected from (a) hydroxyl group, (b) a halogen atom, (c) a C$_{1-6}$ alkyl-sulfonyl group, C$_{1-6}$ alkenyl-sulfonyl group and C$_{1-6}$ alkynyl-sulfonyl group, which may be halogenated, (d) a C$_{1-4}$ alkylenedioxy group which may be halogenated, (e) a C$_{1-6}$ alkoxy group which may be halogenated, (f) a C$_{1-6}$ hydrocarbon-thio group which may be halogenated, (g) a C$_{1-6}$ alkoxy-carbonyl group, (h) a C$_{6-14}$ aryl-C$_{1-6}$ alkoxy group, (i) a C$_{1-7}$ alkanoylamino group, (j) a C$_{1-6}$ alkyl-carbamoyl group, (k) a C$_{1-6}$ alkenyl-carbamoyl group, (l) a C$_{1-6}$ alkynyl-carbamoyl group and (m) an amino group which may be substituted with a C$_{1-6}$ hydrocarbon group, (9) a 5- to 14-membered aromatic heterocyclic group which may be substituted with one or more groups selected from (a) hydroxyl group, (b) a halogen atom, (c) nitrile group, (d) a C$_{1-6}$ alkyl group, C$_{1-6}$ alkenyl group or C$_{1-6}$ alkynyl group, which may be halogenated, (e) a C$_{1-6}$ alkoxy group which may be halogenated, (f) a C$_{1-6}$ alkylthio group, C$_{1-6}$ alkenylthio group or C$_{1-6}$ alkynylthio group which may be halogenated, (g) a C$_{1-6}$ alkoxy-C$_{1-6}$ alkyl group, (h) acetyl group, (i) an C$_{1-6}$ alkanoyl group, (j) a mono-(C$_{1-6}$ hydrocarbon)-amino group, (k) a di-(C$_{1-6}$ hydrocarbon)-amino group and (l) a tri-(C$_{1-6}$ hydrocarbon)-amino group, (10) a 4- to 10-membered non-aromatic heterocyclic group which may be substituted with one or more groups selected from (a) hydroxyl group, (b) a halogen atom, (c) nitrile group, (d) a C$_{1-6}$ alkyl group, C$_{1-6}$ alkenyl group or C$_{1-6}$ alkynyl group, which may be halogenated, (e) a C$_{1-6}$ alkoxy group which may be halogenated, (f) a C$_{1-6}$ alkylthio group, C$_{1-6}$ alkenylthio group or C$_{1-6}$ alkynylthio group, which may be halogenated, (g) a C$_{1-6}$ alkoxy-C$_{1-6}$ alkyl group, (h) acetyl group, (i) a C$_{1-6}$ alkanoyl group, (j) a mono-(C$_{1-6}$ hydrocarbon)-amino group, (k) a di-(C$_{1-6}$ hydrocarbon)-amino group and (l) a tri-(C$_{1-6}$ hydrocarbon)-amino group, (m) a C$_{1-4}$ alkylenedioxy group and (n) an oxo group, (11) a C$_{1-6}$ alkoxy group which may be substituted with one or more groups selected from (a) hydroxyl group, (b) a halogen atom, (c) a C$_{1-6}$ alkyl group, C$_{1-6}$ alkenyl group or C$_{1-6}$ alkynyl group, which may be substituted with a group selected from hydroxyl group, a halogen atom, a 5- to 14-membered aromatic heterocyclic group and a 4 to 10-membered non-aromatic heterocyclic group, (d) a C$_{3-8}$ cycloalkyl group or C$_{3-8}$ cycloalkenyl group which may be hydroxylated or halogenated, (e) a C$_{1-6}$ alkoxy group which may be hydroxylated or halogenated, (f) a C$_{1-6}$ alkylthio group, C$_{1-6}$ alkenylthio group or C$_{1-6}$ alkynylthio group, which may be halogenated, (g) a C$_{3-8}$ cycloalkyloxy group or C$_{3-8}$ cycloalkenyloxy group which may be halogenated, (h) a C$_{3-8}$ cycloalkylthio group or C$_{3-8}$ cycloalkenylthio group which may be halogenated, (i) a C$_{6-14}$ aryl group, (j) a C$_{1-6}$ alkanoyl group which may be halogenated, (k) a 5- to 14-membered aromatic heterocyclic group and (l) a 4- to 10-membered non-aromatic heterocyclic group, (12) a C$_{3-8}$ cycloalkyloxy group which may be substituted with one or two groups selected from (a) hydroxyl group, (b) a halogen atom, (c) a C$_{1-6}$ a hydrocarbon group which may be substituted with a group selected from hydroxyl group, a halogen atom, a C$_{1-6}$ alkoxy group and a C$_{1-6}$ alkanoyl group, (d) a C$_{1-6}$ alkoxy group which may be substituted with a group selected from a halogen atom, a C$_{1-6}$ alkoxy group and a C$_{1-6}$ alkanoyl group and (e) a C$_{1-6}$ hydrocarbon-thio group which may be substituted with a group selected from a halogen atom, a C$_{1-6}$ alkoxy group and a C$_{1-6}$ alkanoyl group, (13) a C$_{1-6}$ alkylthio group, C$_{1-6}$ alkenylthio group or C$_{1-6}$ alkynylthio group, which may be substituted with one or two groups selected from (a) hydroxyl group, (b) a halogen atom, (c) a C$_{1-6}$ alkyl group, C$_{1-6}$ alkenyl group or C$_{1-6}$ alkynyl group which may be substituted with a group selected from hydroxyl group, a halogen atom, a 5- to 14-membered aromatic heterocyclic group and 4- to 10-membered non-aromatic heterocyclic group, (d) a $C_{3-8}$ cycloalkyl group, $C_{3-8}$ cycloalkenyl group or $C_{3-8}$ cycloalkynyl group, which may be hydroxylated or halogenated, (e) a $C_{1-6}$ alkoxy group which may be hydroxylated or halogenated, (f) a $C_{1-6}$ alkylthio group, $C_{1-6}$ alkenylthio group or $C_{1-6}$ alkynylthio group, which may be halogenated, (g) a $C_{3-8}$ cycloalkyloxy group or $C_{3-8}$ cycloalkenyloxy group which may be halogenated, (h) a $C_{3-8}$ cycloalkylthio group or $C_{3-8}$ cycloalkenylthio group which may be halogenated, (i) a $C_{6-14}$ aryl group, (j) a $C_{1-6}$ alkanoyl group which may be halogenated, (k) a 5- to 14-membered aromatic heterocyclic group and (l) a 4- to 10-membered non-aromatic heterocycle, (14) a $C_{3-8}$ cycloalkylthio group or a $C_{3-8}$ cycloalkenylthio group which may be substituted with one or two groups selected from (a) hydroxyl group, (b) a halogen atom, (c) a $C_{3-8}$ alkyl group, $C_{3-8}$ alkenyl group or $C_{3-8}$ alkynyl group, which may be halogenated, (d) a $C_{1-6}$ alkoxy group which may be halogenated, (e) a $C_{1-6}$ hydrocarbon-thio group which may be halogenated and (f) a $C_{1-6}$ alkanoyl group which may be halogenated, (15) an amino group represented by the formula —N($R^3$)$R^4$ (wherein $R^3$ and $R^4$ are the same as or different from each other and each represents a group selected from (a) an aromatic heterocyclic group, (b) a non-aromatic heterocyclic group, (c) a $C_{1-6}$ alkyl group, $C_{1-6}$ alkenyl group or $C_{1-6}$ alkynyl group, which may be substituted with a halogen atom or a $C_{1-6}$ alkoxy group, (d) a $C_{3-8}$ cycloalkyl group or a $C_{3-8}$ cycloalkenyl group which may be halogenated, (e) a carbonyl group which is substituted with a $C_{1-6}$ alkyl group, $C_{1-6}$ alkenyl group or $C_{1-6}$ alkynyl group, which may be halogenated, a $C_{3-8}$ cycloalkyl group or $C_{3-8}$ cycloalkenyl group, which may be halogenated, a $C_{1-6}$ alkoxy group which may be halogenated, a $C_{6-14}$ aryl group or an aromatic heterocyclic group, (f) a $C_{1-6}$ alkanoyl group which may be substituted with a group selected from a $C_{6-14}$ aryl group and an aromatic heterocyclic group, (g) a carbamoyl group which may be substituted with a $C_{1-6}$ alkyl group, a $C_{1-6}$ alkenyl group, a $C_{1-6}$ alkynyl group, a $C_{6-14}$ aryl group or an aromatic heterocyclic group and (h) a sulfonyl group which is substituted with a $C_{1-6}$ alkyl group, a $C_{1-6}$ alkenyl group or a $C_{1-6}$ alkynyl group, and also, (i) $R^3$ and $R^4$ may be combined and united to form a 3- to 10-membered ring and the cyclic amino group may be substituted with one or more groups selected from hydroxyl group, a halogen atom, a $C_{1-6}$ alkyl group, a $C_{1-6}$ alkenyl group, a $C_{1-6}$ alkynyl group, a $C_{1-6}$ alkoxy group, a $C_{1-6}$ hydrocarbon-thio group and a $C_{1-4}$ alkylenedioxy group), (16) a $C_{6-14}$ aryl-oxy group which may be substituted with one or more groups selected from (a) hydroxyl group, (b) a halogen atom, (c) a $C_{1-6}$ alkyl-sulfonyl group, $C_{1-6}$ alkenyl-sulfonyl group or $C_{1-6}$ alkynyl-sulfonyl group which may be halogenated, (d) a $C_{1-4}$ alkylenedioxy group which may be halogenated, (e) a $C_{1-6}$ alkoxy group which may be halogenated, (f) a $C_{1-6}$ hydrocarbon-thio group which may be halogenated, (g) a $C_{1-6}$ alkoxy-carbonyl group, (h) a $C_{6-14}$ aryl-$C_{1-6}$ alkoxy group, (i) a $C_{1-7}$ alkanoylamino group, (j) a $C_{1-6}$ alkyl-carbamoyl group, (k) a $C_{1-6}$ alkenyl-carbamoyl group, (l) a $C_{1-6}$ alkynyl-carbamoyl group and (m) an amino group which may be substituted with a $C_{1-6}$ hydrocarbon group, (17) a $C_{6-14}$ aryl-thio group which may be substituted with one or more groups selected from (a) hydroxyl group, (b) a halogen atom, (c) a $C_{1-6}$ alkyl-sulfonyl group, $C_{1-6}$ alkenyl-sulfonyl group or $C_{1-6}$ alkynyl-sulfonyl group, which may be halogenated, (d) a $C_{1-4}$ alkylenedioxy group which may be halogenated, (e) a $C_{1-6}$ alkoxy group which may be halogenated, (f) a $C_{1-6}$ hydrocarbon-thio group which may be halogenated, (g) a $C_{1-6}$ alkoxy-carbonyl group, (h) a $C_{6-14}$ aryl-$C_{1-6}$ alkoxy group, (i) a $C_{1-7}$ alkanoylamino group (j) a $C_{1-6}$ alkyl-carbamoyl group, (k) a $C_{1-6}$ alkenyl-carbamoyl group, (l) a $C_{1-6}$ alkynyl-carbamoyl group and (m) an amino group which may be substituted with a $C_{1-6}$ hydrocarbon group, (18) a 5- to 15-membered aromatic heterocycle-oxy group which may be substituted one or more groups selected from (a) hydroxyl group, (b) a halogen atom, (c) nitrile group, (d) a $C_{1-6}$ alkyl group, $C_{1-6}$ alkenyl group or $C_{1-6}$ alkynyl group, which may be halogenated, (e) a $C_{1-6}$ alkoxy group which may be halogenated, (f) a $C_{1-6}$ alkylthio group, $C_{1-6}$ alkenylthio group or $C_{1-6}$ alkynylthio group, which may be halogenated, (g) a $C_{1-6}$ alkoxy-$C_{1-6}$ alkyl group, (h) acetyl group, (i) a $C_{1-6}$ alkanoyl group, (j) a mono-($C_{1-6}$ hydrocarbon)-amino group, (k) a di-($C_{1-6}$ hydrocarbon)-amino group and (l) a tri-($C_{1-6}$ hydrocarbon)-amino group, (19) a 5- to 15-membered aromatic heterocycle-thio group which may be substituted one or more groups selected from (a) hydroxyl group, (b) a halogen atom, (c) nitrile group, (d) a $C_{1-6}$ alkyl group, $C_{1-6}$ alkenyl group or $C_{1-6}$ alkynyl group, which may be halogenated, (e) a $C_{1-6}$ alkoxy group which may be halogenated, (f) a $C_{1-6}$ alkylthio group, $C_{1-6}$ alkenylthio group or $C_{1-6}$ alkynylthio group, which may be halogenated, (g) a $C_{1-6}$ alkoxy-$C_{1-6}$ alkyl group, (h) acetyl group, (i) a $C_{1-6}$ alkanoyl group, (j) a mono-($C_{1-6}$ hydrocarbon)-amino group, (k) a di-($C_{1-6}$ hydrocarbon)-amino group and (l) a tri-($C_{1-6}$ hydrocarbon)-amino group, (20) a 4- to 10-membered non-aromatic heterocycle-oxy group which may be substituted one or more groups selected from (a) hydroxyl group, (b) a halogen atom, (c) nitrile group, (d) a $C_{1-6}$ alkyl group, $C_{1-6}$ alkenyl group or $C_{1-6}$ alkynyl group, which may be halogenated, (e) a $C_{1-6}$ alkoxy group which may be halogenated, (f) a $C_{1-6}$ alkylthio group, $C_{1-6}$ alkenylthio group or $C_{1-6}$ alkynylthio group which may be halogenated, (g) a $C_{1-6}$ alkoxy-$C_{1-6}$ alkyl group, (h) acetyl group, (i) a $C_{1-6}$ alkanoyl group, (j) a mono-($C_{1-6}$ hydrocarbon)-amino group, (k) a di-($C_{1-6}$ hydrocarbon)-amino group and (l) a tri-($C_{1-6}$ hydrocarbon)-amino group, (21) a 4- to 10-membered non-aromatic heterocycle-thio group which may be substituted one or more groups selected from (a) hydroxyl group, (b) a halogen atom, (c) nitrile group, (d) a $C_{1-6}$ alkyl group, $C_{1-6}$ alkenyl group or $C_{1-6}$ alkynyl group, which may be halogenated, (e) a $C_{1-6}$ alkoxy group which may be halogenated, (f) a $C_{1-6}$ alkylthio group, $C_{1-6}$ alkenylthio group or $C_{1-6}$ alkynylthio group which may be halogenated, (g) a $C_{1-6}$ alkoxy-$C_{1-6}$ alkyl group, (h) acetyl group, (i) a $C_{1-6}$ alkanoyl group, (j) a mono-($C_{1-6}$ hydrocarbon)-amino group, (k) a di-($C_{1-6}$ hydrocarbon)-amino group and (l) a tri-($C_{1-6}$ hydrocarbon)-amino group, (22) azide group, (23) guanidino group, (24) carbamide group, (25) formyl group, (26) a $C_{1-6}$ imidoyl group which may be substituted, (27) a $C_{1-6}$ alkanoyl group which may be substituted with a $C_{1-6}$ alkoxy group, (28) a $C_{1-6}$ alkanoyl-oxy group which may be substituted with a $C_{1-6}$ alkoxy group, (29) a carboxyl group which may form a salt, (30) a carbonyl group which is substituted with a group selected from (a) a $C_{1-6}$ alkoxy group, (b) a $C_{6-14}$ aryl group and (c) a 5- to 14-membered aromatic heterocyclic group, (31) a carbamoyl group represented by the formula —CO—N($R^5$)$R^6$ (wherein $R^5$ and $R^6$ are the same as or different from each other and each represents a group selected from (a) hydrogen atom, (b) a $C_{1-6}$ alkyl group, (c) a $C_{1-6}$ alkenyl group, (d) a $C_{1-6}$ alkynyl group, (e) a $C_{3-8}$ cycloalkyl group, (f) a $C_{3-8}$ cycloalkenyl group, (g) a $C_{6-14}$ aryl group and (h) an aromatic heterocyclic group or (i) $R^5$ and $R^6$ may be combined and united to form a 3- to 8-membered ring), (32) a $C_{1-4}$ alkylenedioxy group which may be substituted with (a) hydroxyl group or (b) a halogen atom, (33) a sulfinyl group which may be substituted with a group selected from (a) a $C_{1-6}$ hydrocarbon group which may be halogenated and (b) an amino group which may be mono-substituted or di-substituted with a $C_{1-6}$ hydrocarbon group which may be halogenated and (34) a sulfonyl group which may be substituted with (a) a $C_{1-6}$ hydrocarbon group which may be halogenated or (b) an amino group which may be mono-substituted or di-substituted with a $C_{1-6}$ hydrocarbon group which may be halogenated, (7) the compound described in (1) or (2), a salt thereof or a hydrate of them, wherein HAr is a 5- to 14-membered aromatic heterocycle which may be substituted with, in addition to a substituent —X—Ar, 1 to 3 groups selected from (1) a 5- or 6-membered aromatic heterocycle which may be substituted with a $C_{1-6}$ alkyl group, (2) a 5- to 6-membered non-aromatic heterocycle which may be substituted with one or more groups selected from (a) hydroxyl group, (b) a $C_{1-6}$ alkyl group and (c) a $C_{1-6}$ alkoxy group, (3) a $C_{6-10}$ aromatic hydrocarbon ring which may be substituted with one or more groups selected from (a) a halogen atom, (b) a $C_{1-6}$ alkoxy group, (c) a $C_{1-4}$ alkylenedioxy group and (d) a sulfonyl group which may be substituted with a $C_{1-6}$ alkyl group, (4) a $C_{1-6}$ alkyl group which may be substituted with one or more groups selected from (a) hydroxyl group, (b) a halogen atom, (c) a 5- or 6-membered aromatic heterocycle and (d) a $C_{1-6}$ alkoxy group and (5) a $C_{1-6}$ alkoxy group which may be substituted with (a) a halogen atom or (b) a $C_{1-6}$ alkoxy group, (8) the compound described in (1) or (2), a salt thereof or a hydrate of them, wherein HAr is a 5- to 10-membered aromatic heterocycle which may be substituted with, in addition to a substituent —X—Ar, 1 to 3 groups selected from (1) a benzene ring which may be substituted with a $C_{1-4}$ alkylenedioxy group, (2) pyridine ring, (3) pyrimidine ring, (4) pyridazine ring, (5) pyrazine ring, (6) thiophene ring, (7) a piperidine ring which may be substituted with a $C_{1-6}$ alkoxy group, (8) a piperazine ring which may be substituted with a $C_{1-6}$ alkoxy group, (9) a pyrrolidine ring which may be substituted with a $C_{1-6}$ alkoxy group, (10) a piperidine ring which is substituted with hydroxyl group and a $C_{1-6}$ alkoxy group, (11) a piperazine ring which is substituted with hydroxyl group and a $C_{1-6}$ alkoxy group, (12) a pyrrolidine ring which is substituted with hydroxyl group and a $C_{1-6}$ alkoxy group, (13) morpholine ring, (14) a $C_{1-6}$ alkyl group which may be substituted with a $C_{1-6}$ alkoxy group and (15) a $C_{1-6}$ alkoxy group which may be substituted with hydroxyl group or a $C_{1-6}$ alkoxy group, (9) the compound described in (1) or (2), a salt thereof or a hydrate of them, in which HAr is a pyridine ring, pyrimidine ring, pyridazine ring, pyrazine ring, indole ring, quinoline ring, thiophene ring or benzothiophene ring which may be substituted with 1 to 3 groups,

(10) the compound described in (1) or (2), a salt thereof or a hydrate of them, wherein HAr is a pyridine ring, pyrimidine ring, pyridazine ring, pyrazine ring, indole ring, quinoline ring, thiophene ring or benzothiophene ring, which may be substituted with, in addition to a substituent —X—Ar, 1 to 3 groups selected from (1) a 5- or 6-membered aromatic heterocycle which may be substituted with a $C_{1-6}$ alkyl group, (2) a 5- or 6-membered aromatic heterocycle which may be substituted with one or more groups selected from (a) hydroxyl group, (b) a $C_{1-6}$ alkyl group and (c) a $C_{1-6}$ alkoxy group, (3) a $C_{6-10}$ aromatic hydrocarbon ring which may be substituted with one or more groups selected from (a) a halogen atom, (b) a $C_{1-6}$ alkoxy group, (c) a $C_{1-4}$ alkylenedioxy group and (d) a sulfonyl group which may be substituted with a $C_{1-6}$ alkyl group, (4) a $C_{1-6}$ alkyl group which may be substituted with one or more groups selected from (a) hydroxyl group, (b) a halogen atom, (c) a 5- or 6-membered heterocycle and (d) a $C_{1-6}$ alkoxy group and (5) a $C_{1-6}$ alkoxy group which may be substituted with (a) a halogen atom and (b) a $C_{1-6}$ alkoxy group,

(11) the compound described in (1) or (2), a salt thereof or a hydrate of them, wherein Ar is a $C_{6-14}$ aromatic hydrocarbon ring or 5- to 14-membered aromatic heterocycle, which may have 1 to 3 substituents selected from (1) a halogen atom, (2) a $C_{1-6}$ alkyl group, $C_{2-6}$ alkenyl group or $C_{2-6}$ alkynyl group, which may be substituted with one or more groups selected from (a) a halogen atom, (b) a $C_{1-6}$ alkoxy group and (c) a sulfonyl group which may be substituted, (3) a $C_{1-6}$ alkoxy group which may be halogenated, (4) a mono-($C_{1-6}$ alkyl)-amino group, (5) a di-($C_{1-6}$ alkyl)-amino group and (6) a $C_{1-4}$ alkylenedioxy group which may be halogenated,

(12) the compound described in (1) or (2), a salt thereof or a hydrate of them, in which Ar is an optionally substituted benzene ring or pyridine ring,

(14) the compound described in (1) or (2), a salt thereof or a hydrate of them, in which X is —$CH_2$—; and Ar is benzene ring,

(15) the compound described in (1) or (2) in which the compound is represented by the following formula:

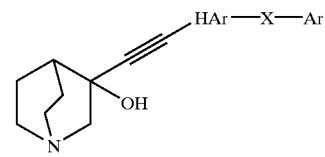

(in the formula, HAr represents a 5- to 10-membered aromatic heterocycle containing 1 to 4 atoms selected from nitrogen atom, sulfur atom and oxygen atom and may be substituted with 1 to 3 groups selected from (1) a halogen atom, (2) hydroxyl group, (3) thiol group, (4) nitro group, (5) nitrile group, (6) a $C_{1-6}$ chain hydrocarbon group which may be substituted, (7) a $C_{3-8}$ cyclic hydrocarbon group which may be substituted, (8) a $C_{6-14}$ aromatic cyclic hydrocarbon group which may be substituted, (9) a 5- to 14-membered aromatic heterocyclic group which may be substituted, (10) a 4- to 10-membered non-aromatic heterocyclic group which may be substituted, (11) a $C_{1-6}$ alkoxy group which may be substituted, (12) a $C_{3-8}$ cycloalkyloxy group which may be substituted, (13) a $C_{1-6}$ chain hydrocarbon-thio group which may be substituted, (14) a $C_{3-8}$ cyclic hydrocarbon-thio group which may be substituted, (15) a $C_{6-14}$ aromatic hydrocarbon-oxy group which may be substituted, (16) a 5- to 14-membered heterocycle-oxy group which may be substituted, (17) a $C_{6-14}$ aromatic hydrocarbon-thio group which may be substituted, (18) a 5- to 14-membered heterocycle-thio group which may be substituted, (19) an amino group which may be substituted, (20) azide group, (21) guanidino group, (22) carbamide group, (23) a formyl group, (24) a $C_{1-6}$ imidoyl group which may be substituted, (25) a substituted carbonyl group, (26) a substituted carbonyl-oxy group, (27) a carboxyl group which may form a salt, (28) a carbamoyl group which may be substituted, (29) a $C_{1-4}$ alkylenedioxy group which may be substituted, (30) a sulfinyl group which may be substituted and (31) a sulfonyl group which may be substituted; Ar is a $C_{6-14}$ aromatic hydrocarbon ring or 5- to 14-membered aromatic heterocycle, which may be substituted with a group selected from (1) hydroxyl group, (2) a halogen atom, (3) a $C_{1-6}$ chain hydrocarbon group which may be substituted, (4) a $C_{3-8}$ cyclic hydrocarbon group which may be substituted, (5) a $C_{1-6}$ alkoxy group which may be substituted, (6) a $C_{3-8}$ cycloalkyloxy group which may be substituted, (7) a $C_{1-6}$ chain hydrocarbon-thio group which may be substituted, (8) a $C_{3-8}$ cyclic hydrocarbon-thio group, (9) a $C_{6-14}$ aromatic hydrocarbon cyclic group which may be substituted, (10) a 5- to 14-membered heterocyclic group which may be substituted, (11) an amino group which may be substituted with a $C_{1-6}$ alkyl group and (12) a $C_{1-4}$ alkylenedioxy group; and X represents a chain represented by (1) a single bond, (2) a $C_{1-6}$ alkylene chain which may be substituted, (3) a $C_{2-6}$ alkenylene chain which may be substituted, (4) a $C_{2-6}$ alkynylene chain which may be substituted, (5) the formula —Q— (wherein Q represents oxygen atom, sulfur atom, CO or $N(R^2)$ (wherein $R^2$ represents a $C_{1-6}$ alkyl group or a $C_{1-6}$ alkoxy group)), (6) —NH—CO—, (7) —CO—NH—, (8) —NH—CH$_2$—, (9) —CH$_2$—NH—, (10) —CH$_2$—CO—, (11) —CO—CH$_2$—, (12) —NH—S(O)$_m$—, (13) —S(O)$_m$—NH—, (14) —CH$_2$—S(O)$_m$—, (15) —S(O)$_m$—CH$_2$— (wherein m is 0, 1 or 2) or (16) —(CH$_2$)$_n$—O— (wherein n denotes an integer from 1 to 6)), a salt thereof or a hydrate of them,

(16) the compound described in (15), a salt thereof or a hydrate of them, in which HAr is a pyridine ring, pyrazine ring, pyrimidine ring or pyridazine ring, which may be substituted with, in addition to a substituent —X—Ar, one or more groups selected from (1) a 5- or 6-membered aromatic heterocycle, (2) a 5- or 6-membered non-aromatic heterocycle which may be substituted with a $C_{1-6}$ alkoxy group and (3) a $C_{6-10}$ aromatic hydrocarbon ring; Ar is a benzene ring or pyridine ring which may be halogenated; and X is —CH$_2$—,

(17) the compound described in (15), a salt thereof or a hydrate of them, in which HAr is a pyridine ring, pyrazine ring, pyrimidine ring or pyridazine ring, which may be substituted with, in addition to a substituent —X—Ar, a group selected from (1) a $C_{1-6}$ alkoxy group which may be substituted with hydroxyl group, (2) a $C_{1-6}$ alkoxy-$C_{1-6}$ alkoxy group and (3) a $C_{1-6}$ alkoxy-$C_{1-6}$ alkyl-amino group; Ar is an optionally halogenated benzene or pyridine ring; and X is —CH$_2$—,

(18) the compound described in (15), a salt thereof or a hydrate of them, wherein HAr is a pyridine ring, pyrazine ring, pyrimidine ring or pyridazine ring, which may be substituted with, in addition to a substituent —X—Ar, 1 to 3 groups selected from (1) a benzene ring which may be substituted with a $C_{1-4}$ alkylenedioxy group, (2) pyridine ring, (3) pyrimidine ring, (4) pyridazine ring, (5) pyrazine ring, (6) thiophene ring, (7) a piperidine ring which may be substituted with a $C_{1-6}$ alkoxy group, (8) a piperazine ring which may be substituted with a $C_{1-6}$ alkoxy group, (9) a pyrrolidine ring which may be substituted with a $C_{1-6}$ alkoxy group, (10) a piperidine ring which is substituted with hydroxyl group and a $C_{1-6}$ alkoxy group, (11) a piperazine ring which is substituted with hydroxyl group and a $C_{1-6}$ alkoxy group, (12) a pyrrolidine ring which is substituted with hydroxyl group and a $C_{1-6}$ alkoxy group, (13) morpholine ring, (14) a $C_{1-6}$ alkyl group which may be substituted with a $C_{1-6}$ alkoxy group and (15) a $C_{1-6}$ alkoxy group which may be substituted with hydroxyl group or a $C_{1-6}$ alkoxy group; Ar is a benzene ring or pyridine ring, which may be halogenated; and X is —CH$_2$—,

(19) the compound described in (1), a salt thereof or a hydrate of them, in which the compound is any one selected from 3-(4-benzyl-2-phenyl-5-pyrimidyl)ethynyl-3-quinuclidinol; 3-[4-benzyl-2-(2-pyridyl)-5-pyrimidyl]ethynyl-3-quinuclidinol; 3-[3-benzyl-5-(2-pyridyl)-2-pyridyl]ethynyl-3-quinuclidinol; 3-(3-benzyl-5-phenyl-2-pyridyl)ethynyl-3-quinuclidinol; 3-[3-benzyl-5-(3-pyridyl)-2-pyridyl]ethynyl-3-quinuclidinol; 3-[3-benzyl-5-(4-pyridyl)-2-pyridyl]ethynyl-3-quinuclidinol; 3-(3-benzyl-5-pyrazyl-2-pyridyl)ethynyl-3-quinuclidinol; 3-[3-benzyl-5-(2-ethoxycarbonylethyl)-2-pyridyl]ethynyl-3-quinuclidinol; 3-[3-benzyl-5-(3-oxobutyl)-2-pyridyl]ethynyl-3-quinuclidinol; 3-[3-benzyl-5-(3-hydroxybutyl)-2-pyridyl]ethynyl-3-quinuclidinol; 3-[2-benzyl-6-(3-methoxypropylamino)-3-pyridyl]ethynyl-3-quinuclidinol; 3-[2-benzyl-6-(2-methoxyethyloxy)-3-pyridyl]ethynyl-3-quinuclidinol; 3-[2-benzyl-6-(3-methoxypropyloxy)-3-pyridyl]ethynyl-3-quinuclidinol; 3-[2-benzyl-6-(4-pyridyl)-3-pyridyl]ethynyl-3-quinuclidinol; 3-[2-benzyl-6-(3-pyridyl)-3-pyridyl]ethynyl-3-quinuclidinol; 3-(2-benzyl-6-pyrazyl-3-pyridyl)ethynyl-3-quinuclidinol; 3-[2-benzyl-6-(2-pyridyl)-3-pyridyl]ethynyl-3-quinuclidinol; 3-[4-benzyl-2-(3-pyridyl)-5-pyrimidyl]ethynyl-3-quinuclidinol; 3-[4-benzyl-2-(3,4-methylenedioxyphenyl)-5-pyrimidyl]ethynyl-3-quinuclidinol; 3-[4-benzyl-2-(3,4-methylenedioxyphenyl)-5-pyridyl]ethynyl-3-quinuclidinol; 3-[4-benzyl-2-(2-pyridyl)-5-pyridyl]ethynyl-3-quinuclidinol; 3-[4-benzyl-2-(3-pyridyl)-5-pyridyl]ethynyl-3-quinuclidinol; 3-(4-benzyl-2-pyrazyl-5-pyridyl)ethynyl-3-quinuclidinol; 3-[4-benzyl-2-(4-pyridyl)-5-pyridyl]ethynyl-3-quinuclidinol; 3-[4-benzyl-2-(2-methoxyethoxy)-5-pyridyl]ethynyl-3-quinuclidinol; 3-[2-benzyl-6-(4-ethoxycarbonylpiperidino)-3-pyridyl]ethynyl-3-quinuclidinol; 3-(2-benzyl-6-morpholino-3-pyridyl)ethynyl-3-quinuclidinol; 3-[2-benzyl-6-(4-methoxypiperidino)-3-pyridyl]ethynyl-3-quinuclidinol; (3R)-3-[2-benzyl-6-(2-methoxyethyl)oxy-3-pyridyl]ethynyl-3-quinuclidinol; (3R)-3-[2-benzyl-6-(3-methoxypropyl)oxy-3-pyridyl]ethynyl-3-quinuclidinol; (3S)-3-[2-benzyl-6-(3-methoxypropyl)oxy-3-pyridyl]ethynyl-3-quinuclidinol; (3R)-3-[2-benzyl-6-(3-fluoropropyl)oxy-3-pyridyl]ethynyl-3-quinuclidinol; (3R)-3-[2-benzyl-6-(1,3-dioxolan-2-yl)methyloxy-3-pyridyl]ethynyl-3-quinuclidinol; (3R)-3-[2-benzyl-6-(3-hydroxypropyl)oxy-3-pyridyl]ethynyl-3-quinuclidinol; 3-[2-benzyl-6-[3-(3-methoxycarbonylpropanoyloxy)propyl]oxy-3-pyridyl]ethynyl-3-quinuclidinol; 3-[2-benzyl-6-[3-[N-(tert-butoxycarbonyl)alanyloxy]propyl]oxy-3-pyridyl]ethynyl-3-quinuclidinol; (3R)-3-[4-benzyl-2-(3-pyridyl)-5-pyridyl]ethynyl-3-quinuclidinol; (3R)-3-[4-benzyl-2-(2-pyridyl)-5-pyridyl]ethynyl-3-quinuclidinol; (3R)-3-[4-benzyl-2-(3,4-methylenedioxyphenyl)-5-pyridyl]ethynyl-3-quinuclidinol; (3R)-3-[2-benzyl-6-[(3R,4S)-3-hydroxy-4-methoxypyrrolidine-1-yl]-3-pyridyl]ethynyl-3-quinuclidinol; (3R)-3-[2-benzyl-6-[(3S,4R)-3-fluoro-4- methoxypyrrolidine-1-yl]-3-pyridyl]ethynyl-3-quinuclidinol; (3R)-3-[2-benzyl-6-[(3R,4R)-3-hydroxy-4-methoxypyrrolidine-1-yl]-3-pyridyl]ethynyl-3-quinuclidinol; (3R)-3-[2-benzyl-6-[(3R,4R)-3,4-dimethoxypyrrolidine-1-yl]-3-pyridyl]ethynyl-3-quinuclidinol; (3R)-3-[2-benzyl-5-chloro-6-[(3R,4R)-3-hydroxy-4-methoxypyrrolidine-1-yl]-3-pyridyl]ethynyl-3-quinuclidinol; (3R)-3-[2-benzyl-5-bromo-6-[(3R,4R)-3-hydroxy-4-methoxypyrrolidine-1-yl]-3-pyridyl]ethynyl-3-quinuclidinol; (3R)-3-[2-benzyl-6-(3,3-ethylenedioxypyrrolidine-1-yl)-3-pyridyl]ethynyl-3-quinuclidinol; (3R)-3-[2-benzyl-5-chloro-6-(3,3-ethylenedioxypyrrolidine-1-yl)-3-pyridyl]ethynyl-3-quinuclidinol; (3R)-3-[2-benzyl-6-(cis-3,4-dimethoxypyrrolidine-1-yl)-3-pyridyl]ethynyl-3-quinuclidinol; (3R)-3-[2-benzyl-6-[(3R,4R)-3,4-dimethoxy-2-pyrrolidinone-1-yl]-3-pyridyl]ethynyl-3-quinuclidinol; (3R)-3-[2-benzyl-6-[(3R,4R)-4-hydroxy-3-methoxy-2-pyrrolidinone-1-yl]-3-pyridyl]ethynyl-3-quinuclidinol; (3R)-3-[2-benzyl-6-(3,3-ethylenedioxy-2-pyrrolidinone-1-yl)-3-pyridyl]ethynyl-3-quinuclidinol; (3R)-3-[2-benzyl-6-[(3R)-3-hydroxy-2-pyrrolidinone-1-yl]-3-pyridyl]ethynyl-3-quinuclidinol; (3R)-3-[2-benzyl-6-[(3R)-3-methoxy-2-pyrrolidinone-1-yl]-3-pyridyl]ethynyl-3-quinuclidinol; (3R)-3-[4-benzyl-2-(1,4-dioxene-2-yl)-5-pyridyl]ethynyl-3-quinuclidinol; and (3R)-3-[4-benzyl-2-[(3R,4R)-3-hydroxy-4-methoxypyrrolidine-1-yl]-3-pyrimidyl]ethynyl-3-quinuclidinol,

(20) a squalene synthesizing enzyme inhibitor comprising the compound described in any of (1) to (19), a salt thereof or a hydrate of them,

(21) a medicinal composition comprising a compound (I) represented by the following formula:

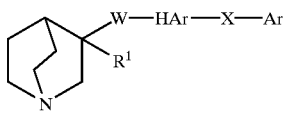

(I)

(in which $R^1$ represents (1) hydrogen atom or (2) hydroxyl group; HAr represents an aromatic heterocycle which may be substituted with 1 to 3 groups; Ar represents an optionally substituted aromatic ring; W represents a chain represented by (1) —CH$_2$—CH$_2$— which may be substituted, (2) —CH=CH— which may be substituted, (3) —C≡C—, (4) —NH—CO—, (5) —CO—NH—, (6) —NH—CH$_2$—, (7) —CH$_2$—NH—, (8) —CH$_2$—CO—, (9) —CO—CH$_2$—, (10) —NH—S(O)$_l$—, (11) —S(O)$_l$—NH—, (12) —CH$_2$—S(O)$_l$— or (13) —S(O)$_l$—CH$_2$— (l denotes 0, 1 or 2); and X represents a chain represented by (1) a single bond, (2) an optionally substituted $C_{1-6}$ alkylene chain, (3) an optionally substituted $C_{2-6}$ alkenylene chain, (4) an optionally substituted $C_{2-6}$ alkynylene chain, (5) a formula —Q— (wherein Q represents oxygen atom, sulfur atom, CO or $N(R^2)$ (wherein $R^2$ represents a $C_{1-6}$ alkyl group or a $C_{1-6}$ alkoxy group)), (6) —NH—CO—, (7) —CO—NH—, (8) —NH—CH$_2$—, (9) —CH$_2$—NH—, (10) —CH$_2$—CO—, (11) —CO—CH$_2$—, (12) —NH—S(O)$_m$—, (13) —S(O)$_m$—NH—, (14) —CH$_2$—S(O)$_m$—, (15) —S(O)$_m$—CH$_2$— (wherein m denotes 0, 1 or 2) or (16) —(CH$_2$)$_n$—O— (wherein n denotes an integer from 1 to 6)), a salt thereof or a hydrate of them,

(22) the medicinal composition described in (21), which is a preventive or curative agent for a disease against which squalene synthesizing enzyme inhibition is efficacious,

(23) the medicinal composition described in (21), which is a cholesterol biosynthesis inhibitor,

(24) the medicinal composition described in (21), which is a triglyceride biosynthesis inhibitor,

(25) the medicinal composition described in (21), which is an agent for preventing or curing hyper lipidemia,

(26) the medicinal composition described in (21), which is an agent for preventing or curing arterial sclerosis diseases or ischemic heart diseases,

(27) the medicinal composition described in (21), which is an agent for preventing or curing hypertension, coronary diseases, cerebrovascular diseases, aortic diseases, peripheral arterial diseases, angina pectoris, acute coronary syndromes or cardiac infarction,

(28) a method for producing a quinuclidine compound (IV) represented by the following formula:

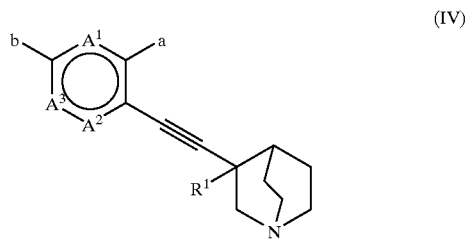

(IV)

(in which $A^1$, $A^2$, $A^3$, a, b and $R^1$ have the same meanings as defined above), a salt thereof or a hydrate of them, which comprises the step of reacting an aromatic heterocyclic compound (II) represented by the following formula:

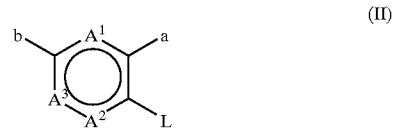

(II)

(in which $A^1$ and $A^3$ are the same as or different from each other and each means 1) an optionally substituted carbon atom or 2) a hetero atom; $A^2$ means 1) an optionally substituted carbon atom, 2) a hetero atom or 3) a single bond; L means a leaving group; and a and b are different from each other and each means 1) a group —X—Ar (in which X represents a chain represented by (1) a single bond; (2) an optionally substituted $C_6$ alkylene chain; (3) an optionally substituted $C_{2-6}$ alkenylene chain; (4) an optionally substituted $C_{2-6}$ alkynylene chain; (5) a formula —Q— (wherein Q represents oxygen atom, sulfur atom, CO or $N(R^2)$ (wherein $R^2$ represents a $C_{1-6}$ alkyl group or a $C_{1-6}$ alkoxy group)); (6) —NH—CO—; (7) —CO—NH—; (8) —NH—CH$_2$—; (9) —CH$_2$—NH—; (10) —CH$_2$—CO—; (11) —CO—CH$_2$—; (12) —NH—S(O)$_m$—; (13) —S(O)$_m$—NH—; (14) —CH$_2$—S(O)$_m$—; (15) —S(O)$_m$—CH$_2$— (wherein m denotes 0, 1 or 2); or (16) —(CH$_2$)$_n$—O— (wherein n denotes an integer from 1 to 6); and Ar represents an optionally substituted aromatic ring, respectively), or 2) any one group selected from: (1) a halogen atom; (2) hydroxyl group; (3) thiol group; (4) nitro group; (5) nitrile group; (6) an optionally substituted linear $C_{1-6}$ hydrocarbon group; (7) an optionally substituted $C_{3-8}$ cyclic hydrocarbon group; (8) an optionally substituted $C_{6-14}$ aromatic hydrocarbon cyclic group; (9) an optionally substituted 5- to 14-membered aromatic heterocyclic group; (10) an optionally substituted 4- to 10-membered non-aromatic heterocyclic group; (11) an optionally substituted $C_{1-6}$ alkoxy group; (12) an optionally substituted $C_{3-8}$ cycloalkyloxy group;

(13) an optionally substituted linear $C_{1-6}$ hydrocarbon-thio group; (14) an optionally substituted $C_{3-8}$ cyclic hydrocarbon-thio group; (15) an optionally substituted $C_{6-14}$ aromatic hydrocarbon-oxy group; (16) an optionally substituted 5- to 14-membered heterocyclic-oxy group; (17) an optionally substituted $C_{6-14}$ aromatic hydrocarbon-thio group; (18) an optionally substituted 5- to 14-membered heterocyclic-thio group; (19) an optionally substituted amino group; (20) an azide group; (21) guanidino group; (22) carbamide group; (23) formyl group; (24) an optionally substituted $C_{1-6}$ imidoyl group; (25) a substituted carbonyl group; (26) a substituted carbonyl-oxy group; (27) a carboxyl group which may form a salt; (28) an optionally substituted carbamoyl group; (29) an optionally substituted $C_{1-4}$ alkylenedioxy group; (30) an optionally substituted sulfinyl group; and (31) an optionally substituted sulfonyl group, respectively) and a quinuclidine compound (III) represented by the following formula:

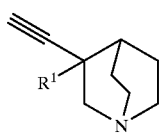
(III)

(wherein $R^1$ means hydrogen atom or hydroxyl group) in the presence of a Pd catalyst, a copper salt and a base,

(29) a method for producing a quinuclidine compound (VI) represented by the following formula:

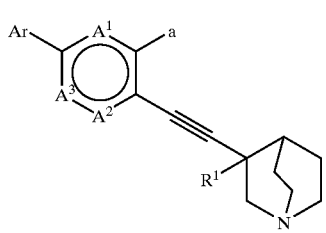
(VI)

(in which $A^1$, $A^2$, $A^3$, a, Ar and $R^1$ have the same meanings as defined above), a salt thereof or a hydrate of them, which comprises the step of reacting a quinuclidine compound (V) represented by the following formula:

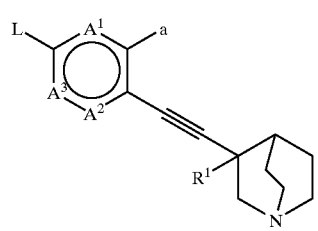
(V)

(in which $A^1$ and $A^3$ are the same as or different from each other and each means 1) an optionally substituted carbon atom or 2) a hetero atom; $A^2$ represent 1) an optionally substituted carbon atom, 2) a hetero atom or 3) a single bond; L means a leaving group; a means a group —X—Ar (wherein X and Ar have the same meanings as defined above); and $R^1$ means hydrogen atom or hydroxyl group, respectively) and an aromatic cyclic compound represented by the following formula:

Ar—M (in which Ar means an optionally substituted aromatic ring; and M means an optionally substituted metal atom, respectively) in the presence of a Pd catalyst, and

(30) a method for producing a quinuclidine compound (VIII) represented by the following formula:

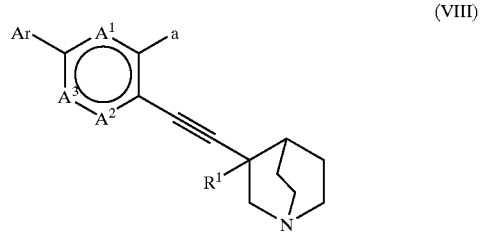
(VIII)

(in which $A^1$, $A^2$, $A^3$, a, Ar and $R^1$ have the same meanings as defined above), a salt thereof or a hydrate of them, which comprises the step of reacting a quinuclidine compound (VII) represented by the following formula:

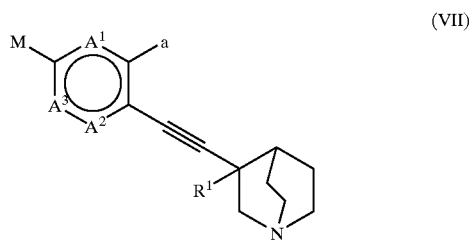
(VII)

(in which $A^1$ and $A^3$ are the same as or different from each other and each means 1) an optionally substituted carbon atom or 2) a hetero atom; $A^2$ means 1) an optionally substituted carbon atom, 2) a hetero atom or 3) a single bond; M means an optionally substituted metal atom; a means 1) a group —X—Ar (wherein X and Ar have the same meanings as defined above); and $R^1$ means hydrogen atom or hydroxyl group, respectively) and an aromatic cyclic compound represented by the following fromula:

Ar—L (in which Ar means an optionally substituted aromatic ring; and L means a leaving group, respectively) in the presence of a Pd catalyst. Also, the present invention provides a method of preventing and curing a disease on which squalene synthesizing enzyme inhibition is effective by administering the compound represented by the above formula (I), its salt or hydrates of these compounds to a patient in a pharmacologically effective amount and a use of the compound represented by the above formula (I), its salt or hydrates thereof for producing a preventive and curing agent for a disease on which squalene synthesizing enzyme inhibition is effective.

In the specification of the present invention, there is the case where the structural formula of a compound represents a definite isomer. However, the present invention includes isomers such as geometrical isomers, optical isomers based on asymmetric carbon, stereoisomers and tautomers and is not limited by the description of the formula illustrated for the sake of convenience.

The definitions of the terms used in the specification of the present invention will be explained below.

In the specification of the present invention, the group represented by $R^1$ in the above formula (I) means hydrogen atom or hydroxyl group and preferably hydroxyl group.

In the specification of the present invention, the "aromatic heterocycle which may be substituted with 1 to 3 groups" represented by HAr in the aforementioned formula (I) is preferably, for example, a 5- to 14-membered aromatic heterocycle which has 1 to 4 atoms selected optionally from nitrogen atom, sulfur atom and oxygen atom and may be substituted with 1, 2 or 3 substituents, and more preferably, an aromatic heterocycle which may be substituted with 1 to 3 groups selected from (1) halogen atom, (2) hydroxyl group, (3) thiol group, (4) nitro group, (5) nitrile group, (6) a $C_{1-6}$ chain hydrocarbon group which may be substituted, (7) a $C_{3-8}$ cyclic hydrocarbon group which may be substituted, (8) a $C_{6-14}$ aromatic hydrocarbon cyclic group which may be substituted, (9) a 5- to 14-membered aromatic heterocyclic group which may be substituted, (10) a 4- to 10-membered non-aromatic heterocyclic group which may be substituted, (11) a $C_{1-6}$ alkoxy group which may be substituted, (12) a $C_{3-8}$ cycloalkoxy group which may be substituted, (13) a $C_{1-6}$ chain hydrocarbon-thio group which may be substituted, (14) a $C_{3-8}$ cyclic hydrocarbon-thio group which may be substituted, (15) a $C_{6-14}$ aromatic hydrocarbon-oxy group which may be substituted, (16) a 5- to 14-membered heterocycle-oxy group which may be substituted, (17) a $C_{6-14}$ aromatic hydrocarbon-thio group which may be substituted, (18) a 5- to 14-membered heterocycle-thio group which may be substituted, (19) an amino group which may be substituted, (20) azide group, (21) guanidino group, (22) carbamide group, (23) formyl group, (24) a $C_{1-6}$ imidoyl group which maybe substituted, (25) a carbonyl group which is substituted, (26) a carbonyloxy group which is substituted, (27) a carboxy group which may form a salt, (28) a carbamoyl group which may be substituted, (29) a $C_{1-4}$ alkylenedioxy group which may be substituted, (30) a sulfinyl group which may be substituted and (31) a sulfonyl group which may be substituted.

In the above-mentioned definition of HAr, the "aromatic heterocycle" means monocyclic type, dicyclic type or tricyclic type aromatic heterocycles. Examples thereof include 5- to 14-membered aromatic heterocyclic groups containing 1 to 4 atoms selected from nitrogen atom, sulfur atom and oxygen atom. Specifically, aromatic heterocycles containing two or more different atoms selected from nitrogen atom, sulfur atom and oxygen atom, such as nitrogen-containing aromatic heterocycles, e.g., pyrrole ring, pyridine ring, pyridone ring, pyridazine ring, pyrimidine ring, pyrazine ring, pyrazole ring, imidazole ring, indole ring, isoindolyl ring, indolizine ring, purine ring, indazole ring, quinoline ring, isoquinoline ring, quinolizine ring, phthalazine ring, naphthyridine ring, quinoxaline ring, quinazoline ring, cinnoline ring, pteridine ring, imidazotriazine ring, pyrazinopyridazine ring, acridine ring, phenanthridine ring, carbazole ring, carbazoline ring, perimidine ring, phenanthroline ring and phenarsine ring; sulfur-containing aromatic heterocycles, e.g., a thiophene ring and benzothiophene ring; oxygen-containing aromatic heterocycles, e.g., a furan ring, pyran ring, cyclopentapyran ring, benzofuran ring, isobenzofuran ring; thiazole ring, isothiazole ring, benzthiazole ring, benzthiadiazole ring, phenothiazine ring, isoxazole ring, furazane ring, phenoxazine ring, pyrazoloxazole ring, imidazothiazole ring, thienofuran ring, furopyrrole ring and pyridoxazine ring. As preferable examples thereof pyrrole ring, pyridine ring, pyridone ring, pyrimidine ring, imidazole ring, indole ring, quinoline ring, isoquinoline ring, quinolizine ring, phthalazine ring, naphthyridine ring, quinazoline ring, acridine ring, phenarsine ring, thiophene ring, benzothiophene ring, furan ring, pyran ring, benzofuran ring, thiazole ring, benzthiazole ring and phenothiazine ring are given. As more preferable examples thereof, pyrrole ring, pyridine ring, thiophene ring, benzothiophene ring, thiazole ring and benzthiazole ring are given.

In the above definition, the "halogen atom" means halogen atoms such as fluorine atom, chlorine atom, bromine atom and iodine atom and is preferably fluorine atom, chlorine atom and bromine atom.

The "$C_{1-6}$ chain hydrocarbon group" in the "$C_{1-6}$ chain hydrocarbon group which may be substituted" given as the substituent of HAr means "a $C_{1-6}$ alkyl group", "a $C_{2-6}$ alkenyl group" and "a $C_{2-6}$ alkynyl group". As the "$C_{1-6}$ alkyl group", for example, straight-chain or branched $C_{1-6}$ alkyl groups such as methyl group, ethyl group, n-propyl group, i-propyl group, sec-propyl group, n-butyl group, i-butyl group, sec-butyl group, t-butyl group, n-pentyl group, i-pentyl group, sec-pentyl group, t-pentyl group, n-hexyl group, i-hexyl group, 1,2-dimethylpropyl group, 2-ethylpropyl group, 1-methyl-2-ethylpropyl group, 1-ethyl-2-methylpropyl group, 1,1,2-trimethylpropyl group, 1,1,2-triethylpropyl group, 1,1-dimethylbutyl group, 2,2-dimethylbutyl group, 2-ethylbutyl group, 1,3-dimethylbutyl group, 2-methylpentyl group and 3-methylpentyl group are preferable. As the "$C_{2-6}$ alkenyl group", straight-chain or branched $C_{2-6}$ alkenyl groups such as vinyl group, allyl group, isopropenyl group, 1-propene-2-yl group, 1-butene-1-yl group, 1-butene-2-yl group, 1-butene-3-yl group, 2-butene-1-yl group and 2-butene-2-yl group are preferable. As the "$C_{2-6}$ alkynyl group", ethynyl group, propynyl group, butynyl group, pentynyl group and hexynyl group are preferable. Also, the term "may be substituted" implies that may be substituted with one or two groups selected from, for example, (1) a hydroxyl group which may be protected, (2) halogen atom, (3) nitrile group, (4) carboxyl group, (5) a $C_{3-8}$ cycloalkyl group, $C_{3-8}$ cycloalkenyl group or $C_{3-8}$ cycloalkynyl group, which may be hydroxylated or halogenated, (6) a $C_{1-6}$ alkoxy group which may be substituted with a group selected from a halogen atom, hydroxyl group, a $C_{6-14}$ aryl group, 5- to 14-membered heteroaryl group and a $C_{6-14}$ aryl-$C_{1-6}$ alkoxy group, (7) a $C_{3-8}$ cycloalkyloxy group which may be halogenated or hydroxylated, (8) a $C_{3-8}$ cycloalkenyloxy group which may be halogenated or hydroxylated, (9) a $C_{1-6}$ alkoxy-carbonyl group, (10) a $C_{1-4}$ alkylenedioxy group which may be halogenated, (11) a $C_{1-6}$ alkanoyl group which may be substituted with a group selected from hydroxyl group, a $C_{1-6}$ alkoxy group and a $C_{1-6}$ alkanoyloxy group, (12) a $C_{6-14}$ aryl group which may be substituted with a group selected from a halogen atom, a $C_{1-6}$ alkyl group and a $C_{1-6}$ alkoxy group, (13) a 5- to 14-membered aromatic heterocyclic group which may be substituted with a group selected from a halogen atom, a $C_{1-6}$ alkyl group, a $C_{3-8}$ alkenyl group, a $C_{3-8}$ alkynyl group and a $C_{1-6}$ alkoxy group, (14) a 4- to 10-membered non-aromatic heterocyclic group which may be substituted with a group selected from a halogen atom, a $C_{1-6}$ alkyl group, a $C_{3-8}$ alkenyl group, a $C_{3-8}$ alkynyl group and a $C_{1-6}$ alkoxy group, (15) a group $(EtO)_2PO-$, (16) acetyl group, (17) a sulfonyl group which may be substituted with a group selected from a $C_{1-6}$ hydrocarbon group, a mino-($C_{1-6}$ hydrocarbon)-amino group and a di-($C_{1-6}$ hydrocarbon)-amino group, (18) an amino group which may be substituted with $C_{1-6}$ hydrocarbon group, (19) a $C_{1-6}$ hydrocarbon group-thio group which may be hydroxylated or halogenated and (20) a carbamoyl group which may be substituted with a $C_{1-6}$ hydrocarbon group.

The "$C_{1-6}$ chain hydrocarbon group which may be substituted" is preferably a $C_{1-6}$ chain hydrocarbon groups which may substituted with one or two groups selected from (1) hydroxyl group, (2) a halogen atom, (3) nitrile group, (4) a $C_{1-6}$ cycloalkyl group, (5) a $C_{1-6}$ alkoxy group, (6) a $C_{1-6}$ alkoxy-$C_{1-6}$ alkoxy group, (7) a $C_{1-4}$ alkylenedioxy group, (8) a $C_{1-6}$ alkoxy-carbonyl group, (9) a $C_{1-6}$ alkanoyl group, (10) a $C_{1-6}$ alkoxy-$C_{1-6}$ alkanoyl group, (11) a $C_{1-6}$ alkanoyl-oxy group, (12) a $C_{1-6}$ alkanoyl-oxy-$C_{1-6}$ alkanoyl group, (13) a 5- to 14-membered heterocyclic group, (14) a 5- to 10-membered condensed heterocyclic group which may substituted with a $C_{1-6}$ alkoxy group, (15) carboxyl group, (16) $(EtO)_2PO$— and (17) a $C_{1-6}$ alkyl-sulfonyl group, and more preferably a substituted $C_{1-6}$ chain hydrocarbon group such as (1) unsubstituted $C_{1-6}$ chain hydrocarbon groups such as ethyl group, propyl group and 2-propene-1-yl group, (2) $C_{1-6}$ chain hydrocarbon groups substituted with a $C_{6-14}$ aromatic hydrocarbon group such as phenyl group, (3) $C_{1-6}$ chain hydrocarbon groups substituted with a 5- to 14-membered aromatic heterocyclic group such as pyridyl group and (4) substituted $C_{1-6}$ chain hydrocarbon groups such as a $C_{1-6}$ alkoxy-$C_{1-6}$ chain hydrocarbon group.

In the above-mentioned definition, for example, the "$C_{1-6}$ chain hydrocarbon group which may be halogenated" means that any one of the carbons of the "$C_{1-6}$ chain hydrocarbon group" may be substituted with a halogen atom. Specific examples thereof include trifluoromethyl group, 2-chloroethyl group, 1,2-dichloroethyl group, 2-bromoethyl group, 3-bromopropyl group, 3,3,3-trifluoropropyl group, 4-chlorobutyl group, 2,2-dimethyl-4-bromobutyl group and 3-chloro-2-propenyl group. Also, the "$C_{1-6}$ alkoxy group which may be halogenated" means that any one of the carbons of the "$C_{1-6}$ alkoxy group" may be substituted with a halogen atom. Specific examples thereof include trifluoromethoxy group, 2-chloroethoxy group, 1,2-dichloroethoxy group, 2-bromoethoxy group, 3-bromopropyloxy group, 3,3,3-trifluoropropyloxy group, 4-chlorobutyloxy group, and 2,2-dimethyl-4-bromobutyloxy group.

The "$C_{3-8}$ cyclic hydrocarbon group" in the "$C_{3-8}$ cyclic hydrocarbon group which may be substituted" which is given as the substituent of HAr means a "$C_{3-8}$ cycloalkyl group", a "$C_{3-8}$ cycloalkenyl group" and the like. As the "$C_{3-8}$ cycloalkyl group", 3- to 8-membered cycloalkyl groups such as cyclopropanyl group, cyclobutanyl group, cyclopentanyl group, cyclohexanyl group and cycloheptanyl group are preferable. As the "$C_{3-8}$ cycloalkenyl group", 3- to 8-membered cycloalkenyl groups such as cyclopropenyl group, cyclobutenyl group, cyclopentenyl group, cyclohexenyl group and cycloheptenyl group are preferable. Also, the term "may be substituted" implies that the above "$C_{3-8}$ cyclic hydrocarbon group" may be substituted with one or two groups selected from, for example, (1) a hydroxyl group which may be protected, (2) a halogen atom, (3) nitrile group, (4) carboxy group, (5) a $C_{1-6}$ alkyl group which may be substituted with a group selected from hydroxyl group, a halogen atom, a $C_{1-6}$ alkoxy group which may be halogenated, a $C_{1-6}$ hydrocarbon-thio group which may be halogenated, an amino group which may be substituted with a $C_{1-6}$ hydrocarbon group and a $C_{1-6}$ alkanoyl group, (6) a $C_{1-6}$ alkenyl group which may be substituted with a group selected from hydroxyl group, a halogen atom, a $C_{1-6}$ alkoxy group which may be halogenated, a $C_{1-6}$ hydrocarbon-thio group which may be halogenated, an amino group which may be substituted with a $C_{1-6}$ hydrocarbon group and a $C_{1-6}$ alkanoyl group, (7) a $C_{1-6}$ alkynyl group which may be substituted with a group selected from hydroxyl group, a halogen atom, a $C_{1-6}$ alkoxy group which may be halogenated, a $C_{1-6}$ hydrocarbon-thio group which may be halogenated, an amino group which may be substituted with a $C_{1-6}$ hydrocarbon group and a $C_{1-6}$ alkanoyl group, (8) an amino group which may be substituted with a group selected from hydroxyl group, a halogen atom, a $C_{1-6}$ alkoxy group which may be halogenated, a $C_{1-6}$ hydrocarbon-thio group which may be halogenated, a $C_{1-6}$ alkanoyl group and a $C_{1-6}$ hydrocarbon group, (9) a $C_{1-6}$ alkoxy group which may be substituted with a group selected from hydroxyl group, a halogen atom, a $C_{1-6}$ alkyl group which may be halogenated, a $C_{1-6}$ alkoxy group which may be hydroxylated or halogenated, a $C_{1-6}$ hydrocarbon-thio group which may be halogenated, an amino group which may be substituted with a $C_{1-6}$ hydrocarbon group and a $C_{1-6}$ alkanoyl group, (10) a $C_{1-6}$ hydrocarbon-thio group which may be substituted with a group selected from hydroxyl group, a halogen atom, a $C_{1-6}$ alkyl group which may be halogenated, a $C_{1-6}$ alkenyl group which may be halogenated, a $C_{1-6}$ alkynyl group which may be halogenated, a $C_{1-6}$ alkoxy group which may be hydroxylated and halogenated, a $C_{1-6}$ hydrocarbon-thio group which may be halogenated, an amino group which may be substituted with a $C_{1-6}$ hydrocarbon group and a $C_{1-6}$ alkanoyl group, (11) a $C_{1-6}$ alkanoyl group which may be substituted with a group selected from hydroxyl group, a $C_{1-6}$ alkoxy group and a $C_{1-6}$ alkanoyloxy group, (12) a $C_{6-14}$ aryl group which may be substituted with a group selected from a halogen atom, a $C_{1-6}$ alkyl group and a $C_{1-6}$ alkoxy group, (13) a 5- to 14-membered aromatic heterocyclic group which may be substituted with a halogen group, a $C_{1-6}$ alkyl group, a $C_{3-8}$ alkenyl group, a $C_{3-8}$ alkynyl group and a $C_{1-6}$ alkoxy group, (14) a non-aromatic heterocyclic group which may be substituted with a group selected from a halogen atom, a $C_{1-6}$ alkyl group, a $C_{3-8}$ alkenyl group, a $C_{3-8}$ alkynyl group and a $C_{1-6}$ alkoxy group, (15) a $C_{1-6}$ alkoxy-carbonyl group, (16) a $C_{1-4}$ alkylenedioxy group which may be halogenated, (17) the formula $(EtO)_2PO$— and (18) acetyl group.

It is to be noted that in the specification of the present invention, the "hydrocarbon group" shown in the formula (I) implies both of the "$C_{1-6}$ chain hydrocarbon group" and the "$C_{3-8}$ cyclic hydrocarbon group" which have the same definitions as above.

Preferable examples of the "$C_{6-14}$ aromatic hydrocarbon cyclic group" in the "$C_{6-14}$ aromatic hydrocarbon cyclic group which may be substituted" which is given as the substituent of HAr include phenyl group, pentalenyl group, indenyl group, naphthyl group, azulenyl group, heptalenyl group, benzocyclooctenyl group and phenanthrenyl group. Among these groups, a phenyl group and naphthyl group are more preferable. Also, the term "may be substituted" implies that the above "$C_{6-14}$ aromatic hydrocarbon cyclic group" may be substituted with one or more groups selected from, for example, (1) hydroxyl group, (2) a halogen atom, (3) a $C_{1-6}$ alkyl-sulfonyl group, a $C_{1-6}$ alkenyl-sulfonyl group or a $C_{1-6}$ alkynyl-sulfonyl group which may be halogenated, (4) a $C_{1-4}$ alkylenedioxy group which may be halogenated, (5) a $C_{1-6}$ alkoxy group which may be halogenated, (6) a $C_{1-6}$ hydrocarbon-thio group which may be halogenated, (7) a $C_{1-6}$ alkoxy-carbonyl group, (8) a $C_{6-14}$ aryl-$C_{1-6}$ alkoxy group, (9) a $C_{1-7}$ alkanoylamino group, (10) a $C_{1-6}$ alkyl-carbamoyl group, (11) a $C_{1-6}$ alkenyl-carbamoyl group, (12) a $C_{1-6}$ alkynyl-carbamoyl group and (13) an amino group which may be substituted with a $C_{1-6}$ hydrocarbon group. Preferable examples of the "$C_{6-14}$ aromatic hydrocarbon cyclic group which is substituted" include phenyl groups converted into nitriles, halogenated phenyl group, phenyl group substituted with a $C_{1-6}$ alkyl group such as an ethyl group, phenyl group substituted with a $C_{1-6}$ alkoxy group such as methoxy group, phenyl group substituted with an alkylenedioxy group such as 2,4-methylenedioxy group and phenyl group substituted with a di-($C_{1-6}$ alkyl)-amino group such as dimethylamino group.

It is to be noted that, in the present invention, the "$C_{6-14}$ aryl group" shown in the formula (I) has the same meaning as the above-mentioned "$C_{6-14}$ aromatic hydrocarbon cyclic group" and excludes aromatic heterocyclic groups.

The "5- to 14-membered aromatic heterocyclic group" in the "5- to 14-membered aromatic heterocyclic group which may be substituted" which is given as the substituent of HAr means an aromatic heterocycle having 1 to 4 atoms selected from nitrogen atom, oxygen atom and sulfur atom. Specific examples thereof include pyrrolyl group, pyridinyl group, pyridazinyl group, pyrimidinyl group, pirazinyl group, thiazolyl group and oxazolyl group. Also, the term "may be substituted" means that the above-mentioned "5- to 14-membered aromatic heterocyclic group" may be substituted with one or more groups selected from (1) hydroxyl group, (2) a halogen atom, (3) nitrile group, (4) a $C_{1-6}$ alkyl group, $C_{1-6}$ alkenyl group or $C_{1-6}$ alkynyl group, which may be halogenated, (5) a $C_{1-6}$ alkoxy group which may be halogenated, (6) a $C_{1-6}$ alkyl-thio group, $C_{1-6}$ alkenyl-thio group or $C_{1-6}$ alkynyl-thio group, which may be halogenated, (7) a $C_{1-6}$ alkoxy-$C_{1-6}$ alkyl group, (8) acetyl group, (9) a $C_{1-6}$ alkanoyl group, (10) a mono-($C_{1-6}$ hydrocarbon)-amino group, (11) a di-($C_{1-6}$ hydrocarbon)-amino group and (12) a tri-($C_{1-6}$ hydrocarbon)-amino group. Preferable examples of the "substituted 5- to 14-membered aromatic heterocyclic group" include aromatic heterocycles converted to nitrites, aromatic heterocycles substituted with a $C_{1-6}$ alkyl group, aromatic heterocycles substituted with a $C_{1-6}$ alkoxy group, aromatic heterocycles substituted with a $C_{1-6}$ alkoxy-$C_{1-6}$ alkyl group, aromatic heterocycles substituted with a mono-($C_{1-6}$ alkyl)-amino group and aromatic heterocycles substituted with a di-($C_{1-6}$ alkyl)-amino group.

In the specification of the present invention, the "$C_{6-14}$ heteroaryl group" shown in the formula (I) has the same meaning as the above-mentioned "5- to 14-membered aromatic heterocyclic group".

It is to be noted that in the specification of the present invention, the "aromatic ring" shown in the formula (I) implies all rings having the same meanings as the above-mentioned "$C_{6-14}$ aromatic hydrocarbon ring" and "5- to 14-membered aromatic heterocyclic group".

The "4- to 10-membered non-aromatic heterocyclic group" in the "4- to 10-membered non-aromatic heterocyclic group which may be substituted" which is given as the substituent of HAr means a ring which has the same meaning as the aforementioned "$C_{3-8}$ cyclic hydrocarbon group" and in which 1 to 4 carbon atoms are substituted with an atom selected from nitrogen atom, oxygen atom and sulfur atom and also means that it includes a unsaturated condensed ring. Preferable specific examples thereof include pyrrolidinyl group, pyrrolinyl group, piperidinyl group, piperazinyl group, imidazolinyl group, pyrazolidinyl group, imidazolydinyl group, morpholinyl group, tetrahydropyranyl group, azetidinyl group, oxetanyl group, oxathiolanyl group, phthalimide and succinimide. More preferable examples include pyrrolidinyl group, piperidinyl group and morpholinyl group. Also, the term "may be substituted" means that the above-mentioned "4- to 10-membered aromatic heterocyclic group" may be substituted with one or more groups selected from (1) hydroxyl group, (2) a halogen atom, (3) nitrile group, (4) a $C_{1-6}$ alkyl group, $C_{1-6}$ alkenyl group or $C_{1-6}$ alkynyl group which may be halogenated, (5) a $C_{1-6}$ alkoxy group which may be halogenated, (6) a $C_{1-6}$ alkyl-thio group, $C_{1-6}$ alkenyl-thio group or $C_{1-6}$ alkynyl-thio group which may be halogenated, (7) a $C_{1-6}$ alkoxy-$C_{1-6}$ alkyl group, (8) acetyl group, (9) a $C_{1-6}$ alkanoyl group, (10) a mono-($C_{1-6}$ hydrocarbon)-amino group, (11) a di-($C_{1-6}$ hydrocarbon)-amino group, (12) a tri-($C_{1-6}$ hydrocarbon group-amino group and (13) an oxo group forming carbonyl group, N-oxide group, sulfoxide group or sulfonic group.

It is to be noted that in the specification of the present invention, the "heterocycle" shown in the formula (I) implies both of the "5- to 14-membered heterocyclic group" and the "4- to 10-membered non-aromatic heterocyclic group" which have the same definitions as above.

The "$C_{1-6}$ alkoxy group" in the "$C_{1-6}$ alkoxy group which may be substituted" given as the substituent of HAr means the "alkoxy group" corresponding to the "$C_{1-6}$ chain hydrocarbon group" in the aforementioned definition. Preferable examples thereof include $C_{1-6}$ alkyl-oxy groups such as methoxy group, ethoxyl group, n-propoxy group, i-propoxy group, sec-propoxy group, n-butoxy group, i-butoxy group, sec-butoxy group, t-butoxy group, n-pentoxy group, i-pentoxy group, sec-pentoxy group, t-pentoxy group, n-hexoxy group, i-hexoxy group, 1,2-dimethylpropoxy group, 2-ethylpropoxy group, 1-methyl-2-ethylpropoxy group, 1-ethyl-2-methylpropoxy group, 1,1,2-trimethylpropoxy group, 1,1-dimethylbutoxy group, 2,2-dimethylbutoxy group, 2-ethylbutoxy group, 1,3-dimethylbutoxy group, 2-methylpentoxy group and 3-methylpentoxy group; $C_{2-6}$ alkenyl-oxy groups such as vinyloxy group, allyloxy group, isopropoxyl group, 1-propenyl-2-oxy group, 1-butenyl-1-oxy group, 1-butenyl-2-oxy group, 1-butenyl-3-oxy group, 2-butenyl-1-oxy group and 2-butenyl-2-oxy group; and $C_{2-6}$ alkynyl-oxy groups such as ethynyloxy group, propinyloxy group, butynyloxy group, pentynyloxy group and hexynyloxy group. The term "may be substituted" means that may be substituted with one or more groups selected from, for example, (1) hydroxyl group, (2) a halogen atom, (3) a $C_{1-6}$ alkyl group, $C_{2-6}$ alkenyl group or $C_{2-6}$ alkynyl group, which may be substituted with a group selected from hydroxyl group, a halogen atom, a 5- to 14-membered aromatic heterocyclic group and a 4- to 10-membered non-aromatic heterocyclic group, (4) a $C_{3-8}$ cycloalkyl group or $C_{3-8}$ cycloalkenyl group, which may be hydroxylated or halogenated, (5) a $C_{1-6}$ alkoxy group which may be hydroxylated or halogenated, (6) a $C_{1-6}$ alkylthio group, $C_{1-6}$ alkenylthio group or $C_{1-6}$ alkynylthio group, which may be halogenated, (7) a $C_{3-8}$ cycloalkyloxy group, $C_{3-8}$ cycloalkenyloxy group or $C_{3-8}$ cycloalkynyloxy group which may be halogenated, (8) a $C_{3-8}$ cycloalkylthio group, $C_{3-8}$ cycloalkenylthio group or $C_{3-8}$ cycloalkynylthio group, which may be halogenated, (9) a $C_{6-14}$ aryl group, (10) a $C_{1-6}$ alkanoyl group which may be halogenated, (11) a 5- to 14-membered aromatic heterocyclic group and (12) a 4- to 10-membered non-aromatic heterocycle. Preferable examples of the "$C_{1-6}$ alkoxy group which is substituted" include a $C_{1-6}$ alkoxy group which is hydroxylated, a $C_{1-6}$ alkoxy group which is halogenated, a $C_{1-6}$ alkoxy group substituted with a hydroxy-$C_{3-8}$ cycloalkyl group, a $C_{1-6}$ alkoxy group substituted with a non-aromatic heterocycle-oxy group, a $C_{1-6}$ alkoxy-$C_{1-6}$ alkoxy group, a $C_{1-6}$ alkoxy group substituted with a $C_{1-6}$ alkoxy-carbonyl group, a $C_{1-6}$ alkoxy group substituted with a non-aromatic heterocyclic group and a $C_{1-6}$ alkoxy group which is formyl-aminated.

The "$C_{3-8}$ cycloalkoxy group" in the "$C_{3-8}$ cycloalkoxy group which may be substituted" given as the substituent of HAr means the "cycloalkoxy group" corresponding to the "$C_{1-6}$ cyclic hydrocarbon group" in the above definition. Preferable examples thereof include $C_{3-8}$ cycloalkyloxy groups such as cyclopropyloxy group, cyclobutyoxy group, cyclopentyloxy group and cyclohexyloxy group and $C_{3-8}$ cycloalkenyloxy groups such as cyclopropenyloxy group, cyclobutenyloxy group, cyclopentenyloxy group and cyclohexenyloxy group. Also, the term "may be substituted" means that the above-mentioned $C_{3-8}$ alkoxy group may be substituted with one or two groups selected from, for example, (1) hydroxyl group, (2) a halogen atom, (3) a $C_{1-6}$ hydrocarbon group which may be substituted with a group selected from hydroxyl group, a halogen atom, a $C_{1-6}$ alkoxy group and a $C_{1-6}$ alkanoyl group, (4) a $C_{1-6}$ alkoxy group which may be substituted with a group selected from a halogen atom, a $C_{1-6}$ alkoxy group and a $C_{1-6}$ alkanoyl group and (5) a $C_{1-6}$ hydrocarbon-thio group which may be substituted with a group selected from a halogen atom, a $C_{1-6}$ alkoxy group and a $C_{1-6}$ alkanoyl group. A $C_{3-8}$ cycloalkoxy group which may be substituted with a $C_{1-6}$ alkoxy group and the like are preferable.

The "$C_{1-6}$ chain hydrocarbon-thio group" in the "$C_{1-6}$ chain hydrocarbon-thio group which may be substituted" given as the substituent of HAr means the "$C_{1-6}$ chain hydrocarbon-thio group" corresponding to the "$C_{1-6}$ chain hydrocarbon group" in the above definition, that is, a "$C_{1-6}$ alkyl-thio group", "$C_{1-6}$ alkenyl-thio group" and "$C_{1-6}$ alkynyl-thio group". Specific examples thereof include methylthio group, ethylthio group, n-propylthio group, i-propylthio group, sec-propylthio group, n-butylthio group, i-butylthio group, sec-butylthio group, t-butylthio group, 1,2-dimethylpropylthio group, 2-ethylpropylthio group, 1,1-dimethylbutylthio group, 2,2-dimethylbutylthio group, 2-tylbutylthio group, 1,3-dimethylbutylthio group, isopropenylthio group, ethynylthio group and propinylthio group. Also, the term "may be substituted" implies that may be substituted with one or two groups selected from, for example, (1) hydroxyl group, (2) a halogen atom, (3) a $C_{1-6}$ alkyl group, $C_{1-6}$ alkenyl group or $C_{1-6}$ alkynyl group, which may be substituted with a group selected from hydroxyl group, a halogen atom, a 5- to 14-membered aromatic heterocyclic group and a 4- to 10-membered non-aromatic heterocyclic group, (4) a $C_{3-8}$ cycloalkyl group, $C_{3-8}$ cycloalkenyl group or $C_{3-8}$ cycloalkynyl group, which may be hydroxylated or halogenated, (5) a $C_{1-6}$ alkoxy group which may be hydroxylated or halogenated, (6) a $C_{1-6}$ alkylthio group, $C_{1-6}$ alkenylthio group or $C_{1-6}$alkynylthio group, which may be halogenated, (7) a $C_{3-8}$ cycloalkyloxy group, $C_{3-8}$ cycloalkenyloxy group or $C_{3-8}$ cycloalkynyloxy group which may be halogenated, (8) a $C_{3-8}$ cycloalkylthio group, $C_{3-8}$ cycloalkenylthio group or $C_{3-8}$ cycloalkynylthio group, which may be halogenated, (9) a $C_{6-14}$ aryl group, (10) a $C_{1-6}$ alkanoyl group which may be halogenated, (11) a 5- to 14-membered aromatic heterocyclic group and (12) a 4- to 10-membered non-aromatic heterocyclic group. The "$C_{1-6}$ chain hydrocarbon-thio group which may be substituted" is preferably a $C_{1-6}$ chain hydrocarbon-thio group which may be hydroxylated, a $C_{1-6}$ chain hydrocarbon-thio group which may be substituted with a $C_{1-6}$ alkoxy group and the like.

The "$C_{3-8}$ cyclic hydrocarbon-thio group" in the "$C_{3-8}$ cyclic hydrocarbon-thio group which may be substituted" given as the substituent to HAr means the "$C_{1-6}$ cyclic hydrocarbon-thio group" corresponding to the "$C_{1-6}$ cyclic hydrocarbon group" in the above definition, that is, a "$C_{1-6}$ cycloalkyl-thio group" and "$C_{1-6}$ cyclic alkenyl-thio group". Specific examples thereof include cyclopropanylthio group, cyclobutanylthio group, cyclohexanylthio group, cyclopropenylthio group, cyclobutenylthio group, cyclopentenylthio group and cyclohexenylthio group. The "$C_{3-8}$ cyclic hydrocarbon-thio group which may be substituted" is preferably a "$C_{3-8}$ cyclic hydrocarbon-thio group" substituted with one or two groups selected from (1) hydroxyl group, (2) a halogen atom, (3) a $C_{3-8}$ alkyl group, $C_{3-8}$ alkenyl group or $C_{3-8}$ alkynyl group, which may be halogenated, (4) a $C_{1-6}$ alkoxy group which may be halogenated, (5) a $C_{1-6}$ hydrocarbon-thio group which may be halogenated and (6) a $C_{1-6}$ alkanoyl group which may be halogenated.

The "$C_{6-14}$ aromatic hydrocarbon-oxy group" in the "$C_{6-14}$ aromatic hydrocarbon-oxy group which may be substituted" given as the substituent of HAr means the "$C_{1-6}$ cyclic hydrocarbon-oxy group" corresponding to the "$C_{6-14}$ aromatic hydrocarbon group" in the above definition. For example, phenyloxy group, pentalenyloxy group and naphthyloxy group are preferable. As the "$C_{6-14}$ aromatic hydrocarbon-oxy group which may be substituted", a "$C_{6-14}$ aromatic hydrocarbon-oxy group" which is substituted with one or more groups selected from (1) hydroxyl group, (2) a halogen atom, (3) a $C_{1-6}$ alkyl-sulfonyl group, $C_{1-6}$ alkenyl-sulfonyl group or $C_{1-6}$ alkynyl-sulfonyl group, which may be halogenated, (4) a $C_{1-4}$ alkylenedioxy group which may be halogenated, (5) a $C_{1-6}$ alkoxy group which may be halogenated, (6) a $C_{1-6}$ hydrocarbon-thio group which may be halogenated, (7) a $C_{1-6}$ alkoxy-carbonyl group, (8) $C_{6-14}$ aryl-$C_{1-6}$ alkoxy group, (9) a $C_{1-7}$ alkanoylamino group, (10) a $C_{1-6}$ alkyl-carbamoyl group, (11) a $C_{1-6}$ alkenyl-carbamoyl group, (12) a $C_{1-6}$ alkynyl-carbamoyl group and (13) an amino group which may be substituted with a $C_{1-6}$ hydrocarbon group is preferable.

It is to be noted that in the specification of the present invention, the "$C_{6-14}$ aryloxy group" shown in the formula (I) has the same meaning as the "$C_{6-14}$ aromatic hydrocarbon-oxy group" in the above definition.

The "5- to 14-membered heterocycle-oxy group" in the "5- to 14-membered heterocycle-oxy group which may be substituted" which is given as the substituent of HAr means a "5- to 14-membered heterocycle-oxy group" corresponding to a ring having the same meaning as the "5- to 14-membered heterocyclic group" and the "4- to 10-membered non-aromatic heterocyclic group" in the aforementioned definition. Specific examples thereof include an "aromatic heterocycle-oxy group" such as pyrrolyloxy group, pyridinyloxy group, pyridazinyloxy group, pyrimidinyloxy group, pirazinyloxy group and thiazolyloxy group; and a "non-aromatic heterocycle-oxy group" such as pyrrolidinyloxy group, pyrrolinyloxy group, piperidinyloxy group, piperazinyloxy group, imidazolinyloxy group, imidazolydinyloxy group, morpholinyloxy group and tetrahydropyranyloxy group. As the "5- to 14-membered heterocycle-oxy group which may be substituted", a "5- to 14-membered heterocycle-oxy group" which may be substituted with one or more groups selected from (1) hydroxyl group, (2) a halogen atom, (3) nitrile group, (4) a $C_{1-6}$ alkyl group, $C_{1-6}$ alkenyl group or $C_{1-6}$ alkynyl group which may be halogenated, (5) a $C_{1-6}$ alkoxy group which may be halogenated, (6) a $C_{1-6}$ alkyl-thio group, $C_{1-6}$ alkenyl-thio group or $C_{1-6}$ alkynyl-thio group which may be halogenated, (7) a $C_{1-6}$ alkoxy-$C_{1-6}$ alkyl group, (8) acetyl group, (9) a $C_{1-6}$ alkanoyl group, (10) a mono-($C_{1-6}$ hydrocarbon)-amino group, (11) a di-($C_{1-6}$ hydrocarbon)-amino group and (12) a tri-($C_{1-6}$ hydrocarbon)-amino group is preferable.

The "$C_{6-14}$ aromatic hydrocarbon-thio group" in the "$C_{6-14}$ aromatic hydrocarbon-thio group which maybe substituted" given as the substituent of HAr means the "$C_{1-6}$ cyclic hydrocarbon-thio group" corresponding to the "$C_{6-14}$ aromatic hydrocarbon group" in the above definition. For example, phenylthio group, pentalenylthio group and naphthylthio group are preferable. As the "$C_{6-14}$ aromatic hydrocarbon-thio group which may be substituted", a $C_{6-14}$ aromatic hydrocarbon-thio group" which may be substituted with one or more groups selected from (1) hydroxyl group, (2) a halogen atom, (3) a $C_{1-6}$ alkyl-sulfonyl group, $C_{1-6}$ alkenyl-sulfonyl group or $C_{1-6}$ alkynyl-sulfonyl group which may be halogenated, (4) a $C_{1-4}$ alkylenedioxy group which may be halogenated, (5) a $C_{1-6}$ alkoxy group which may be halogenated, (6) a $C_{1-6}$ hydrocarbon-thio group which may be halogenated, (7) a $C_{1-6}$ alkoxy-carbonyl group, (8) a $C_{6-14}$aryl-$C_{1-6}$ alkoxy group, (9) a $C_{1-7}$ alkanoylamino group, (10) a $C_{1-6}$ alkyl-carbamoyl group, (11) a $C_{1-6}$ alkenyl-carbamoyl group, (12) a $C_{1-6}$ alkynyl-carbamoyl group and (13) an amino group which may be substituted with a $C_{1-6}$ hydrocarbon group is preferable.

The "5- to 14-membered heterocycle-thio group[ in the "5- to 14-membered heterocycle-thio group which may be substituted" which is given as the substituent of HAr means a "5- to 14-membered heterocycle-thio group" corresponding to a ring having the same meaning as the "5- to 14-membered aromatic heterocyclic group" and the "4- to 10-membered non-aromatic heterocyclic group" in the aforementioned definition. Specific examples thereof include an "aromatic heterocycle-thio group" such as pyrrolylthio group, pyridinylthio group, pyridazinylthio group, pyrimidinylthio group, pirazinylthio group and thiazolylthio group; and an "non-aromatic heterocycle-thio group" such as pyrrolidinylthio group, pyrrolinylthio group, piperidinylthio group, piperazinylthio group, imidazolinylthio group, imidazolydinylthio group and morpholinylthio group. Also, as the "5- to 14-membered heterocycle-thio group which may be substituted", a "5- to 14-membered heterocycle-thio group" which may be substituted with one or more groups selected from (1) hydroxyl group, (2) a halogen atom, (3) nitrile group, (4) a $C_{1-6}$ alkyl group, $C_{1-6}$ alkenyl group or $C_{1-6}$ alkynyl group which may be halogenated, (5) a $C_{1-6}$ alkoxy group which may be halogenated, (6) a $C_{1-6}$ alkyl-thio group, $C_{1-6}$ alkenyl-thio group or $C_{1-6}$ alkynyl-thio group which may be halogenate (7) a $C_{1-6}$ alkoxy-$C_{1-6}$ alkyl group, (8) acetyl group, (9) a $C_{1-6}$ alkanoyl group, (10) a mono-($C_{1-6}$ hydrocarbon)-amino group, (11) a di-($C_{1-6}$ hydrocarbon)-amino group and (12) a tri-($C_{1-6}$ hydrocarbon)-amino group and (13) an oxo group is preferable. amino group and (3) an oxo group is preferable.

The "amino group which may be substituted" given as the substituent of HAr means an amino group represented by the formula —N($R^3$)$R^4$ (wherein $R^3$ and $R^4$ are the same as or different from each other and each is a group selected from (1) an aromatic heterocyclic group, (2) a non-aromatic heterocyclic group, (3) a $C_{1-6}$ alkyl group, $C_{1-6}$ alkenyl group or $C_{1-6}$ alkynyl group which may be substituted with a halogen atom or a $C_{1-6}$ alkoxy group, (4) a $C_{3-8}$ cycloalkyl group, $C_{3-8}$ cycloalkenyl group or $C_{3-8}$ cycloalkynyl group which may be halogenated, (5) a carbonyl group which is substituted with a $C_{1-6}$ alkyl group, $C_{1-6}$ alkenyl group or $C_{1-6}$ alkynyl group which may be halogenated, a $C_{3-8}$ cycloalkyl group, $C_{3-8}$ cycloalkenyl group or $C_{3-8}$ cycloalkynyl group which may be halogenated, a $C_{1-6}$ alkoxy group which may be halogenated, a $C_{6-14}$ aryl group or an aromatic heterocyclic group, (6) a $C_{1-6}$ alkanoyl group which may be substituted with a group selected from a $C_{6-14}$ aryl group and an aromatic heterocyclic group, (7) a carbamoyl group which may be substituted with a $C_{1-6}$ alkyl group, a $C_{1-6}$ alkenyl group, a $C_{1-6}$ alkynyl group, a $C_{6-14}$ aryl group or an aromatic heterocyclic group and (8) a sulfonyl group which is substituted with a $C_{1-6}$ alkyl group, a $C_{1-6}$ alkenyl group or a $C_{1-6}$ alkynyl group. Also, (9) $R^3$ and $R^4$ may be combined and united to form a 3- to 10-membered ring, and the cyclic amino group may be substituted with one or more groups selected from hydroxyl group, a halogen atom, a $C_{1-6}$ alkyl group, a $C_{1-6}$ alkenyl group, a $C_{1-6}$ alkynyl group, a $C_{1-6}$ alkoxy group, a $C_{1-6}$ hydrocarbon-thio group and a $C_{1-4}$ alkylenedioxy group). An amino group, $R^3$ and $R^4$ are the same as or different from each other and each is a group selected from a $C_{1-6}$ alkyl group, a $C_{1-6}$ alkoxy-$C_{1-6}$ alkyl group, a $C_{1-6}$ alkoxy-carbonyl group, a $C_{1-6}$ alkanoyl group, a $C_{6-14}$ aryl-carbonyl group, a heteroaryl-carbonyl group, a $C_{1-6}$ alkyl-carbamoyl group, a $C_{6-14}$ alkyl-carbamoyl group, a $C_{6-14}$ aryl-sulfonyl group and a 5- to 14-membered heterocyclic group.

Given as example of the "$C_{1-6}$ imidoyl group" in the "$C_{1-6}$ imidoyl group which may be substituted" given as the substituent of HAr are formimidoyl, hexaneimidoyl and succinimidoyl. As the "$C_{1-6}$ imidoyl group which may be substituted", a $C_{1-6}$ imidoyl group which may be substituted with a halogen atom is preferable.

Examples of the "substituted carbonyl group" given as the substituent of HAr include carbonyl groups substituted with a group selected from a $C_{1-6}$ alkyl group, a $C_{2-6}$ alkenyl group, a $C_{26}$ alkynyl group, a $C_{1-6}$ alkoxy-$C_{1-6}$ alkyl group, a $C_{1-6}$ alkoxy group, a $C_{6-4}$ aryl group and a 5- to 14-membered aromatic heterocyclic group.

The "substituted carbonyl group" in the "the "substituted carbonyl-oxy group" given as the substituent of HAr is a carbonyl having the same meaning as the "substituted carbonyl group" in the aforementioned definition. Examples of the "substituted carbonyl-oxy group" include a $C_{1-6}$ alkyl-carbonyl-oxy group, a $C_{2-6}$ alkenyl-carbonyl-oxy group, a $C_{2-6}$ alkynyl-carbonyl-oxy group, a $C_{1-6}$ alkoxy-$C_{1-6}$ alkyl-carbonyl-oxy group, a $C_{1-6}$ alkoxy-carbonyl-oxy group, a $C_{6-14}$ aryl-carbonyl-oxy group and 5- to 14-membered aromatic heterocycle-carbonyl-oxy group. Preferable examples are a $C_{1-6}$ alkyl-carbonyl-oxy group, a $C_{2-6}$ alkenyl-carbonyl-oxy group and a $C_{2-6}$ alkynyl-carbonyl-oxy group.

Examples of the "carboxyl group which may form a salt" given as the substituent of HAr include salts of alkali metals such as lithium, sodium and potassium, salts of alkali earth metals such as magnesium and calcium, tetramethylammonium salts, quaternary ammonium salts such as a tetraethylammonium salt, amino acid salts such as alginates, aspartates, glutamate and a proline salt, and further betaines with amino groups in a molecule.

The "carbamoyl group which may be substituted" given as the substituent of HAr is, specifically, carbamoyl groups represented by the formula —CO—N($R^5$)$R^6$ (wherein $R^5$ and $R^6$ are the same as or different from each other and each represents a group selected from (1) hydrogen atom, (2) a $C_{1-6}$ alkyl group, (3) a $C_{1-6}$ alkenyl group, (4) a $C_{1-6}$ alkynyl group, (5) a $C_{3-8}$ cycloalkyl group, (6) a $C_{3-8}$ cycloalkenyl group, (7) a $C_{3-8}$ cycloalkynyl group, (8) a $C_{6-14}$ aryl group and (9) an aromatic heterocyclic group or (10) $R^5$ and $R^6$ may be combined and united to form a 3- to 8-membered ring). A carbamoyl group, wherein $R^5$ and $R^6$ are the same as or different from each other and each is a group selected from a $C_{1-6}$ alkynyl group, a $C_{3-8}$ cycloalkyl group, a $C_{6-14}$ aryl group which may be halogenated etc., is preferable.

Given as examples of the "$C_{1-4}$ alkylenedioxy group" in the "$C_{1-4}$ alkylenedioxy group which may be substituted" given as the substituent of HAr are a methylenedioxy group, ethylenedioxy group and propylenedioxy group. As the "$C_{1-4}$ alkylenedioxy group which may be substituted", a $C_{3-4}$ alkylenedioxy group which may be hydroxylated or halogenated is preferable.

As the "sulfinyl group which may be substituted" given as the substituent of HAr, a sulfinyl group which may be substituted with a group selected from (1) a $C_{1-6}$ hydrocarbon group which may be halogenated and (2) an amino group which may be mono- or di-substituted with a $C_{1-6}$ hydrocarbon group which may be halogenated is preferable.

As the "sulfonyl group which may be substituted" given as the substituent of HAr, a sulfonyl group which may be substituted with a group selected from (1) a $C_{1-6}$ hydrocarbon group which may be halogenated and (2) an amino group which E may be mono- or di-substituted with a $C_{1-6}$ hydrocarbon group which may be halogenated is preferable.

The definition of the "aromatic heterocycle which may be substituted" represented by HAr in the formula (I) is as above-mentioned. Preferable examples of the substituent of the "aromatic heterocycle" include (1) a $C_{1-6}$ alkyl group, $C_{1-6}$ alkenyl group or $C_{1-6}$ alkynyl group, which may be substituted with one or two groups selected from (a) hydroxyl group, (b) a halogen atom, (c) a 5- to 14-aromatic heterocyclic group, (d) a 4- to 10-membered non-aromatic heterocyclic group, (e) a 5- to 10-membered condensed heterocyclic group which may be substituted with a $C_{1-6}$ alkoxy group and (f) a $C_{1-6}$ alkyl-sulfonyl group, (2) a $C_{1-6}$ alkoxy group which may be substituted with one or more groups selected from (a) hydroxyl group, (b) a halogen atom, (c) a 4- to 10-membered non-aromatic heterocycle-oxy group, (d) a $C_{1-6}$ alkoxy group, (e) a $C_{1-6}$ alkoxy-carbonyl group and (f) a 4- to 10-membered non-aromatic heterocycle, (3) a $C_{6-14}$ aromatic hydrocarbon cyclic group which may be substituted with one or more groups selected from (a) a halogen atom, (b) a $C_{1-6}$ alkoxy group and (c) a $C_{1-4}$ alkylenedioxy group, (4) a 5- to 14-membered aromatic heterocyclic group which may be substituted with one or more groups selected from (a) hydroxyl group, (b) nitrile group, (c) a $C_{1-6}$ alkyl group, (d) a $C_{1-6}$ alkoxy group, (e) a $C_{1-6}$ alkoxy-$C_{1-6}$ alkyl group, (f) a $C_{1-6}$ alkanoyl group, (g) a $C_{1-4}$ alkylenedioxy group, (h) a mono-($C_{1-6}$ alkyl)-amino group and (i) a di-($C_{1-6}$ alkyl)-amino group and (5) a 4- to 10-membered non-aromatic heterocyclic group which may be substituted with one or more groups selected from (a) hydroxyl group, (b) nitrile group, (c) a $C_{1-6}$ alkyl group, (d) a $C_{1-6}$ alkoxy group, (e) a $C_{1-6}$ alkoxy-$C_{1-6}$ alkyl group, (f) a $C_{1-6}$ alkanoyl group, (g) a $C_{1-4}$ alkylenedioxy group, (h) a mono-($C_{1-6}$ alkyl)-amino group and (i) a di-($C_{1-6}$ alkyl)-amino group. More preferable examples include a $C_{1-6}$ alkyl group which may be halogenated, a $C_{2-6}$ alkenyl group which may be halogenated, a $C_{1-6}$ alkoxy-$C_{1-6}$ alkyl group, a $C_{1-6}$ alkyl group substituted with a $C_{6-14}$ aromatic hydrocarbon cyclic group, a $C_{1-6}$ alkyl group substituted with 5- or 6-membered aromatic heterocycle, a $C_{1-6}$ alkoxy group which may be halogenated, a $C_{1-6}$ alkoxy-$C_{1-6}$ alkoxy group, a $C_{6-14}$ aromatic hydrocarbon group, a 5- or 6-membered aromatic heterocycle which may be substituted with a $C_{1-6}$ alkyl group and a 4- to 10-membered non-aromatic heterocyclic group which may be substituted with one or more groups selected from (a) hydroxyl group, (b) nitrile group and (c) a $C_{1-6}$ alkoxy group.

The terms "halogen atom", "$C_{1-6}$ hydrocarbon group", "$C_{1-6}$ alkyl group", "$C_{3-8}$ alkenyl group", "$C_{3-8}$ alkynyl group", "$C_{3-8}$ cycloalkyl group", "$C_{3-8}$ cycloalkenyl group", "$C_{3-8}$ cycloalkynyl group", "$C_{6-14}$ aromatic hydrocarbon group", $C_{6-14}$ aryl group", "5- to 14-membered aromatic heterocyclic group", "5- to 14-membered heteroaryl group", "4- to 10-membered non-aromatic heterocyclic group", "$C_{1-6}$ alkoxy group", "$C_{3-8}$ cycloalkoxy group", "$C_{3-8}$ cycloalkyloxy group", "$C_{3-8}$ cycloalkenyloxy group", "$C_{1-6}$ hydrocarbon-thio group", "$C_{1-6}$ alkylthio group", "$C_{1-6}$ alkenylthio group", "$C_{1-6}$ alkynylthio group", "$C_{3-8}$ cycloalkylthio group", "$C_{3-8}$ cycloalkenylthio group", "$C_{1-6}$ alkoxycarbonyl group", "$C_{1-6}$ alkanoyl group", "$C_{1-6}$ alkanoyloxy group", "carbamoyl group", "$C_{1-6}$ imidoyl group", "carboxyl group which may form a salt", "$C_{1-4}$ alkylenedioxy group", "sulfonyl group" and "sulfinyl group", which are all used in the above-mentioned definitions concerning the substituents of the aromatic heterocycle HAr have the same meanings as defined above.

In the specification of the present invention, the "aromatic ring" in the "aromatic ring which may be substituted" represented by Ar in the formula (I) means a ring having the same meaning as the "aromatic ring" in the above definition. For example, benzene ring, a pyridine ring and the like are preferable. Examples of the "aromatic ring which may be substituted" include aromatic rings which may be substituted with one or more groups selected from (1) hydroxyl group, (2) a halogen atom, (3) a $C_{1-6}$ chain hydrocarbon group which may be substituted, (4) a $C_{3-8}$ cyclic hydrocarbon group which may be substituted, (5) a $C_{1-6}$ alkoxy group which may be substituted, (6) a $C_{3-8}$ cycloalkoxy group which may be substituted, (7) a $C_{1-6}$ chain hydrocarbon-thio group which may be substituted, (8) a $C_{3-8}$ cyclic hydrocarbon-thio group, (9) a $C_{6-14}$ aromatic hydrocarbon cyclic group which may be substituted, (10) a 5- to 14-membered heterocyclic group which may be substituted, (11) an amino group which may be substituted with a $C_{1-6}$ alkyl group and (12) a $C_{1-4}$ alkylenedioxy group which may be substituted.

The "$C_{1-6}$ chain hydrocarbon group which may be substituted" given as the substituent of Ar means a group having the same meaning as the "$C_{1-6}$ chain hydrocarbon group which may be substituted" shown in the definition of HAr. As the "$C_{1-6}$ chain hydrocarbon group which may be substituted", a $C_{1-6}$ alkyl group which may be halogenated, a $C_{1-6}$ alkenyl group which may be halogenated, a $C_{1-6}$ alkynyl group which may be halogenated and the like are preferable.

The "$C_{3-8}$ cyclic hydrocarbon group which may be substituted" given as the substituent of Ar means a group having the same meaning as the "$C_{3-8}$ cyclic hydrocarbon group which may be substituted" shown in the definition of HAr. As the "$C_{3-8}$ cyclic hydrocarbon group which may be substituted", a $C_{3-8}$ cycloalkyl group which may be halogenated, a $C_{3-8}$ cycloalkenyl group which may be halogenated and the like are preferable.

The "$C_{1-6}$ alkoxy group which may be substituted" given as the substituent of Ar means a group having the same meaning as the "$C_{1-6}$ alkoxy group which may be substituted" shown in the definition of HAr. As the "$C_{1-6}$ alkoxy group which may be substituted", a $C_{1-6}$ alkoxy group which may be halogenated and the like are preferable.

The "$C_{1-6}$ cycloalkoxy group which may be substituted" given as the substituent of Ar means a group having the same meaning as the "$C_{3-8}$ cycloalkoxy group which may be substituted" shown in the definition of HAr. As the "$C_{3-8}$ cycloalkoxy group which may be substituted", a $C_{3-8}$ cycloalkyloxy group which may be halogenated, a $C_{3-8}$ cycloalkenyloxy group which may be halogenated and the like are preferable.

The "$C_{1-6}$ chain hydrocarbon-thio group which may be substituted" given as the substituent of Ar means a group having the same meaning as the "$C_{1-6}$ chain hydrocarbon-thio group which may be substituted" shown in the definition of HAr. As the "$C_{1-6}$ chain hydrocarbon-thio group which may be substituted", a $C_{1-6}$ alkyl-thio group which may be halogenated, a $C_{1-6}$ alkenyl-thio group which may be halogenated, a $C_{1-6}$ alkynyl-thio group which may be halogenated and the like are preferable.

The "$C_{3-8}$ cyclic hydrocarbon-thio group" given as the substituent of Ar means a group having the same meaning as the "$C_{3-8}$ cyclic hydrocarbon-thio group which may be substituted" shown in the definition of HAr. As the "$C_{3-8}$ cyclic hydrocarbon-thio group which may be substituted", a $C_{3-8}$ cycloalkylthio group which may be halogenated, a $C_{3-8}$ cycloalkenylthio group which may be halogenated and the like are preferable.

The "$C_{6-14}$ aromatic hydrocarbon cyclic group which may be substituted" and "5- to 14-membered heterocyclic group which may be substituted" which are given as the substituents of Ar mean groups having the same meanings as the "$C_{6-14}$ aromatic hydrocarbon cyclic group which may be substituted" and the "5- to 14-membered heterocyclic group which may be substituted" shown in the definitions of HAr respectively.

The "amino group which may be substituted with a $C_{1-6}$ alkyl group" given as the substituent of Ar means an amino group mono-substituted with a $C_{1-6}$ alkyl group such as methylamino group and ethylamino group and an amino group di-substituted with a $C_{1-6}$ alkyl group such as dimethylamino group and diethylamino group. Further, the nitrogen atom may be tri-substituted with a $C_{1-6}$ alkyl group to form an ammonium salt.

The "$C_{1-4}$ alkylenedioxy group which may be substituted" given as the substituent of Ar means a group having the same meaning as the "$C_{1-4}$ alkylenedioxy group which may be substituted" shown in the definition of HAr. For example, a $C_{1-4}$ alkylenedioxy group which may be substituted with a halogen atom etc. is preferable.

As above-mentioned, the "aromatic ring which may be substituted" represented by Ar in the formula (I) is defined. Preferable examples of Ar include a benzene ring, pyridine ring, pyrazine ring, thiophene ring and thiazole ring, which maybe substituted with a group selected from hydroxyl group, a halogen atom, a $C_{1-6}$ alkyl group, a $C_{1-6}$ alkoxy group and the like.

In the specification of the present invention, W in the formula (I) means a connecting chain in which the primary chain is constituted of two or more atoms. Examples thereof include preferably a chain represented by (1) —$CH_2$—$CH_2$— which may be substituted, (2) —CH=CH— which may be substituted, (3) —C≡C—, (4) —NH—CO—, (5) —CO—NH—, (6) —NH—$CH_2$—, (7) —$CH_2$—NH—, (8) —$CH_2$—CO—, (9) —CO—$CH_2$—, (10) —NH—$S(O)_1$—, (11) —$S(O)_1$—NH—, (12) —$CH_2$—$S(O)_1$— and (13) —$S(O)_1$—$CH_2$— (1 denotes 0, 1 or 2), more preferably (1) —$CH_2$—$CH_2$—, (2) —CH=CH— and (3) —$C^{57}$ C—, and further preferably —C≡C—.

In the specification of the present invention, examples of the connecting group X in the formula (I) include chains represented by (1) a single bond, (2) a $C_{1-6}$ alkylene chain which may be substituted, (3) a $C_{2-6}$ alkenylene chain which may be substituted, (4) a $C_{2-6}$ alkynylene chain which may be substituted, (5) a formula —Q— (wherein Q represents oxygen atom, sulfur atom, CO or N(R) (wherein R represents a $C_{1-6}$ alkyl group or a $C_{1-6}$ alkoxy group)), (6) —NH—CO—, (7) —CO—NH—, (8) —NH—$CH_2$—, (9) —$CH_2$—NH—, (10) —$CH_2$—CO—, (11) —CO—$CH_2$—, (12) —NH—$S(O)_m$—, (13) —$S(O)_m$—NH—, (14) —$CH_2$—$S(O)_m$—, (15) —$S(O)_m$—$CH_2$— (wherein m denotes 0, 1 or 2) or (16) —$(CH_2)_n$—O— (wherein n denotes an integer from 1 to 6). Here, the "$C_{1-6}$ alkylene chain", the "$C_{1-6}$ alkenylene chain" and the "$C_{1-6}$ alkynylene chain" mean chains corresponding to $C_{1-6}$ hydrocarbon groups having the same meanings as the "$C_{1-6}$ alkyl group", the "$C_{1-6}$ alkenyl group" and the "$C_{1-6}$ alkynyl group" in the above definitions. The connecting chain X represents preferably a single bond, a $C_{1-6}$ alkylene chain, a $C_{2-6}$ alkynylene chain, —CO— or the like and more preferably a simple bond, methylene chain, ethylene chain or —CO—.

The amino group in the "amino group which may be substituted with a $C_{1-6}$ alkyl group or an acyl group" means an amino group which may be substituted with a $C_{1-6}$ alkyl group having the same meaning as the aforementioned definition or an acyl group having the same meaning as the above definition. Specific examples thereof include an N-formylamino group, N-acetylamino group, N-propionylamino group, N-pivaloylamino group, N-benzoylamino group, N-methyl-N-formylamino group, N-methyl-N-benzoylamino group, N-methylamino group, N,N-dimethylamino group, N-methyl-N-ethylamino group, N-(n-propyl)amino group, N-(i-propyl)amino group and N-(t-butyl)amino group.

The "$C_{1-6}$ alkoxycarbonyl group" is an alkoxycarbonyl group corresponding to the $C_{1-6}$ alkoxy group in the above definition. Specific examples thereof include methoxycarbonyl group, ethoxycarbonyl group, n-propoxycarbonyl group, i-propoxycarbonyl group, sec-propoxycarbonyl group, n-butoxycarbonyl group, i-butoxycarbonyl group, 1,2-dimethylpropoxycarbonyl group and 2-ethylpropoxycarbonyl group.

The definitions of $R^1$, HAr, Ar, W and X to be used in the formula (I) have been described as above. To state more preferable examples, as examples of —X—Ar, a benzyl group (X=methylene chain; Ar=benzene ring) which may be substituted is given and as examples of HAr, besides a substituent —X—Ar, a pyridine ring, pyrimidine ring, pyridazine ring, pyrazine ring, indole ring, quinoline ring, thiophene ring or benzothiophene ring which may be substituted with one or two groups selected from (1) a 5- or 6-membered aromatic heterocycle which may be substituted with a $C_{1-6}$ alkyl group, (2) a 5- or 6-membered non-aromatic heterocycle which may be substituted one or more groups selected from (a) hydroxyl group, (b) a $C_{1-6}$ alkyl group and (c) a $C_{1-6}$ alkoxy group, (3) a $C_{6-10}$ aromatic hydrocarbon ring which may be substituted with one or more groups selected from (a) a halogen atom, (b) a $C_{1-6}$ alkoxy group, (c) a $C_{1-4}$ alkylenedioxy group and (d) a sulfonyl group which may be substituted with a $C_{1-6}$ alkyl group, (4) a $C_{1-6}$ alkyl group which may be substituted with one or two groups selected from (a) hydroxyl group, (b) a halogen atom, (c) a 5- or 6-membered aromatic heterocycle and (d) a $C_{1-6}$ alkoxy group and (5) a $C_{1-6}$ alkoxy group which may be substituted with (a) a halogen atom and (b) a $C_{1-6}$ alkoxy group. More preferable examples of HAr include a pyridine ring, pyrimidine ring, pyridazine ring, pyrazine ring, indole ring, quinoline ring, thiophene ring or benzothiophene ring which may be substituted with one or two groups selected from (1) a benzene ring which may be substituted with a $C_{1-4}$ alkylenedioxy group, (2) pyridine ring, (3) pyrimidine ring, (4) pyridazine ring, (5) pyrazine ring, (6) thiophene ring, (7) a piperidine ring which may be substituted with a $C_{1-6}$ alkoxy group, (8) a piperazine ring which may be substituted with a $C_{1-6}$ alkoxy group, (9) a pyrrolidine ring which may be substituted with a $C_{1-6}$ alkoxy group, (10) a piperidine ring substituted with hydroxyl group and a $C_{1-6}$ alkoxy group, (11) a piperazine ring substituted with hydroxyl group and a $C_{1-6}$ alkoxy group, (12) a pyrrolidine ring substituted with hydroxyl group and a $C_{1-6}$ alkoxy group, (13) morpholine ring, (14) a $C_{1-6}$ alkyl group which may be substituted with a $C_{1-6}$ alkoxy group and (15) a $C_{1-6}$ alkoxy group which may be substituted with hydroxyl group or a $C_{1-6}$ alkoxy group.

The salts in the present invention mean generally pharmacologically acceptable salts. Examples of these salts include hydrohalides such as hydrofluorides, hydrochlorides, hydrobromides and hydroiodides; inorganic acid salts such as sulfates, nitrates, perchlorates, phosphates, carbonates and bicarbonates; organic carboxylates such as acetates, maleates, tartrates and fumarates; organic sulfonates such as methanesulfonates, trifluoromethanesulfonates, ethanesulfonates, benzene sulfonates and toluene sulfonates; amino acid salts such as alginates, aspartates and glutamates; salts with amines such as trimethylamine salts, triethylamine salts, procaine salts, pyridium salts and phenethylbenzylamine salts; alkali metal salts such as sodium salts and potassium salts; and alkali earth metal salts such as magnesium salts and calcium salts.

General Production Method

Various methods are considered as a method for producing the compound represented by the formula (I) according to the present invention and the compound can be produced by a usual organic synthetic method. To state a typical method, for example, the following method may be used to produce the compound.

Production method 1

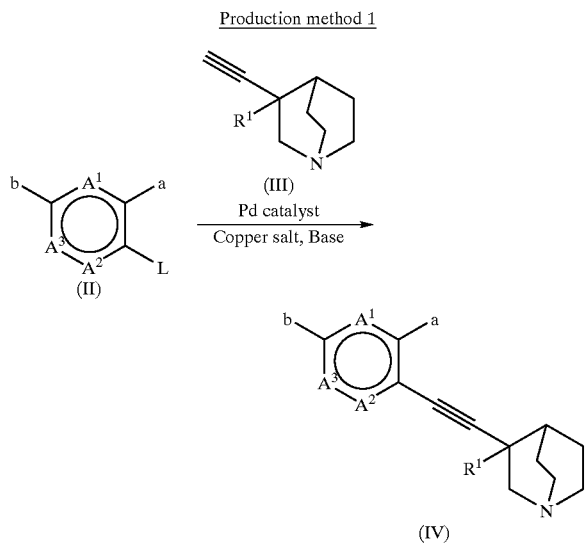

The above production method is a method of producing the compound (IV) according to the invention of the patent application of this case by coupling the aromatic heterocyclic compounds (II) and (III) with each other. In the formula, $A^1$, $A^2$ and $A^3$ are the same as or different form each other and each means (1) a carbon atom which may be substituted or (2) a heteroatom such as nitrogen atom, sulfur atom or oxygen atom, wherein there is the case where $A^2$ further means a single bond. When $A^2$ means a single bond, the ring to which $A^1$, $A^2$ and $A^3$ belong is a 5-membered ring. Here, in the case where $A^1$, $A^2$ and $A^3$ respectively represent the "carbon atom which may be substituted", the term "may be substituted" means that it may be substituted with the substituent shown in HAr defined above. Specifically, the carbon atom may be substituted with a group selected from (1) halogen atom, (2) hydroxyl group, (3) thiol group, (4) nitro group, (5) nitrile group, (6) a $C_{1-6}$ chain hydrocarbon group which may be substituted, (7) a $C_{3-8}$ cyclic hydrocarbon group which may be substituted, (8) a $C_{6-14}$ aromatic hydrocarbon cyclic group which may be substituted, (9) a 5- to 14-membered aromatic heterocyclic group which may be substituted, (10) a 4- to 10-membered non-aromatic heterocyclic group which may be substituted, (11) a $C_{1-6}$ alkoxy group which may be substituted, (12) a $C_{3-8}$ cycloalkyloxy group which may be substituted, (13) a $C_{1-6}$ chain hydrocarbon-thio group which may be substituted, (14) a $C_{3-8}$ cyclic hydrocarbon-thio group which may be substituted, (15) a $C_{6-4}$ aromatic hydrocarbon-oxy group which may be substituted, (16) a 5- to 14-membered heterocycle-oxy group which may be substituted, (17) a $C_{6-14}$ aromatic hydrocarbon-thio group which may be substituted, (18) a 5- to 14-membered heterocycle-thio group which may be substituted, (19) an amino group which may be substituted, (20) azide group, (21) guanidino group, (22) carbamide group, (23) formyl group, (24) a $C_{1-6}$ imidoyl group which may be substituted, (25) a carbonyl group which is substituted, (26) a carbonyl-oxy group which is substituted, (27) a carboxyl group which may form a salt, (28) a carbamoyl group which may be substituted, (29) a $C_{1-4}$ alkylenedioxy group which may be substituted, (30) a sulfinyl group which may be substituted and (31) a sulfonyl group which may be substituted. * L means a leaving group and $R^1$ means hydrogen atom or hydroxyl group, a and b respectively mean a group —X—Ar (wherein X and Ar have the same meaning as defined above) and the substituent of HAr of the formula (I) described in the aforementioned definition, or respectively mean the substituent of HAr and group —X—Ar (wherein X and Ar have the same meaning as defined above) of the formula (I) described in the above definition. The leaving group L may be any group so long as it is known as a leaving group in organic synthesis and no particular limitation is imposed. Examples thereof include halogen atoms such as chlorine atom, bromine atom and iodine atom; substituted or unsubstituted acetoxy groups such as acetoxy group and trifluoroacetoxy group; substituted sulfonyloxy groups such as methanesulfonyloxy group trifluoromethanesulfonyloxy group, benzenesulfonyloxy group and p-toluenesulfonyloxy group; and substituted phosphoryloxy groups such as diphenoxyphosphoryloxy. Among these groups, halogen atoms such as chlorine atom, bromine atom and iodine atom and trifluoromethanesulfonyloxy group are preferable. As the palladium catalyst, for example, tetrakis(triphenylphosphine)palladium(0) or bis(triphenylphosphine)palladium(II) chloride may be used in an amount of 0.00001 to 0.1 mol equivalents. For example, 0.0001 to 0.1 mol equivalents of cuprous iodide or cuprous chloride may be used as the copper salt and for example, 1 to 5 equivalents of triethyl amine or N,N-diisopropylethylamine may be used as the base. As the solvent, N,N-dimethylformamide, N-methylpyrrolidone, tetrahydrofuran, methanol or a mixture of these solvents is used. The reaction temperature is preferably 0° C. to 140° C.

Production method 2

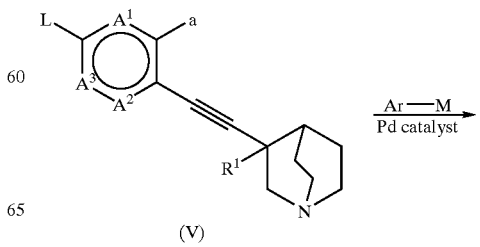

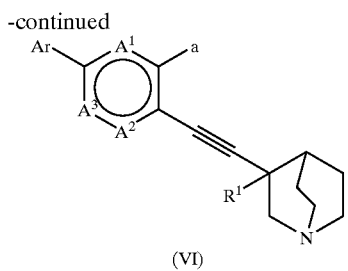

(VI)

Production method 3

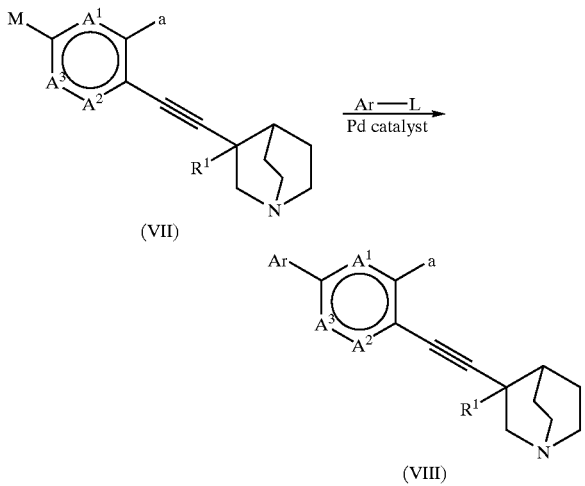

The above production methods ensure that the compounds (VI) and (VIII) according to the present invention may be produced. In the reaction formula, L and a have the same meanings as those in the above definition. As L, for example, chlorine atom, bromine atom, iodine atom or trifluoromethanesulfonyloxy group may be used. M means a metal atom which may have a substituent. For example, trinbutyltin or dihydroxyboron is preferable. As the palladium catalyst, for example, tetrakis triphenylphosphine)palladium (0) or bis(triphenylphosphine)palladium(II) chloride may be used in an amount of 0.0001 to 0.1 mol equivalents. Examples of the solvent include toluene, xylene, N,N-dimethylformamide and N-methylpyrrolidone. A reaction temperature ranging from 50° C. to 150° C. is adopted. When the metal M is boron, an inorganic base such as sodium carbonate or an organic base such as triethylamine is used as the base. As the solvent, an organic solvent containing water is also used.

No particular limitation is imposed on the dosage form of the compound according to the present invention and either oral administration or parenteral administration according to a method which is usually used is acceptable. The compound may be made into preparations of a tablet, powder, granule, capsule agent, syrup agent, troche, inhalant, suppository, injection, ointment, ophthalmic ointment, ophthalmic solution, collunarium, ear drop, cataplasm and lotion, and administered. In the preparation of these forms, fillers, binders, lubricants, colorants, flavoring agents, and if necessary, stabilizers, emulsifiers, absorbefacient agents, surfactants, pH regulators, antiseptics and antioxidants etc. may be used and components which are usually used as raw materials of medicinal preparations are formulated to prepare a medicine by a usual method. Examples of these components include animal or vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicon resins; silicon oils; surfactants such as polyoxyethylene fatty acid ester, sorbitan fatty acid ester, glycerol fatty acid ester, polyoxyethylenesorbitan fatty acid ester, polyoxyethylene hydrogenated castor oil and polyoxyethylene/polyoxypropylene block copolymers; water-soluble polymers such as hydroxyethyl cellulose, polyacrylic acid, carboxyvinyl polymers, polyethylene glycol, polyvinylpyrrolidone and methyl cellulose; lower alcohols such as ethanol and isopropanol; polyhydric. alcohols such as glycerol, propylene glycol, dipropylene glycol and sorbitol; sugars such as glucose and cane sugar; inorganic powders such as silicic acid anhydride, aluminum magnesium silicate and aluminum silicate; and purified water.

The medicine according to the present invention is administered to an adult patient at a dose of generally about 30 $\mu$g to 10 g, preferably 100 $\mu$g to 5 g and more preferably 100 $\mu$g to 100 mg in the case of oral administration and about 30 $\mu$g to 1 g, preferably 100 $\mu$g to 500 mg and more preferably 100 $\mu$g to 30 mg in the case of injection in one to several parts a day although the dose differs depending on the degree of a symptom, age, sex, weight, dosage form and type of disease.

The biochemical activities of the compound according to the present invention and the effects (squalene synthesizing enzyme activity, cholesterol biosynthesis inhibitive activity and cholesterol and triglyceride biosynthesis inhibitive activity) of the compound as a medicine may be evaluated by the following methods.

TEST EXAMPLE 1

Measurement of Squalene Synthesizing Enzyme Inhibitive Activity by Using a Rat Liver Microsome (I) The reaction was run on a scale of 500 $\mu$l. 200 $\mu$l of a solution containing 125 mM tris-hydrochloric acid (pH: 7.3), 2.5 mM magnesium chloride, 5 mM potassium fluoride and 10 mM reduction type nicotinamidoadenine dinucleotide phosphoric acid, 100 $\mu$l of the specimen solution with a 5-fold concentration, 100 $\mu$l of distilled water and 50 $\mu$l of 0.4 to 1 mg/ml rat liver microsome prepared by the following method were mixed.

(II) The above mixture was pre-incubated at 37° C. for 10 minutes and thereafter, 50 $\mu$l of 100 $\mu$M [$^3$H]-farnesylpyrophosphoric acid (30 mCi/mmol, NEN) was added to the mixture to start a reaction. The reaction was continued at 37° C. for 10 minutes. 1 ml of ethanol was added to the resulting mixture to terminate the reaction and then 1 ml of distilled water and 3 ml of petroleum ether were added to the reaction solution, which was then shaken for 30 minutes. The water phase was separated from the oil phase, the water phase was frozen at −70° C. in dry ice/methanol and the radiative activity of the organic phase was measured using a liquid scintillator. Or the organic phase was evaporated to dryness using nitrogen gas and the residue was dissolved as a marker in 25 $\mu$l of chloroform containing squalene, farnesol and cholesterol. This sample was spotted on a TCL plate (Merck) and developed using heptane for 15 to 20 minutes. A band of squalene was cut from the plate to measure the radiative activity by using a liquid scintillation

Method of the Preparation of a Rat Liver Microsome

The following operations were all carried out on ice and the centrifugation was performed at 4° C. The liver was excised from a male Spraugue-Dawly rat (hereinafter referred to as SD rat) (8 to 9 weeks age) and perfused with 1.15% potassium chloride to remove the blood. Then, the liver was minced using a forceps and the minced liver was homogenized using a Teflon homogenizer. The resulting sample was centrifuged at 16000×g twice for 15 minutes. The supernatant was further centrifuged at 105000×g for 60 minutes. The obtained deposit was determined as a microsome fraction, which was then suspended in a 25 mM tris-hydrochloric acid solution. The concentration of protein was measured quantitatively by a Bradford method and the concentration of protein was adjusted to 20 mg/ml by using the same solution. The resulting solution was stored at 70° C.

TEST EXAMPLE 2

Measurement of Cholesterol Biosynthesis Inhibitive Activity in a Rat (I) An SPF grade male SD rat (4 weeks age, SLC) was bred for more than one week in a day-night-reversal room and subjected to an experiment made in the daytime. The compound dissolved in a 2% Tween 80 solution was administered (5 ml/kg) to the rat using an oral sonde. After one hour, a [1-$^{14}$C]Acetic acid, sodium salt (1.67–2.22 GBq/mmol, 37 MBq/ml, NEN) prepared by diluting to 1.85 MBq/ml by using physiological saline was intraabdominally administered (300 μl/animal). After one hour, the rat was anesthetized by diethyl ether to carry out exsanguination from the aorta abdominalis. The collected blood was centrifuged at 3000 rpm for 10 minutes to prepare blood plasma.

(II) 1 ml of 4N KOH and 1 ml of ethanol were added to 2 ml of the blood plasma, which was then incubated at 65° C. for one hour and there after, 3 ml of petroleum ether was added. The plasma was shaken for 30 minutes. After the water phase was separated from the organic phase by centrifugation, it was frozen at −80° C. and the radiative activity of the organic phase was measured using a liquid scintillation counter. Or the organic phase was evaporated to dryness using nitrogen gas and the residue was dissolved as a marker in 25 μl of chloroform containing squalene, farnesol and cholesterol. This sample was applied to a TCL plate (Merck) and developed using toluene and isopropyl ether (1:1) for 15 to 20 minutes. A band of cholesterol was cut from the plate to measure the radiative activity by using a liquid scintillation counter. The cholesterol biosynthesis inhibition activity was expressed by an inhibition rate (%) to a control group.

TEST EXAMPLE 3

Measurement of Cholesterol and Triglyceride Biosynthesis Inhibitive Activities in a Rat Liver Cell A liver cell was isolated from a male SD rat according to a usual method (collagenase perfusion method) and subjected to an experiment.

The isolated liver cells were planted in an amount of 500 μl every well on a Type collagen coated 24 well plate (cell density: 4×10$^5$ cell/ml). As the cell culture solution, a Williams'E medium (adjusted to pH 7.4) containing 10% FCS, 1 μM insulin, 1 μM dexamethasone, 100 units/ml penicillin and 10 μg/ml streptomycin was used. After the liver cells were incubated in a $CO_2$ incubator for 2 hours, unstuck cells were removed and the liver cells were further incubated overnight.

After the culture medium was exchanged, the specimen diluted in a 10% DMSO-90% cell culture solution was added to each well in an amount of 5 μl. DMSO (final concentration: 0.1%) was added to a control group. A [1-$^{14}$C]Acetic acid, sodium salt (5 μCi/well) was added to the media 10 minutes and 4 hours after the specimen was added for the measurement of cholesterol synthesis inhibitive action and for the measurement of triglyceride synthesis inhibitive action respectively, followed by culturing for further 2 hours.

After the cultivation was finished, the supernatant was removed and the cells were washed using PBS(−)(Phosphate buffered saline ($Ca^{2+}$, $Mg^{2+}$free) twice. Hexane/isopropyl alcohol (3:2, v/v) was added to the cells and the cells were then allowed to stand for 10 minutes to extract intracellular lipid. The extract was transferred to a glass tube and exsiccated under a nitrogen gas stream. Further, the exsiccated extract was washed with 25 mL of petroleum ether and then dissolved in petroleum ether containing the following components: 0.01% squalene, 0.3% free cholesterol, 0.3% cholesterol acetate, 0.1% triolein, 0.01% farnesol and 0.3% lanosterol.

The resulting solution was spotted on a TLC plate to perform an isolating operation. The spotted solution was developed for 10 minutes by using toluene/isopropyl ether (1:1, v/v) as the solvents and for further 15 minutes by using heptane in place of the above solvent after it was dried using air.

After the development was finished, the TLC plate was subjected to iodine color development. After each position of free cholesterol and triolein which were used as standards was confirmed, the image of the TLC plate was transferred to a BAS 2000 (Fuji Film) imaging plate by exposure performed for 16 hours. This transferred image was analyzed using a BAS 2000 IP Reader and an Imaging analyzer II to measure radiative activities contained in the free cholesterol and triglyceride fractions.

The cholesterol biosynthesis inhibitive activity was expressed by a concentration ($IC_{50}$) at which 50% of the radiative activity of the control group was inhibited and the triceride biosynthesis inhibitive activity was expressed by an inhibition rate (%) to the control group.

The test results based on Test Example 1 (Measurement of squalene synthesizing enzyme inhibitive activity by using a rat liver microsome), Test Example 2 (Measurement of cholesterol biosynthesis inhibitive activity in a rat) and Teat Example 3 (Measurement of cholesterol and triglyceride biosynthesis inhibitive activities in a rat liver cell) are shown below.

TABLE 1

| Example | Squalene synthesizing enzyme inhibitive activity $IC_{50}$ (nM) |
| --- | --- |
| 1 | 10 |
| 2 | 20 |
| 9 | 34 |
| 10 | 2 |
| 18 | 25 |

TABLE 1-continued

| Example | Squalene synthesizing enzyme inhibitive activity IC$_{50}$ (nM) |
|---|---|
| 19 | 10 |
| 104 | 6.7 |
| 106 | 6.9 |
| 110 | 2.1 |
| 116 | 0.77 |
| 117 | 4.5 |
| 118 | 2.5 |
| 119 | 3.9 |
| 124 | 1.8 |
| 138 | 0.35 |
| 142 | 5 |
| 144 | 2.6 |
| 153 | 11 |
| 166 | 15 |
| 180 | 6.3 |
| 201 | 1.6 |

TABLE 2

| Example | Dose (mg/kg) | Cholesterol biosynthesis inhibitive activity inhibition (%) |
|---|---|---|
| 6 | 3 | 73 |
| 11 | 3 | 72 |
| 12 | 3 | 78 |
| 13 | 3 | 87 |
| 104 | 2 | 88 |
| 123 | 3 | 86 |
| 142 | 3 | 82 |
| 147 | 3 | 87 |
| 148 | 3 | 92 |
| 150 | 1 | 73 |
| 153 | 1 | 82 |
| 168 | 3 | 89 |
| 169 | 3 | 92 |

TABLE 3

| Example | Cholesterol biosynthesis inhibitive activity IC$_{50}$ ($\mu$M) |
|---|---|
| 116 | 0.072 |
| 117 | 0.079 |
| 118 | 0.075 |
| 120 | 0.075 |
| 124 | 0.081 |
| 138 | 0.014 |
| 148 | 0.16 |
| 149 | 0.59 |
| 153 | 0.055 |
| 179 | 0.13 |
| 186 | 0.069 |

TABLE 4

| Example | Triglyceride biosynthesis inhibitive activity inhibition in 1 $\mu$M of the specimen |
|---|---|
| 106 | 81 |
| 110 | 84 |
| 118 | 85 |
| 120 | 80 |
| 124 | 79 |
| 150 | 80 |
| 153 | 85 |
| 166 | 82 |
| 176 | 74 |
| 179 | 84 |
| 201 | 85 |

The compound according to the present invention is very useful as a squalene synthesizing enzyme inhibitor (Table 1) and also as a cholesterol biosynthesis inhibitor in actual (Table 2 and Table 3). Further, it is very useful also as an inhibitor of the synthesis of triglyceride as neutral fat (Table 4). Accordingly, the compound according to the present invention is useful as preventive and curative agents for a disease on which squalene synthesizing inhibition, cholesterol biosynthesis inhibition or triglyceride biosynthesis inhibition is effective. From the above results, the compound according to the present invention is useful as a preventive and curative agent for hyper lipidemia and also as a preventive and curative agent for arterial sclerosis diseases or ischemic heart diseases.

EXAMPLES

The present invention will be explained in more detail and concretely by way of the following Examples, however, the present invention is not limited by them. The structural formulae of compounds in these Examples are listed in Tables 5 to 10 shown below.

PRODUCTION EXAMPLES

PRODUCTION EXAMPLE 1

4-Benzyl-5-bromo-2-pyridyl Trifluoromethanesulfonate a) 4-Benzoyl-2-chloropyridine 102 g of 2-chloronicotinic acid was suspended in 250 ml of benzene. 50 ml of thionyl chloride was added thereto, followed by heating under reflux for 7 hours. After cooling as it was, the reaction solution was evaporated. The residue was dissolved in 250 ml of benzene, followed by adding 200 g of anhydrous aluminum chloride little by little under stirring in a water bath. After leaving the reaction solution as it was overnight at room temperature, 2 L of ice-water was added thereto little by little and the mixture was extracted with ethyl acetate. The organic phase was washed with dilute hydrochloric acid, an aqueous sodium bicarbonate solution and brine, dried over anhydrous magnesium sulfate and the solvent was removed, to give 135 g of the target compound.

$^1$H-NMR (CDCl$_3$) δ ppm=7.50–7.56 (3H, m), 7.61 (1H, dd, J=0.8, 1.2 Hz), 7.68 (1H, t, J=8 Hz), 7.81 (2H, d, J=8 Hz), 8.58 (1H, dd, J=0.8, 5.2 Hz).

b) 4-Benzoyl-2-methoxypyridine

While heating under reflux a 28% sodium methoxide methanol solution mildly, a mixture of 135 g of 4-benzoyl-2-chloropyridine and 150 ml of methanol was added dropwise thereinto over one hour, followed by heating under reflux for further 2 hours. After cooling as it was, the reaction solution was filtered to remove insoluble matters and the solvent was removed. To the residue was added an aqueous sodium bicarbonate solution and the mixture was extracted with ethyl acetate. The organic phase was washed with brine, dried over anhydrous magnesium sulfate and then the solvent was removed, to give 130 g of the target compound.

$^1$H-NMR (CDCl$_3$) δ ppm=4.00 (3H, s), 7.00 (1H, dd, J=0.8, 1.2 Hz), 7.16 (1H, dd, J=1.2, 5.2 Hz), 7.50 (2H, t, J=8 Hz), 7.63 (1H, t, J=8 Hz), 7.83 (2H, d, J=8 Hz), 8.32 (1H, dd, J=0.8, 5.2 Hz).

c) 4-(α-Hydroxybenzyl)-2-methoxypyridine 9.4 g of sodium borohydride was added little by little to a mixture of 130 g of 4-benzoyl-2-methoxypyridine and 300 ml of methanol under stirring in an ice bath. After the dropwise addition was completed, the mixture was stirred at room temperature overnight. The reaction solution was added to 1 L of water and then extracted with ethyl acetate. The organic phase was washed with brine, dried over anhydrous magnesium sulfate and then the solvent was removed, to give 104 g of the target compound.

$^1$H-NMR (CDCl$_3$) δ ppm=2.39 (1H, d, J=3 Hz), 3.92 (3H, s), 5.74 (1H, d, J=3 Hz), 6.82 (1H, s), 6.86 (1H, d, J=5 Hz), 7.28–7.36 (5H, m); 8.08 (1H, d, J=5 Hz).

d) 4-(α-Acetoxybenzyl)-2-methoxypyridine

A mixture of 104 g of 4-(α-hydroxybenzyl)-2-methoxypyridine, 100 ml of acetic acid anhydride and 100 ml of pyridine was heated under stirring for 5 hours in an oil bath kept at 110° C. After the reaction solution was evaporated, water was added to the residue and the mixture was extracted with ethyl acetate. The extract was washed with an aqueous sodium bicarbonate solution and brine, dried over anhydrous magnesium sulfate and the solvent was removed. The residue was subjected to silica gel column chromatography using 5–20% ethyl acetate/hexane, to give 112 g of the target compound.

$^1$H-NMR (CDCl$_3$) δ ppm=2.18 (3H, s), 3.92 (3H, s), 6.73–6.76 (2H, m); 6.79 (1H, d, J=5 Hz), 7.28–7.38 (5H, m), 8.10 (1H, d, J=5 Hz).

e) 4-Benzyl-2-methoxypyridine 5 g of 10% palladium carbon and 500 ml of methanol were added to 112 g of 4-(α-acetoxybenzyl)-2-methoxypyridine, followed by conducting hydrocracking in a hydrogen atmosphere. The catalyst was filtered off and the filtrate was evaporated. Then, the residue was neutralized by an aqueous saturated sodium bicarbonate solution and the mixture was extracted with ethyl acetate. The extract was washed with brine, dried over anhydrous magnesium sulfate and the solvent was removed, to give 73 g of the target compound.

$^1$H-NMR (CDCl$_3$) δ ppm=3.90 (5H, s), 6.55 (1H, s), 6.70 (1H, d, J=5 Hz), 7.17 (2H, d, J=8 Hz), 7.22 (1H, t, J=8 Hz), 7.30 (2H, t, J=8 Hz), 8.04 (1H, d, J=5 Hz).

f) 4-Benzyl-5-bromo-2-methoxypyridine

A mixed solution of 22 ml of bromine, 90 g of potassium bromide and 500 ml of water was added dropwise into a mixture of 73 g of 4-benzyl-2-methoxypyridine, 28 g of potassium hydroxide, 1.7 g of tetraethylammonium chloride, 90 g of potassium bromide and 500 ml of water under stirring in an ice bath. After stirring overnight, sodium sulfite was added thereto and the mixture was extracted with ethyl acetate. The extract was washed with brine, dried over anhydrous magnesium sulfate and the solvent was removed. The residue was subjected to silica gel column chromatography using 5–10% ethyl acetate/hexane, to give 62 g of the target compound.

$^1$H-NMR (CDCl$_3$) δ ppm=3.87 (3H, s), 4.00 (2H, s), 6.46 (1H, s), 7.19 (2H, d, J=7 Hz), 7.25 (1H, t, J=7 Hz), 7.32 (2H, t, J=7 Hz), 8.22 (1H, s).

g) 4-Benzyl-5-bromo-2-hydroxypyridine 250 ml of 47% hydrobromic acid was added to 62 g of 4-benzyl-5-bromo-2-methoxypyridine, followed by heating under stirring for 3 hours in an oil bath kept at 100° C. After cooling as it was, the reaction solution was added to an aqueous potassium carbonate solution little by little and neutralized. The resulting precipitates were collected by filtration, to give 59 g of the target compound.

$^1$H-NMR (DMSO-d$_6$) δ ppm=3.87 (2H, s), 6.20 (1H, s), 7.21–7.36 (5H , m), 7.72 (1H, s).

h) 4-Benzyl-5-bromo-2-pyridyl Trifluoromethanesulfonate 100 g of N-phenyltrifluoromethanesulfonimide was added to a suspension of 200 ml of dichloromethane containing 59 g of 4-benzyl-5-bromo-2-hydroxypyridine, 100 ml of triethylamine and 8 g of 4-dimethylaminopyridine little by little. After stirring at room temperature for 7 hours, the reaction solution was evaporated. The residue was subjected to silica gel column chromatography using 5–10% ethyl acetate/hexane, to give 82 g of the target compound.

$^1$H-NMR (CDCl$_3$) δ ppm=4.11 (2H, s), 6.82 (1H, s), 7.18 (2H, d, J=7 Hz), 7.32 (1H, t, J=7 Hz), 7.38 (2H, t, J=7Hz), 8.46 (1H, s).

PRODUCTION EXAMPLE 2

2-Benzyl-6-pyridyl Trifluoromethanesulfonate a) 2-Bromo-6-methoxypyridine 250 ml of 28% sodium methoxide methanol solution was added dropwise into a mixture of 200 g of 2,6-dibromopyridine and 150 ml of methanol while heating at 80° C. stirring in an oil bath, followed by stirring under heating for 2 hours as it was. After cooling as it was, the mixture was extracted with diethyl ether-water, and the organic phase was washed with water and brine, dried over anhydrous magnesium sulfate and the solvent was removed, to give 150 g of the target compound.

H $^1$H-NMR (CDCl$_3$) δ ppm=3.94 (3H, s), 6.68 (1H, d, J=7 Hz), 7.06 (1H, d, J=8 Hz), 7.40 (1H, t, J=8 Hz).

b) 2-Benzyl-6-methoxypyridine

A Grignard's reagent prepared from 123 ml of benzyl bromide, 30 g of magnesium and 400 ml of diethylether was slowly added dropwise into a mixture of 150 g of 2-bromo-6-methoxypyridine, 4.3 g of 1,3-bis(diphenylphosphino)propanenickel(II) chloride and 500 ml of tetrahydrofuran under stirring in an ice bath. After stirring overnight as it was, the mixture was extracted with an aqueous ammonium chloride solution and hexane. The organic phase was washed with water and then brine, dried over anhydrous magnesium sulfate and the solvent was removed. The residue was subjected to silica gel column chromatography using 1% and 1.5% of ethyl acetate/hexane, to give 150 g of the target compound.

$^1$H-NMR (CDCl$_3$) δ ppm=3.92 (3H, s), 4.03 (2H, s), 6.54 (1H, d, J=8 Hz), 6.65 (1H, d, J=7 Hz), 7.18–7.32 (5H, m), 7.44 (1H, dd, J=7, 8 Hz).

c) 2-Benzyl-6-hydroxypyridine

A mixture of 59 g of 2-benzyl-6-methoxypyridine and 200 ml of 47% hydrobromic acid was heated under stirring for 7 hours in an oil bath kept at 100° C. After cooling as it was, 250 ml of water was added thereto, and the resulting crystals were collected by filtration, washed with water and vacuum-dried, to give 38.9 g of the target compound.

$^1$H-NMR (DMSO-d$_6$) δ ppm=3.78 (2H, s), 5.96 (1H, d, J=7 Hz), 6.15 (1H, d, J=9 Hz), 7.20–7.36 (6H, m).

d) 2-Benzyl-6-pyridyl Trifluoromethanesulfonate

A mixture of 10 g of 2-benzyl-6-hydroxypyridine, 23 g of N-phenyltrifluoromethanesulfonimide, 0.66 g of 4-dimethylaminopyridine, 23 ml of triethylamine and 100 ml of dichloromethane was stirred at room temperature in a water bath for one hour. The reaction solution was evaporated and the residue was subjected to silica gel column chromatography using 2–3% ethyl acetate/hexane and further filtered through NH-silica gel (Fuji Silicia Kagaku) and eluted with 3% ethyl acetate/hexane. The eluate was evaporated, to give 11.7 g of the target compound.

$^1$H-NMR (CDCl$_3$) δ ppm=4.13 (2H, s), 6.99 (1H, d, J=8 Hz), 7.16 (1H, d, J=8 Hz), 7.22–7.34 (5H, m), 7.75 (1H, t, J=8 Hz).

PRODUCTION EXAMPLE 3

2-Benzyl-3-bromo-6-pyridyl Trifluoromethanesulfonate a) 2-Benzyl-1-bromo-6-methoxypyridine A mixed solution of 17 ml of bromine, 90 g of potassium bromide and 450 ml of water was added dropwise into a mixture of 60 g of 2-benzyl-6-methoxypyridine (Production Example 2-b), 90 g of potassium bromide, 450 ml of water, 20 g of potassium hydroxide and 2.5 g of tetraammonium chloride over 2 hours under stirring in an ice bath. After stirring overnight as it was, sodium sulfite was added thereto and the mixture was extracted with hexane. The organic phase was washed with water and brine, dried over anhydrous magnesium sulfate and the solvent was removed. The residue was subjected to silica gel column chromatography to elute with 0.5–1.5% of ethyl acetate/hexane, to give 72.5 g of the target compound.

$^1$H-NMR (CDCl$_3$) δ ppm=3.88 (3H, s), 4.20 (2H, s), 6.48 (1H, d, J=8 Hz), 7.17–7.38 (5H, m), 7.62 (1H, d, J=8 Hz).

b) 2-Benzyl-3-bromo-6-hydroxypyridine

A mixture of 72.5 g of 2-benzyl-3-bromo-6-methoxypyridine and 300 ml of 47% hydrobromic acid was heated under stirring for 4 hours in an oil bath kept at 100° C. After cooling as it was, 500 ml of water was added thereto. The resulting crystals were collected by filtration, washed with water and diethyl ether, air-dried and then dried under heating under reduced pressure, to give 63.8 g of the target compound.

$^1$H-NMR (DMSO-d$_6$) ppm=3.97 (2H, s), 6.25 (1H, d, J=9 Hz), 7.20–7.35 (5H, m), 7.58 (1H, d, J=9 Hz).

c) 2-Benzyl-3-bromo-6-pyridyl Trifluoromethanesulfonate

A mixture of 1.2 g of 2-benzyl-3-bromo-6-hydroxypyridine, 1.7 g of N-phenyltrifluoromethanesulfonimide, 1.9 ml of triethylamine, 28 mg of 4-dimethylaminopyridine and 15 ml of dichloromethane was stirred at room temperature for 3 hours. Silica gel was added to the reaction solution and the solvent was removed. The residue was subjected to silica gel column chromatography using 5% ethyl acetate/hexane, to give 1.6 g of the target compound.

$^1$H-NMR (CDCl$_3$) δ ppm=4.28 (2H, s), 6.92 (1H, d, J=8 Hz), 7.22–7.33 (5H, m), 7.97 (1H, d, J=8 Hz).

PRODUCTION EXAMPLE 4

4-Benzyl-5-bromo-2-iodopyrimidine a) tert-Butyl 2-(Dimethylaminomethylene)-3-oxo-4-phenylbutyrate Phenylacetyl chloride was slowly added dropwise into a mixture of 110 g of Meldrum's acid, 120 ml of pyridine and 500 ml of dichloromethane under stirring in an ice bath. After stirring overnight as it was, 650 ml of an aqueous 1.2 N hydrochloric acid solution was added to the mixture. The organic phase was washed with water and brine, dried over anhydrous magnesium sulfate and the solvent was removed. To the residue was added 600 ml of tert-butanol, followed by heating under reflux for 3 hours. After cooling as it was, the solvent was removed while ethanol was added. To the residue were added 600 ml of toluene and 110 ml of N,N-dimethylformamidodimethylacetal, followed by heating under stirring for 2 hours in an oil bath kept at 100° C. while removing methanol by using Dean-Stark apparatus. The reaction solution was evaporated, and the residue was subjected to silica gel column chromatography using 50–70% ethyl acetate/hexane, to give 93 g of the target compound.

b) 4-Benzyl-2-aminopyrimidine

Trifluoroacetic acid was slowly added dropwise into a mixture of 93 g of tert-butyl 2-(dimethylaminomethylene)-3-oxo-4-phenylbutyrate and 400 ml of dichloromethane under stirring in an ice bath. After stirring overnight as it was, the solvent was removed and the residue was extracted with an aqueous sodium bicarbonate solution, ethyl acetate and tetrahydrofuran. The organic phase was washed with water and brine, dried over anhydrous magnesium sulfate and the solvent was removed. To the residue were added 500 ml of ethanol, 110 g of guanidine hydrochloride and 96 g of sodium ethoxide, followed by heating under reflux vigorously for 20 hours. After cooling as it was, 800 ml of water, 150 ml of hexane and 30 ml of diethyl ether were added thereto. After stirring at room temperature for 30 minutes, the resulting crystals were collected by filtration, washed with water, air-dried and then vacuum-dried under heating, to give 26 g of the target compound.

$^1$H-NMR (CDCl$_3$) δ ppm=3.91 (2H, s), 5.01 (2H, s), 6.41 (1H, d, J=5 Hz), 7.23–7.35 (5H, m), 8.15 (1H, d, J=5 Hz).

c) 4-Benzyl-5-bromo-2-iodopyrimidine

A solution of 60 ml of a methanol containing 7.3 ml of bromine was slowly added dropwise into a mixture of 26 g of 4-benzyl-2-aminopyrimidine, 24 g of sodium bicarbonate and 150 ml of N,N-dimethylformamide while stirring in an ice bath. After stirring for 10 minutes in an ice bath, an aqueous sodium thiosulfate solution was added thereto. After stirring at room temperature for 30 minutes, insoluble matters were filtered and vacuum-dried under heating. A mixture of the resulting crude compound, 51 ml of isoamyl nitrite, 51 ml of diiodomethane, 24 g of cuprous iodide and 400 ml of tetrahydrofuran was heated under stirring for 2 hours in a 65° C. oil bath. After cooling as it was, 400 ml of ethyl acetate was added thereto and insoluble matters were filtered through Celite. The filtrate was partitioned by adding an aqueous sodium thiosulfate solution and an aqueous ammonium chloride solution thereto. The organic phase was washed with brine and the solvent was removed. The residue was subjected to silica gel column chromatography and eluted with 6% ethyl acetate/hexane, to give 20 g of the target compound.

$^1$H-NMR (CDCl$_3$) δ ppm=4.20 (2H, s), 7.23–7.35 (5H, m), 8.42 (1H, s).

PRODUCTION EXAMPLE 5

3-Benzyl-5-bromo-2-pyridyl Trifluoromethane Sulfonate a) 3-Benzyl-2-methoxypyridine 16 g of aluminum chloride was added to a mixture of 8.6 g of 2-chloronicotinic acid and 120 ml of benzene in an ice bath under stirring. After stirring at room temperature for 2 hours, water and ethyl acetate were added thereto. Insoluble matters were filtered off using Celite, and the organic phase was washed with brine, dried over anhydrous magnesium sulfate and the solvent was removed. To the residue were added 100 ml of methanol and 30 ml of 28% sodium methoxide methanol solution, followed by heating under reflux overnight. After cooling as it was, the solvent was removed and the mixture was partitioned by adding water and ethyl acetate thereto. The organic phase was washed with water and brine, dried over anhydrous magnesium sulfate and the solvent was removed. To the residue were added 90 ml of diethylene glycol, 6.8 g of potassium carbonate and 4.3 ml of hydrazine mono hydrate. The mixture was heated under stirring for one hour in a 100° C. oil bath and then for 3 hours in a 170° C. oil bath. After cooling as it was, the mixture was partitioned by adding water and ethyl acetate thereto. The organic phase was washed with brine, dried over anhydrous magnesium sulfate and the solvent was removed. The residue was subjected to silica gel column chromatography and eluted with 10% ethyl acetate/hexane, to give 4.2 g of the target compound.

$^1$H-NMR (CDCl$_3$) δ ppm=3.91 (2H, s), 3.97 (3H, s), 6.79 (1H, dd, J=5, 7 Hz), 7.18–7.32 (6H, m), 8.03 (1H, dd, J=2, 5 Hz).

b) 3-Benzyl-5-bromo-2-methoxypyridine 0.12 ml of bromine was added to a mixture of 430 mg of 3-benzyl-2-methoxypyridine, 460 mg of sodium bicarbonate and 10 ml of methanol under stirring in an ice bath, followed by stirring at room temperature for 8 hours. The mixture was partitioned by adding an aqueous sodium thiosulfate solution and ethyl acetate thereto. The organic phase was washed with saturated brine, dried over anhydrous magnesium sulfate and the solvent was removed. The residue was subjected to silica gel column chromatography and eluted with 5% ethyl acetate/hexane, to give 140 mg of the target compound.

$^1$H-NMR (CDCl$_3$) δ ppm=3.87 (2H, s), 3.92 (3H, s), 7.17–7.34 (6H, m), 8.05 (1H, d, J=2 Hz).

c) 3-Benzyl-5-bromo-2-pyridyl Trifluoromethanesulfonate

A mixture of 190 mg of 3-benzyl-5-bromo-2-methoxypyridine and 2 ml of 47% hydrobromic acid was stirred under heating in an oil bath kept at 70° C. for 2 hours. After cooling as it was, the mixture was partitioned by adding an aqueous potassium carbonate solution and ethyl acetate were added thereto. The organic phase was washed with water and brine, dried over anhydrous magnesium sulfate and the solvent was removed. To the residue were added 300 mg of N-phenyltrifluoromethanesulfonimide, 8.4 mg of 4-dimethylaminopyridine, 0.29 mg of triethylamine and 2 ml of dichloromethane, followed by stirring at room temperature for one hour. Silica gel was added to the reaction solution and the solvent was removed. The residue was subjected to silica gel column chromatography using 5% ethyl acetate/hexane, to give 220 mg of the target compound.

$^1$H-NMR (CDCl$_3$) δ ppm=4.01 (2H, s), 7.17–7.20 (2H, m), 7.28–7.39 (3H, m), 7.65–7.67 (1H, m), 8.27 (1H, d, J=2 Hz).

PRODUCTION EXAMPLE 6

(3-Pyridyl)tributyltin 1.45 ml of a hexane solution containing 1.54 M normal butyl lithium was added dropwise into 200 ml of diethyl solution containing 10.0 g of 3-bromopyridine at −78° C. in a nitrogen atmosphere over 10 minutes. After the dropwise addition, the mixture was stirred for 10 minutes and then 20 ml of tributyltin chloride was added dropwise thereinto over 10 minutes. Then, after stirring for 30 minutes, water was added to the reaction mixture and then extracted with ethyl acetate. The extract was washed with brine and the solvent was removed. The residue was subjected to silica column chromatography and eluted with hexane and then with hexane/ethyl acetate (7:1), to give 21.9 g of the target compound.

$^1$H-NMR (CDCl$_3$) δ ppm=0.87–0.94 (9H, m), 1.07–1.11 (6H, m), 1.26–1.38 (6H, m), 1.50–1.58 (6H, m), 7.22 (1H, m), 7.73 (1H, m) 8.50 (1H, m), 8.59 (1H, s).

PRODUCTION EXAMPLE 7

(2-Pyridyl)tributyltin

The title compound was synthesized in the same manner as in Production Example 6.

$^1$H-NMR (CDCl$_3$) δ ppm=0.87–0.94 (9H, m), 1.09–1.14 (6H, m), 1.28–1.37 (6H, m), 1.52–1.58 (6H, m), 7.10 (1H, m), 7.40 (1H, m), 7.48 (1H, m), 8.73 (1H, m).

PRODUCTION EXAMPLE 8

(3,4-Methylenedioxyphenyl)tributyltin

The title compound was synthesized in the same manner as in Production Example 6 except that the reaction solvent (diethyl ether) was altered to tetrahydrofuran.

$^1$H-NMR (CDCl$_3$) δ ppm=0.87–0.90 (9H, m), 1.00–1.04 (6H, m), 1.30–1.37 (6H, m), 1.49–1.56 (6H, m), 5.61 (2H, s), 6.83–6.93 (3H, m).

PRODUCTION EXAMPLE 9

(4-Pyridyl)tributyltin 9.0 ml of a hexane solution of 2.52 M of normal butyllithium was added dropwise into 20 ml of a tetrahydrofuran solution of 3.2 ml of diisopropylamine under ice-cooling over10 minutes in a nitrogen atmosphere. After stirring under ice-cooling for 20 minutes, 6.3 ml of hydrogenated tributyltin was added dropwise thereinto over 10 minutes, followed by stirring under ice-cooling for further 20 minutes. Then, under cooling to −78 ° C., a suspension of 2.0 g of 4-bromopyridine hydrochloride and 30 ml of tetrahydrofuran was added dropwise thereto over 10 minutes. After stirring for 2 hours, water was added to the reaction mixture and the mixture was extracted with ethyl acetate. The extract was washed with brine and the solvent was removed. Then, the residue was subjected to NH-silica gel column chromatography to elute with hexane/ethyl acetate (7:1) and further subjected to silica column chromatography and eluted with hexane/ethyl acetate (2:1), to give 580 mg (15%) of the target compound.

$^1$H-NMR (CDCl$_3$) δ ppm=0.87–0.91 (9H, m), 1.07–1.11 (6H, m), 1.30–1.35 (6H, m), 1.49–1.60 (6H, m), 7.35–7.37 (2H, m), 8.47–8.48 (2H, m).

PRODUCTION EXAMPLE 10

Pyrazyltributyltin 5.0 g of tetrakistriphenylphosphinepalladium(0) was added to 50 ml of a xylene solution containing 8.0 g of chloropyrazine and 200 g of bis (tributylthin), followed by heating under stirring at 140° C. for one hour in a nitrogen atmosphere. After cooling the reaction mixture to room temperature, the solvent was removed. The residue was subjected to silica column chromatography and eluted with hexane and then with hexane/ethyl acetate (10:1), to give 9.5 g of pyrazyltributyltin.

$^1$H-NMR (CDCl$_3$) δ ppm=0.87–0.94 (9H, m), 1.15–1.19 (6H, m), 1.26–1.38 (6H, m), 1.53–1.60 (6H, m), 8.36 (1H, m), 8.54 (1H, m), 8.71 (1H, m).

PRODUCTION EXAMPLE 11

2-Benzyl-3-methoxymethyloxypyridine-6-carboxyaldehyde a) 3-Benzyloxy-2-hydroxymethyl-6-methylpyridine 100 g of 3-hydroxy-6-methyl-2-pyridine methanol and 150 g of potassium carbonate were suspended in 400 ml of N,N-dimethylformamide. Under heating under stirring 60° C. in an oil bath, 85 ml of benzyl bromide was added dropwise thereinto. Further, after heating under stirring for 30 minutes, insoluble matters were filtered off. Water was added to the filtrate, and the mixture was extracted with ethyl acetate. The organic phase was washed with water and brine, dried over anhydrous magnesium sulfate and the solvent was removed. The residue was recrystallized from ethanol/hexane, to give 145 g of the target compound.

$^1$H-NMR (CDCl$_3$) δ=2.49 (3H, s), 4.48 (1H, t, J=4 Hz), 4.77 (2H, d, J=4 Hz), 5.09 (2H, s), 6.98 (1H, d, J=8Hz), 7.08 (1H, d, J=8 Hz), 7.28–7.45 (5H, m).

b) 3-Benzyloxy-6-methylpyridine-2-carboxyaldehyde 145 g of 3-benzyloxy-2-hydroxymethyl-6-methylpyridine was dissolved in 500 ml of chloroform. 400 g of manganese dioxide was added thereto under heating under stirring at 60° C. in an oil bath, followed by heating under stirring as it was for one hour. After cooling as it was, the reaction solution was filtered to remove insoluble matters, and the solvent was removed. The resulting crystals were vacuum-dried, to give 139 g of the target compound.

$^1$H-NMR (CDCl$_3$) δ=2.57 (3H, s), 5.22 (2H, s), 7.25–7.46 (7H, m), 10.41 (1H, s).

c) 3-Benzyloxy-2-(α-hydroxybenzyl)-6-methylpyridine 139 g of 3-benzyloxy-6-methylpyridine-2-carboxyaldehyde was dissolved in 700 ml of tetrahydrofuran, followed by cooling to −60° C. or less. Under stirring using a mechanical stirrer, 400 ml of a cyclohexane/ether solution containing 1.8 mol of phenyl-lithium was added dropwise thereinto. After stirring for 30 minutes under cooling as it was, an aqueous saturated ammonium chloride solution was added thereto and the temperature was returned to room temperature. Further, water was added thereto and the mixture was extracted with ethyl acetate. The resulting organic phase was washed with water and brine, dried over anhydrous magnesium sulfate and the solvent was removed. The residue was recrystallized from ethanol under cooling, to give 116 g of the target compound.

$^1$H-NMR (CDCl$_3$) δ=2.53 (3H, s), 4.92 (1H, d, J=12 Hz), 4.98 (1H, d, J=12 Hz), 5.80 (1H, d, J=7 Hz), 5.91 (1H, d, J=7 Hz), 6.99 (1H, d, J=8 Hz), 7.04 (1H, d, J=8 Hz), 7.07–7.14 (2H, m), 7.20–7.36 (8H, m).

d) 2-Benzoyl-3-benzyloxy-6-methylpyridine 116 g of 3-benzyloxy-2-(α-hydroxybenzyl)-6-methylpyridine was dissolved in 500 ml of chloroform. 400 g of manganese dioxide was added under stirring, followed by heating under stirring at 60 ° C. for one hour in an oil bath. After cooling as it was, the reaction solution was filtered to remove insoluble matters, and the solvent was removed. The resulting crystals were vacuum-dried, to give 113 g of the target compound.

$^1$H-NMR (CDCl$_3$) δ=2.53 (3H, s), 5.06 (2H, s), 7.13–7.30 (7H, m), 7.45 (2H, t, J=8 Hz), 7.58 (1H, t, J=8 Hz), 7.87 (2H, d, J=8 Hz).

e) 6-Hydroxymethyl-2-benzoyl-3-benzyloxypyridine 113 g of 2-benzoyl-3-benzyloxy-6-methylpyridine was dissolved in 600 ml of dichloromethane. 96 g of 3-chloroperbenzoic acid was added thereto, followed by stirring under heating at 50° C. in an oil bath. After cooling in a water bath, an aqueous sodium sulfite solution and further an aqueous saturated sodium bicarbonate solution were added to the reaction solution. The organic phase was separated, further washed with an aqueous saturated sodium bicarbonate solution and brine. Then, it was dried over anhydrous magnesium sulfate and the solvent was removed. The resulting residue was dissolved in 200 ml of acetic acid anhydride, followed by heating under stirring at 150° C. for 3 hours in an oil bath. Then, the solvent was removed and 400 ml of methanol and 200 ml of an aqueous 2N sodium hydroxide solution were further added thereto, followed by heating under stirring at 60° C. for 3 hours in an oil bath. Activated carbon was added to the reaction solution. After stirring for a while, it was filtered off. Water was added to the filtrate to precipitate crystals. The resulting crystals were collected by filtration and vacuum-dried, to give 116 g of the target compound.

$^1$H-NMR (CDCl$_3$) δ=3.18 (1H, t, J=5 Hz), 4.74 (2H, d, J=5 Hz), 5.12 (2H, s), 7.17–7.30 (5H, m), 7.32 (1H, d, J=9 Hz), 7.39 (1H, d, J=9 Hz), 7.46 (2H, t, J=8 Hz), 7.60 (1H, t, J=8 Hz), 7.85 (2H, d, J=8 Hz).

f) 2-Benzoyl-6-(tert-butyldimethylsilyl)oxymethyl-3-benzyloxypyridine 116 g of 6-hydroxymethyl-2-benzoyl-3-benzyloxypyridine was dissolved in 450 ml of N,N-dimethylformamide. 100 g of imidazole and 85 g of tert-butyldimethylsilyl chloride was added thereto, followed by stirring at room temperature overnight. The solvent was removed, water was added thereto and the mixture was extracted with ethyl acetate. Further, the organic phase was washed with dilute hydrochloric acid, water, an saturated sodium bicarbonate solution and brine, dried over anhydrous magnesium sulfate and evaporated. The residue was dried, to give 141 g of the target compound.

$^1$H-NMR (CDCl$_3$) δ=0.11 (6H, s), 0.95 (9H, s), 4.80 (2H, s), 5.10 (2H, s), 7.15–7.32 (5H, m), 7.39 (1H, d, J=9 Hz), 7.44 (2H, t, J=8 Hz) 7.53–7.61 (2H, m), 7.85 (2H, d, J=8 Hz).

g) 2-(α-Acetoxybenzyl)-6-(tert-butlydimethylsilyl)oxymethyl-3-benzyloxypyridine 141 g of 2-benzoyl-6-(tert-butyldimethylsilyl)oxymethyl-3-benzyloxypyridine was dissolved in 500 ml of methanol. Under ice-cooling, 4.9 g of sodium boron hydride thereto, followed by stirring for 2 hours. After returning to room temperature, water was added thereto and the mixture was extracted with ethyl acetate. Further, the organic phase was washed with brine, dried over anhydrous magnesium sulfate and evaporated. The resulting residue was dissolved in 200 ml of pyridine and 100 ml of acetic acid anhydride was added thereto, followed by heating under stirring for one hour at 150° C in an oil bath. The Solvent was removed, water was added thereto and the mixture was extracted with ethyl acetate. Further, the organic phase was washed with dilute hydrochloric acid, water, an aqueous saturated sodium bicarbonate solution and brine, dried over anhydrous magnesium sulfate and evaporated. The residue was dried, to give 160 g of the target compound.

$^1$H-NMR (CDCl$_3$) δ=0.10 (6H, s), 0.94 (9H, s), 2.17 (3H, s), 4.79 (2H, s), 5.04 (1H, d, J=12 Hz), 5.09 (1H, d, J=12 Hz), 7.14–7.46 (13H, m).

h) 2-Benzyl-6-(tert-butyldimethylsilyl)oxymethyl-3-hydroxypyridine 160 g of 2-(α-acetoxybenzyl)-6-tert-butyldimethylsilyl) oxymethyl-3-benzyloxypyridine was dissolved in a mixed solvent of 200 ml of tetrahydrofuran and 200 ml of methanol. 8 g of 10% palladium carbon was added thereto to conduct hydrocracking. After the atmosphere in the reaction system was replaced by nitrogen, the catalyst was filtered off and the filtrate was evaporated. The residue was dissolved in ethyl acetate, washed with an aqueous saturated sodium bicarbonate solution and brine, dried over anhydrous magnesium sulfate and evaporated, to give 100 g of the target compound.

$^1$H-NMR (CDCl$_3$) δ=0.11 (6H, s), 0.95 (9H, s), 4.19 (2H, s), 4.79 (2H, s), 7.09 (1H, d, J=8 Hz), 7.10–7.34 (6H, m).

i) 2-Benzyl-6-hydroxymethyl-3-methoxymethyloxypyridine 63 g of potassium carbonate and 300 ml of N,N-dimethylformamide were added to 100 g of 2-benzyl-6-(tert-butyldimethylsilyl)oxymethyl-3-hydroxypyridine and 23 ml of chloromethyl methyl ether was added dropwise into the mixture at room temperature under stirring using a mechanical stirrer. After heating under stirring at 50° C. for 2 hours in an oil bath, water was added thereto and the mixture was extracted with ethyl acetate. Further, the organic phase was washed with water and brine, dried over anhydrous magnesium sulfate and the solvent was removed. The resulting residue was dissolved by adding 400 ml of tetrahydrofuran and 300 ml of a tetrahydrofuran solution containing 1 mol of tetra-n-butylammonium fluoride was added thereto under ice-cooling. After stirring under ice-cooling, water was added thereto and the mixture was extracted with ethyl acetate. Further, the organic phase was washed with water and brine, dried over anhydrous magnesium sulfate and evaporated. The residue was dissolved in 50% ethyl acetate/hexane and filtered through silica gel. The filtrate was evaporated and dried, to give 73 g of the target compound.

$^1$H-NMR (CDCl$_3$) δ=3.29 (3H, s), 4.17 (2H, s), 4.79 (2H, s), 5.12 (2H, s), 7.14 (1H, t, J=7 Hz), 7.18–7.32 (5H, m), 7.37 (1H, d, J=8 Hz).

j) 2-Benzyl-3-methoxymethyloxypyridine-6-carboxyaldehyde 73 g of 2-benzyl-6-hydroxymethyl-3-methoxymethyloxypyridine was dissolved in 300 ml of chloroform, followed by adding 220 g of manganese dioxide under stirring. Then, the mixture was heated under stirring at 50° C. for 1.5 hours in an oil bath. After cooling as it was, the reaction solution was filtered to remove insoluble matters and the solvent was removed. The resulting crystals were recrystallized from ether/hexane, to give 30 g of the target compound. The filtrate obtained during recrystallization was concentrated. The residue was subjected to silica gel column chromatography using 5–10% ethyl acetate/hexane as an eluent for separation and purification and recrystallized from ether/hexane, to give 11 g of the target compound.

$^1$H-NMR (CDCl$_3$) δ=3.29 (3H, s), 4.27 (2H, s), 5.25 (2H, s), 7.18 (1H, t, J=7 Hz), 7.26 (2H, t, J=7 Hz), 7.31 (2H, d, J=7 Hz), 7.45 (1H, d, J=8 Hz), 7.85 (1H, d, J=8 Hz), 10.00 (1H, s).

PRODUCTION EXAMPLE 12

Benzyl-3-methoxymethyloxy-6-iodopyridine a) 2-Bromo-3-methoxymethyloxypyridine 50 g of 2-bromo-3-hydroxypyridine was suspended in 200 ml of tetrahydrofuran, followed by adding 33 ml of chloromethyl methyl ether. While cooling to −20° C. and stirring, 17 g of 60% oily sodium hydride was added thereto little by little. After adding sodium hydride, the cooling medium was removed, followed by stirring at room temperature for 3.5 hours. Under cooling, ice water was added thereto little by little and the mixture was extracted with ethyl acetate. The organic phase was further washed with brine, dried over anhydrous sodium sulfate and the solvent was removed. The residue was subjected to silica gel column chromatography using 10–15% ethyl acetate/hexane as an eluent for separation and purification, to give 35 g of the target compound.

$^1$H-NMR (CDCl$_3$) δ=3.53 (3H, s), 5.28 (2H, s), 7.21 (1H, dd, J=4.6, 8.2 Hz), 7.43 (1H, dd, J=1.6, 8.2 Hz), 8.05 (1H, dd, J=1.6, 4.6 Hz).

b) 2-Benzyl-3-methoxymethyloxypyridine

A diethyl ether solution of magnesium benzyl bromide prepared from 38 ml of benzyl bromide, 8 g of magnesium and 250 ml of anhydrous diethyl ether was slowly added dropwise into a mixture of 35 g of 2-bromo-3-methoxymethyloxypyridine, 5 g of 1,3-bis(diphenylphosphino)propanenickel(II) chloride and 200 ml of tetrahydrofuran under stirring under ice-cooling in a nitrogen atmosphere. After stirring for 4.5 hours, an aqueous saturated ammonium chloride solution was added thereto and the mixture was extracted with ethyl acetate. The organic phase was further washed with brine, dried over anhydrous sodium sulfate and the solvent was removed. The residue was subjected to silica gel column chromatography using 8–20% ethyl acetate/hexane as an eluent for separation and purification, to give 27 g of the target compound.

$^1$H-NMR (CDCl$_3$) δ=3.34 (3H, s), 4.21 (2H, s), 5.17 (2H, s), 7.11–7.38 (7H, m), 8.20 (1H, dd, J=1.3, 4.8 Hz).

c 2-Benzyl-3-hydroxy-6-iodopyridine 60 ml of trifluoroacetic acid was added to 27 g of 2-benzyl-3-methoxymethyloxypyridine, followed by stirring at room temperature for 2 hours and then heating under stirring for one hour at 50° C. in an oil bath. The reaction solution was added to an aqueous potassium carbonate solution which was ice-cooled, and the resulting crystals were collected by filtration. The filtrate was evaporated, and to the resulting crystals were added 19 g of sodium iodide, 5 g of sodium hydroxide and 200 ml of methanol. Under stirring under ice-cooling, 158 ml of an aqueous 5% sodium hypochlorite solution was added dropwise thereinto over 30 minutes. After stirring overnight as it was, 60 ml of 5N hydrochloric acid was added thereto and an aqueous saturated sodium thiosulfate solution was further added thereto, followed by extracting with ethyl acetate. The organic phase was washed further with brine, dried over anhydrous sodium sulfate and the solvent was removed. The resulting crystals were collected by filtration and vacuum-dried, to give 17 g of the target compound.

d) 2-Benzyl-3-methoxymethyloxy-6-iodopyridine 12 g of 2-benzyl-3-hydroxy-6-iodopyridine was dissolved in 50 ml of tetrahydrofuran, followed by adding 3.8 ml of chloromethyl methyl ether. 2 g of 60% oily sodium hydride was added little by little thereto to under stirring under ice-cooling. After adding sodium hydride, the cooling medium was removed and the mixture was stirred at room temperature for 2.5 hours. Then, ice water was added thereto little by little under cooling, followed by extracting with ethyl acetate. The organic phase was further washed brine, dried over anhydrous sodium sulfate and the solvent was removed. The residue was subjected to silica gel column chromatography using 15% ethyl acetate/hexane as an eluent for separation and purification, to give 13 g of the target compound.

$^1$H-NMR (CDCl$_3$) δ=3.28 (3H, s), 4.14 (2H, s), 5.11 (2H, s), 7.04 (1H, d, J=8.4 Hz), 7.14–7.30 (5H, m), 7.48 (1H, d, J=8.4 Hz)

PRODUCTION EXAMPLE 13

2-(4-Fluorobenzyl)-3-bromo-6-hydroxypyridine

Benzyl bromide in Production Example 2-b) was altered to 4-fluorobenzyl chloride and in succession, the same procedures as in Production Examples 3-a) and 3-b) were conducted to synthesize the title compound.

$^1$H-NMR (CDCl$_3$) δ=4.15 (2H, s), 6.36 (1H, d, J=9 Hz), 6.99–7.03 (2H, m), 7.33–7.37 (2H, m), 7.51 (1H, d, J=9 Hz).

PRODUCTION EXAMPLE 14

2-(3-Fluorobenzyl)-3-bromo-6-hydroxypyridine

Benzyl bromide in Production Example 2-b) was alerted to 3-fluorobenzyl chloride and then the same procedures as in Production Examples 3-a) and 3-b) were conducted, to synthesize the title compound.

$^1$H-NMR (CDCl$_3$) δ=4.18 (2H, s), 6.37 (1H, d, J=9 Hz), 6.92–6.97 (1H, m), 7.06–7.17 (2H, m), 7.26–7.31 (1H, m), 7.52 (1H, d, J=9 Hz).

PRODUCTION EXAMPLE 15

4-Benzyl-5-bromo-2-chloropyrimidine

The title compound was synthesized in the same manner as in Production Example 4 except that isoamyl nitrite was altered to tert-butyl nitrite, diiodomethane and cuprous iodide were altered to copper chloride and tetrahydrofuran as the solvent was altered to acetonitrile.

$^1$H-NMR (CDCl$_3$) δ=4.75 (2H, s), 7.25–7.35 (5H, m), 7.70 (1H, s).

PRODUCTION EXAMPLE 16

2-Benzyl-3-bromo-6-hydroxy-5-iodopyridine 1.19 g of N-iodosuccinimide was added to a mixture of 1.16 g of 2-benzyl-3-bromo-6-hydroxypyridine (Production Example 3-b) and 10 ml of N,N-dimethylformamide at room temperature, followed by stirring at the same temperature overnight. 50 ml of water was added to the reaction solution and the resulting crystals were collected by filtration, washed with water and then vacuum-dried, to give 1.47 g of the target compound.

$^1$H-NMR (CDCl$_3$) δ=4.02 (2H, s), 7.30–7.37 (5H, m), 8.11 (1H, s).

PRODUCTION EXAMPLE 17

2-Bromo-6-iodo-3-pyridyl-trifluoromethanesulfonate a) 2-Bromo-3-hydroxy-6-iodopyridine 17.6 g of Chloramine T was added to a mixture of 10.9 g of 2-bromo-3-hydroxypyridine, 9.35 g of sodium iodide and 110 ml of N,N-dimethylformamide under stirring in an ice bath, followed by stirring at the same temperature for 30 minutes and then at room temperature for 10 minutes. Water, ethyl acetate and 11 ml of an aqueous 6N hydrochloric acid solution were added thereto, and the organic phase was washed with brine and the solvent was removed. The residue was subjected to silica gel column chromatography and eluted with 30% ethyl acetate/hexane, to give 16.5 g of the target compound.

$^1$H-NMR (CDCl$_3$) δ=5.58 (1H, br s), 6.98–7.01 (1H, m), 7.55–7.58 (1H, m).

b) 2-Bromo-6-iodo-3-pyridyl Trifluoromethanesulfonate 19.7 g of N-phenyltrifluoromethanesulfonimide, 336 mg of 4-dimethylaminopyridine and 23.0 ml of triethylamine were added to a mixture of 16.5 g of 2-bromo-3-hydroxy-6-iodopyridine and 150 ml of dichloromethane at room temperature, followed by stirring at room temperature for 1.5 hours. Silica gel was added to the reaction solution and the solvent was removed. The residue was subjected to silica gel column chromatography using 5% ethyl acetate/hexane, to give 19.9 g of the target compound.

$^1$H-NMR (CDCl$_3$) δ=7.30 (1H, d, J=9 Hz), 7.78 (1H, d, J=9 Hz).

PRODUCTION EXAMPLE 18

(2-Benzyl-3-methoxymethyloxy-6-pyridyl)tributyltin

The title compound was synthesized in the same manner as in Production Example 6 except that 3-bromopyridine was altered to 2-benzyl-6-iodo-3-methoxymethyloxypyridine (Production Example 12).

$^1$H-NMR (CDCl$_3$) δ=0.84–0.89 (9H, m), 1.03–1.08 (6H, m), 1.28–1.38 (6H, m), 1.51–1.59 (6H, m), 3.32 (3H, s), 4.20 (2H, s), 5.12 (1H, s), 7.10–7.36 (7H, m).

PRODUCTION EXAMPLE 19

Pyrazylacetylene a) Pyrazyltrimethylsilylacetylene 10.1 g of trimethylsilylacetylene and 28.6 ml of triethylamine were added to a mixture of 6.11 ml of chloropyrazine, 653 mg of cuprous iodide, 3.96 g of tetrakis(triphenylphosphine)palladium(0) and 100 ml of N,N-dimethylformamide, followed by stirring at 50° C. for 3.5 hours. After cooling as it was at room temperature, Celite and hexane were added thereto, followed by filtering off insoluble matters through Celite. After evaporating the solvent, the residue was subjected to silica gel column chromatography and eluted with 10% ethyl acetate/hexane, to give 9.58 g of the target compound.

$^1$H-NMR (CDCl$_3$) d=0.31 (9H, s), 8.47 (1H, s), 8.53 (1H, s), 8.68 (1H, s).

b) Pyrazylacetylene 7.51 g of potassium carbonate was added to a mixture of 9.58 g of pyrazyltrimethylsilylacetylene and 70 ml of methanol at 0° C., followed by stirring at room temperature for 30 minutes. Water and diethyl ether were added thereto, and the organic layer was washed with brine, dried over anhydrous magnesium sulfate and the solvent was evaporated, to give 2.50 g of the title compound.

$^1$H-NMR (CDCl$_3$) d=3.20 (1H, s), 8.38 (1H, s), 8.41 (1H, s), 8.57 (1H, s).

PRODUCTION EXAMPLE 20

2-Methoxymethyloxy-1-iodobenzene 216 mg of 60% oily sodium hydride was added to a mixture of 1.65 of 2-iodophenol and 20 ml of N,N-dimethylformamide under ice-cooling followed by stirring at room temperature for 30 minutes. Under ice-cooling, 570 μl of chloromethyl methyl ether was added thereto, followed by stirring for 30 minutes at room temperature. Water and ethyl acetate were added thereto. The organic phase was washed with water and brine, dried over anhydrous magnesium sulfate and the solvent was removed, to give 2.12 g of the target compound.

$^1$H-NMR (CDCl$_3$) d=3.52 (3H, s), 5.24 (2H, s), 6.76 (1H, dt, J=1, 8 Hz), 7.07 (1H, dd, J=1, 8 Hz), 7.26–7.30 (1H, m), 7.78 (1H, dd, J=1, 8 Hz).

PRODUCTION EXAMPLE 21

2-Methyl-2-propenyltributyltin 1,2-dibromomethan 140 μl and 0.400 ml of 1-chloro-2-methyl-2-propene was added to a mixture of 505 mg of magnesium and 2 ml of tetrahydrofuran, followed by heating. After initiating, the heating was stopped. The reaction solution was diluted with 5 ml of tetrahydrofuran, followed by adding dropwise 8 ml of a tetrahydrofuran solution of 1.18 ml of 1-chloro-2-methyl-2-propene thereinto. After stirring at room temperature for 30 minutes, tributyltin chloride was added to the reaction solution, followed by stirring at room temperature for 4 hours. An aqueous ammonium chloride solution and ethyl acetate were added thereto, and the organic phase was washed with an aqueous saturated sodium bicarbonate and brine, dried over anhydrous magnesium sulfate and the solvent was removed, to give 5.29 g of the target compound.

$^1$H-NMR (CDCl$_3$) δ=0.85–0.98 (9H, m), 1.25–1.78 (23H, m), 4.43–4.48 (2H, m).

PRODUCTION EXAMPLE 22

2-Iodo-1,3,4-thiadiazole

A mixture of 19.2 g of 2-amino-1,3,4-thiadiazole, 35.0 g of cuprous iodide, 74.0 ml of diiodomethane, 74.0 ml of isopentyl nitrite and 500 ml of tetrahydrofuran was heated under reflux for 5 hours. After cooling as it was, 200 ml of ethyl acetate was added to the reaction solution. After filtering off the insoluble matters, the filtrate was subjected to silica gel column chromatography and eluted with hexane/ethyl acetate (10:1) and then with hexane/ethyl acetate (1:2). Then the eluate was crystallized from ethyl acetate/methanol/hexane, to give 15.7 g of the target compound.

$^1$H-NMR (CDCl$_3$) δ=9.13 (1H, s).

PRODUCTION EXAMPLE 23

(2-Pyrmidyl)tri-n-butyltin 3.2 ml of a hexane solution containing 1.57 mol of n-butyllithium was slowly added dropwise into a solution of 20 ml of tetrahydrofuran containing 707 μl of diisopropylamine under ice-cooling. After stirring at 0° C. for 30 minutes, 1.4 ml of tri-n-butyltin hydride was slowly added dropwise thereinto. After stirring at 0° C. for 30 minutes, the mixture cooled to −78° C. and a suspension of 30 ml of tetrahydrofuran containing 2-chloropyrimidine was slowly added drowise thereinto. After stirring at −78° C. for one hour as it was and then at 0° C. for 2 hours, water was added to the reaction solution. The mixture was extracted with ethyl acetate, and the organic phase was washed with brine and the solvent was removed. Then, the residue was subjected to silica gel column chromatography and eluted with hexane/ethyl acetate (10:1) and then with hexane/ethyl acetate (7:1), to give 654 mg of the target compound.

$^1$H-NMR (CDCl$_3$) δ=0.86–0.90 (9H, m), 1.15–1.20 (6H, m), 1.30–1.36 (6H, m), 1.54–1.61 (6H, m), 7.12 (1H, t, J=5 Hz), 8.68 (2H, d, J=5 Hz).

PRODUCTION EXAMPLE 24

(5-Pyrmidyl)tri-n-butyltin

The title compound was synthesized in the same manner as in the synthesis of (2-pyrimidyl)tri-n-butyltin.

$^1$H-NMR (CDCl$_3$) δ=0.87–0.91 (9H, m), 1.12–1.16 (6H, m), 1.30–1.38 (6H, m), 1.50–1.59 (6H, m), 8.67–8.71 (2H, m), 9.12 (1H, s).

PRODUCTION EXAMPLE 25

(4-Pyrmidyl)tri-n-butyltin 5.8 ml of a hexane solution containing 2.52 mol of n-butyllithium was slowly added dropwise into a solution of 20 ml of tetrahydrofuran containing 2.5 ml of 2,2,6,6-tetramethylpiperidine. After stirring at 0° C. for 30 minutes, a mixture of 0.98 ml of pyrimidine, 4.6 ml of tri-n-butyltin chloride and 20 ml of tetrahydrofuran was slowly added dropwise thereinto. After stirring at −78° C. for 4 hours, water was added to the reaction solution and then extracted with ethyl acetate. The organic phase was washed with brine and the solvent was removed. Then, the residue was subjected to silica gel column chromatography to elute with hexane/ethyl acetate (10:1), to give 474 mg of the target compound.

$^1$H-NMR (CDCl$_3$) δ=0.86–0.91 (9H, m), 1.14–1.18 (6H, m), 1.30–1.38 (6H, m), 1.52–1.60 (6H, m), 7.44 (1H, dd, J=4.8 Hz, 1.6 Hz), 8.47 (1H, d, J=4.8 Hz), 9.23 (1H, d, J=1.6 Hz).

PRODUCTION EXAMPLE 26

(3-Pyrmidyl)tri-n-butyltin 11.2 ml of a hexane solution containing 2.52 mol of n-butyllithium was slowly added to a solution of 30 ml of tetrahydrofuran containing 4.8 ml of 2,2,6,6-tetramethylpiperidine at −30° C., followed by stirring at 0° C. for 30 minutes. Thereafter, 7.3 ml of N,N,N',N'-tetramethylethylenediamine was added and then a mixture of 1.74 ml of pyridazine, 10.3 ml of tri-n-butyltin chloride and 10 ml of tetrahydrofuran was slowly added to the mixture at −78° C., followed by stirring at −78° C. for 3 hours, Then, water was added to the reaction solution, and then extracted with ethyl acetate. The organic phase was washed with brine and the solvent was removed. Then, the residue was subjected to NH-silica gel (Fuji Silicia) column chromatography and eluted with hexane/ethyl acetate (10:1), and then subjected to silica gel chromatography and eluted with hexane/ethyl acetate (10:1) and then with hexane/ethyl acetate (1:1), to give 660 mg of the target compound.

$^1$H-NMR (CDCl$_3$) δ=0.86–0.91 (9H, m), 1.14–1.22 (6H, m), 1.24–1.38 (6H, m), 1.54–1.61 (6H, m), 7.24–7.28 (1H, m), 7.48–7.50 (1H, m), 9.03–9.04 (1H, m).

PRODUCTION EXAMPLE 27

(4-Pyrmidyl)tri-n-butyltin 58.0 ml of a hexane solution containing 2.52 mol of n-butyllithium was slowly added dropwise into a solution of 200 ml of tetrahydrofuran containing 25.0 mol of 2,2,6,6-tetramethylpiperidine at −30° C. After stirring at 0° C. for 30 minutes, a mixture of 9.1 ml of pyridazine, 46.0 ml of tri-n-butyltin chloride and 100 ml of tetrahydrofuran was slowly added dropwise thereinto at −78° C. After stirring at −78° C. for 4 hours, water was added to the reaction solution and then extracted with ethyl acetate. The organic phase was washed with brine and the solvent was removed. Then, the residue was subjected to NH-silica gel (Fuji Silicia) column chromatography and eluted with hexane/ethyl acetate (10:1). Then, it was subjected to silica gel chromatography and eluted with hexane/ethyl acetate (10:1) and then with hexane/ethyl acetate (1:1), to give 6.6 g of the target compound.

$^1$H-NMR (CDCl$_3$) δ=0.87–0.91 (9H, m), 1.13–1.18 (6H, m), 1.31–1.36 (6H, m), 1.50–1.58 (6H, m), 7.53 (1H, d, J=5 Hz), 9.02 (1H, d, J=5 Hz), 9.17 (1H, s).

PRODUCTION EXAMPLE 28

(1,4-Dioxene-2-yl)tri-n-butyltin 5.8 ml of a pentane solution containing 1.51 mol of tert-biutyllithium was slowly added to 30 ml of a tetrahydrofuran solution containing 1.0 g of 1,4-dioxene at −40° C. After stirring at −40° C. for one hour, 1.7 ml of tri-n-butyltin chloride was slowly added dropwise thereinto at −78° C. After stirring at −78° C. for 3 hours, water was added to the reaction solution and then extracted with ethyl acetate. The organic phase was washed with brine and the solvent was removed. Then, the residue was filtered through silica gel and the solvent was removed, to give 1.5 g of the target compound.

$^1$H-NMR (CDCl$_3$) δ=0.87–1.56 (27H, m), 4.00–4.11 (4H, m), 5.69 (1H, s).

PRODUCTION EXAMPLE 29

(3R)-3-Ethynyl-3-quinuclidinol a) (3R)-3-Ethynyl-3-quinuclidinol $^+$L-(+)-tartaric Acid 15.1 g of 3-ethynyl-3-quinuclidinol and 15 g of L-(+)-tartaric acid were dissolved under heating in 300 ml of methanol. After cooling as it was, the resulting crystals were collected by filtration and recrystallized from methanol three times, to give 2.07 g of the title compound.

$^1$H-NMR (DMSO-d$_6$) δ ppm=1.45–1.54 (1H, m), 1.68–1.78 (1H, m), 1.83–2.03 (3H, m), 2.83–3.01 (5H, m), 3.21 (1H, dd, J=2, 14 Hz), 3.50 (1H, s), 4.05 (2H, s).

b) (3R)-3-Ethynyl-3-quinuclidinol 15.6 g of (3R)-3-ethynyl-3-quinuclidinol $^+$L-(+)-tartrate was dissolved in 150 ml of water and 20 g of anhydrous potassium carbonate was added little by little under stirring. The resulting crystal were collected by filtration, washed with water and then dried, to give 6.88 g of the title compound.

$^1$H-NMR (DMSO-d$_6$) δ ppm=1.20–1.30 (1H, m), 1.47–1.55 (1H, m), 1.70–1.90 (3.H, m), 2.54–2.70 (4H, m), 2.72 (1H, dd, J=2, 14 Hz), 2.93 (1H, d, J=14 Hz), 3.29 (1H, s), 5.47 (1H, s); $[α]^{24}_{589}$=+58.3 (c=1.02, MeOH); (literature; $[α]^{24}_{589}$=+54.5 (c=0.99, MeOH); Tetrahedron: Asymmetry, 6 (6), 1393, 1995).

PRODUCTION EXAMPLE 30

(3s)-3-Ethynyl-3-quinuclidinol

The title compound was synthesized from 3-ethynyl-3-quinuclidinol in the same manner as in Production Example 29 using D-(−)-tartaric acid was used as an optical resolution agent.

$^1$H-NMR (DMSO-d$_6$) δ=1.20–1.30 (1H, m), 1.47–1.55 (1H, m), 1.70–1.90 (3.H, m), 2.54–2.70 (4H, m), 2.72 (1H, dd, J=2, 14 Hz), 2.93 (1H, d, J=14 Hz), 3.29 (1H, s), 5.47 (1H, s); $[α]^{22.5}_{589}$=−56.9 (c=1.00, MeOH); (literature; $[α]^{20}_{589}$=−56.1 (c=1.02, MeOH); Tetrahedron: Asymmetry, 6 (6), 1393, 1995).

EXAMPLES

Example 1

3-[4-Benzyl-2-(3,4-methylenedioxyphenyl)-5-pyridyl]ethynyl-3-quinuclidinol a) 4-Benzyl-5-bromo-2-(3,4-methylenedioxyphenyl)pyridine A mixture of 400 mg of 4-benzyl-5-bromo-2-pyridyl trifluoromethanesulfonate, 410 mg of (3,4-methylenedioxyphenyl)tributyltin, 300 mg of tetrabutylammonium chloride, 20 mg of tetrakis(triphenylphsphine)palladium(0) and 2 ml of xylene was stirred under heating for 3 hours in an oil bath kept at 140° C. in a nitrogen atmosphere. The reaction solution was subjected to silica gel column chromatography using 5–10% ethyl acetate/hexane, to give 140 mg of the title compound.

$^1$H-NMR (CDCl$_3$) δ ppm=4.12 (2H, s), 6.00 (2H, s), 6.85 (1H, d, J=8 Hz), 7.23 (2H, d, J=8 Hz), 7.27 (1H, t, J=7 Hz), 7.32–7.41 (5H, m), 8.68 (1H, s).

b) 3-[4-Benzyl-2-(3,4-methylenedioxyphenyl)-5-pyridyl]ethynyl-3-quinuclidinol

A mixture of 140 mg of 4-benzyl-5-bromo-2-(3,4-methylenedioxyphenyl)pyridine, 70 mg of 3-ethynyl-3-quinucllidinol, 10 mg of tetrakis(triphenylphosphine)palladium(0), 1 mg of cuprous iodide, 0.5 ml of triethylamine and 1 ml of N,N-dimethylformamide was stirred under heating for 2 hr in an oil bath kept at 100° C. in a nitrogen atmosphere. After cooling as it was, aqueous dilute ammonia was added thereto, followed by extracting with ethyl acetate. The extract was washed with brine, dried over anhydrous magnesium sulfate and the solvent was evaporated. The residue was subjected to NH-silica gel column chromatography using 50% ethyl acetate/hexane and then ethyl acetate, to give 40 mg of the title compound.

$^1$H-NMR (CDCl$_3$) δ ppm=1.30–1.95 (3H, m), 2.00–2.15 (2H, m), 2.65–2.95 (4H, m), 3.03 (1H, d, J=14 Hz), 3.23 (1H, d, J=14 Hz), 4.15 (2H, s), 6.01 (2H, s), 6.87 (1H, d, J=8 Hz), 7.19 (2H, d, J=8 Hz), 7.22–7.28 (1H, m), 7.32 (2H, t, J=7 Hz), 7.40 (1H, s), 7.42–7.46 (2H, m), 8.65 (1H, s).

Example 2

3-[4-Benzyl-2-(2-pyridyl)-5-pyridyl]ethynyl-3-quinuclidinol

The title compound was synthesized in the same manner as in Example 1.

$^1$H-NMR (CDCl$_3$) δ ppm=1.35–1.90 (3H, m), 2.00–2.15 (2H, m), 2.70–2.95 (4H, m), 3.03 (1H, d, J=14 Hz), 3.23 (1H, dd, J=2, 14 Hz), 4.21 (2H, s), 7.20–7.32 (6H, m), 7.81 (1H, dt, J=2, 8 Hz), 8.29 (1H, s), 8.38 (1H, d, J=8 Hz), 8.64–8.67 (1H, m), 8.68 (1H, s).

Example 3

3-[4-Benzyl-2-(3-pyridyl)-5-pyridyl]ethynyl-3-quinuclidinol

The title compound was synthesized in the same manner as in Example 1.

$^1$H-NMR (CDCl$_3$) δ ppm=1.38–1.92 (3H, m), 2.00–2.11 (2H, m), 2.70–3.00 (4H, m), 3.06 (1H, d, J=14 Hz), 3.25 (1H, dd, J=2, 14 Hz), 4.18 (2H, s), 7.20 (2H, d, J=7 Hz), 7.22–7.29 (1H, m), 7.32 (2H, t, J=7 Hz), 7.39 (1H, dd, J=5, 7 Hz), 7.49 (1H, s), 8.22–8.27 (1H, m), 8.63 (1H, dd, J=2, 5 Hz), 8.74 (1H, s), 9.13 (1H, dd, J=1, 2 Hz).

Example 4

3-[4-Benzyl-2-pyrazyl-5-pyridyl]ethynyl-3-quinuclidinol

The title compound was synthesized in the same manner as in Example 1.

$^1$H-NMR (CDCl$_3$) δ ppm=1.37–1.90 (3H, m), 2.00–2.11 (2H, m), 2.70–2.96 (4H, m), 3.05 (1H, d, J=14 Hz), 3.24 (1H, dd, J=2, 14 Hz), 4.20 (2H, s), 7.18–7.33 (5H, m), 8.20 (1H, s), 8.56–8.60 (2H, m) 8.73 (1H, s), 9.61 (1H, d, J=2 Hz).

Example 5

3-[4-Benzyl-2-(4-pyridyl)-5-pyridyl]ethynyl-3-quinuclidinol

The title compound was synthesized in the same manner as in Example 1.

$^1$H-NMR (CDCl$_3$) δ ppm=1.41–1.43 (1H, m), 1.61–1.67 (1H, m), 1.84–1.87 (1H, m), 2.04–2.06 (2H, m), 2.77–2.85 (4H, m), 3.05 (1H, dd, J=2, 14 Hz), 3.25 (1H, dd, J=2, 14 Hz), 4.20 (2H, s), 7.19–7.35 (5H, m), 7.55 (1H, s), 7.80–7.82 (2H, m), 8.69–8.70 (2H, m), 8.74 (1H, s).

Example 6

3-[4-Benzyl-2-(2-methoxyethoxy)-5-pyridyl]ethynyl-3-quinuclidinol a) 4-(a-Hydroxybenzyl)-2-(2-methoxyethoxy)pyridine 3 g of sodium was added to 50 ml of methoxy ethanol and the mixture was stirred under heating in an oil bath kept at 100° C. in a nitrogen atmosphere for 1 hr. After sodium was dissolved, a mixture of 5.6 g of 4-benzoyl-2-chloropyridine (Production Example 1-a) and 10 ml of methoxy ethanol was added dropwise thereinto, followed by stirring under heating in an oil bath kept at 100° C. in a nitrogen atmosphere for 3 hours. The reaction solution was evaporated and an aqueous sodium hydrogencarbonate solution was added thereto. The mixture was extracted with ethyl aceate, and the organic layer was washed with brine and subjected to silica gel column chromatography using 10–50% ethyl acetate/hexane, to give 5.9 g of the title compound.

$^1$H-NMR (CDCl$_3$) δ ppm=2.55 (1H, brs), 3.42 (3H, s), 3.70–3.75 (2H, m), 4.40–4.45 (2H, m), 5.96 (1H, brs), 7.18 (1H, s), 7.24–7.40 (6H, m), 8.12 (1H, s).

b) 4-Benzyl-5-bromo-2-(2-methoxyethoxy)pyridine 7.32 g of the title compound was obtained from 11.8 g of 4-(a-hydroxybenzyl)-2-(2-methoxyethoxy)pyridine in the same manner as in Production Examples (1-d, e and f).

$^1$H-NMR (CDCl$_3$) δ ppm=3.40 (3H, s), 3.66–3.70 (2H, m), 3.98 (2H, s), 4.37–4.42 (2H, m), 6.50 (1H, s), 7.15–7.35 (5H, m), 8.18 (1H, s).

c) 3-[4-Benzyl-2-(2-methoxyethoxy)-5-pyridyl]ethynyl-3-quinuclidinol 310 mg of the title compound was obtained from 1.38 g of 4-benzyl-5-bromo-2-(2-methoxyethoxy)pyridine in the same manner as in Example 12.

$^1$H-NMR (CDCl$_3$) δ ppm=1.35–1.90 (3H, m), 1.98–2.08 (2H, m), 2.70–2.96 (4H, m), 3.02 (1H, d, J=14 Hz), 3.24 (1H, dd, J=2, 14 Hz), 3.42 (3H, s), 3.69–3.73 (2H, m), 4.04 (2H, s), 4.42–4.46 (2H, m), 6.55 (1H, s), 7.16 (2H, d, J=7 Hz), 7.23 (1H, t, J=7 Hz), 7.30 (2H, t, J=7 Hz), 8.18 (1H, s).

Example 7

3-[2-Benzyl-6-(4-ethoxycarbonylpiperidino)-3-pyridyl]ethynyl-3-quinuclidinol a) 2-Benzyl-6-(4-ethoxycarbonylpiperidino)pyridine A mixture of 5 g of 2-benzyl-6-pyridyl trifluoromethanesulfonate, 3.6 ml of ethyl isonipecotinate, 3.3 g of potassium carbonate and 15 ml of N-methylpyrrolidone was heated under stirring in an oil bath kept at 100° C. in a nitrogen atmosphere. After cooling as it was, the mixture was extracted with ethyl acetate/water. The organic phase was washed with water and brine, dried over anhydrous magnesium sulfate and evaporated. The residue was subjected to silica gel column chromatography and eluted with 1–5% ethyl acetate/hexane, to give 4.7 g of the target compound.

$^1$H-NMR (CDCl$_3$) δ ppm=1.26 (3H, t, J=7 Hz), 1.70–1.82 (2H, m), 1.94–2.01 (2H, m), 2.51 (1H, tt, J=4, 11 Hz), 2.88–2.97 (2H, m), 3.97 (2H, s), 4.15 (2H, q, J=7 Hz), 4.22–4.29 (2H, m), 6.38 (1H, d, J=7 Hz), 6.46 (1H, d, J=9 Hz), 7.16–7.22 (1H, m), 7.26–7.31 (4H, m), 7.34 (1H, dd, J=7, 9 Hz).

b) 2-Benzyl-3-iodo-6-(4-ethoxycarbonylpiperidino)pyridine

Under stirring in an ice bathe, 1.25 g of N-iodosuccinimide was added little by little to a mixture of 1.2 g of 2-benzyl-6-(4-ethoxycarbonylpiperidino)pyridine and 10 ml of N,N-dimethylformamide, followed by stirring as it was overnight. Sodium sulfite was added thereto, and the mixture was extracted with ethyl acetate-water. The organic phase was washed with water and brine, dried over anhydrous magnesium sulfate and evaporated. The residue was subjected to silica gel column chromatography and eluted with 1–5% ethyl acetate/hexane, to give 1.42 g of the target compound.

$^1$H-NMR (CDCl$_3$) δ ppm=1.26 (3H, t, J=7 Hz), 1.64–1.76 (2H, m), 1.90–1.98 (2H, m), 2.50 (1H, tt, J=11 Hz, 4 Hz), 2.87–2.96 (2H, m), 4.10–4.20 (6H, m), 6.27 (1H, d, J=9 Hz), 7.18 (1H, t, J=7 Hz), 7.26 (2H, t, J=7 Hz), 7.32 (2H, d, J=7 Hz), 7.70 (1H, d, J=9 Hz).

c) 3-[2-Benzyl-6-(4-ethoxycarbonylpiperidino)-3-pyridyl]ethynyl-3-quinuclidinol

A mixture of 1.42 g of 2-benzyl-3-iodo-6-(4-ethoxycarbonylpiperidino)pyridine, 520 mg of 3-ethynyl-3-quinuclidinol, 110 mg of tetrakis(triphenylphosphine)palladium(0), 3 mg of cuprous iodide, 1.3 ml of triethylamine and 6 ml of N,N-dimethylformamide was heated under stirring in an oil bath kept at 80° C. for 3 hours in a nitrogen atmosphere. After cooling as it was, the mixture was extracted with ethyl acetate-dilute aqueous ammonia. The organic phase was washed with water and brine, dried over anhydrous magnesium sulfate and evaporated. The residue was subjected to NH-silica gel column chromatography and eluted with 20–100% ethyl acetate/hexane and then with 2.5% methanol/ethyl acetate, to give 700 mg of the target compound.

$^1$H-NMR (CDCl$_3$) δ ppm=1.26 (3H, t, J=7 Hz), 1.34–1.45 (1H, m), 1.53–1.78 (3H, m), 1.83–2.08 (5H, m), 2.53 (1H, tt, J=4, 11 Hz), 2.69–3.04 (7H, m), 3.23 (1H, dd, J=2, 14 Hz), 4.10–4.18 (4H, m), 4.22–4.30 (2H, m), 6.43 (1H, d, J=9 Hz), 7.16 (1H, t, J=7 Hz), 7.25 (2H, t, J=7 Hz), 7.30 (2H, d, J=7 Hz), 7.43 (1H, d, J=9 Hz).

Example 8

3-(2-Benzyl-6-morpholino-3-pyridyl)ethynyl-3-quinuclidinol

The title compound was synthesized in the same manner as in Example 7.

$^1$H-NMR (CDCl$_3$) δ ppm=1.35–1.45 (1H, m), 1.54–1.64 (1H, m), 1.83–1.93 (1H, m), 1.98–2.08 (2H, m), 2.68–2.94 (4H, m), 3.02 (1H, d, J=14 Hz), 3,24 (1H, dd, J=2, 14 Hz), 3.52 (4H, t, J=5 Hz), 3.79 (4H, t, J=5 Hz), 4.16 (2H, s), 6.40 (1H, d, J=8 Hz), 7.14–7.31 (5H, m), 7.47 (1H, d, J=8 Hz).

Example 9

3-[2-Benzyl-6-(4-methoxypiperidino)-3-pyridyl)ethynyl-3-quinuclidinol

The title compound was synthesized in the same manner as in Example 7.

$^1$H-NMR (CDCl$_3$) δ ppm=1.35–1.45 (1H, m), 1.52–1.65 (3H, m), 1.83–1.96 (3H, m), 1.98–2.08 (2H, m), 2.70–2.93

(4H, m), 3.02 (1H, d, J=14 Hz), 3.19–3.27 (3H, m), 3.38 (3H, s), 3.39–3.46 (1H, m), 3.96–4.04 (2H, m), 4.15 (2H, s), 6.44 (1H, d, J=9 Hz), 7.16 (1H, t, J=7 Hz), 7.25 (2H, t, J=7 Hz), 7.30 (2H, d, J=7 Hz), 7.42 (1H, d, J=9 Hz).

Example 10

(3R)-3-[2-Benzyl-6-[(3R,4R)-3-hydroxy-4-methoxypyrrolidine-1-yl]-3-pyridyl)ethynyl-3-quinuclidinol a) 2-Benzyl-6-[(3R,4R)-3,4-dihydroxyrrolidine-1-yl] pyridine 11 ml of 1,8-diazabicyclo[5.4.0]-7-undecene was added dropwise into a mixture of 11.3 g of 2-benzyl-6-pyridyl trifluoromethanesulfonate, 11.3 g of (3R,4R)-3,4-dihydroxypyrrolidine acetate (synthesized from D-tartaric acid as starting material, Angew. Chem. Int. Ed. Engl., 23 (6), 435, 1984) and 10 ml of N-methylpyrrolidone in an oil bath kept at 100° C. in a nitrogen atmosphere, followed by stirring for 6 hours. After cooling as it was, the mixture was extracted with ethyl acetate-water. The organic phase was washed with water and brine, dried over anhydrous magnesium sulfate and evaporated. The residue was subjected to silica gel column chromatography and eluted with ethyl acetate, to give 5.35 g of the target compound.

$^1$H-NMR (CDCl$_3$) δ ppm=3.47 (2H, dd, J=2, 11 Hz), 3.79 (2H, dd, J=4, 11 Hz), 3.97 (2H, s), 4.26–4.30 (2H, m), 6.17 (1H, d, J=8 Hz), 6.38 (1H, d, J=8 Hz), 7.19 (1H, t, J=7 Hz), 7.26–7.36 (5H, m).

b) 2-Benzyl-6-[(3R,4R)-3-hydroxy-4-methoxypyrrolidine-1-yl]pyridine 800 mg of oily (60%) sodium hydride was added little by little to a mixture of 5.35 g of 2-benzyl-6-[(3R,4R)-3,4-dihydroxypyrrolidine-1-yl]pyridine and 40 ml of tetrahydrofuran while stirring, followed by stirring as it was for one hour. Then 1.24 ml of methyl iodide was added thereto, followed by stirring as it was overnight. The mixture was extracted with ethyl acetate-water, and the organic phase was washed with water and brine, dried over anhydrous magnesium sulfate and evaporated. The residue was subjected to silica gel column chromatography and eluted with 30% ethyl acetate/hexane, to give 2.18 g of the target compound.

$^1$H-NMR (CDCl$_3$) δ ppm=3.42 (3H, s), 3.47–3.55 (2H, m), 3.69–3.78 (2H, m), 3.85–3.89 (1H, m), 3.97 (2H, s), 4.38–4.42 (1H, m), 6.17 (1H, d, J=8 Hz), 6.35 (1H, d, J=7 Hz), 7.19 (1H, t, J=7 Hz), 7.26–7.35 (5H, m).

c) 2-Benzyl-3-iodo-6-[(3R,4R)-3-hydroxy-4-methoxypyrrolidine-1-yl]pyridine

Under stirring in an ice bath, 2.5 g of N-iodosuccinimide was added little by little to a mixture of 3.11 g of 2-benzyl-6-[(3R,4R)-3-hydroxy-4-methoxypyrrolidine-1-yl]pyridine and 10 ml of N,N-dimethylformamide, followed by stirring as it was overnight. Sodium sulfite was added thereto and the mixture was extracted with ethyl acetate-water. The organic phase was washed with water and brine, dried over anhydrous magnesium sulfate and evaporated. The residue was subjected to silica gel column chromatography and eluted with 30% ethyl acetate/hexane, to give 4.19 g of the target compound.

$^1$H-NMR (CDCl$_3$) δ ppm=3.41 (3H, s), 3.42–3.51 (2H, m), 3.64–3.71 (2H, m), 3.84–3.87 (1H, m), 4.19 (2H, s), 4.38–4.42 (1H, m), 5.98 (1H, d, J=8 Hz), 7.18 (1H, t, J=7 Hz), 7.26 (2H, t, J=7 Hz), 7.37 (2H, d, J=7 Hz), 7.69 (1H, d, J=8 Hz).

d) (3R)-3-[2-Benzyl-6-[(3R,4R)-3-hydroxy-4-methoxypyrrolidine-1-yl]-3-pyridyl)ethynyl-3-quinuclidinol A mixture of 4.19 g of 2-benzyl-3-iodo-6-[(3R,4R)-3-hydroxy-4-methoxypyrrolidine-1-yl]pyridine, 1.7 g of (3R)-3-ethynyl-3-quinuclidinol, 500 mg of tetrakis(triphenylphosphine)palladium(0), 10 mg of cuprous iodide, 4.2 ml of triethylamine and 13 ml of N,N-dimethylformamide was heated under stirring in an oil bath kept at 70° C. for 3 hours in a nitrogen atmosphere. After cooling as it was, the mixture was extracted with ethyl acetate-dilute aqueous ammonia. The organic phase was washed with water and brine, dried over anhydrous magnesium sulfate and evaporated. The residue was subjected to NH-silica gel column chromatography and eluted with 20–100% ethyl acetate/hexane and then with 5% methanol/ ethyl acetate, to give 1.54 g of the target compound.

$^1$H-NMR (CDCl$_3$) δ ppm=1.34–1.44 (1H, m), 1.50–1.60 (1H, m), 1.80–1.90 (1H, m), 1.97–2.08 (2H, m), 2.60–2.90 (4H, m), 2.97 (1H, d, J=14 Hz), 3.19 (1H, dd, J=2, 14 Hz), 3.40 (3H, s), 3.41–3.54 (2H, m), 3.62–3.73 (2H, m), 3.82–3.85 (1H, m), 4.13 (2H, s), 4.34–4.37 (1H, m), 6.09 (1H, d, J=9 Hz), 7.14 (1H, t, J=7 Hz), 7.23 (2H, t, J=7 Hz), 7.29 (2H, d, J=7 Hz), 7.39 (1H, d, J=9 Hz).

Example 11

3-[2-Benzyl-6-(3-methoxypropylamino)-3-pyridyl) ethynyl-3-quinuclidinol

The title compound was synthesized in the same manner as in Example 7.

$^1$H-NMR (CDCl$_3$) δ ppm=1.34–1.44 (1H, m), 1.52–1.66 (1H, m), 1.81–1.91 (3H, m), 1.97–2.07 (2H, m), 2.67–2.93 (4H, m), 3.01 (1H, dd, J=2, 14 Hz), 3.21 (1H, dd, J=2, 14 Hz), 3.34 (3H, s), 3.36 (2H, q, J=6 Hz), 3.48 (2H, t, J=6 Hz), 4.93 (1H, t, J=6 Hz), 6.20 (1H, d, J=8 Hz), 7.16 (1H, t, J=7 Hz), 7.22–7.31 (4H, m), 7.42 (1H, d, J=8 Hz).

Example 12

3-[2-Benzyl-6-(2-methoxyethyloxy)-3-pyridyl) ethynyl-3-quinuclidinol a) 2-Benzyl-3-bromo-6-(2-methoxyethoxy)pyridine A mixture of 5 g of 2-benzyl-3-bromo-6-hydroxypyridine, 3.9 g of anhydrous potassium carbonate, 2.7 ml of 2-bromoethyl methyl ether and 20 ml of N,N-dimethylformamide was heated under stirring in an oil bat kept at 80° C. for one hour. After cooling as it was, the mixture was extracted with ethyl acetate-water. The organic phase was washed with water and brine, dried over anhydrous magnesium sulfate and evaporated. The residue was subjected to silica gel column chromatography and eluted with 1–3% ethyl acetate/hexane, to give 4.2 g of the target compound.

$^1$H-NMR (CDCl$_3$) δ ppm=3.41 (3H, s), 3.68 (2H, t, J=5 Hz), 4.19 (2H, s), 4.41 (2H, t, J=5 Hz), 6.54 (1H, d, J=9 Hz), 7.20 (1H, t, J=7 Hz), 7.27 (2H, t, J=7 Hz), 7.32 (2H, d, J=7 Hz), 7.63 (1H, d, J=9 Hz).

b) 3-[2-Benzyl-6-(2-methoxyethyloxy)-3-pyridyl)ethynyl-3-quinuclidinol

A mixture of 720 mg of 2-benzyl-3-bromo-6-(2-methoxyethyloxy)pyridine, 340 mg of 3-ethynyl-3-quinuclidinol, 130 mg of tetrakis(triphenylphosphine) palladium(0), 42 mg of cuprous iodide, 0.93 ml of triethylamine and 3 ml of N,N-dimethylformamide was heated under stirring in an oil bath kept at 80° C. for 2 hours in a nitrogen atmosphere. After cooling as it was, the mixture was extracted with ethyl acetate-dilute aqueous ammonia. The organic phase was washed with water and brine, dried over anhydrous magnesium sulfate and evaporated. The residue was subjected to NH-silica gel column chromatography and eluted with 20–100% ethyl acetate/hexane and then with 2.5% methanol/ethyl acetate, to give 500 mg of the target compound.

$^1$H-NMR (CDCl$_3$) δ ppm=1.35–1.45 (1H, m), 1.55–1.65 (1H, m), 1.83–1.93 (1H, m), 1.98–2.08 (2H, m), 2.7–2.93 (4H, m), 3.02 (1H, d, J=14 Hz), 3.23 (1H, dd, J=2, 14 Hz), 3.41 (3H, s), 3.69 (2H, t, J=5 Hz), 4.19 (2H, s), 4.45 (2H, t, J=5 Hz), 6.59 (1H, d, J=8 Hz), 7.14–7.3 (5H, m), 7.53 (1H, d, J=8 Hz).

Example 13

3-[2-Benzyl-6-(3-methoxypropyloxy)-3-pyridyl]ethynyl-3-quinuclidinol

The title compound was synthesized in the same manner as in Example 12.

$^1$H-NMR (CDCl$_3$) δ ppm=1.38–1.48 (1H, m), 1.58–1.69 (1H, m), 1.82–1.93 (1H, m), 2.00 (2H, quint, J=6.4 Hz), 2.72–2.94 (6H, m), 3.03 (1H, dd, J=1.2, 14 Hz), 3.24 (1H, dd, J=2.0, 14 Hz), 3.34 (3H, s), 3.51 (2H, t, J=6.4 Hz), 4.20 (2H, s), 4.37 (2H, t, J=6.4 Hz), 6.53 (1H, d, J=8.4 Hz), 7.18–7.31 (5H, m), 7.54 (1H, d, J=8.4 Hz).

Example 14

3-[2-Benzyl-6-(4-pyridyl)-3-pyridyl]ethynyl-3-quinuclidinol a) 2-Benzyl-3-bromo-6-(4-pyridyl)pyridine A mixture of 298 mg of 2-benzyl-3-bromo-6-pyridyl trifluoromethanesulfonate, 277 mg of (4-pyridyl)tributyltin, 87 mg of tetrakis(triphenylphosphine)palladium(0), 209 mg of tetrabutylammonium chloride and 5.0 ml of xylene was heated under stirring in an oil bath kept at 140° C. for one hour in a nitrogen atmosphere. After cooling as it was, the solvent was removed, and the residue was subjected to NH-silica gel column chromatography and eluted with hexane/ethyl acetate (5:1) and then with hexane/ethyl acetate (3:1), to give 196 mg of the target compound.

$^1$H-NMR (CDCl$_3$) δ ppm=4.42 (2H, s), 7.23–7.39 (5H, m), 7.54 (1H, d, J=8 Hz), 7.88–7.90 (2H, m), 7.93 (1H, d, J=8 Hz), 8.71–8.72 (2H, m).

b) 3-[2-Benzyl-6-(4-pyridyl)-3-pyridyl]ethynyl-3-quinuclidinol

A mixture of 196 mg of 2-benzyl-3-bromo-6-(4-pyridyl)pyridine, 100 mg of 3-ethynyl-3-quinuclidinol, 70 mg of tetrakis(triphenylphosphine)palladium(0), 11 mg of cuprous iodide, 0.25 ml of triethylamine and 3.0 ml of N,N-dimethylformamide was heated under stirring in an oil bath kept at 85° C. for one hour in a nitrogen atmosphere. After cooling as it was, the mixture was extracted with ethyl acetate-dilute aqueous ammonia. The organic phase was washed with brine and the solvent was removed. The residue was subjected to NH-silica gel column chromatography and eluted with hexane/ethyl acetate (1:1) and then with methanol/ethyl acetate (20:1). After removing the solvent, the residue was recrystallized from hexane/ethyl acetate, to give 178 mg of the target compound.

$^1$H-NMR (CDCl$_3$) δ ppm=1.39–1.45 (1H, m), 1.62–1.67 (1H, m), 1.83–1.88 (1H, m), 2.02–2.75 (2H, m), 2.78–2.89 (4H, m), 3.03 (1H, d, J=14 Hz), 3.25 (1H, dd, J=2, 14 Hz), 4.41 (2H, s), 7.19–7.33 (5H, m), 7.63 (1H, d, J=8 Hz), 7.78 (1H, d, J=8 Hz), 7.90–7.92 (2H, m), 8.70–8.72 (2H, m).

Example 15

3-[2-Benzyl-6-(3-pyridyl)-3-pyridyl]ethynyl-3-quinuclidinol

The title compound was synthesized in the same manner as in Example 14.

$^1$H-NMR (CDCl$_3$) δ ppm=1.43–1.47 (1H, m), 1.57–1.62 (1H, m), 1.80–1.94 (1H, m), 2.05–2.07 (2H, m), 2.77–2.90 (4H, m), 3.05 (1H, d, J=14 Hz), 3.25 (1H, d, J=14 Hz), 4.40 (2H, s), 7.18–7.34 (5H, m), 7.39–7.42 (1H, m), 7.56 (1H, d, J=8 Hz), 7.75 (1H, d, J=8 Hz), 8.34–8.37 (1H, m), 8.63 (1H, dd, J=2, 5 Hz), 9.21 (1H, d, J=2 Hz).

Example 16

3-(2-Benzyl-6-pyrazyl-3-pyridyl)ethynyl-3-quinuclidinol

The title compound was synthesized in the same manner as in Example 14.

$^1$H-NMR (DMSO-d$_6$) δ ppm=1.27–1.36 (1H, m), 1.52–1.60 (1H, m), 1.72–1.82 (1H, m), 1.87–1.96 (1H, m), 1.99–2.03 (1H, m), 2.56–2.72 (4H, m), 2.87 (1H, d, J=14 Hz), 3.07 (1H, d, J=14 Hz), 4.39 (2H, s), 5.80 (1H, s), 7.18–7.41 (5H, m), 7.99 (1H, d, J=8 Hz), 8.20 (1H, d, J=8 Hz), 8.72 (1H, d, J=3 Hz), 8.75 (1H, m), 9.51 (1H, s).

Example 17

3-[2-Benzyl-6-(2-pyridyl)-3-pyridyl]ethynyl-3-quinuclidinol

The title compound was synthesized in the same manner as in Example 14.

$^1$H-NMR (CDCl$_3$) δ ppm=1.40–1.93 (3H, m), 2.00–2.11 (2H, m), 2.70–2.95 (4H, m), 3.02 (1H, d, J=14 Hz), 3.22 (1H, dd, J=2, 14 Hz), 4.42 (2H, s), 7.18–7.34 (6H, m), 7.81 (1H, d, J=8 Hz), 7.81 (1H, dt, J=2, 8 Hz), 8.27 (1H, d, J=8 Hz), 8.46 (1H, d, J=8 Hz), 8.65–8.68 (1H, m).

Example 18

3-[4-Benzyl-2-(3-pyridyl)-5-pyridyl]ethynyl-3-quinuclidinol a) 4-Benzyl-5-bromo-2-(3-pyridyl)pyridine A mixture of 440 mg of 4-benzyl-5-bromo-2-iodopyrimidine, 430 mg of (3-pyridyl)tributyltin, 68 mg of tetrakis (triphenylphosphine)palladium(0) and 5 ml of xylene was heated under ref lux for one hour in a nitrogen atmosphere. After cooling as it was, silica gel was added to the reaction solution and the solvent was removed. The residue was subjected to silica gel column chromatography using 30% ethyl acetate/hexane, to give 110 mg of the target compound.

$^1$H-NMR (CDCl$_3$) δ ppm=4.33 (2H, s), 7.21–7.42 (6H, m), 8.66 (1H, td, J=2, 8 Hz), 8.71 (1H, dd, J=2, 5 Hz), 8.80 (1H, s), 9.62 (1H, d, J=2 Hz).

b) 3-[4-Benzyl-2-(3-pyridyl)-5-pyrimidyl]ethynyl-3-quinuclidinol

A mixture of 110 mg of 4-benzyl-5-bromo-2-(3-pyridyl)pyrimidine, 59 mg of 3-ethynyl-3-quinuclidinol, 19 mg of tetrakis(triphenylphosphine)palladium(0), 10 mg of cuprous iodide, 0.14 ml of triethylamine and 1.5 ml of N,N-dimethylformamide was heated under stirring in an oil bath kept at 100° C. for 2 hours in a nitrogen atmosphere. After cooling as it was, NH-silica gel was added to the reaction solution and the solvent was removed. The residue was subjected to NH-silica gel column chromatography using 2.5% methanol/ethyl acetate, to give 62 mg of the target compound.

$^1$H-NMR (CDCl$_3$) δ ppm=1.42–1.92 (3H, m), 2.05–2.12 (2H, m), 2.76–2.99 (4H, m), 3.10 (1H, d, J=14 Hz) 3.28 (1H, dd, J=2, 14 Hz), 4.32 (2H, s), 7.21–7.35 (5H, m), 7.40–7.43 (1H, m), 8.68–8.70 (2H, m), 8.74 (1H, s), 9.65–9.66 (1H, m).

Example 19

3-[4-Benzyl-2-(3,4-methylenedioxyphenyl)-5-pyrimidyl]ethynyl-3-quinuclidinol

The title compound was synthesized in the same manner as in Example 18.

$^1$H-NMR (CDCl$_3$) δ ppm=1.40–1.70 (2H, m), 1.84–1.92 (1H, m), 2.04–2.12 (2H, m), 2.74–2.91 (4H, m), 3.05 (1H, d, J=14 Hz), 3.25 (1H, dd, J=2, 14 Hz), 4.29 (2H, s), 6.04 (2H, s), 6.91 (1H, d, J=8 Hz), 7.21–7.34 (5H, m), 7.94 (1H, d, J=2 Hz), 8.08 (1H, dd, J=2, 8 Hz), 8.66 (1H, s).

Example 20

3-(4-Benzyl-2-phenyl-5-pyrimidyl)ethynyl-3-quinuclidinol

The title compound was synthesized in the same manner as in Example 18.

$^1$H-NMR (CDCl$_3$) δ ppm=1.43–1.70 (2H, m), 1.84–1.92 (1H, m), 2.02–2.11 (2H, m), 2.75–2.92 (4H, m), 3.06 (1H, d, J=14 Hz), 3.26 (1H, dd, J=2, 14 Hz), 4.33 (2H, s), 7.21–7.36 (5H, m), 7.48–7.50 (3H, m), 8.45–8.48 (2H, m), 8.73 (1H, s).

Example 21

3-[4-Benzyl-2-(2-pyridyl)-5-pyridyl]ethynyl-3-quinuclidinol

The title compound was synthesized in the same manner as in Example 18.

$^1$H-NMR (CDCl$_3$) δ ppm=1.40–1.48 (1H, m), 1.61–1.88 (2H, m), 2.00–2.08 (2H, m), 2.76–2.95 (4H, m), 3.06 (1H, d, J=14 Hz), 3.25 (1H, dd, J=2, 14 Hz), 4.40 (2H, s), 7.21–7.33 (5H, m), 7.39–7.42 (1H, m), 7.86 (1H, td, J=2, 8 Hz), 8.54 (1H, d, J=8 Hz), 8.85–8.87 (2H, m).

Example 22

3-[3-Benzyl-5-(2-pyridyl)-2-pyridyl]ethynyl-3-quinuclidinol a) 3-(3-Benzyl-5-bromo-2-pyridyl)ethynly-3-quinuclidinol A mixture of 2.2 g of 3-benzyl-5-bromo-2-pyridyl trifluoromethanesulfonate, 840 mg of 3-ethynyl-3-quinuclidinol, 920 mg of tetrakis(triphenylphosphine) palladium(0), 170 mg of cuprous iodide, 2.3 ml of triethylamine and 25 ml of N,N-dimethylformamide was stirred at room temperature for one hour in a nitrogen atmosphere. NH-silica gel was added to the reaction solution and the solvent was removed. The residue was subjected to NH-silica gel column chromatography using 3.5% methanol/ethyl acetate, to give 940 mg of the target compound.

$^1$H-NMR (CDCl$_3$) δ ppm=1.35–1.44 (1H, m), 1.56–1.65 (1H, m), 1.80–1.90 (1H, m), 1.98–2.09 (2H, m), 2.70–2.92 (4H, m), 3.04 (1H, d, J=14 Hz), 3.25 (1H, dd, J=2, 14 Hz), 4.11 (2H, s), 7.14–7.17 (2H, m), 7.23–7.34 (3H, m), 7.57 (1H, d, J=2 Hz), 8.50 (1H, d, J=2 Hz).

b) 3-[3-Benzyl-5-(2-pyridyl)-2-pyridyl]ethynyl-3-quinuclidinol

A mixture of 150 mg of 3-(3-benzyl-5-bromo-2-pyridyl) ethynyl-3-quinuclidinol, 150 mg of (2-pyridyl)tributyltin, 86 mg of tetrakis(triphenylphosphine)palladium(0) and 3.5 ml of toluene was heated under stirring in an oil bath kept at 110° C. for 2 hours in a nitrogen atmosphere. After cooling as it was, NH-silica gel was added to the reaction solution and the solvent was removed. The residue was subjected to NH-silica gel column chromatography using 2.5% methanol/ethyl acetate, to give 100 mg of the target compound.

$^1$H-NMR (CDCl$_3$) δ ppm=1.35–1.43 (1H, m), 1.54–1.63 (1H, m), 1.83–1.92 (1H, m), 1.99–2.10 (2H, m), 2.71–2.94 (4H, m), 3.07 (1H, d, J=14 Hz), 3.26 (1H, dd, J=2, 14 Hz), 4.21 (2H, s), 7.19–7.30 (6H, m), 7.70 (1H, d, J=8 Hz), 7.76 (1H, td, J=2, 8 Hz), 8.16 (1H, d, J=2 Hz), 8.68–8.70 (1H, m), 9.02 (1H, d, J=2 Hz).

Example 23

3-(3-Benzyl-5-phenyl-2-pyridyl)ethynyl-3-quinuclidinol

The title compound was synthesized in the same manner as in Example 22.

$^1$H-NMR (CDCl$_3$) δ ppm=1.36–1.44 (1H, m), 1.56–1.64 (1H, m), 1.86–1.95 (1H, m), 1.98–2.11 (2H, m), 2.71–2.95 (4H, m), 3.08 (1H, d, J=14 Hz), 3.28 (1H, dd, J=2, 14 Hz), 4.21 (2H, s), 7.19–7.53 (10H, m), 7.64 (1H, d, J=2 Hz), 8.69 (1H, d, J=2 Hz).

Example 24

3-[3-Benzyl-5-(3-pyridyl)-2-pyridyl]ethynyl-3-quinuclidinol

The title compound was synthesized in the same manner as in Example 22.

$^1$H-NMR (CDCl$_3$) δ ppm=1.37–1.45 (1H, m), 1.56–1.64 (1H, m), 1.84–1.92 (1H, m), 2.04–2.12 (2H, m), 2.73–2.94 (4H, m), 3.09 (1H, d, J=14 Hz), 3.28 (1H, dd, J=2, 14 Hz), 4.21 (2H, s), 7.18–7.31 (5H, m), 7.38 (1H, ddd, J=1, 5, 8 Hz), 7.61 (1H, d, J=2 Hz), 7.82 (1H, td, J=2, 8 Hz), 8.62 (1H, dd, J=2, 5 Hz), 8.64 (1H, d, J=2 Hz), 8.87 (1H, dd, J=1, 2 Hz).

Example 25

3-[3-Benzyl-5-(4-pyridyl)-2-pyridyl]ethynyl-3-quinuclidinol

The title compound was synthesized in the same manner as in Example 22.

$^1$H-NMR (CDCl$_3$) δ ppm=1.37–1.45 (1H, m), 1.57–1.65 (1H, m), 1.85–1.92 (1H, m), 2.00–2.11 (2H, m), 2.73–2.93 (4H, m), 3.08 (1H, d, J=14 Hz), 3.28 (1H, dd, J=2, 14 Hz), 4.22 (2H, s), 7.18–7.34 (5H, m), 7.42–7.44 (2H, m), 7.67 (1H, d, J=2 Hz), 8.67–8.69 (2H, m), 8.70 (1H, d, J=2 Hz).

Example 26

3-(3-Benzyl-5-pyrazyl-2-pyridyl)ethynyl-3-quinuclidinol

The title compound was synthesized in the same manner as in Example 22.

$^1$H-NMR (CDCl$_3$) δ ppm=1.36–1.44 (1H, m), 1.56–1.64 (1H, m), 1.85–1.93 (1H, m), 2.01–2.11 (2H, m), 2.73–2.95 (4H, m), 3.08 (1H, d, J=14 Hz), 3.27 (1H, dd, J=2, 14 Hz), 4.23 (2H, s), 7.19–7.32 (5H, m), 8.13 (1H, d, J=2 Hz), 8.54 (1H, d, J=2 Hz), 8.64 (1H, dd, J=1, 2 Hz), 9.04 (1H, d, J=1 Hz), 9.08 (1H, d, J=2 Hz).

Example 27

3-[3-Benzyl-5-(2-ethoxycarbonylethyl)-2-pyridyl]ethynyl-3-quinuclidinol a) 3-Benzyl-5-formyl-2-methoxypryridine 4.6 ml of a hexane solution of 1.6 M normal butyllithium was added dropwise into a mixture of 1.0 g of 3-benzyl-5-bromo-2-methoxypyridine (Production Example 5-b) and 10 ml of diethyl ether at −78° C. After stirring at the same temperature for one hour, 0.56 ml of N,N-dimethylformamide was added thereto, followed by heating gradually to room temperature. The reaction mixture was partitioned by adding water and ethyl acetate thereto. The organic phase was washed with water and brine, dried over anhydrous magnesium sulfate and the solvent was removed.

$^1$H-NMR (CDCl$_3$) δ ppm=3.94 (2H, s), 4.03 (3H, s), 4.00 (3H, s), 7.19–7.33 (5H, m), 7.77–7.78 (1H, m), 8.49 (1H, d, J=4 Hz), 9.90 (1H, s).

b) 3-Benzyl-5-(2-ethoxycarbonylethyl)-2-methoxypyridine

To 3-benzyl-5-formyl-2-methoxypryridine were added 0.92 ml of triethylphosphono acetate, 11 ml of methanol and 2.9 ml of a 21% sodium ethoxide ethanol solution, followed by stirring at room temperature for one hour. The mixture was partitioned by adding water and ethyl acetate thereto, and the organic phase was washed with water and brine, dried over anhydrous magnesium sulfate and the solvent was removed. The residue was subjected to silica gel column chromatography and eluted with 5% ethyl acetate/hexane, to give 950 mg of the target compound.

$^1$H-NMR (CDCl$_3$) δ ppm=1.32 (3H, t, J=7 Hz), 3.92 (2H, s), 4.00 (3H, s), 4.23 (2H, q, J=7 Hz), 6.23 (1H, d, J=16 Hz), 7.19–7.34 (5H, m), 7.45 (1H, d, J=2 Hz), 7.57 (1H, d, J=16 Hz), 8.14 (1H, d, J=2 Hz).

c) 3-Benzyl-5-(2-ethoxycarbonylethyl)-2-methoxypyridine

A mixture of 950 mg of 3-benzyl-5-(2-ethoxycarbonylethenyl)-2-methoxypyridine, 90 mg of 10% palladium carbon and 10 ml of ethanol was stirred at room temperature for one hour in a hydrogen atmosphere. After the atmosphere in the system was replaced by nitrogen, the mixture was filtered through Celite. The solvent was removed, to give 950 mg of the target compound.

$^1$H-NMR (CDCl$_3$) δ ppm=1.21 (3H, t, J=7 Hz), 2.52 (2H, t, J=7 Hz), 2.80 (2H, t, J=7 Hz), 3.88 (2H, s), 3.93 (3H, s), 4.09 (2H, q, J=7 Hz), 7.12 (1H, s), 7.18–7.30 (5H, m), 7.86 (1H, s).

d) 3-Benzyl-5-(2-ethoxycarbonylethyl)-2-hydroxypyridine

A mixture of 240 mg of 3-benzyl-5-(2-ethoxycarbonylethyl)-2-methoxypyridine, 2.5 ml of 1,2-dichloroethane and a solution of 1.0 M boron tribromide in 0.39 ml of dichloromethane was stirred at 50° C. for 8 hours. Water and silica gel were added to the reaction solution, and the solvent was removed. The residue was subjected to silica gel column chromatography using 75% ethyl acetate/hexane, to give 86 mg of the target compound.

$^1$H-NMR (CDCl$_3$) δ ppm=1.21 (3H, t, J=7 Hz), 2.45 (2H, t, J=7 Hz), 2.66 (2H, brs), 3.89 (2H, brs), 4.08 (2H, q, J=7 Hz), 6.99–7.34 (7H, m).

e) 3-Benzyl-5-(2-ethoxycarbonylethyl)-2-pyridyl Trifluoromethanesulfonate

A mixture of 86 mg of 3-benzyl-5-(2-ethoxycarbonylethyl)-2-hydroxypyridine, 130 mg of N-phenyltrifluoromethanesulfonimide, 0.13 ml of triethylamine, 3.7 mg of 4-dimethylaminopyridine and 1.5 ml of dichloromethane was stirred at room temperature for one hour. Silica gel was added to the reaction solution and the solvent was removed. The residue was subjected to silica gel column chromatography using 15% ethyl acetate/hexane, to give 130 mg of the target compound.

$^1$H-NMR (CDCl) δ ppm=1.21 (3H, t, J=7 Hz), 2.58 (2H, t, J=7 Hz), 2.92 (2H, t, J=7 Hz), 4.00 (2H, s), 4.09 (2H, q, J=7 Hz), 7.15–7.19 (2H, m), 7.24–7.36 (3H, m), 7.42 (1H, d, J=2 Hz), 8.06 (1H, d, J=2 Hz).

f) 3-[3-Benzyl-5-(2-ethoxycarbonylethyl)-2-pyridyl]ethnyl-3-quinuclidinol

A mixture of 180 mg of 3-benzyl-5-(2-ethoxycarbonylethyl)-2-pyridyl trifluoromethanesulfonate, 66 mg of 3-ethynyl-3-quinuclidinol, 100 mg of tetrakis (triphenylphosphine)palladium(0), 17 mg of cuprous iodide, 0.18 ml of triethylamine and 2 ml of N,N-dimethylformamide was heated under stirring at 70° C. in an oil bath for one hour in a nitrogen atmosphere. After cooling as it was, NH-silica gel was added thereto and the solvent was removed. The residue was subjected to NH-silica gel column chromatography using 2.5% methanol/ethyl acetate, to give 120 mg of the target compound.

$^1$H-NMR (CDCl$_3$) δ ppm=1.20 (3H, t, J=7 Hz), 1.33–1.42 (1H, m), 1.53–1.61 (1H, m), 1.82–1.91 (1H, m), 1.98–2.08 (2H, m), 2.57 (2H, t, J=7 Hz), 2.68–2.92 (6H, m), 3.05 (1H, d, J=14 Hz), 3.23 (1H, dd, J=2, 14 Hz), 4.08 (2H, q, J=7 Hz), 7.12–7.16 (2H, m), 7.19–7.31 (4H, m), 8.31 (1H, d, J=2 Hz).

Example 28

3-[3-Benzyl-5-(3-oxobutyl)-2-pyridyl]ethynyl-3-quinuclidinol

The title compound was synthesized in the same manner as in Example 27.

$^1$H-NMR (CDCl$_3$) δ ppm=1.36–1.47 (1H, m), 1.55–1.63 (1H, m), 1.80–1.92 (1H, m), 2.00–2.10 (2H, m), 2.12 (3H, s), 2.68–3.05 (8H, m), 3.08 (1H, dd, J=1.6, 14 Hz), 3.25 (1H, dd, J=2.0, 14 Hz), 4.11 (2H, s), 7.12–7.16 (2H, m), 4.20–7.32 (4H, m), 8.30 (1H, d, J=2.2 Hz).

Example 29

3-[3-Benzyl-5-(3-hydroxybutyl)-2-pyridyl]ethynyl-3-quinuclidinol

A mixture of 314 mg of 3-[3-benzyl-5-(3-oxobutyl)-2-pyridyl]ethynyl-3-quinuclidinol hydrochloride, 129 mg of potassium carbonate, 35 mg of sodium borohydride and 10 ml of methanol was stirred at room temperature for one hour. A small amount of water was added thereto, and the mixture was evaporated. The residue was subjected to NH-silica gel column chromatography using chloroform and then chloroform/methanol/aqueous concentrated ammonia (46:1:0.1), to give 340 mg of the target compound.

$^1$H-NMR (CDCl$_3$) δ ppm=1.21 (3H, d, J=6.0 Hz), 1.33–1.41 (1H, m), 1.52–1.61 (1H, m), 1.65–1.80 (2H, m), 1.80–1.91 (1H, m), 2.00–2.10 (2H, m), 2.58–2.94 (6H, m), 3.06 (1H, dd, J=1.2, 14 Hz), 3.24 (1H, dd, J=2.0, 14 Hz), 3.72–3.81 (1H, m), 4.11 (2H, s), 7.13–7.30 (6H, m), 8.30 (1H, d, J=2.2 Hz).

Example 30

3-[3-(2-Thienylmethyl)-2-pyridyl]ethynyl-3-quinuclidinol a) 2-Chloro-3-(2-thienylcarbonyl)pyridine 10 g of 2-chloronicotinic acid chloride was added to a mixture of 7.2 g of aluminum chloride and 100 ml of carbon disulfide under ice-cooling, followed by adding 8.8 ml of thiophene was slowly added dropwise thereinto. After stirring at room temperature for two nights, the reaction solution was slowly poured into ice water. The mixture was extracted with ethyl acetate, and the organic phase was successively washed with aqueous saturated sodium bicarbonate and brine. After removing the solvent, the residue was subjected to silica gel column chromatography and eluted with hexane/ethyl acetate (3:1) and then with hexane/ethyl acetate (2:1), to give 1.64 g of the target compound.

$^1$H-NMR (CDCl$_3$) δ=7.15–7.17 (1H, m), 7.37–7.40 (1H, m), 7.42–7.44 (1H, m), 7.78–7.83 (2H, m), 8.54–8.57 (1H, m).

b) 2-Methoxy-3-(2-thienylcarbonyl)pyridine

A mixture of 1.64 g of 2-chloro-3-(2-thienylcarbonyl)pyridine, 4.5 ml of a methanol solution of 28% sodium methoxide and 2.0 ml of methanol was heated under stirring for 30 minutes. After cooling as it was, water was added to the reaction solution and the mixture was extracted with ethyl acetate. The organic phase was washed with brine and the solvent was removed, to give 1.46 g of the target compound.

$^1$H-NMR (CDCl$_3$) δ=3.96 (3H, s), 6.90–7.05 (1H, m), 7.11–7.14 (1H, m), 7.48–7.50 (1H, m), 7.72–7.76 (2H, m), 8.30–8.33 (1H, m).

c) 2-Methoxy-3-[2-thienyl(hydroxy)methyl]pyridine 303 mg of sodium borohydride was added little by little to a solution containing 1.46 g of 2-methoxy-3-(2-thienylcarbonyl)pyridine and 10 ml of ethanol under ice-cooling. After stirring at room temperature for 2 hours, water was slowly added thereto and the mixture was extracted with ethyl acetate. The organic phase was washed with brine and the solvent was removed, to give 1.47 g of the target compound.

$^1$H-NMR (CDCl$_3$) δ=3.99 (3H, s), 6.26 (1H, d), 6.88–6.96 (3H, m), 7.25 (1H, m), 7.64 (1H, dd), 8.12 (1H, dd).

d) 2-Methoxy-3-[2-thienylmethyl]pyridine

A mixture of 1.47 g of 2-methoxy-3-[2-thienyl(hydroxy)methyl]pyridine, 3.2 g of zinc iodide, 3.4 g of sodium cyanoborohydride and 30 ml of 1,2-dichloroethane was stirred at room temperature for two nights. Insoluble matters were filtered off, and to the filtrate was added an aqueous sodium hydroxide solution. The mixture was extracted with ethyl acetate, and the organic phase was washed with brine and the solvent was evaporated. Then, the residue was subjected to silica gel column chromatography and eluted with hexane and then with hexane/ethyl acetate (40:1), to give 734 mg of the target compound.

$^1$H-NMR (CDCl$_3$) δ=3.99 (3H, s), 4.10 (2H, s), 6.79–6.84 (2H, m), 6.92–6.95 (1H, m), 7.13–7.16 (1H, m), 7.35–7.36 (1H, m), 8.04 (1H, dd).

e) 3-(2-Thienylmethyl)-2-pyridyl Trifluoromethanesulfonate 10 ml of 47% hydrobromic acid was added to 216 mg of 2-methoxy-3-(2-thienylmethyl)pyridine, followed by heating under stirring for 4 hours in an oil bath kept at 80° C. After cooling as it was, the reaction mixture was neutralized by adding potassium carbonate thereto carefully. Water was added thereto, and the mixture was extracted with ethyl acetate/tetrahydrofuran. The organic phase was washed with brine, dried over anhydrous magnesium sulfate and the solvent was removed, to give 140 mg of a crude product. A mixture of 140 mg of the crude product, 314 mg of N-phenyltrifluoromethanesulfonimide, 153 μl of triethylamine, 27 mg of 4-dimethylaminopyridine and 5.0 ml of dichloromethane was stirred at room temperature for 3 hours. Water was added to the reaction solution and extracted with ethyl acetate. The organic phase was washed with brine and the solvent was removed. The residue was subjected to NH-silica gel (Fuji Silicia) column chromatography and eluted with hexane and then with hexane/ethyl acetate (40:1), to give 89 mg of the target compound.

$^1$H-NMR (CDCl$_3$) δ=4.23 (2H, s), 6.86–6.89 (1H, m), 6.96–6.99 (1H, m), 7.21–7.24 (1H, m), 7.29–7.33 (1H, m), 7.66–7.69 (1H, m), 8.25 (1H, dd).

f) 3-[3-(2-Thienylmethyl)-2-pyridyl]ethynyl-3-quinuclidinol

A mixture of 89 mg of 3-(2-thienylmethyl)-2-pyridyl trifluoromethanesulfonate, 50 mg of 3-ethynyl-3-quinuclidinol, 64 mg of tetrakis (triphenylphosphine) palladium(0), 11 mg of cuprous iodide, 105 μl of triethylamine and 3.0 ml of N,N-dimethylformamide was heated under stirring at 70° C. for 1.5 hours in a nitrogen atmosphere. The reaction solution was poured into aqueous dilute ammonia, followed by extracting with ethyl acetate. Then, the organic phase was washed with brine and the solvent was removed, and the residue was subjected to NH-silica gel (Fuji silicia) column chromatography and eluted with hexane/ethyl acetate (1:1) and then with ethyl acetate/methanol (15:1), to give 88 mg of the target compound.

$^1$H-NMR (CDCl$_3$) δ=1.35–1.45 (1H, m), 1.56–1.68 (1H, m), 1.86–1.99 (1H, m), 2.02–2.13 (2H, m), 2.73–2.94 (4H, m), 3.05–3.10 (1H, m), 3.29–3.33 (1H, m), 4.32 (2H, s), 6.76–6.79 (1H, m), 6.92–6.95 (1H, m), 7.15–7.23 (2H, m), 7.55 (1H, d), 8.46 (1H, d).

Example 31

3-[6-pyrazyl-3-benzyl-2-pyridyl]ethynyl-3-quinuclidinol a) 6-Chloro-3-(α-hydroxybenzyl)-2-methoxypyridine 100 ml of a pentane solution containing 1.56 mol of tert-butyllithium was slowly added dropwise into a solution of 200 ml of tetrahydrofuran containing 11.9 ml of 2-bromomesitylene at −78° C. under cooling. After stirring at the same temperature for one hour, 7.2 ml of 2-chloro-6-methoxypyridine was slowly added dropwise thereinto. After stirring under ice-cooling for one hour and then at room temperature for one hour, 8.5 ml of benzaldehyde was added thereto under ice-cooling, followed by stirring at room temperature for further one hour. Water was added to the reaction solution, followed by extracting with ethyl acetate. The organic phase was washed with brine and the solvent was removed. The residue was subjected to silica gel column chromatography and eluted with hexane and then with hexane/ethyl acetate (7:1), to give 15.0 g of the target compound.

$^1$H-NMR (CDCl$_3$) δ=3.95 (3H, s), 5.96 (1H, d, J=4 Hz), 6.90–6.92 (1H, m), 7.25–7.37 (5H, m), 7.54–7.57 (1H, m).

b) 6-Chloro-3-benzoyl-2-methoxypyridine 36.0 g of manganese(IV) oxide was added to a solution of 3.7 g of 6-chloro-3-(α-hydroxybenzyl)-2-methoxypyridine in 80 ml of tetrahydrofuran, followed by stirring at room temperature for 2 hours. Insoluble matters were filtered off and then the solvent was evaporated, to give 3.6 g of the title compound.

$^1$H-NMR (CDCl$_3$) δ=3.90 (3H, s), 7.04 (1H, dd, J=0.4 Hz, 8 Hz), 7.44–7.48 (2H, m), 7.56–7.62 (1H, m), 7.70 (1H, dd, J=0.4 Hz, 8 Hz), 7.76–7.81 (2H, m).

c) (3-Benzoyl-2-methoxy-6-pyridyl)tributyltin

A mixture of 3.6 g of 6-chloro-3-benzoyl-2-methoxypyridine, 42.1 g of bis(tributyltin), 1.7 g of tetrakis (triphenylphosphine)palladium(0) and 20 ml of toluene was heated under reflux for 2 hours. After cooling as it was, the solvent was removed, and the residue was subjected to silica gel column chromatography and eluted with hexane and then with hexane/ethyl acetate (2:1), to give 5.1 g of the target compound.

$^1$H-NMR (CDCl$_3$) δ=0.85–1.65 (27H, m), 3.90 (3H, s), 7.12–7.14 (1H, m), 7.28–7.59 (4H, m), 7.79–7.82 (2H, m).

d) 6-Pyrazyl-3-benzoyl-2-methoxypyridine

A mixture of 5.1 g of (3-benzoyl-2-methoxy-6-pyridyl) tributyltin, 5.4 ml of chloropyrazine, 1.8 g of tetrakis (triphenylphosphine)palladium(0) and 30 ml of xylene was heated under reflux for 2 hours. After cooling as it was, the solvent was removed, and the residue was subjected to silica gel column chromatography and eluted with hexane and then with hexane/ethyl acetate (1:1), to give 1.3 g of the target compound.

$^1$H-NMR (CDCl$_3$) δ=4.02 (3H, s), 7.45–7.50 (2H, m), 7.59–7.63 (1H, m), 7.83–7.91 (3H, m), 8.10–8.13 (1H, m), 8.63–8.66 (2H, m), 9.66 (1H, d, J=1.4 Hz).

e) 6-Pyrazyl-3-benzyl-2-methoxypyridine

A mixture of 806 mg of 6-pyrazyl-3-benzoyl-2-methoxypyridine, 177 μl of hydrazine, 421 mg of potassium carbonate and 35 ml of diethylene glycol was heated under stirring at 100° C. for one hour and then at 170° C. for 3 hours. After cooling as it was, water was added to the reaction solution, followed by extracting with ethyl acetate. The organic phase was washed with brine and the solvent was removed, and the residue was subjected to silica gel column chromatography and eluted with hexane/ethyl acetate (5:1) and then with hexane/ethyl acetate (4:1), to give 234 mg of the target compound.

$^1$H-NMR (CDCl$_3$) δ=3.98 (2H, s), 4.08 (3H, s), 7.21–7.33 (5H, m), 7.44 (1H, d, J=8 Hz), 7.89 (1H, d, J=8 Hz), 8.53–8.57 (2H, m), 9.60 (1H, d, J=1.5 Hz).

f) 6-Pyrazyl-3-benzyl-2-hydroxypyridine 5.0 ml of 47% hydrobromic acid was added to 234 mg of 6-pyrazyl-3-benzyl-2-methoxypyridine, followed by heating under stirring for one hour in an oil bath kept at 80° C. After cooling as it was, the reaction solution was slowly added to an aqueous potassium carbonate solution. The resulting crystals were collected by filtration and dried, to give 222 mg of the target compound.

$^1$H-NMR (CDCl$_3$) δ=3.95 (2H, s), 6.83 (1H, d, J=7 Hz), 7.12–7.15 (1H, m), 7.21–7.36 (5H, m), 8.59–8.61 (2H, m), 9.07 (1H, d, J=1.3 Hz).

g) 6-Pyrazyl-3-benzyl-2-pyridyl Trifluoromethanesulfonate 222 mg of 6-pyrazyl-3-benzyl-2-hydroxypyridine, 365 mg of N-phenyltrifluoromethanesulfonimide, 178 μl of triethylamine, 31 mg of 4-dimethylaminopyridine, 10 ml of dichloromethane and 3.0 ml of N,N-dimethylformamide were added, followed by stirring at room temperature for 3 hours. Water was added to the reaction solution, followed by extracting with ethyl acetate. The extract was washed with brine and the solvent was removed. The residue was subjected to silica gel column chromatography and eluted with hexane and then with hexane/ethyl acetate (4:1), to give 336 mg of the target compound.

$^1$H-NMR (CDCl$_3$) δ=4.11 (2H, s), 7.22–7.42 (5H, m), 7.75 (1H, d, J=8 Hz), 8.36 (1H, d, J=8 Hz), 8.59–8.63 (2H, m), 9.50 (1H, d, J=1.3 Hz).

h) 3-[6-Pyrazyl-3-benzyl-2-pyridyl]ethynyl-3-quinuclidinol

A mixture of 336 mg of 6-pyrazyl-3-benzyl-2-pyridyl trifluoromethanesulfonate, 161 mg of 3-ethynyl-3-quinuclidinol, 205 mg of tetrakis (triphenylphosphine) palladium(0), 34 mg of cuprous iodide, 370 μl of triethylamine and 5.0 ml of N,N-dimethylformamide was heated under stirring at 80° C. for 3 hours in a nitrogen atmosphere. After cooling as it was, the solvent was removed, and the residue was subjected to NH-silica gel (Fuji silicia) column chromatography and eluted with ethyl acetate/methanol (20:1), to give 204 mg of the target compound.

$^1$H-NMR (CDCl$_3$) δ=1.39–1.79 (2H, m), 1.89–1.96 (1H, m), 2.06–2.14 (2H, m), 2.75–2.94 (4H, m), 3.07 (1H, d, J=14 Hz), 3.29 (1H, d, J=14 Hz), 4.23 (2H, s), 7.18–7.34 (5H, m), 7.62 (1H, d, J=8 Hz), 8.25 (1H, d, J=8 Hz), 8.59 (2H, s), 9.64 (1H, s).

Example 32

3-[3-Benzyl-5-(3-thienyl)-2-pyridyl]ethynyl-3-quinuclidinol

A mixture of 127 mg of 3-(3-benzyl-5-bromo-2-pyridyl) ethynyl-3-quinuclidinol (Example 22-a), 61.4 mg of 3-thiopheneboronic acid, 55.4 mg of tetrakis (triphenylphosphine)palladium(0), 2 ml of toluene, 0.5 ml of methanol and 1 ml of aqueous 2 mol sodium carbonate solution was stirred at 80° C. for 2 hours in a nitrogen atmosphere. NH-silica gel was added to the reaction solution and the solvent was removed. The residue was subjected to NH-silica gel column chromatography using 3% methanol/ethyl acetate, to give 83.9 mg of the target compound.

$^1$H-NMR (CDCl$_3$) δ=1.35–1.42 (1H, m), 1.54–1.62 (1H, m), 1.84–1.92 (1H, m), 2.00–2.10 (2H, m), 2.68–2.83 (3H, m), 2.87–2.94 (1H, m), 3.09 (1H, d, J=14 Hz), 3.26 (1H, dd, J=2, 14 Hz), 4.18 (2H, s), 7.17–7.33 (6H, m), 7.39–7.42 (1H, m), 7.47–7.49 (1H, m), 7.61 (1H, s), 8.70 (1H, d, J=2 Hz).

Example 33

3-[6-(Methylamino-3-benzyl-5-pyrazyl-2-pyridyl] ethynyl-3-quinuclidinol a) 6-(Acetoxymethyl)-3-benzoyl-2-methoxypyridine A mixture of 5 g of 6-methyl-3-benzoyl-2-methoxypyridine synthesized in the same manner as in Production Example-1b, 4.3 g of N-bromosuccinimide and 100 ml of benzene was irradiated with light of 200 W tungsten lamp for 30 minutes and refluxed. After cooling, insoluble matters were filtered off, and the filtrate was concentrated. To the residue were added 30 ml of acetic acid and 5 g of sodium acetate, followed by heating in an oil bath kept at 100° C. overnight. After concentrating the reaction solution, it was extracted with ethyl acetate-aqueous saturated sodium bicarbonate. The organic phase was washed with brine, dried over anhydrous magnesium sulfate and evaporated. The residue was subjected to silica gel column chromatography using 5–10% ethyl acetate/hexane, to give 3.69 g of the target compound.

$^1$H-NMR (CDCl$_3$) δ=2.21 (3H, s), 3.87 (3H, s), 5.20 (2H, s), 7.02 (1H, d, J=8 Hz), 7.45 (2H, t, J=8 Hz), 7.58 (1H, t, J=8 Hz), 7.73 (1H, d, J=8 Hz), 7.79 (2H, d, J=8 Hz).

b) 6-(Acetoxymethyl)-3-benzoyl-2-methoxy-5-pyrazypyridine

A mixture of 3.93 g of 6-(acetoxymethyl)-3-benzoyl-2-methoxypyridine, 8.81 ml of triethylsilane and 30 ml of trifluoroacetic acid was stirred at 60° C. for one hour. After cooling as it was, the mixture was neutralized by adding an aqueous potassium carbonate thereto. Ethyl acetate was added thereto, and the organic phase was washed with water and brine, dried over anhydrous magnesium sulfate and the solvent was removed. After adding 20 ml of methanol and 3.48 g of sodium bicarbonate to the residue, 1.07 ml of bromine was added thereto under ice-cooling, followed by stirring at room temperature for 30 minutes. An aqueous sodium thiosulfate solution and ethyl acetate were added to the reaction solution. The organic phase was washed with water and brine, dried over anhydrous magnesium sulfate and the solvent was removed. To the residue were added 3.10 g of pyrazyltrubutyltin, 1.46 g of tetrakis (triphenylphosphine)palladium(0) and 40 ml of xylene, followed by heating under reflux for 2.5 hours. Silica gel was added to the reaction solution and the solvent was removed. The residue was subjected to silica gel column chromatography using 30% ethyl acetate/hexane, to give 2.18 g of the target compound.

¹H-NMR (CDCl₃) δ=2.02 (3H, s), 3.96 (2H, s), 4.01 (3H, s), 5.29 (2H, s), 7.21–7.33 (5H, m), 7.46 (1H, s), 8.50 (1H, d, J=2 Hz), 8.59–8.60 (1H, m), 8.66 (1H, d, J=1 Hz).

c) 3-Benzyl-6-(tert-butoxycarbonylamino)-2-methoxy-5-pyrazylpyridine 6.24 ml of an aqueous 1N sodium hydroxide solution was added to a mixture of 2.18 g of 6-(acetoxymethyl)-3-benzyl-2-methoxy-5-pyrazylpyridine and 20 ml of methanol at ambient temperature, followed by stirring at the same temperature. Water and ethyl acetate were added to the reaction solution, and the organic phase was washed with water and brine, dried over anhydrous magnesium sulfate and the solvent was removed. 14.1 ml of a Jone's reagent was added to a solution of the residue in 20 ml of acetone, followed by stirring at room temperature overnight. 6 ml of 2-propanol was added to the reaction mixture, followed by extracting with ethyl acetate. The organic phase was washed with water and brine, dried over anhydrous magnesium sulfate and the solvent was removed. A mixture of the residue, 25 ml of tert-butanol, 733 μl of triethylamine and 1.13 g of diphenyl phosphorylazide was stirred at room temperature for 3 hours. After evaporating the solvent, the residue was subjected to silica gel column chromatography using 25% ethyl acetate/hexane, to give 212 mg of the target compound.

¹H-NMR (CDCl₃) δ=1.51 (9H, s), 3.93 (2H, s), 4.08 (3H, s), 7.19–7.31 (5H, m), 7.65 (1H, s), 8.42 (1H, d, J=2 Hz), 8.52–8.54 (1H, m), 8.80 (1H, d, J=1 Hz).

d) 3-[6-(Methyamino)-3-benzy-5-pyrazyl-2-pyridyl]ethynyl-3-quinuclidinol 11.8 mg of 60% oily sodium hydride was added to a mixture of 77.2 mg of 3-benzyl-6-(tert-butoxycarbonylamino)-2-methoxy-5-pyrazylpyridine and 1 ml of N,N-dimethylformamide under ice-cooling. After stirring at the same temperature for 5 minutes, 14.7 μl of methyl iodide was added thereto. After stirring at room temperature for 2 hours, water and ethyl acetate were added thereto. The organic phase was washed with water and brine, dried over anhydrous magnesium sulfate and the solvent was removed. A mixture of the residue and 2 ml of 48% hydrobromic acid was stirred at 80° C. for 2 hours. After cooling as it was, it was neutralized using an aqueous potassium carbonate solution. The resulting crystals were collected by filtration and vacuum-dried. Then, 3 ml of N,N-dimethylformamide, 40.4 mg of N-phenyltrifluoromethanesulfonimide, 47.2 μl of triethylamine and 1.4 mg of 4-dimethylaminopyridine were added thereto, followed by stirring at room temperature for 13 hours. The reaction solution was filtered through silica gel, and the solvent was evaporated. A mixture of the residue, 12.1 mg of 3-ethynyl-3-quinuclidinol, 16.9 mg of tetrakis(triphenylphosphine)palladium(0), 2.8 mg of cuprous iodide, 30.5 μl of triethylamine and 1 ml of N,N-dimethylformamide was stirred at 70° C. for one hour in a nitrogen atmosphere. To the reaction mixture was added NH-silica gel, followed by removing the solvent. The residue was subjected to NH-silica gel column chromatography using 3% methanol/ethyl acetate, to give 15.9 mg of the target compound.

¹H-NMR (CDCl₃) δ=1.34–1.42 (1H, m), 1.52–1.60 (1H, m), 1.83–1.92 (1H, m), 1.98–2.07 (2H, m), 2.70–2.82 (4H, m), 3.02 (1H, d, J=14 Hz), 3.11 (3H, d, J=5 Hz), 3.25 (1H, dd, J=2, 14 Hz), 4.09 (2H, s), 7.18–7.22 (3H, m), 7.26–7.31 (2H, m), 7.68 (1H, s), 8.44 (1H, d, J=2 Hz), 8.50–8.51 (1H, m), 8.53–8.55 (1H, m), 8.92 (1H, d, J=1 Hz).

Example 34

3-[3-Benzyl-5-(1-hydroxycyclopentyl)ethynyl-2-pyridyl]ethynyl-3-quinuclidinol 100 mg of 3-(3-benzyl-5-bromo-2-pyridyl)ethynyl-3-quinuclidinol (Example 22-a), 55 mg of 1-ethynylcyclopentanol, 50 mg of tetrakis(triphenylphosphine)palladium(0), 10 mg of cuprous iodide and 1 ml of triethylamine were mixed in 5 ml of N,N-dimethylformamide, followed by stirring in an oil bath kept at 80° C. for one hour. An aqueous sodium carbonate solution was added thereto, followed by extracting with ethyl acetate. The extract was washed with brine, dried over anhydrous magnesium sulfate and evaporated. The residue was subjected to NH-silica gel column chromatography and eluted with 10% methanol/ethyl acetate, to give 93 mg of the target compound.

¹H-NMR (CDCl₃) δ=1.33–1.43 (1H, m), 1.52–1.62 (1H, m), 1.70–1.92 (5H, m), 1.95–2.10 (6H, m), 2.69–2.94 (4H, m), 3.07 (1H, d, J=14 Hz), 3.26 (1H, dd, J=2, 14 Hz), 4.03 (2H, s), 7.12 (2H, d, J=7 Hz), 7.22 (1H, t, J=7 Hz), 7.29 (2H, t, J=7 Hz), 7.43 (1H, d, J=2 Hz), 8.50 (1H, d, J=2 Hz).

Example 35

3-[3-Benzyl-5-(N-phenylcarbomyl)-2-pyridyl]ethynyl-3-quinclidinol a) 3-Benzyl-2-methoxpyridine-5-carbomyl Acid 11.1 g of 3-benzyl-5-bromo-2-methoxypyridine (Production Example 5-b) was dissolved in 70 ml of diethyl ether. 30 ml of a hexane solution containing 1.6 mol of n-butyllithium was added dropwise thereinto in a dry ice-acetone bath. After one hour, carbon dioxide was blown into the reaction solution, followed by adding water. After washing the aqueous phase with diethyl ether, 50 ml of 1N hydrochloric acid was added thereto, followed by extracting with ethyl acetate. The extract was washed with brine, dried over anhydrous magnesium sulfate anhydride and evaporated. The residue was crystallized from hexane-ethyl acetate, to give 7.76 g of the target compound.

¹H-NMR (CDCl₃) δ=3.93 (2H, s), 4.04 (3H, s), 7.18–7.33 (5H, m), 7.92 (1H, d, J=2 Hz), 8.77 (1H, d, J=2 Hz).

b) 3-Benzyl-5-(N-phenylcaramoyl)-2-methoxypyridine 200 mg of 3-benzyl-2-methoxypyridine-5-carboxylic acid and 0.25 ml of pyridine were dissolved in 5 ml of dichloromethane. Under ice-cooling, 0.073 ml of thionyl chloride was added dropwise thereinto. After stirring for 30 minutes, 0.1 ml of aniline was added thereto. The temperature was raised to room temperature and the mixture was stirred for 30 minutes. After adding water, the mixture was extracted with ethyl acetate. The extract was washed with 1N hydrochloric acid and brine, dried over anhydrous magnesium sulfate and evaporated, to give 275 mg of the target compound.

¹H-NMR (CDCl₃) δ=3.97 (2H, s), 4.04 (3H, s), 7.15 (1H, t, J=7 Hz) 7.20–7.40 (7H, m), 7.58 (2H, d, J=7 Hz), 7.81 (1H, d, J=2 Hz), 8.55 (1H, d, J=2 Hz).

c) 3-Benzyl-5-(N-phenylcarbomyl)-2-pyridyl Trifluoromethesulfonate 275 mg of 3-benzyl-5-(N-phenylcarbamoyl)-2-methoxypyridine was dissolved in 5 ml of 1,2-dichloroethane. 0.5 ml of dichloromethane solution containing 1 mol of boron tribromide was added thereto, follwed by stirring at 50° C. for 3 hours. Aqueous ammonium chloride was added thereto and the mixture was extracted with ethyl acetate. The extract was washed with brine and then evaporated. To the residue were added 360 mg of N-phenyltrifluoromethanesulfonimide, 10 mg of 4-dimethylaminopyridine, 0.4 ml of triethylamine and 5 ml of dichloromethane, followed by stirring at room temperature overnight. The reaction solution was subjected to silica gel column chromatography and eluted with 30% ethyl acetate/hexane, to give 150 mg of the target compound.

¹H-NMR (CDCl₃) δ=4.09 (2H, s), 7.17–7.42 (8H, m), 7.57 (2H, d, J=8 Hz), 7.69 (1H, brs), 8.10 (1H, d, J=2 Hz), 8.65 (1H, d, J=2 Hz).

d) 3-[3-Benzyl-5-(N-phenylcarbamoyl)-2-pyridyl]ethynyl-3-quinuclidinol 150 mg of 3-benzyl-5-(N-phenylcarbamoyl)-2-pyridyl trifluoromethanesulfonate, 60 mg of 3-ethynyl-3-quinuclidinol, 50 mg of tetrakis (triphenylphosphine) palladium(0), 10 mg of cuprous iodide and 0.15 ml of triethylamine were added to 2 ml of N,N-dimethylformamide, followed by stirring for 3 hours in an oil bath kept at 50° C. After cooling as it was, aqueous ammonia was added thereto and the mixture was extracted with ethyl acetate. The extract was washed with brine, dried over anhydrous magnesium sulfate and evaporated. The residue was subjected to NH-silica gel column chromatography, to synthesize 90 mg of the target compound.

¹H-NMR (CDCl₃) δ=1.35–1.92 (3H, m), 1.98–2.10 (2H, m), 2.70–2.95 (4H, m), 3.07 (1H, d, J=14 Hz), 3.27 (1H, dd, J=2, 14 Hz), 4.20 (2H, s), 7.14–7.19 (3H, m), 7.24 (1H, t, J=7 Hz), 7.31 (2H, t, J=7 Hz), 7.36 (2H, t, J=8 Hz), 7.58 (2H, d, J=8 Hz), 7.98 (1H, d, J=2 Hz), 8.00 (1H, brs), 8.87 (1H, d, J=2 Hz).

Example 36

3-[3-Benzyl-5-[N-(4-fluorophenyl)carbamoyl]-2-pyridyl)ethynyl-3-quinclidinol

The title compound was synthesized in the same manner as in Example 35.

¹H-NMR (CDCl₃) δ=1.34–1.44 (1H, m), 1.54–1.64 (1H, m), 1.78–1.89 (1H, m), 1.99–2.09 (2H, m), 2.66–2.95 (4H, m), 3.08 (1H, d, J=14 Hz), 3.25 (1H, dd, J=2, 14 Hz), 4.15 (2H, s), 7.00 (2H, t, J=8 Hz), 7.13 (2H, d, J=7 Hz), 7.22 (1H, t, J=7 Hz), 7.28 (2H, t, J=7 Hz), 7.48–7.56 (2H, m), 7.93 (1H, d, J=2 Hz), 8.48 (1H, brs), 8.80 (1H, d, J=2 Hz).

Example 37

3-[3-Benzyl-5-(N-cyclohexlcarbamoyl)-2-pyridyl]ethynyl-3-quinclidinol

The target compound was synthesized in the same manner as in Example 35.

¹H-NMR (CDCl₃) δ=1.24–190 (11H, m), 1.97–2.10 (4H, m), 2.65–2.95 (4H, m), 3.06 (1H, dd, J=2, 14 Hz), 3.24 (1H, dd, J=2, 14 Hz), 3.88–4.00 (1H, m), 4.16 (2H, S), 6.10 (1H, d, J=8 Hz), 7.14 (2H, d, J=7 Hz), 7.22 (1H, t, J=7 Hz), 7.28 (2H, t, J=7 Hz), 7.89 (1H, d, J=2 Hz), 8.72 (1H, d, J=2 Hz).

Example 38

3-[3-Benzyl-5-(1-pyrrolidinylcarbamoyl)-2-pyridyl]ethynyl-3-quinclidinol

The target compound was synthesized in the same manner as in Example 35.

¹H-NMR (CDCl₃) δ=1.35–1.65 (2H, m), 1.83–2.10 (7H, m), 2.70–2.95 (4H, m), 3.04 (1H, d, J=14 Hz), 3.27 (1H, dd, J=2, 14 Hz), 3.38 (2H, t, J=7 Hz), 3.62 (2H, t, J=7 Hz), 4.18 (2H, s), 7.17 (2H, d, J=7 Hz), 7.24 (1H, t, J=7 Hz), 7.31 (2H, t, J=7 Hz), 7.63 (1H, d, J=2 Hz), 8.62 (1H, d, J=2 Hz).

Example 39

3-[3-Benzyl-5-methoxcarbonyl-2-pyridyl)ethynyl-3-quinuclidinol a) 3-Benzyl-2-methoxy-5-methoxycarbonylpyridine A mixture of 2.1 g of 3-benzyl-2-methoxypyridine-5-carboxylic acid and 2.9 g of potassium carbonate was suspended in 40 ml of N,N-dimethylformamide. 1.1 ml of methyl iodide was added-thereto at room temperature under stirring. After stirring for 40 minutes, water was added thereto and extracted with ethyl acetate. The organic phase was further washed with brine, dried over anhydrous sodium sulfate and the solvent was evaporated. The residue was subjected to silica gel column chromatography using 11–14% ethyl acetate/hexane as an eluent for separation and purification, to give 2.2 g of the target compound.

¹H-NMR (CDCl₃) δ=3.87 (3H, s), 3.92 (2H, s), 4.02 (3H, s), 7.18–7.32 (5H, m), 7.90 (1H, dd, J=2.3 Hz, 0.7 Hz), 8.70 (1H, d, J=2.3 Hz).

b) 3-Benzyl-2-hydroxy-5-methoxycarbonylridine 2.2 g of 3-benzyl-2-methoxy-5-methoxycarbonylpyridine was dissolved in 40 ml of 1,2-dichloroethane. 8.5 ml of a dichloromethane solution containing 1.0 mol of boron tribromide was added thereto in a nitrogen atmosphere, followed by heating under stirring at 50° C. in an oil bath overnight. After cooling as it was, water was added thereto and the solvent was removed at a low temperature. The residue was subjected to silica gel column chromatography using 50–60% ethyl acetate/hexane as an eluent for separation and purification to give 1.2 g of the target compound.

¹H-NMR (CDCl₃) δ=3.83 (3H, s), 3.87 (2H, s), 7.20–7.34 (5H, m), 7.73 (1H, d, J=2.4 Hz), 8.11 (1H, d, J=2.4 Hz).

c) 3-Benzyl-5-methoxycarbonyl-2-pyridyl Trifluoromethanesulfonate 1.2 g of 3-benzyl-2-hydroxy-5-methoxycarbonylpyridine was dissolved in 40 ml of 1,2-dichloroethane. 2.3 g of N-phenyltrifluoromethanesulfonimide, 202 mg of 4-dimethylaminopyridine and 0.9 ml of triethylamine were added thereto, followed by stirring at room temperature for 3 hours. Then, the solvent was removed, and the residue was subjected to silica gel column chromatography using 11% ethyl acetate/hexane as an eluent for separation and purification, to give 2.0 g of the target compound.

¹H-NMR (CDCl₃) δ=3.93 (3H, s), 4.05 (2H, s), 7.16–7.43 (5H, m), 8.20 (1H, d, J=2.3 Hz), 8.82 (1H, d, J=2.3 Hz).

d) 3-[Benzyl-5-methoxycarbonyl-2-pyridyl]ethynyl-3-quinuclidinol 50 ml of N,N-dimethylformamide was added to a mixture of 2.0 g of 3-benzyl-5-methoxycarbonyl-2-pyridyl trifluoromethanesulfonate, 742 mg of 3-ethynyl-3-quinuclidinol, 1.5 g of tetrakis(triphenylphosphine) palladium(0), 374 mg of cuprous iodide and 2.7 ml of triethylamine, followed by heating under stirring for one hour in an oil bath kept at 60° C. in a nitrogen atmosphere. After cooling as it was, ethyl acetate and aqueous ammonia were added thereto and the mixture was extracted with ethyl acetate. The organic phase was further washed with brine, dried over anhydrous magnesium sulfate and the solvent was removed. The residue was subjected to silica gel column chromatography using chloroform/methanol/aqueous 36% ammonia (46:3:0.3) as an eluent for separation and purification, to give 1.1 g of the target compound.

¹H-NMR (CDCl₃) δ=1.38–1.48 (1H, m), 1.58–1.68 (1H, m), 1.82–1.92 (1H, m), 2.00–2.14 (2H, m), 2.70–2.98 (4H, m), 3.09 (1H, dd, J=14 Hz, 1.8 Hz), 3.27 (1H, dd, J=14 Hz, 2.0 Hz), 3.92 (3H, s), 4.19 (2H, s), 7.12–7.74 (5H, m), 8.09 (1H, d, J=2.0 Hz), 9.04 (1H, d, J=2.0 Hz).

Example 40

3-[3-Benzyl-5-(N-methoxcarbonylamino)-2-pyridyl]ethynyl-3-quinuclidinol a) 3-Benzyl-5-tert-butoxycarbonylamino-2-methoxypyridine 7.34 g of 3-benzyl-2-methoxypyridine-5-carboxylic acid (Example 35-a), 6.5 ml of diphenylphosphorylazide and 4.2 ml of triethylamine were mixed in 100 ml of tert-butanol, followed by heating under reflux overnight. After evaporating the reaction solution, it was partitioned by adding water and ethyl acetate thereto, washed with brine, dried over anhydrous magnesium sulfate and then evaporated. The residue was subjected to silica gel column chromatography, to synthesize 9.37 g of the target compound.

$^1$H-NMR (CDCl$_3$) δ=1.48 (9H, s), 3.89 (2H, s), 3.92 (3H, s), 6.25 (1H, brs), 7.17–7.31 (5H, m), 7.48 (1H, brs), 7.92 (1H, brs).

b) 3-Benzyl-5-(N-methyl-tert-butoxycarbonylamino)-2-methoxypyridine 970 mg of 3-benzyl-5-tert-butoxycarbonylamino-2-methoxypyridine was dissolved in 10 ml of N,N-dimethylformamide, followed by. adding 200 mg of 60% oily sodium hydride thereto. After stirring at room temperature, 0.192 ml of methyl iodide was added thereto in an ice bath. After the returned to room temperature, water was added and the mixture was extracted with ethyl acetate. The extract was washed with brine, dried over anhydrous magnesium sulfate and evaporated, to give 920 mg of the target compound.

$^1$H-NMR (CDCl$_3$) δ=1.37 (9H, brs), 3.17 (3H, s), 3.89 (2H, s), 3.96 (3H, s), 7.13 (1H, brs), 7.18–7.25 (3H, m), 7.30 (2H, d, J=7 Hz), 7.88 (1H, d, J=2 Hz).

c) 3-Benzyl-5-(N-methylamino)-2-methoxypyridine 920 mg of 3-benzyl-5-(N-methyl-tert-butoxycarbonylamino)-2-methoxypyridine was dissolved in 5 ml of ethyl acetate, followed by adding 10 ml of 4N hydrochloric acid/ethyl acetate thereto. The resulting solid (640 mg) was collected by filtration. To the solid (230 mg) were added 10 ml of ethyl acetate, 150 mg of benzoyl chloride and 0.5 ml of pyridine in an ice bath, followed by stirring. After adding water thereto, the mixture was extracted with ethyl acetate. The extract was washed with 1N hydrochloric acid, aqueous saturated sodium hydrogencarbonate and brine, dried over anhydrous magnesium sulfate and then evaporated, to give 270 mg of the target compound.

$^1$H-NMR (CDCl$_3$) δ=3.42 (3H, s), 3.75 (2H, s), 3.89 (3H, s), 6.80–6.95 (3H, m), 7.15–7.30 (8H, m), 7.80 (1H, brs).

d) 3-[3-Benzyl-5-(N-methylbenzoylamino)-2-pyridyl]ethynyl-3-quinuclidinol

The target compound was synthesized in the same manner as in Example 35-c.

$^1$H-NMR (CDCl$_3$) δ=1.35–1.46 (1H, m), 1.54–1.64 (1H, m), 1.75–1.85 (1H, m), 2.01–2.12 (2H, m), 2.60–2.90 (4H, m), 2.98 (1H, dd, J=2, 14 Hz), 3.15 (1H, dd, J=2, 14 Hz), 3.47 (3H, s), 4.00 (2H, s), 6.85–6.89 (2H, m), 7.04 (1H, d, J=2 Hz), 7.18–7.27 (7H, m), 7.31–7.35 (1H, m), 8.19 (1H, d, J=2 Hz)

Example 41

3-(3-Benzyl-5-(N-methylbenensulfonylamino)-2-pyridyl)ethynyl-3-quinuclidinol The target compound was synthesized in the same manner as in Example 40.

$^1$H-NMR (CDCl$_3$) δ=1.35–1.95 (3H, m), 1.98–2.08 (2H, m), 2.70–2.95 (4H, m), 3.03 (1H, d, J=14 Hz), 3.15 (3H, s), 3.25 (1H, dd, J=2, 14 Hz), 4.11 (2H, s), 7.11 (2H, d, J=7 Hz), 7.22–7.33 (4H, m), 7.42 (2H, t, J=7 Hz), 7.50 (2H, dd, J=2, 8 Hz), 7.57 (1H, t, J=7 Hz), 8.16 (1H, d, J=3 Hz).

Example 42

3-(2-Allyl-6-pyrazyl-3-pyridyl)ethynyl-3-quinuclidinol

2-Allyl-6-pyrazyl-3-pyridyl Trifluoromethane Sulfonate

A mixture of 1.22 g of 2-bromo-6-iodo-3-pyridyl trifluoromethanesulfonate (Production Example 17), 1.04 g of pyrazyltributyltin, 326 g of tetrakis(triphenylphosphine)palladium(0) and 10 ml of xylene was stirred at 140° C. for 2 hours. After cooling to room temperature as it was, the mixture was filtered using silica gel and the solvent was evaporated. A mixture of the residue, 868 μl of allyltributyltin, 324 mg of tetrakis(triphenylphosphine)palladium(0) and 10 ml of toluene was heated under reflux for 1.5 hours. After cooling to room temperature as it was, silica gel was added to the mixture and the solvent was evaporated. The residue was subjected to silica gel column chromatography and eluted with 20% ethyl acetate/hexane, to give 500 mg of the target compound.

$^1$H-NMR (CDCl$_3$) δ=3.79 (2H, d, J=6 Hz), 5.20–5.26 (2H, m), 6.11–6.21 (1H, m), 7.75 (1H, d, J=12 Hz), 8.37 (1H, d, J=12 Hz), 8.60–8.63 (2H, m), 9.68 (1H, s).

b) 3-(2-Allyl-6-pyrazyl-3-pyridyl)ethynyl-3-quinuclidinol

A mixture of 500 mg of 2-allyl-6-pyrazyl-3-pyridyl trifluoromethanesulfonate, 203 mg of 3-ethynyl-3-quinuclidinol, 155 mg of tetrakis(triphenylphosphine)palladium(0), 25.5 mg of cuprous iodide, 0.560 ml of triethylamine and 5 ml of N,N-dimethylformamide was stirred at 65° C. for 20 minutes in a nitrogen atmosphere. After cooling as it was, NH-silica gel was added to the reaction mixture and the solvent was removed. The residue was subjected to NH-silica gel column chromatography using 2.5% methanol/ethyl acetate, to give 428 mg of the target compound.

$^1$H-NMR (CDCl$_3$) δ=1.42–1.50 (1H, m), 1.66–1.75 (1H, m), 1.97–2.14 (3H, m), 2.82–2.98 (4H, m), 3.11 (1H, d, J=14 Hz), 3.36 (1H, dd, J=2, 14 Hz), 3.84 (2H, d, J=6 Hz), 5.14–5.20 (2H, m), 6.13–6.22 (1H, m), 7.83 (1H, d, J=12 Hz), 8.19 (1H, d, J=12 Hz), 8.57–8.60 (2H, m), 9.68 (1H, s).

Example 43

3-(3-Allyl-6-phenyl-3-pyridyl)ethynyl-3-quinuclidinol

The title compound was synthesized in the same manner as in Example 42.

$^1$H-NMR (CDCl$_3$) δ=1.42–2.16 (5H, m), 2.82–2.96 (4H, m), 3.10 (1H, d, J=14 Hz), 3.34 (1H, dd, J=2, 14 Hz), 3.83 (2H, d, J=6 Hz), 5.14–5.18 (2H, m), 6.13–6.23 (1H, m), 7.39–7.57 (5H, m), 7.73 (1H, d, J=8 Hz), 8.03 (1H, d, J=8 Hz).

Example 44

3-[2-Allyl-6-(3-pyridyl)-3-pyridyl]ethynyl-3-quinuclidinol

The title compound was synthesized in the same manner as in Example 42.

$^1$H-NMR (CDCl$_3$) δ=1.42–1.50 (1H, m), 1.65–1.74 (1H, m), 1.96–2.13 (3H, m), 2.81–2.95 (4H, m), 3.10 (1H, d, J=14 Hz), 3.34 (1H, dd, J=2, 14 Hz), 3.79–3.80 (2H, m), 5.11–5.19 (2H, m), 6.11–6.21 (1H, m), 7.39–7.42 (1H, m), 7.52–7.56 (1H, m), 7.72–7.76 (1H, m), 8.35–8.37 (1H, m), 8.63–8.64 (1H, m), 9.21 (1H, s).

Example 45

3-[2-(2-Methyl-2-propenyl)-6-pyrazyl-3-pyridyl]ethynyl-3-quinuclidinol a) 2-(2-methyl-2-propenyl)-6-pyrazyl-3-pyridyl Trifluoromethanesulfonate A mixture of 220 mg of 2-bromo-6-iodo-3-pyridyl trifluoromethane sulfonate, 187 mg of pyrazyltributyltin, 58.7 mg of tetrakis(triphenylphosphine)palladium(0) and 2ml of xylene was stirred at 140° C. for 2 hours. After cooling to room temperature as it was, the mixture was filtered through silica gel and the solvent was evaporated. To the residue were added 1.20 ml of 2-methyl-2-propenyltributyltin (Production Example 21), 60.2 mg of tetrakis(triphenylphosphine)palladium(0) and 3 ml of xylene, followed by heating under reflux for 2 hours. After cooling to room temperature as it was, silica gel was added thereto and the solvent was evaporated. The residue was subjected to silica gel column chromatography and eluted with 20% ethyl acetate/hexane, to give 83.1 mg of the target compound.

$^1$H-NMR (CDCl$_3$) δ=1.83 (3H, s), 3.71 (2H, s), 4.73 (1H, s), 4.92 (1H, s), 7.75 (1H, d, J=8 Hz), 8.36 (1H, d, J=8 Hz), 8.60–8.62 (2H, m), 9.66 (1H, s).

b) 3-[2-(2-Methyl-2propenyl)-6-pyrazyl-3-pyridyl]ethynyl-3-quinuclidionol

A mixture of 83.1 mg of 2-(2-methyl-2-propenyl)-6-pyrazyl-3-pyridyl trifluoromethane sulfonate, 35.0 mg of 3-ethynyl-3-quinuclidinol, 13.3 mg of tetrakis(triphenylphosphine)palladium(0), 2.2 mg of cuprous iodide, 96.6 μl of triethylamine and 1 ml of N,N-dimethylformamide was stirred at room temperature for one hour in a nitrogen atmosphere. NH-silica gel was added to the reaction solution, and the solvent was removed. The residue was subjected to NH-silica gel column chromatography using 2.5% methanol/ethyl acetate, to give 71.2 mg of the target compound.

$^1$H-NMR (CDCl$_3$) δ=1.42–1.49 (1H, m), 1.65–1.74 (1H, m), 1.85 (3H, s), 1.97–2.12 (3H, m), 2.78–2.95 (4H, m), 3.10 (1H, d, J=14 Hz), 3.34 (1H, dd, J=2, 14 Hz), 3.78 (2H, s), 4.70 (1H, s), 4.88 (1H, s), 7.83 (1H, d, J=8 Hz), 8.19 (1H, d, J=8 Hz), 8.58–8.60 (2H, m), 9.67 (1H, d, J=2 Hz).

Example 46

3-2-[2-Benzyl-6-(4-pyridazyl)-3-pyridyl]ethynyl-3-quinuclidinol

The target compound was synthesized in the same manner as in Example 14.

$^1$H-NMR (CDCl$_3$) δ=1.41–1.48 (1H, m), 1.63–1.91 (2H, m), 2.04–2.09 (2H, m), 2.76–2.92 (4H, m), 3.07 (1H, d, J=14 Hz), 3.26 (1H, d, J=14 Hz), 4.41 (2H, s), 7.19–7.33 (5H, m), 7.65 (1H, d, J=8 Hz) 7.80 (1H, d, J=8 Hz), 8.04–8.06 (1H, m), 9.27–9.29 (1H, m), 9.78–9.79 (1H, m).

Example 47

(3R)-3-[2-Benzyl-6-(3-pyridazyl)-3-pyridyl]ethynyl-3-pyridyl]ethynyl-3-quinuclidinol The target compound was synthesized in the same manner as in Example 14.

$^1$H-NMR (CDCl$_3$) δ=1.43–1.47 (1H, m), 1.60–1.87 (2H, m), 2.05–2.08 (2H, m), 2.71–2.99 (4H, m), 3.05 (1H, d, J=14 Hz), 3.25 (1H, dd, J=2, 14 Hz), 4.42 (2H, s), 7.21–7.30 (5H, m), 7.52–7.60 (1H, m), 7.87 (1H, d, J=8 Hz), 8.54–8.58 (2H, m), 9.17–9.19 (1H, m).

Example 48

3-[2-Benzyl-6-(1,4-dioxene-2-yl)-3-pyridyl]ethynyl-3-quinuclidinol

The target compound was synthesized in the same manner as in Example 14.

$^1$H-NMR (CDCl$_3$) δ=1.39–1.41 (1H, m), 1.59–1.61 (1H, m), 1.80–1.87 (1H, m), 2.01–2.05 (2H, m), 2.72–2.87 (4H, m), 3.00 (1H, d, J=14 Hz), 3.20 (1H, dd, J=2, 14 Hz), 4.16–4.27 (6H, m), 7.16–7.27 (6H, m), 7.34 (1H, s), 7.61 (1H, d, J=8 Hz).

Example 49

3-[2-Benzyl-6-(3-oxo-1-cyclohexenyl)-3-pyridyl]ethynyl-3-quinclidinol

The target compound was synthesized in the same manner as in Example 14 by using (3-oxo-1-cyclohexenyl)tributyltin synthesized according to literature (Tetrahedron Letters, Vol. 31, No. 13, 1837 (1990)).

$^1$H-NMR (CDCl$_3$) δ=1.42–1.44 (1H, m), 1.63–1.99 (2H, m), 2.00–2.17 (4H, m), 2.49–2.52 (2H, m), 2.77–2.91 (6H, m), 3.04 (1H, d, J=14 Hz), 3.24 (1H, dd, J=2, 14 Hz), 4.34 (2H, s), 6.81 (1H, t, J=1 Hz), 7.19–7.32 (5H, m), 7.44 (1H, d, J=8 Hz), 7.71 (1H, d, J=8 Hz).

Example 50

3-[2-Benzyl-6-(3,4-dihydro-2H-6-pyranyl)-3-pyridyl]ethynyl-3-quinuclidinol

The target compound was synthesized in the same manner as in Example 14 by using (3,4-dihydro-2H-6-pyranyl)tributyltin synthesized with reference to a literature (Synlett 152 (1994)).

$^1$H-NMR (CDCl$_3$) δ=1.38–1.48 (1H, m), 1.66–1.82 (2H, m), 1.89–2.04 (4H, m), 2.52–2.30 (2H, m), 2.74–2.94 (4H, m), 3.00 (1H, d, J=14 Hz), 3.20 (1H, dd, J=2, 14 Hz), 4.17–4.20 (2H, m), 4.32 (2H, s), 6.15–6.17 (1H, m), 7.17–7.26 (5H, m), 7.38 (1H, d, J=8 Hz), 7.65 (1H, d, J=8 Hz).

Example 51

3-[2-Benzyl-6-(2-hydroxyphenyl)-3-pyridyl]ethynyl-3-quinuclidinol a) 2-Benzyl-3-hydroxy-6-(2-hydroxyphenyl)pyridine A mixture of 641 mg of (2-benzyl-3-methoxymethyloxy-6-pyridyl)tributyltin (Production Example 18), 327 mg of 2-methoxymethyloxyiodobenzene (Production Example 20), 71.6 mg of tetrakis(triphenylphosphine)palladium(0) and 7 ml of xylene was heated under refluxed for one hour in nitrogen atmosphere. After cooling as it was, the mixture was filtered through silica gel and the solvent was removed. To the residue was added 2 ml of trifluoroacetic acid, followed by stirring at room temperature overnight. The reaction solution was neutralized by aqueous potassium carbonate. Ethyl acetate was added thereto, and the organic phase was washed with water and brine, dried over anhydrous magnesium sulfate and the solvent was removed. The residue was subjected to silica gel column chromatography using 30% ethyl acetate/hexane, to give 54.5 mg of the target compound.

$^1$H-NMR (CDCl$_3$) δ=4.24 (2H, s), 6.85–6.90 (1H, m), 6.96–6.99 (1H, m), 7.21–7.27 (3H, m), 7.33–7.34 (4H, m), 7.68–7.70 (2H, m).

b) 2-Benzyl-6-(2-hydroxyphenyl)-3-pyridyl Trifluoromethane Sulfonate

A mixture of 54.5 mg of 2-benzyl-3-hydroxy-6-(2-hydroxyphenyl)pyridine, 70.2 mg of N-phenyltrifluoromethanesulfonimide, 824 µl of triethylamine, 1.2 mg of 4-dimethylaminopyridine and 1.5 ml of dichloromethane was stirred at room temperature for 2.5 hours. Silica gel was added to the reaction solution, and the solvent was removed. The residue was subjected to silica gel column chromatography using 12% ethyl acetate/hexane, to give 68.5 mg of the target compound.

$^1$H-NMR (CDCl$_3$) δ=4.29 (2H, s), 6.88–6.92 (1H, m), 6.95–6.98 (1H, m), 7.28–7.32 (4H, m), 7.35–7.39 (2H, m), 7.70–7.76 (2H, m), 7.83 (1H, d, J=8 Hz), 12.81 (1H, s).

c) 3-[2-Benzyl-6-(2-hydroxyphenyl)-3-pyridyl]ethynyl-3-quinuclidinol

A mixture of 67.0 mg of 2-benzyl-6-(2-hydroxyphenyl)-3-pyridyl trifluoromethane sulfonate, 24.7 mg of 3-ethynyl-3-quinuclidinol, 19.0 mg of tetrakis(triphenylphosphine)palladium(0), 0.1 mg of cuprous iodide, 68.6 µl of triethylamine and 1.5 ml of N,N-dimethylformamide was heated under stirring at 100° C. for 2 hours in a nitrogen atmosphere. NH-silica gel was added to the reaction solution, and the solvent was removed. The residue was subjected to NH-silica gel column chromatography using 3% methanol/ethyl acetate, to give 56.8 mg of the target compound.

$^1$H-NMR (CDCl$_3$) δ=1.40–1.48 (1H, m), 1.52–1.60 (1H, m), 1.88–2.10 (3H, m), 2.80–2.90 (4H, m), 3.08 (1H, d, J=14 Hz), 3.28 (1H, dd, J=2, 14 Hz), 4.36 (2H, s), 6.85–6.89 (1H, m), 6.96 (1H, d, J=8 Hz), 7.24–7.34 (6H, m), 7.67–7.72 (2H, m), 7.78 (1H, d, J=8 Hz), 13.81 (1H, s).

Example 52

(3R)-3-[2-Benzyl-6-(1,3,4-thiadazole-2-yl)-3-pyridyl]ethynyl-3-quinuclidinol

The target compound was synthesized in the same manner as in Example 51 by using 2-iodo-1,3,4-thiadiazole (Production Example 22).

$^1$H-NMR (CDCl$_3$) δ=1.41–1.44 (1H, m), 1.62–1.98 (2H, m), 2.01–2.07 (2H, m), 2.50–2.95 (4H, m), 3.05 (1H, d, J=14 Hz), 3.24 (1H, dd, J=2, 14 Hz), 4.37 (2H, s), 7.19–7.29 (5H, m), 7.82 (1H, d, J=8 Hz), 8.18 (1H, d, J=8 Hz), 9.16 (1H, s).

Example 53

3-[2-(4-Methoxybenzyl)-6-methyl-3-pyridyl]ethynyl-3-quinuclidinol a) 3-Benzyloxy-2-[(4-hydroxyphenyl)hydroxymethyl]-6-methylpyridine A 1.6 mol solution of n-butyllithium in hexane was added dropwise to a mixture of 2.43 g of 4-bromoanisole and 20 ml of diethyl ether at −50° C., followed by stirring at −20° C. for 30 minutes. Further, a mixture of 2.27 g of 3-benzyloxy-6-methylpyridine-2-carboxyaldehyde (Production Example 11-b) and 50 ml of diethyl ether was added thereto at −60° C. over 15 minutes. After stirring at the same temperature for 30 minutes, aqueous saturated ammonium chloride was added to the reaction solution. The mixture was extracted with ethyl acetate, and the organic phase was washed with brine, dried over anhydrous magnesium sulfate and concentrated. The residue was subjected to silica gel column chromatography using 5–20% ethyl acetate/hexane, to give 1.16 g of the target compound.

$^1$H-NMR (CDCl$_3$) δ=2.52 (3H, s), 3.77 (3H, s), 4.92 (1H, d, J=12 Hz) 4.98 (1H, d, J=12 Hz), 5.75 (1H, d, J=6 Hz), 5.87 (1H, d, J=6 Hz), 6.79 (2H, d, J=9 Hz), 6.98 (1H, d, J=8 Hz), 7.03 (1H, d, J=8 Hz), 7.10–7.15 (2H, m), 7.23 (2H, d, J=9 Hz), 7.27–7.34 (3H, m).

b) 3-Hydroxy-2-(4-methoxybenzyl)-6-methylpyridine

A mixture of 0.87 g of 3-benzyloxy-2-[(4-methoxyphenyl)hydroxymethyl]-6-methylpyridine, 2.5 ml of acetic acid anhydride and 20 ml of pyridine was heated under stirring for 4 hours in an oil bath kept at 120° C. After the reaction solution was evaporated, water was added thereto. The mixture was extracted with ethyl acetate, and the organic phase was washed with brine, dried over anhydrous magnesium sulfate and concentrated. To the residue were added 20 ml of methanol, 10 ml of tetrahydrofuran and a catalytic amount of 10% palladium/carbon, followed by stirring for 10 hours in a hydrogen atmosphere. After the catalyst was filtered off, the filtrate was concentrated. Then, the crystals were washed with diethyl ether, to give 320 mg of the target compound.

$^1$H-NMR (d$_6$-DMSO) δ=2.32 (3H, s), 3.69 (3H, s), 3.92 (2H, s), 6.80 (2H, d, J=8 Hz), 6.92 (1H, d, J=7 Hz), 7.07 (1H, d, J=7 Hz), 7.14 (2H, d, J=8 Hz).

c) 2-(4-Methoxybenzyl)-6-methyl-3-pyridyl Trifluoromethanesulfonate

A mixture of 160 mg of 3-hydroxy-2-(4-methoxybenzyl)-6-methylpyridine, 300 mg of N-phenyltrifluoromethanesulfonimide, 146 µl of triethylamine, 26 mg of 4-dimethylaminopyridine and 5.0 ml of dichloromethane was stirred at room temperature for 2 hours. Water was added to the reaction solution, and the mixture was extracted with ethyl acetate. The organic phase was washed with brine and the solvent was removed. The residue was subjected to NH-silica gel (Fuji silicia) column chromatography to elute with hexane and then with hexane/ethyl acetate (2:1), to give 230 mg of the target compound.

$^1$H-NMR (CDCl$_3$) δ=2.57 (3H, s), 3.77 (3H, s), 4.15 (2H, s), 6.80–6.82 (2H, m), 7.08 (1H, d, J=8 Hz), 7.19–7.21 (2H, m), 7.44 (1H, d, J=8 Hz).

d) 3-[2-(4-Methoxybenzyl-6-methyl-3-pyridyl]ethynyl-3-quinuclidinol

A mixture of 230 mg of 2-(4-methoxybenzyl)-6-methyl-3-pyridyl trifluoromethane sulfonate, 116 mg of 3-ethynyl-3-quinuclidinol, 147 mg of tetrakis(triphenylphosphine)palladium(0), 24 mg of cuprous iodide, 266 µl of triethylamine and 5.0 ml of N,N-dimethylformamide was heated under stirring at 80° C. for 3 hours in a nitrogen atmosphere. The reaction solution was poured into aqueous dilute ammonia, and the mixture was extracted with ethyl acetate. Then, the organic phase was washed with brine and the solvent was removed. The residue was subjected to NH-silica gel (Fuji Silicia) column chromatography and eluted with hexane/ethyl acetate (1:1) and then with ethyl acetate/methanol (20:1), to give 192 mg of the target compound.

$^1$H-NMR (CDCl$_3$) δ=1.35–1.44 (1H, m), 1.54–1.65 (1H, m), 1.77–1.89 (1H, m), 2.02–2.04 (2H, m), 2.54 (3H, s), 2.75–2.95 (4H, m), 3.02 (1H, dd, J=2, 14 Hz), 3.23 (1H, dd, J=2, 14 Hz), 3.75 (3H, s), 4.23 (2H, s), 6.77–6.80 (2H, m), 6.97 (1H, d, J=8 Hz), 7.16–7.19 (2H, m), 7.55 (1H, d, J=8 Hz).

Example 54

3-6-Methyl-2-(2-pyridylmethyl)-3-pyridyl]ethynyl-3-quinuclidinol

The target compound was synthesized in the same manner as in Example 53.

$^1$H-NMR (CDCl$_3$) δ=1.38–1.44 (1H, m), 1.53–1.84 (2H, m), 1.96–2.14 (2H, m), 2.58 (3H, s), 2.75–2.95 (4H, m), 3.05

(1H, d, J=14 Hz), 3.16 (1H, dd, J=2, 14 Hz), 4.49 (2H, s), 7.00 (1H, d, J=8 Hz), 7.11–7.15 (1H, m), 7.25–7.30 (1H, m), 7.49 (1H, d, J=8 Hz), 7.55–7.60 (1H, m), 7.44–8.47 (1H, m).

Example 55

3-[6-Methyl-2-(3-pyridylmethyl)-3-pyridylmethyl)-3-pridyl]ehtynyl-3-quinuclidinol The target compound was synthesized in the same manner as in Example 53.

$^1$H-NMR (CDCl$_3$) δ=1.31–1.39 (1H, m), 1.52–1.78 (2H, m), 1.93–2.00 (2H, m), 2.47 (3H, s), 2.63–2.89 (4H, m), 2.98 (1H, dd, J=2, 14 Hz), 3.15 (1H, dd, J=2, 14 Hz), 4.21 (2H, s), 6.93 (1H, d, J=8 Hz), 7.09–7.19 (1H, m), 7.51 (1H, d, J=8 Hz), 7.53–7.63 (1H, m), 8.34–8.36 (1H, m), 8.50 (1H, d, J=2 Hz).

Example 56

3-[6-Methyl-2-(4-pyridylmethyl)-3-pyridyl]ethynyl-3-quinuclidinol

The target compound was synthesized in the same manner as in Example 53.

$^1$H-NMR (CDCl$_3$) δ=1.36–1.45 (1H, m), 1.54–1.80 (2H, m), 1.97–2.06 (2H, m), 2.55 (3H, s), 2.66–2.95 (4H, m), 3.03 (1H, dd, J=2, 14 Hz), 3.19 (1H, dd, J=2, 14 Hz), 4.28 (2H, s), 7.04 (1H, d, J=8 Hz), 7.13–7.15 (2H, m), 7.61 (1H, d, J=8 Hz), 8.40–8.42 (2H, m).

Example 57

3-[2-(2-Phenylethyl)-6-methyl-3-pyridyl]ethynyl-3-quinuclidinol a) 3-Benzyloxy-6-methyl-2-styrylpyridine 1.5 g of diethyl benzylphosphonate was dissolved in 20 ml of tetrahydrofuran, followed by adding 810 mg of potassium tert-butoxide at room temperature. After stirring for 15 minutes, a solution of 10 ml of tetrahydrofuran containing 1,2 g of 3-benzyloxy-6-methylpyridine-2-carboxyaldehyde (Production Example 11-b) was added thereto, followed by stirring for further 1.5 hours. Then, water was added thereto, and the mixture was extracted with ethyl acetate. The organic phase was washed with brine, dried over anhydrous sodium sulfate and the solvent was removed. The residue was subjected to silica gel column chromatography using 10% ethyl acetate/hexane as an eluent, to give 1.2 g of the target compound.

$^1$H-NMR (CDCl$_3$) δ=2.53 (3H, s), 5.13 (2H, s), 6.95 (1H, d, J=8.4 Hz) 7.12 (1H, d, J=8.4 Hz), 7.24–7.48 (8H, m), 7.59 (2H, d, J=8.4 Hz), 7.61 (1H, d, J=16 Hz), 7.80 (1H, d, J=16 Hz).

b) 3-Hydroxy-6-methyl-2-(2-Phenylethyl)pyridine 1.2 g of 3-benzyloxy-6-methyl-2-styrylpyridine was dissolved in 20 ml of methanol. 684 mg of 10% palladium carbon was added thereto, and the mixture was to hydrogenated. The atmosphere in the reaction system was replaced by nitrogen and the catalyst was filtered off. The filtrate was evaporated, to give 695 mg of the target compound.

c) 6-Methyl-2-(2-phenylethyl)pyridyl Trifluoromethane-sulfonate

A mixture of 695 mg of 3-hydroxy-6-methyl-2-(2-phenylethyl)pyridine, 1.5 g of N-phenyltrifluoromethanesulfonimide, 121 mg of 4-dimethylaminopyridine and 0.6 ml of triethylamine was dissolved in 20 ml of dichloromethane, followed by stirring at room temperature for 5 hours. Then, the solvent was removed and the residue was subjected to silica gel column chromatography using 10% ethyl acetate/hexane as an eluent for separation and purification, to give 1.2 g of the target compound.

$^1$H-NMR (CDCl$_3$) δ=2.59 (3H, s), 3.02–3.09 (2H, m), 3.12–3.19 (2H, m), 7.08 (1H, d, J=8.4 Hz), 7.20–7.31 (5H, m), 7.44 (1H, d, J=8.4 Hz).

d) 3-[2-(2-Phenylethyl)-6-methyl-3-pyridyl]ethynyl-3-quinuclidinol 10 ml of N,N-dimethylformamide was added to a mixture of 1.2 g of 6-methyl-2-(2-phenylethyl)pyridyl trifluoromethane sulfonate, 522 mg of 3-ethynyl-3-quinuclidinol, 400 mg of tetrakis(triphenylphosphine)palladium(0), 217 mg of cuprous iodide and 1.7 ml of triethylamine, followed by heating under stirring at 50° C. in an oil bath for one hour in a nitrogen atmosphere. After cooling as it was, the reaction solution was sprinkled over silica gel and subjected to silica gel column chromatography using chloroform/methanol/aqueous 36% ammonia (46:5:0.5) as an eluent for separation and purification, to give 490 mg of the target compound.

$^1$H-NMR (CDCl$_3$) δ=1.42–1.52 (1H, m), 1.61–1.72 (1H, m), 1.89–2.02 (1H, m), 2.04–2.16 (2H, m), 2.56 (3H, s), 2.80–2.95 (4H, m), 3.02–3.11 (3H, m), 3.20–3.32 (3H, m), 6.97 (1H, d, J=8.0 Hz), 7.18–7.28 (5H, m), 7.54 (1H, d, J=8.0 Hz).

Example 58

3-(2-Styryl-6-methyl-3-pyridyl)ethynyl-3-quinuclidinol a) 3-Hydroxy-6-methyl-2-styrylpyridine 875 mg of 3-benzyloxy-6-methyl-2-styrylpyridine (Example 57a) was dissolved in 15 ml of 1,2-dichloroethane and 1.2 ml of a dichloromethane solution containing 1.0 mol of boron tribromide was added thereto in a nitrogen atmosphere, followed by heating under stirring at 50° C. in an oil bath over night. After cooling as it was, an aqueous saturated sodium bicarbonate solution was added thereto, and the mixture was extracted with 5% methanol/dichloromethane. The organic phase was further washed with brine, dried over anhydrous magnesium sulfate and the solvent was removed. The residue was vacuum-dried, to give 200 mg of the target compound.

b) 3-(2-Styryl-6-methyl-3-pyridyl)ethynyl-3-quinuclidinol

The target compound was synthesized in the same manner as in Example 57.

$^1$H-NMR (CDCl$_3$) δ=1.40–1.50 (1H, m), 1.66–1.80 (1H, m), 2.00–2.18 (3H, m), 2.59 (3H, s), 2.80–3.00 (4H, m), 3.12 (1H, d, J=14 Hz), 3.38 (1H, dd, J=2, 14 Hz), 6.96 (1H, d, J=7.9 Hz), 7.30 (1H, d, J=7.3 Hz), 7.37 (2H, dd, J=7.5 Hz, 7.3 Hz), 7.565 (1H, d, J=7.9 Hz), 7.572 (1H, d, J=7 .5 Hz), 7.60 (1H, d, J=16 Hz), 7.97 (1H, d, 16 Hz).

Example 59

3-[2-Benzyl-6-(3-methoxypropyl)-3-pyridyl]ethynyl-3-quinuclidinol a) 2-Benzyl-6-(2-ethoxycarbonylethenyl)-3-methoxymethyloxpyridine 1.3 g of ethyl diethylphosphonoacetate was dissolved in 20 ml of tetrahydrofuran, followed by adding 657 mg of potassium tert-butoxide thereto at room temperature. After stirring for 15 minutes, a solution of 10 ml of tetrahydrofuran containing 1.0 g of 2-benzyl-3-methoxymethyloxypyridine-6-carboxyaldehyde (Production Example 11) was added thereto, followed by stirring for further one hour. Then, water was added thereto, and the mixture was extracted with ethyl acetate. The organic phase was washed with brine, dried over anhydrous sodium sulfate and the solvent was removed. The residue was subjected to silica gel column chromatography using 17% ethyl acetate/hexane as an eluent for separation and purification, to give 1.4 g of the target compound.

b) 2-Benzyl-6-(2-ethoxycarbonylethenyl)-3-methoxymethyloxypyridine 1.4 g of 2-benzyl-6-(2-ethoxycarbonylethenyl)-3-methoxymethyloxypyridine was dissolved in 20 ml of ethyl acetate. 457 mg of 10% palladium carbon was added thereto, and the mixture was hydrogenated. After the atmosphere in the reaction system was replaced by nitrogen, the catalyst was filtered off. The filtrate was further filtered through silica gel, and the filtrate was evaporated, to give 1.3 g of the target compound.

$^1$H-NMR (CDCl$_3$) δ=1.22 (3H, t, J=7.1 Hz), 2.76 (2H, t, J=7.6 Hz), 3.05 (2H, t, J=7.6 Hz), 3.30 (3H, s), 4.13 (2H, q, J=7.1 Hz), 4.15 (2H, s), 5.09 (2H, s), 6.97 (1H, d, J=8.4 Hz), 7.14–7.29 (6H, m).

c) 2-Benzyl-6-(3-hydroxypropyl)3-methoxymethyloxypyridine 205 mg of aluminum lithium hydride was suspended in 20 ml of anhydrous ether. A solution of 10 ml of anhydrous ether containing 1.3 g of 2-benzyl-6-(2-ethoxycarbonylethyl)-3-methoxymethyloxypyridine was added dropwise under ice-cooling. After stirring for one hour as it was, 0.2 ml of water, then 0.2 ml of an aqueous 5N sodium hydroxide solution and then 0.6 ml of water were added thereto under ice-cooling. The reaction solution was filtered through filter paper to remove insoluble matters. After washing with ether, the organic phase was evaporated. The residue was subjected to silica gel column chromatography using 40% ethyl acetate/hexane as an eluent for separation and purification, to give 1.0 g of the target compound.

$^1$H-NMR (CDCl$_3$) δ=1.94 (2H, tt, J=6.5 Hz, 5.7 Hz), 2.91 (2H, t, J=6.5 Hz), 3.34 (3H, s), 3.70 (2H, t, J=5.7 Hz), 4.15 (2H, s), 5.13 (2H, s), 6.97 (1H, d, J=8.4 Hz), 7.15–7.31 (6H, m).

d) 2-Benzyl-6-(3-methoxypropyl)-3-methoxymenthyloxypyridine 527 mg of 2-benzyl-6-(3-hydroxypropyl)-3-methoxymethyloxypyridine was dissolved in 5 ml of N,N-dimethylformamide, and 108 mg of 60% oily sodium hydride was added thereto at room temperature under stirring. After 10 minutes, 0.16 ml of methyl iodide was added thereto, followed by stirring for one hour at room temperature. Then, water was added thereto, and the mixture was extracted with ethyl acetate. The organic phase was further washed with brine, dried over anhydrous sodium sulfate and the solvent was removed. The residue was subjected to silica gel column chromatography using 20% ethyl acetate/hexane as an eluent for separation and purification, to give 389 mg of the target compound.

$^1$H-NMR (CDCl$_3$) δ=1.98 (2H, tt, J=7.8 Hz, 6.6 Hz), 2.79 (2H, t, J=7.8 Hz), 3.31 (3H, s), 3.34 (3H, s), 3.41 (2H, t, J=6.6 Hz), 4.17 (2H, s), 5.09 (2H, s), 6.95 (1H, d, J=8.4 Hz), 7.14–7.30 (6H, m).

e) 3-[2-Benzyl-6-(3-methoxypropyl)-3-pyridyl]ethynyl-3-quinuclidinol

The compound obtained above was deprotected using trifluoroacetic acid and in succession, the same procedures as in Example 57 were carried out to synthesize the target compound.

$^1$H-NMR (CDCl$_3$) δ=1.35–1.45 (1H, m), 1.53–1.63 (1H, m), 1.75–1.88 (1H, m), 1.98–2.05 (4H, m), 2.67–2.92 (4H, m), 2.85 (2H, t, J=7.5 Hz), 3.00 (1H, dd, J=2, 14 Hz), 3.20 (1H, dd, J=2, 14 Hz), 3.32 (3H, s), 3.40 (2H, t, J=6.4 Hz), 4.31 (2H, s), 6.99 (1H, d, J=7.9 Hz), 7.15–7.26 (5H, m), 7.58 (1H, d, J=7.9 Hz).

Example 60

3-[2-Benzyl-6-(5,6-dihydro-2H-pyran-4-yl)-3-pyridyl]ethynyl-3-quinuclidinol a) 2-Benzyl-6-(4-hydroxytetrahydro-4H-pyran-4-yl)-3-methoxymethyloxpyridine A solution of 10 ml of diethyl ether containing 1.79 g of 2-benzyl-6-iodo-3-methoxymethyloxypyridine (Production Example 12) was added dropwise to a mixture of a 4.25 ml hexane solution of 1.54 mol of n-butyllithium and 10 ml of diethyl ether at −78° C. After stirring at the same temperature for 20 minutes, tetrahydro-4H-pyran-4-one was added dropwise thereinto. The temperature of the resulting mixture was raised to room temperature and water and diethyl ether were added thereto. The organic phase was washed with water and brine, dried over anhydrous magnesium sulfate and the solvent was removed. The residue was subjected to silica gel column chromatography using 30% ethyl acetate/hexane, to give 1.39 g of the target compound.

$^1$H-NMR (CDCl$_3$) δ=1.47–1.56 (2H, m), 2.05–2.12 (2H, m), 3.38 (3H, s), 3.90–4.01 (4H, m), 4.19 (2H, s), 5.18 (2H, s), 7.14–7.30 (6H, m), 7.41 (1H, d, J=8 Hz).

b) 2-Benzyl-3-hydroxy-6-(4-hydroxytetrahydro-4H-pyran-4-yl)pyridine

A mixed solution of 377 mg of 2-benzyl-6-(4-hydroxytetrahydro-4H-pyran-4-yl)-3-methoxymethyloxypyridine, 2 ml of dichloromethane and 2 ml of trifluoroacetic acid was stirred at room temperature overnight. The reaction solution was neutralized by an aqueous sodium bicarbonate solution, and ethyl acetate was added thereto. The organic phase was washed with water and brine, dried over anhydrous magnesium sulfate and the solvent was removed. The residue was subjected to silica gel column chromatography using 60% ethyl acetate/hexane, to give 241 mg of the target compound.

$^1$H-NMR (CDCl$_3$) δ=1.51–1.57 (2H, m), 2.05–2.12 (2H, m), 3.90–4.01 (4H, m), 4.21 (2H, s), 5.00 (1H, s), 5.39 (1H, s), 7.12 (2H, s), 7.21–7.30 (5H, m).

c) 2-Benzyl-6-(4-hydroxytetrahydro-4H-4pyran-4-yl)-pyridyl Trifluoromethanesulfonate A mixture of 241 mg of 2-benzyl-3-hydroxy-6-(4-hydroxytetrahydro-4H-pyran-4-yl)pyridine, 302 mg of N-phenyltrifluoromethanesulfonimide, 353 µl of triethylamine, 5.2 mg of 4-dimethylaminopyridine and 3 ml of dichloromethane was stirred at room temperature for 2 hours. Silica gel was added to the reaction solution, and the solvent was removed. The residue was subjected to silica gel column chromatography using 30% ethyl acetate/hexane, to give 332 mg of the target compound.

$^1$H-NMR (CDCl$_3$) δ=1.53–1.56 (2H, m), 2.08–2.17 (2H, m), 3.92–3.97 (4H, m), 4.26 (2H, s), 4.60 (1H, s), 7.23–7.36 (6H, m), 7.65 (1H, d, J=8 Hz).

d) 2-Benzyl-6-(5,6-dihydro-2H-pyran-4-yl)-3-pyridyl Trifluoromethanesulfonate 57.9 µl of methanesulfonyl chloride was added dropwise to a mixture of 104 mg of 2-benzyl-6-(4-hydroxytetrahydro-4H-pyran-4-yl)-3-pyridyl trifluoromethane sulfonate, 139 µl of triethylamine and 2 ml of dichloromethane under ice-cooling. After stirring at room temperature for 3 hours, water and ethyl acetate were added thereto. The organic phase was washed with water and brine, dried over anhydrous magnesium sulfate and the solvent was removed. The residue was subjected to silica gel column chromatography using 15% ethyl acetate/hexane, to give 60.7 mg of the target compound.

$^1$H-NMR (CDCl$_3$) δ=2.60 (2H, br s), 3.92 (2H, t, J=5 Hz), 4.23 (2H, s), 4.37 (2H, s), 6.74 (1H, s), 7.21–7.31 (6H, m), 7.53 (1H, d, J=8 Hz).

e) 3-[2-Benzyl-6-(5,6-dihydro-2H-pyran-4-yl)-3-pyridyl]ethynyl-3-quinuclidinol

A mixture of 60.7 g of 2-benzyl-6-(5,6-dihydro-2H-pyran-4-yl)-3-pyridyl trifluoromethane sulfonate, 23.0 mg of 3-ethynyl-3-quinuclidinol, 17.6 mg of tetrakis (triphenylphosphine)palladium(0), 2.9 mg of cuprous iodide, 63.6 μl of triethylamine and 1 ml of N,N-dimethylformamide was stirred at 60° C. for 1.5 hours in a nitrogen atmosphere. NH-silica gel was added to the reaction solution, and the solvent was removed. The residue was subjected to NH-silica gel column chromatography using 3% methanol/ethyl acetate, to give 40.7 mg of the target compound.

$^1$H-NMR (CDCl$_3$) δ=1.33–1.44 (1H, m), 1.56–1.64 (1H, m), 1.80–1.88 (1H, m), 2.00–2.07 (2H, m), 2.60 (1H, br s), 2.73–2.88 (4H, m), 3.02 (1H, d, J=14 Hz), 3.22 (1H, dd, J=2, 14 Hz), 3.93 (1H, t, J=5 Hz), 4.31 (2H, s), 4.36–4.38 (2H, m), 6.75–6.77 (1H, m), 7.12–7.29 (6H, m), 7.61 (1H, d, J=8 Hz).

Example 61

3-[2-Benzyl-6-(4-hydroxy-1-cyclohexenyl)-3-pyridyl]ethynyl-3-quinuclidinol a) 2-Benzyl-3-hydroxy-6-(4-oxo-1-hydroxycyclohexyl)pyridine The target compound was synthesized in the same manner as in Example 60-a and b except that tetrahydro-4H-pyran-4-one was altered to 1,4-cyclohexanedionemonoethylene ketal.

$^1$H-NMR (CDCl$_3$) δ=2.00–2.06 (2H, m), 2.14–2.22 (2H, m), 2.35–2.41 (4H, m), 2.95–3.04 (2H, m), 4.21 (2H, s), 7.05–7.31 (7H, m).

b) 2-Benzyl-6-(1,4-dihydroxycyclohexyl)-3-hydroxypyridine 67.4 mg of sodium borohydride was added to a mixture of 353 mg of 2-benzyl-3-hydroxy-6-(4-oxo-1-hydroxycyclohexyl)pyridine and 4 ml of methanol under ice-cooling, followed by stirring at the same temperature for one hour. Acetone was added thereto, and the solvent was removed. Then, the residue was subjected to silica gel column chromatography using 20% hexane/ethyl acetate, to give 193 mg of the target compound.

$^1$H-NMR (CDCl$_3$) δ=1.30–1.95 (8H, m), 3.70–3.75 (1H, m), 4.20 (2H, s), 7.06–7.31 (7H, m).

c) 3-[2-Benzyl-6-(4-hydroxy-1-cyclohexynyl)-3-pyridyl]ethynyl-3-quinuclidinol

The target compound was synthesized in the same manner as in Example 60-c, d and e except that 2-benzyl-3-hydroxy-6-(4-hydroxytetrahydro-4H-pyran-4-yl)pyridine was altered to 2-benzyl-6-(1,4-dihydroxycyclohexyl)-3-hydroxypyridine.

$^1$H-NMR (CDCl$_3$) δ=1.37–1.44 (1H, m), 1.56–1.64 (1H, m), 1.77–1.88 (2H, m), 2.00–2.06 (3H, m), 2.24–2.31 (1H, m), 2.51–2.91 (7H, m), 3.01 (1H, d, J=14 Hz), 3.22 (1H, dd, J=2, 14 Hz), 4.04–4.10 (1H, m), 4.31 (2H, s), 6.69 (1H, s), 7.16–7.28 (6H, m), 7.60 (1H, d, J=8 Hz).

Example 62

3-[2-Benzyl-6-(tetrahydro-4H-pyran-4-yl)-3-pyridyl]ethynyl-3-quinuclidinol a) 2-Benzyl-6-(5,6-dihydro-2H-pyran-4-yl)-3-methoxymethyloxypyridine 716 μl of methanesulfonyl chloride was added dropwise into a mixture of 1.02 g of 2-benzyl-6-(4-hydroxytetrahydro-4H-pyran-4-yl)-3-methoxymethyloxypyridine (Example 60a), 1.72 ml of triethylamine and 10 ml of dichloromethane under ice-cooling. After stirring at room temperature overnight, water and ethyl acetate were added thereto. The organic phase was washed with water and brine, dried over anhydrous magnesium sulfate and the solvent was removed. The residue was subjected to silica gel column chromatography using 20% ethyl acetate/hexane, to give 355 mg of the target compound.

$^1$H-NMR (CDCl$_3$) δ=2.59–2.63 (2H, m), 3.33 (3H, s), 3.94 (2H, t, J=5 Hz), 4.19 (2H, s), 4.35–4.38 (2H, m), 5.15 (2H, s), 6.59–6.62 (1H, m), 7.13–7.33 (7H, m).

b) 2-Benzyl-3-methoxymethyloxy-6-(tetrahydro-4H-pyran-4-yl)pyridine 20 mg of 10% palladium carbon was added to a mixture of 197 mg of 2-benzyl-6-(5,6-dihydro-2H-pyran-4-yl)-3-methoxymethyloxypyridine and 3 ml of ethanol, followed by stirring at room temperature overnight in a hydrogen atmosphere. After the atmosphere in the reaction system was replaced by nitrogen, the reaction solution was filtered through Celite. The solvent was removed, and then the residue was subjected to silica gel column chromatography using 20% ethyl acetate/hexane, to give 83.7 mg of the target compound.

$^1$H-NMR (CDCl$_3$) δ=1.83–1.88 (4H, m), 2.88–2.96 (1H, m), 3.32 (3H, s), 3.52–3.58 (2H, m), 4.06–4.17 (4H, m), 5.10 (2H, s), 6.96 (1H, d, J=8 Hz), 7.12–7.16 (1H, m), 7.21–7.31 (5H, m).

c) 3-[2-Benzyl-6-(tetrahydro-4H-pyran-4-yl)-3-pyridyl]ethynyl-3-quinuclidinol

The target compound was synthesized in the same manner as in Example 60-b, c and e.

$^1$H-NMR (CDCl$_3$) δ=1.36–1.44 (1H, m), 1.55–1.63 (1H, m), 1.79–1.90 (5H, m), 1.98–2.04 (2H, m), 2.68–2.87 (5H, m), 3.01 (1H, d, J=14 Hz), 3.22 (1H, dd, J=2, 14 Hz), 3.41–3.58 (2H, m), 4.07–4.11 (2H, m), 4.30 (2H, s), 6.99 (1H, d, J=8 Hz), 7.15–7.27 (5H, m), 7.62 (1H, d, J=8 Hz).

Example 63

3-[2-Benzyl-6-(3-methoxy-1-propinyl)-3-pyridyl]ethynyl-3-quinuclidinol

A mixture of 500 mg of 2-benzyl-3-bromo-6-pyridyl trifluoromethanesulfonate obtained in Production Example 3, 0.12 ml of methyl propargyl ether, 40 mg of tetrakis (triphenylphosphine)palladium(0), 1.2 mg of cuprous iodide, 0.53 ml of triethylamine and 1 ml of N,N-dimethylformamide was stirred at room temperature overnight in a nitrogen atmosphere. Ethyl acetate and aqueous dilute ammonia were added to the reaction solution to separate. The organic phase was washed with water and brine, dried over anhydrous magnesium sulfate and then concentrated. The residue was subjected to silica gel column chromatography using 1–10% ethyl acetate/hexane, to give 170 mg of 2-benzyl-3-bromo-6-(3-methoxy-1-propinyl) pyridine.

Next, a mixture of 170 mg of 2-benzyl-3-bromo-6-(3-methoxy-1-propinyl)pyridine, 90 mg of 3-ethynyl-3-quinuclidinol, 30 mg of tetrakis(triphenylphosphine)

palladium(0), 1 mg of cuprous iodide, 0.22 ml of triethylamine and 1 ml of N,N-dimethylformamide was stirred for 2 hours in an oil bath kept at 85° C. in a nitrogen atmosphere. Ethyl acetate and aqueous dilute ammonia were added to the reaction solution to separate. The organic phase was washed with water and brine, dried over anhydrous magnesium sulfate and then concentrated. The residue was subjected to silica gel column chromatography using NH-silica gel to elute with 20–100% ethyl acetate/hexane and then with 2.5% methanol/ethyl acetate, to give 120 mg of the target compound.

$^1$H-NMR (CDCl$_3$) δ=1.35–1.84 (3H, m), 1.96–2.06 (2H, m), 2.64–2.92 (4H, m), 2.99 (1H, dd, J=2, 14 Hz), 3.17 (1H, dd, J=2, 14 Hz), 3.47 (3H, s), 4.33 (2H, s), 4.36 (2H, s), 7.15–7.28 (5H, m), 7.30 (1H, d, J=8 Hz), 7.64 (1H, d, J=8 Hz).

Example 64

3-[2-Benzyl-6-(4-hydroxy-1-butynyl)-3-pyridyl]ethynyl-3-quinuclidinol

The target compound was synthesized in the same manner as in Example 63.

$^1$H-NMR (CDCl$_3$) δ=1.34–1.84 (3H, m), 1.96–2.06 (2H, m), 2.64–2.92 (4H, m), 2.73 (2H, t, J=6 Hz), 2.99 (1H, dd, J=2, 14 Hz), 3.16 (1H, dd, J=2, 14 Hz), 3.85 (2H, t, J=6 Hz), 4.31 (2H, s), 7.14–7.28 (6H, m), 7.60 (1H, d, J=8 Hz).

Example 65

3-[2-(4-Fluorobenzyl)-6-(3-hydroxy-1-butynyl)-3-pyridyl]ethynyl-3-quinuclidinol

The target compound was synthesized in the same manner as in Example 63.

$^1$H-NMR (CDCl$_3$) δ=1.35–1.85 (6H, m), 1.95–2.08 (2H, m), 2.68–2.93 (4H, m), 3.03 (1H, d, J=14 Hz), 3.21 (1H, dd, J=2, 14 Hz), 4.28 (2H, s), 4.79 (1H, q, J=7 Hz), 6.94 (2H, t, J=8 Hz), 7.20 (2H, dd, J=6,8 Hz), 7.28 (1H, d, J=8 Hz), 7.65 (1H, d, J=8 Hz).

Example 66

3-[2-Benzyl-6-(pyrazylethynyl)-3-pyridyl]ethynyl-3-quinuclidinol a) 2-Benzyl-3-bromo-6-(pyrazylethynyl)pyridine A mixture of 788 mg of 2-benzyl-3-bromo-6-pyridyl trifluoromethane sulfonate (Production Example 3), 207 mg of pyrazylacetylene (Production Example 19), 230 mg of tetrakis(triphenylphosphine)palladium(0), 37.9 mg of cuprous iodide, 832 μl of triethylamine and 6 ml of N,N-dimethylformamide was stirred at 80° C. for one hour in a nitrogen atmosphere. Silica gel was added to the reaction solution, and the solvent was removed. The residue was subjected to silica gel column chromatography using 25% ethyl acetate/hexane, to give 443 mg of the target compound.

$^1$H-NMR (CDCl$_3$) δ=4.39 (2H, s), 7.19–7.39 (6H, m), 7.87 (1H, d, J=8 Hz), 8.54–8.56 (1H, m), 8.61–8.62 (1H, m), 8.86 (1H, s).

b) 3-[2-Benzyl-6-(pyrazylethynyl)-3-pyridyl]ethynyl-3-quinuclidinol

A mixture of 109 mg of 2-benzyl-3-bromo-6-(pyrazylethynyl)pyridine, 47.1 mg of 3-ethynyl-3-quinuclidinol, 35.9 mg of tetrakis(triphenylphosphine)palladium(0), 5.9 mg of cuprous iodide, 130 μl of triethylamine and 1.5 ml of N,N-dimethylformamide was stirred for 5 hours at 70° C. in a nitrogen atmosphere. NH-silica gel was added to the reaction solution, and the solvent was removed. The residue was subjected to NH-silica gel column chromatography using 3% methanol/ethyl acetate, to give 61.0 mg of the target compound.

$^1$H-NMR (CDCl$_3$) δ=1.37–1.43 (1H, m), 1.56–1.64 (1H, m), 1.75–1.83 (1H, m), 1.98–2.04 (2H, m), 2.67–2.88 (4H, m), 3.01 (1H, d, J=14 Hz), 3.19 (1H, dd, J=2, 14 Hz), 4.38 (2H, s), 7.17–7.28 (5H, m), 7.48 (1H, d, J=8 Hz), 7.70 (1H, d, J=8 Hz), 8.53–8.54 (1H, m), 8.61–8.62 (1H, m), 8.85–8.86 (1H, m).

Example 67

3-[2-Benzyl-6-(pyrazylethynyl)-3-pyridyl]ethynyl-3-quinuclidinol 12 mg of platinum oxide was added to a mixture of 230 mg of 2-benzyl-3-bromo-6-pyrazylethynyl)pyridine (Production Example 66-a), 2.5 ml of ethyl acetate and 2 ml of methanol, followed by stirring at room temperature overnight in a hydrogen atmosphere. After the atmosphere in the reaction system was replaced by nitrogen, it was filtered through Celite. After removing the solvent, the residue was subjected to silica gel column chromatography using 50% ethyl acetate/hexane, to give 85.4 mg of the target compound.

$^1$H-NMR (CDCl$_3$) δ=3.20–3.30 (4H, m), 4.30 (2H, s), 6.84 (1H, d, J=8 Hz), 7.17–7.28 (5H, m), 7.66 (1H, d, J=8 Hz), 8.34 (1H, s), 8.38 (1H, d, J=2 Hz), 8.47–8.48 (1H, m).

b) 3-[2-Benzyl-6-(pyrazylethynyl)-3-pyridyl]ethynyl-3-quinuclidinol

A mixture of 85.4 mg of 2-benzyl-3-bromo-6-(2-pyrazylethyl)pyridine, 36.4 mg of 3-ethynyl-3-quinuclidinol, 27.8 mg of tetrakis(triphenylphosphine)palladium(0), 4.6 mg of cuprous iodide, 101 μl of triethylamine and 1.5 ml of N,N-dimethylformamide was stirred for 7 hours at 80° C. in a nitrogen atmosphere. NH-silica gel was added to the reaction solution, and the solvent was removed. The residue was subjected to NH-silica gel column chromatography using 3% methanol/ethyl acetate, to give 45.4 mg of the target compound.

$^1$H-NMR (CDCl$_3$) δ=1.36–1.44 (1H, m), 1.54–1.63 (1H, m), 1.78–1.86 (1H, m), 1.98–2.05 (2H, m), 2.67–2.91 (4H, m), 3.01 (1H, d, J=14 Hz), 3.20 (1H, dd, J=2, 14 Hz), 3.25–3.27 (4H, m), 4.30 (2H, s), 6.92 (1H, d, J=8 Hz), 7.16–7.28 (5H, m), 7.54 (1H, d, J=8 Hz), 8.32 (1H, s), 8.36 (1H, d, J=2 Hz), 8.47–8.48 (1H, m).

Example 68

3-[2-Benzyl-6-(4-methoxy-3-oxobutyl)-3-pyridyl]ethynyl-3-quinuclidinol a) Dimethyl 3-Methoxy-2-oxopropyl Phosphonate B14 insert $^1$H-NMR (CDCl$_3$) δ=3.18 (2H, d, J=23 Hz), 3.44 (3H, s), 3.79 (3H, s), 3.82 (3H, s), 4.14 (2H, s).

b) 2-Benzyl-3-methoxymethyloxy-6-(4-methoxy-3-oxo-1-butenyl)pyridine 6 g of dimethyl 3-methoxy-2-oxopropyl phosphonate was dissolved in 200 ml of tetrahydrofuran, to which was then added 3.2 g of potassium tert-butoxide. After stirring for 15 minutes, a solution of 50 ml of tetrahydrofuran containing 6 g of 2-benzyl-3-methoxymethyloxypyridine-6-carboxyaldehyde (Production Example 11) was added thereto, followed by stirring for further one hour. Then, water was added thereto, the solvent was removed and the mixture was extracted with ethyl acetate. Further, the organic phase was washed with brine, dried over anhydrous sodium sulfate and the solvent was removed. The residue was subjected to silica gel column chromatography using 17–33% ethyl acetate/hexane as an eluent for separation and purification, to give 4.6 g of the target compound.

$^1$H-NMR (CDCl$_3$) δ=3.30 (3H, s), 3.49 (3H, s), 4.21 (2H, s), 4.32 (2H, s), 5.19 (2H, s), 7.15–7.35 (8H, m), 7.64 (1H, d, J=16 Hz).

c) 2-Benzyl-3-methoxmethyloxy-6-(4-methoxy-3-oxobutyl) pyridine 4.6 g of 2-benzyl-3-methoxymethyloxy-6-(4-methoxy-3-oxo-1-butenyl)pyridine was dissolved in 100 ml of ethyl acetate, 976 mg of 10% palladium carbon was added thereto, and then hydrogenated. After the atmosphere in the reaction system was replaced by nitrogen, the catalyst was filtered off, and the filtrate was evaporated. The resulting residue was subjected to silica gel column chromatography using 33% ethyl acetate/hexane as an eluent for separation and purification, to give 1.8 g of the target compound.

$^1$H-NMR (CDCl$_3$) δ=2.86 (2H, t, J=7.0 Hz), 3.05 (2H, t, J=7.0 Hz), 3.31 (3H, s), 3.37 (3H, s), 4.01 (2H, s), 4.14 (2H, s), 5.10 (2H, s), 6.97 (1H, d, J=8.4 Hz), 7.15–7.27 (6H, m).

d) 2-Benzyl-6-(4-methoxy-3-oxobutyl)-3-pyridyl Trifluoromethane Sulfonate 1.8 g of 2-benzyl-3-methoxymethyloxy-6-(4-methoxy-3-oxobutyl)pyridine was dissolved in 50 ml of methanol, and 2 ml of concentrated hydrochloric acid was added thereto, followed by heating under reflux for 1.5 hours. After cooling as it was, it was neutralized by an aqueous saturated sodium bicarbonate solution and extracted with ethyl acetate. Further, the organic phase was washed with brine, dried over anhydrous sodium sulfate and the solvent was removed. The resulting residue was dissolved in 50 ml of dichloromethane. 2.7 g of N-phenyltrifluoromethanesulfonimide, 209 mg of 4-dimethylaminopyridine and 1 ml of triethylamine were added thereto, followed by stirring at room temperature for 1.5 hours. The solvent was removed, and the residue was subjected to silica gel column chromatography using 25% ethyl acetate/hexane as an eluent for separation and purification, to give 2.3 g of the target compound.

$^1$H-NMR (CDCl$_3$) δ=2.91 (2H, t, J=6.8 Hz), 3.13 (2H, t, J=6.8 Hz), 3.37 (3H, s), 3.96 (2H, s), 4.19 (2H, s), 7.14 (1H, d, J=8.4 Hz), 7.20–7.29 (5H, m), 7.46 (1H, d, J=8.4 Hz).

e) 3-[2-Benzyl-6-(4-methoxy-3-oxobutyl)-3-pyridyl]ethynyl-3-quinuclidinol 10 ml of N,N-dimethylformamide was added to a mixture of 1.9 g of 2-benzyl-6-(4-methoxy-3-oxobutyl)-3-pyridyl trifluoromethanesulfonate, 773 mg of 3-ethynyl-3-quinuclidinol, 525 mg of tetrakis(triphenylphosphine) palladium(0), 267 mg of cuprous iodide and 2.2 ml of triethylamine, followed by stirring for one hour at 50° C. in an oil bath in a nitrogen atmosphere. After cooling as it was, ethyl acetate was added thereto. The mixture was filtered through Celite, followed by washing with water. The organic phase was washed with brine, dried over anhydrous sodium sulfate and the solvent was removed. The residue was subjected to silica gel column chromatography using chloroform/methanol/36% aqueous ammonia (46:5:0.5) as an eluent for separation and purification, to give 1.3 g of the target compound.

$^1$H-NMR (CDCl$_3$) δ=1.35–1.45 (1H, m), 1.54–1.64 (1H, m), 1.75–1.86 (1H, m), 1.95–2.05 (2H, m), 2.67–2.90 (4H, m), 2.89 (2H, t, J=7.0 Hz), 3.00 (1H, dd, J=2, 14 Hz), 3.11 (2H, t, J=7.0 Hz), 3.20 (1H, dd, J=2, 14 Hz), 3.37 (3H, s), 4.00 (2H, s), 4.27 (2H, s), 7.01 (1H, d, J=7.9 Hz), 7.17–7.26 (5H, m), 7.57 (1H, d, J=7.9 Hz).

Example 69

3-[2-Benzyl-6-(2-ethoxycarbonylethenyl)-3-pyridyl]ethynyl-3-quinuclidinol

The target compound was synthesized in the same manner as in Example 68.

$^1$H-NMR (CDCl$_3$) δ=1.34 (3H, t, J=7.1 Hz), 1.44–1.53 (1H, m), 1.62–1.72 (1H, m), 1.80–1.89 (1H, m), 2.08–2.17 (2H, m), 2.75–3.05 (4H, m), 3.11 (1H, dd, J=2, 14 Hz), 3.25 (1H, dd, J=2, 14 Hz), 4.28 (2H, q, J=7.1 Hz), 4.33 (2H, s), 6.94 (1H, d, J=16 Hz), 7.18–7.30 (6H, m), 7.63 (1H, d, J=16 Hz), 7.66 (1H, d, J=7.9 Hz).

Example 70

3-[2-Benzyl-6-(2-cyanoethyl)-3-pyridyl]ethynyl-3-quinuclidinol

The target compound was synthesized in the same manner as in Example 68.

$^1$H-NMR (CDCl$_3$) δ=1.36–1.46 (1H, m), 1.56–1.66 (1H, m), 1.76–1.89 (1H, m), 1.98–2.08 (2H, m), 2.69–2.95 (4H, m), 2.84 (2H, t, J=7.3 Hz), 3.02 (1H, dd, J=2, 14 Hz), 3.10 (2H, t, J=7.3 Hz), 3.21 (1H, dd, J=2, 14 Hz), 4.31 (2H, s), 7.04 (1H, d, J=7.9 Hz), 7.18–7.28 (5H, m), 7.64 (1H, d, J=7.9 Hz).

Example 71

3-[2-Benzyl-6-(3-oxobutyl)-3-pyridyl]ethynyl-3-quinuclidinol

The target compound was synthesized in the same manner as in Example 68.

$^1$H-NMR (CDCl$_3$) δ=1.35–1.44 (1H, m), 1.52–1.62 (1H, m), 1.75–1.87 (1H, m), 1.98–2.08 (2H, m), 2.13 (3H, s), 2.68–2.95 (4H, m), 2.88 (2H, t, J=6.9 Hz), 3.00 (1H, dd, J=2, 14 Hz), 3.03 (2H, t, J=6.9 Hz), 3.19 (1H, dd, J=2, 14 Hz), 4.27 (2H, s), 6.99 (1H, d, J=7.9 Hz), 7.16–7.28 (5H, m), 7.55 (1H, d, J=7.9 Hz).

Example 72

3-(2-Phenyl-6-morpholino-3-pyridyl)ethynyl-3-quinuclidinol a) 2-Bromo-6-morpholinopyridine A mixture of 5.7 g of 2,6-dibromopyridine, 2.5 g of 3-hydroxypyrrolidine, 3.6 ml of 1,8-diazbicyclo[5.4.0]-7-undecene (DBU) and 20 ml of tetrahydrofuran was heated under stirring for 11 hours in an oil bath kept at 70° C. The mixture was partitioned between ethyl acetate-water, and the organic layer was washed with water and brine, dried over anhydrous magnesium sulfate and then concentrated. The residue was subjected to silica gel column chromatography using 10–30% ethyl acetate/hexane, to give 5.9 g of 2-bromo-6-(3-hydroxypyrrolidine-1-yl)pyridine.

$^1$H-NMR (CDCl$_3$) δ=3.50 (4H, t, J=5Hz), 3.80 (4H, t, J=5 Hz), 6.50 (1H, d, J=8 Hz), 6.79 (1H, d, J=8 Hz), 7.31 (1H, t, J=8 Hz).

b) 2-Phenyl-6-morpholinopyridine

A mixture of 1 g of 2-bromo-6-morpholinopyridine, 110 mg of 1,3-bis(diphenylphosphino)propanenickel(II) chloride and 4 ml of tetrahydrofuran was stirred in an ice bath in a nitrogen atmosphere. A tetrahydrofuran solution of phenylmagnesium bromide which was prepared from 0.65 ml of bromobenzene, 200 mg of magnesium and 5 ml of tetrahydrofuran was added dropwise into the mixture, followed by stirring at room temperature overnight as it was. The reaction solution was extracted with an aqueous saturated ammonium chloride and ethyl acetate, and the organic phase was washed with water and brine, dried over anhydrous magnesium sulfate and then concentrated. The residue was subjected to silica gel column chromatography using 2–10% ethyl acetate/hexane, to give 750 mg of the target compound.

$^1$H-NMR (CDCl$_3$) δ=3.62 (4H, t, J=5 Hz), 3.86 (4H, t, J=5 Hz), 6.60 (1H, d, J=8 Hz), 7.15 (1H, d, J=8 Hz), 7.37 (1H, t, J=7 Hz), 7.44 (2H, t, J=7 Hz), 7.58 (1H, t, J=8 Hz), 8.01 (2H, d, J=7 Hz).

c) 2-Phenyl-6-morpholino-3-iodopyridine

A solution of 750 mg of 2-phenyl-6-morpholinopyridine and 5 ml of N,N-dimethylformamide was stirred in an ice bath, and to the mixture was added 740 mg of N-iodosuccinimide, followed by stirring at room temperature overnight. Further, 70 mg of N-iodosuccinimide was added thereto, followed by stirring at room temperature for 5 hours. The reaction mixture was extracted by adding ethyl acetate, water and sodium sulfite thereto, and the organic phase was washed with water and brine, dried over anhydrous magnesium sulfate and then concentrated. The residue was subjected to silica gel column chromatography using 5–10% ethyl acetate/hexane, to give 1.1 g of the target compound.

$^1$H-NMR (CDCl$_3$) δ=3.52 (4H, t, J=5 Hz), 3.80 (4H, t, J=5 Hz), 6.37 (1H, d, J=9 Hz), 7.36–7.45 (3H, m), 7.60–7.65 (2H, m), 7.93 (1H, d, J=9 Hz).

d) 3-(2-Phenyl-6-morpholino-3-pyridyl)ethynyl-3-quinuclidinol

A mixture of 500 mg of 2-phenyl-6-morpholino-3-iodopyridine, 230 mg of 3-ethynyl-3-quinuclidinol, 79 mg of tetrakis(triphenylphosphine)palladium(0), 1.3 mg of cuprous iodide, 0.57 ml of triethylamine and 1 ml of N,N-dimethylformamide was heated under stirring for 4 hours in an oil bath kept at 75° C. in a nitrogen atmosphere. The mixture was extracted by adding aqueous dilute ammonia and ethyl acetate thereto, and the organic phase was washed with water and brine, dried over anhydrous magnesium sulfate and then concentrated. The residue was subjected to NH-silica gel column chromatography, and eluted with 50% ethyl acetate/hexane, ethyl acetate and then 2.5% methanol/ethyl acetate, and crystallized from ethyl acetate, to give 296 mg of the target compound.

$^1$H-NMR (CDCl$_3$) δ=1.32–1.82 (3H, m), 1.94–2.03 (2H, m), 2.65–2.91 (4H, m), 2.95 (1H, d, J=14 Hz), 3.19 (1H, dd, J=2, 14 Hz), 3.62 (4H, t, J=5 Hz), 3.82 (4H, t, J=5 Hz), 6.54 (1H, d, J=8 Hz), 7.34–7.44 (3H, m), 7.62 (1H, d, J=8 Hz), 7.92 (2H, d, J=8 Hz).

Example 73

3-(2-Phenyloxy-6-morpholino-3-pyridyl)ethynyl-3-quinuclidinol a) 2-Phenyloxy-6-morpholino-3-pyridine 250 mg of 60% oil sodium hydride was added to a mixture of 1 g of 2-bromo-6-morpholinopyridine obtained in Example 72a, 580 mg of phenol, 80 mg of cuprous iodide, 26 mg of a copper powder and 3 ml of N-methylpyrrolidine. After foaming stopped, the mixture was heated under stirring in an oil bath kept at 150° C. for 3 hours in a nitrogen atmosphere. Aqueous dilute ammonia and ethyl acetate were added thereto, and the mixture was extracted. The organic phase was washed with water and brine, dried over anhydrous magnesium sulfate and then concentrated. The residue was subjected to silica gel chromatography using 5 to 7% ethyl acetate/hexane, to give 1.1 g of the target compound.

$^1$H-NMR (CDCl$_3$) δ=3.40 (4H, t, J=5 Hz), 3.76 (4H, t, J=5 Hz), 6.11 (1H, d, J=8 Hz), 6.28 (1H, d, J=8 Hz), 7.15–7.19 (3H, m), 7.36 (2H, t, J=8 Hz), 7.47 (1H, t, J=8 Hz).

b) 3-(2-Phenyloxy-6-morpholino-3-pyridyl)ethynyl-3-quinuclidinol

The target compound was synthesized in the same manner as in Examples 72 c and d.

$^1$H-NMR (CDCl$_3$) δ=1.34–2.06 (5H, m), 2.74–2.94 (4H, m), 3.00 (1H, d, J=14 Hz), 3.27 (1H, dd, J=2, 14 Hz), 3.34 (4H, t, J=5 Hz), 3.69 (4H, t, J=5 Hz), 6.24 (1H, d, J=8 Hz), 7.09–7.17 (3H, m), 7.34 (2H, t, J=4 Hz), 7.56 (1H, d, J=8 Hz).

Example 74

3-[2-Benzyl-6-(4-piperidinone-1-yl)-3-pyridyl]ethynyl-3-quinuclidinol

The target compound was synthesized in the same manner as in Example 7.

$^1$H-NMR (CDCl$_3$) δ=1.36–1.96 (3H, m), 2.00–2.10 (2H, m), 2.46 (4H, t, J=6 Hz), 2.72–2.96 (4H, m), 3.04 (1H, d, J=14 Hz), 3.26 (1H, dd, J=2, 14 Hz), 3.92 (4H, t, J=6 Hz), 4.18 (2H, s), 6.54 (1H, d, J=8 Hz), 7.14–7.32 (5H, m), 7.52 (1H, d, J=8 Hz).

Example 75

3-[2-Benzyl-6-(2-methoxyethyl)amino-3-pyridyl]ethynyl-3-quinuclidinol

The target compound was synthesized in the same manner as in Example 7.

$^1$H-NMR (CDCl$_3$) δ=1.34–1.92 (3H, m), 1.98–2.07 (2H, m), 2.68–2.92 (4H, m), 3.01 (1H, d, J=14 Hz), 3.22 (1H, dd, J=2, 14 Hz), 3.37 (3H, s), 3.49 (2H, q, J=5 Hz), 3.55 (2H, t, J=5 Hz), 4.14 (2H, s), 4.93 (1H, br.t, J=5 Hz), 6.21 (1H, d, J=8 Hz), 7.13–7.31 (5H, m), 7.40 (1H, d, J=8 Hz).

Example 76

3-[2-Benzyl-6-(4-acetylpiperidine-1-yl)-3-pyridyl]ethynyl-3-quinuclidinol

The target compound was synthesized in the same manner as in Example 7.

$^1$H-NMR (CDCl$_3$) δ=1.34–1.44 (1H, m), 1.53–1.67 (3H, m), 1.83–2.08 (5H, m), 2.17 (3H, s), 2.55 (1H, tt, J=4, 11 Hz), 2.68–2.96 (6H, m), 3.02 (1H, d, J=14 Hz), 3.23 (1H, dd, J=2, 14 Hz), 4.15 (2H, s), 4.35 (2H, d, J=13 Hz), 6.43 (1H, d, J=8 Hz), 7.17 (1H, t, J=7 Hz), 7.22–7.32 (4H, m), 7.43 (1H, d, J=8 Hz).

Example 77

3-[2-Benzyl-6-[(2R)-2-methoxymethylpyrrolidine-1-yl]-3-pyridyl]ethynyl-3-quinuclidinol The target compound was synthesized in the same manner as in Example 7.

$^1$H-NMR (CDCl$_3$) δ=1.36–2.10 (9H, m), 2.74–2.95 (4H, m), 3.04 (1H, d, J=14 Hz), 3.20–3.30 (3H, m), 3.32 (3H, s), 3.40–3.49 (1H, m), 3.53 (1H, dd, J=3, 9 Hz), 4.06–4.30 (3H, m), 6.18 (1H, d, J=9 Hz), 7.16 (1H, t, J=7 Hz), 7.25 (2H, t, J=7 Hz), 7.33 (2H, d, J=7 Hz), 7.40 (1H, d, J=9 Hz).

Example 78

3-[2-Benzyl-6-(thiomorpholino)-3-pyridyl]ethynyl-3-quinuclidinol

The target compound was synthesized in the same manner as in Example 191 using 2-benzyl-3-bromo-6-pyridyl trifluoromethanesulfonate (Production Example-3) as starting material.

$^1$H-NMR (CDCl$_3$) δ=1.36–1.95 (3H, m), 1.97–2.08 (2H, m), 2.58–2.63 (4H, m), 2.70–2.95 (4H, m), 3.03 (1H, d, J=14 Hz), 3.25 (1H, d, J=14 Hz), 3.94–3.99 (4H, m), 4.15 (2H, s),

Example 79

3-[2-Benzyl-6-(3-hydroxypiperidino)-3-pyridyl]ethynyl-3-quinuclidinol

The target compound was synthesized in the same manner as in Example 7.

$^1$H-NMR (CDCl$_3$) δ=1.36–1.98 (7H, m), 1.98–2.08 (2H, m), 2.70–2.95 (4H, m), 3.02 (1H, d, J=14 Hz), 3.23 (1H, d, J=14 Hz), 3.40–3.90 (5H, m), 4.14 (2H, s), 6.47 (1H, d, J=9 Hz), 7.12–7.32 (5H, m), 7.42 (1H, d, J=9 Hz).

Example 80

3-[2-Benzyl-6-(4-cyanopiperidino)-3-pyridyl]ethynyl-3-quinuclidinol

The target compound was synthesized in the same manner as in Example 7.

$^1$H-NMR (CDCl$_3$) δ=1.36–2.10 (9H, m), 2.70–2.95 (5H, m), 3.03 (1H, d, J=14 Hz), 3.24 (1H, dd, J=2, 14 Hz), 3.47–3.55 (2H, m), 3.81–3.89 (2H, m), 4.16 (2H, s), 6.45 (1H, d, J=9 Hz), 7.15–7.31 (5H, m), 7.47 (1H, d, J=9 Hz).

Example 81

3-(2-Benzyl-6-piperidino-3-pyridyl]ethynyl-3-quinuclidinol

The target compound was synthesized in the same manner as in Example 7.

$^1$H-NMR (CDCl$_3$) δ=1.35–1.45 (1H, m), 1.52–1.82 (7H, m), 1.85–1.95 (1H, m), 2.00–2.07 (2H, m), 2.72–2.96 (4H, m), 3.02 (1H, d, J=14 Hz), 3.23 (1H, dd, J=2, 14 Hz), 3.56 (4H, dd, J=5.6 Hz, 4.8 Hz), 4.15 (2H, s), 6.41 (1H, d, J=8.8 Hz), 7.14–7.33 (5H, m), 7.41 (1H, d, J=8.8 Hz).

Example 82

3-[2-Benzyl-6-(N-morpholinoamino)-3-pyridyl]ethynyl-3-quinuclidinol

The target compound was synthesized in the same manner as in Example 7.

$^1$H-NMR (CDCl$_3$) δ=1.35–1.95 (3H, m), 1.98–2.08 (2H, m), 2.70–2.93 (4H, m), 3.02 (1H, d, J=14 Hz), 3.23 (1H, dd, J=2, 14 Hz), 3.53 (4H, t, J=5 Hz), 3.79 (4H, t, J=5 Hz), 4.17 (2H, s), 6.41 (1H, d, J=9 Hz), 7.14–7.32 (5H, m), 7.47 (1H, d, J=9 Hz).

Example 83

3-[2-Benzyl-6-(4-tetrahydropyranyl)amino-3-pyridyl]ethynyl-3-quinuclidinol

The target compound was synthesized in the same manner as in Example 7.

$^1$H-NMR (CDCl$_3$) δ=1.35–1.95 (5H, m), 1.96–2.08 (4H, m), 2.70–2.93 (4H, m), 3.02 (1H, d, J=14 Hz), 3.23 (1H, dd, J=2, 14 Hz), 3.50 (2H, dt, J=2, 12 Hz), 3.75–3.85 (1H, m), 3.98 (2H, td, J=4, 12 Hz), 4.14 (2H, s), 4.53 (1H, d, J=8 Hz), 6.18 (1H, d, J=8 Hz), 7.14–7.32 (5H, m), 7.41 (1H, d, J=8 Hz).

Example 84

3-[2-Benzyl-6-(1-pyrrolidinyl)-3-pyridyl]ethynyl-3-quinuclidinol

The target compound was synthesized in the same manner as in Example 7.

$^1$H-NMR (CDCl$_3$) δ=1.38–1.48 (1H, m), 1.57–1.67 (1H, m), 1.89–1.95 (1H, m), 1.98 (4H, t, J=6.2 Hz), 2.01–2.10 (2H, m), 2.72–2.98 (4H, m), 3.05 (1H, d, J=14 Hz), 3.25 (1H, d, J=14 Hz), 3.45 (4H, t, J=6.2 Hz), 4.16 (2H, s), 6.14 (1H, d, J=8.6 Hz), 7.16–7.35 (5H, m), 7.40 (1H, d, J=8.6 Hz).

Example 85

3-[2-Benzyl-6-(3-hydroxypyrrolidine)-1-yl)-3-pyridyl]ethynyl-3-quinuclidinol The target compound was synthesized in the same manner as in Example 7.

$^1$H-NMR (CDCl$_3$) δ=1.35–1.95 (3H, m), 1.98–2.20 (4H, m), 2.70–2.95 (4H, m), 3.02 (1H, d, J=14 Hz), 3.23 (1H, d, J=14 Hz), 3.50–3.65 (4H, m), 4.16 (2H, s), 4.57–4.61 (1H, m), 6.16 (1H, d, J=9 Hz), 7 16 (1H, t, J=7 Hz), 7.24 (2H, t, J=7 Hz), 7.32 (2H, d, J=7 Hz), 7.42 (1H, d, J=9 Hz).

Example 86

(3R)-3-[2-Benzyl-6-[(3R)-3-hydroxypyrrolidine)-1-yl)-3-pyridyl]ethynyl-3-quinuclidinol The target compound was synthesized in the same manner as in Example 7.

$^1$H-NMR (CDCl$_3$) δ=1.35–1.95 (3H, m), 1.98–2.20 (4H, m), 2.70–2.95 (4H, m), 3.02 (1H, d, J=14 Hz), 3.23 (1H, d, J=14 Hz), 3.50–3.65 (4H, m), 4.16 (2H, s), 4.57–4.61 (1H, m), 6.16 (1H, d, J=9 Hz), 7.16 (1H, t, J=7 Hz), 7.24 (2H, t, J=7 Hz), 7.32 (2H, d, J=7 Hz), 7.42 (1H, d, J=9 Hz).

Example 87

(3)-3-[2-Benzyl-6-[(3S-3-hydroxypyrrolidine)-1-yl)-3-pyridyl]ethynyl-3-quinuclidinol The target compound was synthesized in the same manner. as in Example 7.

$^1$H-NMR (CDCl$_3$) δ=1.35–1.95 (3H, m), 1.98–2.20 (4H, m), 2.70–2.95 (4H, m), 3.02 (1H, d, J=14 Hz), 3.23 (1H, d, J=14 Hz), 3.50–3.65 (4H, m), 4.16 (2H, s), 4.57–4.61 (1H, m), 6.16 (1H, d, J=9 Hz), 7.16 (1H, t, J=7 Hz), 7.24 (2H, t, J=7 Hz), 7.32 (2H, d, J=7 Hz), 7.42 (1H, d, J=9 Hz).

Example 88

3-[2-Benzyl-6-(1-hydroxypyrrolidine)-1-yl)-3-pyridyl]ethynyl-3-quinuclidinol The target compound was synthesized in the same manner as in Example 7.

$^1$H-NMR (CDCl$_3$) δ=1.37–1.42 (1H, m), 1.52–1.62 (1H, m), 1.78–1.86 (1H, m), 1.98–2.07 (2H, m), 2.37 (2H, quint, J=7.4 Hz), 2.70–2.92 (4H, m), 3.00 (1H, d, J=14 Hz), 3.21 (1H, dd, J=2, 14 Hz), 4.03 (4H, t, J=7.4 Hz), 4.16 (2H, s), 6.05 (1H, d, J=8.5 Hz), 7.14–7.32 (5H, m), 7.40 (1H, d, J=8.5 Hz).

(Note: preceding fragment) 6.40 (1H, d, J=9 Hz), 7.14–7.32 (5H, m), 7.45 (1H, d, J=9 Hz).

Example 89

(3R)-3-[2-Benzyl-6-(1-azetinidyl)-3-pyridyl]ethynyl-3-quinuclidinol

The target compound was synthesized in the same manner as in Example 7.

¹H-NMR (CDCl₃) δ=1.37–1.42 (1H, m), 1.52–1.62 (1H, m), 1.78–1.86 (1H, m), 1.98–2.07 (2H, m), 2.37 (2H, quint, J=7.4 Hz), 2.70–2.92 (4H, m), 3.00 (1H, d, J=14 Hz), 3.21 (1H, dd, J=2, 14 Hz), 4.03 (4H, t, J=7.4 Hz), 4.16 (2H, s), 6.05 (1H, d, J=8.5 Hz), 7.14–7.32 (5H, m), 7.40 (1H, d, J=8.5 Hz).

Example 90

(3R)-3-[2-Benzyl-6-(1-hydroxyazetidine-1-yl)-3-pyridyl]ethynyl-3-quinuclidinol

The target compound was synthesized in the same manner as in Example 7.

¹H-NMR (CDCl₃) δ=1.40–1.95 (3H, m), 2.05–2.15 (2H, m), 2.65–2.95 (4H, m), 2.98–3.22 (2H, m), 3.88 (2H, dd, J=5, 10 Hz), 4.17 (2H, s), 4.26 (2H, dd, J=6, 10 Hz), 4.65–4.75 (1H, m), 6.13 (1H, d, J=9 Hz), 7.10–7.20 (1H, m), 7.20–7.30 (4H, m), 7.44 (1H, d, J=9 Hz).

Example 91

3-[2-Benzyl-6-(1-methoxypyrrolidine)-1-yl)-3-pyridyl]ethynyl-3-quinuclidinol

The target compound was synthesized in the same manner as in Example 10.

¹H-NMR (CDCl₃) δ=1.37–1.42 (1H, m), 1.52–1.62 (1H, m), 1.84–1.94 (1H, m), 1.98–2.20 (4H, m), 2.72–2.94 (4H, m), 3.01 (1H, d, J=14 Hz), 3.23 (1H, dd, J=2, 14 Hz), 3.36 (3H, s), 3.46–3.64 (4H, m), 4.02–4.08 (1H, m), 4.15 (2H, s), 6.13 (1H, d, J=8.6 Hz), 7.13–7.34 (5H, m), 7.40 (1H, d, J=8.6 Hz).

Example 92

3-[2-Benzyl-6-[(3S)-methoxypyrrolidine)-1-yl)-3-pyridyl]ethynyl-3-quinuclidinol

The target compound was synthesized in the same manner as in Example 10.

¹H-NMR (CDCl₃) δ=1.37–1.42 (1H, m), 1.52–1.62 (1H, m), 1.84–1.94 (1H, m), 1.98–2.20 (4H, m), 2.72–2.94 (4H, m), 3.01 (1H, d, J=14 Hz), 3.23 (1H, dd, J=2, 14 Hz), 3.36 (3H, s), 3.46–3.64 (4H, m), 4.02–4.08 (1H, m), 4.15 (2H, s), 6.13 (1H, d, J=8.6 Hz), 7.13–7.34 (5H, m), 7.40 (1H, d, J=8.6 Hz).

Example 93

(3R)-3-[2-Benzyl-6-[(3R)-3-methoxypyrrolidine)-1-yl)-3-pyridyl]ethynyl-3-quinuclidinol The target compound was synthesized in the same manner as in Example 10.

¹H-NMR (CDCl₃) δ=1.37–1.42 (1H, m), 1.52–1.62 (1H, m), 1.84–1.94 (1H, m), 1.98–2.20 (4H, m), 2.72–2.94 (4H, m), 3.01 (1H, d, J=14 Hz), 3.23 (1H, dd, J=2, 14 Hz), 3.36 (3H, s), 3.46–3.64 (4H, m), 4.02–4.08 (1H, m), 4.15 (2H, s), 6.13 (1H, d, J=8.6 Hz), 7.13–7.34 (5H, m), 7.40 (1H, d, J=8.6 Hz).

Example 94

3-[2-Benzyl-6-(3-ethoxypyrrolidine)-1-yl)-3-pyridyl]ethynyl-3-quinuclidinol

The target compound was synthesized in the same manner as in Example 10.

¹H-NMR (CDCl₃) δ=1.21 (3H, t, J=7.0 Hz), 1.35–1.45 (1H, m), 1.54–1.62 (1H, m), 1.85–1.95 (1H, m), 1.98–2.15 (4H, m), 2.72–2.94 (4H, m), 3.01 (1H, d, J=14 Hz), 3.23 (1H, dd, J=2, 14 Hz), 3.48–3.62 (6H, m), 4.12–4.20 (3H, m), 6.13 (1H, d, J=8.6 Hz), 7.13–7.34 (5H, m), 7.40 (1H, d, J=8.6 Hz).

Example 95

(3)-3-[2-Benzyl-6-[(3R)-3-ethoxypyrrolidine)-1-yl)-3-pyridyl]ethynyl-3-quinuclidinol The target compound was synthesized in the same manner as in Example 10.

¹H-NMR (CDCl₃) δ=1.21 (3H, t, J=7.0 Hz), 1.35–1.45 (1H, m), 1.54–1.62 (1H, m), 1.85–1.95 (1H, m), 1.98–2.15 (4H, m), 2.72–2.94 (4H, m), 3.01 (1H, d, J=14 Hz), 3.23 (1H, dd, J=2, 14 Hz), 3.48–3.62 (6H, m), 4.12–4.20 (3H, m), 6.13 (1H, d, J=8.6 Hz), 7.13–7.34 (5H, m), 7.40 (1H, d, J=8.6 Hz).

Example 96

3-[2-Benzyl-6-[(3S)-3-ethoxypyrrolidine)-1-yl)-3-pyridyl]ethynyl-3-quinuclidinol The target compound was synthesized in the same manner as in Example 10.

¹H-NMR (CDCl₃) δ=1.21 (3H, t, J=7.0 Hz), 1.35–1.45 (1H, m), 1.54–1.62 (1H, m), 1.85–1.95 (1H, m), 1.98–2.15 (4H, m), 2.72–2.94 (4H, m), 3.01 (1H, d, J=14 Hz), 3.23 (1H, dd, J=2, 14 Hz), 3.48–3.62 (6H, m), 4.12–4.20 (3H, m), 6.13 (1H, d, J=8.6 Hz), 7.13–7.34 (5H, m), 7.40 (1H, d, J=8.6 Hz).

Example 97

(3R)-3-[2-Benzyl-6-(4-ethoxypyrrolidino)-3-pyridyl]ethynyl-3-quinuclidinol

The target compound was synthesized in the same manner as in Example 7 by using (3R)-3-ethynyl-3-quinuclidinol.

¹H-NMR (CDCl₃) δ=1.22 (3H, t, J=7 Hz), 1.35–1.44 (1H, m), 1.51–1.62 (3H, m), 1.73–1.96 (3H, m), 1.97–2.08 (2H, m), 2.70–2.95 (4H, m), 3.01 (1H, d, J=14 Hz), 3.14–3.26 (3H, m), 3.48–3.58 (3H, m), 4.00–4.09 (2H, m), 4.15 (2H, s), 6.43 (1H, d, J=9 Hz), 7.16 (1H, t, J=7 Hz), 7.24 (2H, t, J=7 Hz), 7.30 (2H, d, J=7 Hz), 7.42 (1H, d, J=9 Hz).

Example 98

3-[2-Benzyl-6-(3-methoxypyrrolidine-1-yl)-3-pyridyl]ethynyl-3-quinuclidinol

The target compound was synthesized in the same manner as in Example 10.

¹H-NMR (CDCl₃) δ=1.35–1.90 (3H, m), 1.97–2.08 (2H, m), 2.70–2.95 (4H, m), 3.01 (1H, d, J=14 Hz), 3.21 (1H, dd, J=2, 14 Hz), 3.34 (3H, s), 3.90 (2H, dd, J=4, 10 Hz), 4.16 (2H, s), 4.21 (2H, dd, J=6, 10 Hz), 4.30–4.35 (1H, m), 6.10 (1H, d, J9 9 Hz), 7.16 (1H, t, J=7 Hz), 7.22–7.32 (4H, m), 7.42 (1H, d, J=9 Hz).

Example 99

(3R)-3-[2-Benzyl-6-(3-methoxypyrrolidine-1-yl)-3-pyridyl]ethynyl-3-quinuclidinol The target compound was synthesized in the same manner as in Example 10 by using (3R)-3-ethynyl-3-quinuclidinol.

¹H-NMR (CDCl₃) δ=1.35–1.90 (3H, m), 1.97–2.08 (2H, m), 2.70–2.95 (4H, m), 3.01 (1H, d, J=14 Hz), 3.21 (1H, dd, J=2, 14 Hz), 3.34 (3H, s), 3.90 (2H, dd, J=5, 10 Hz), 4.16 (2H, s), 4.21 (2H, dd, J=6, 10 Hz), 4.30–4.35 (1H, m), 6.10 (1H, d, J=9 Hz), 7.16 (1H, t, J=7 Hz), 7.22–7.32 (4H, m), 7.42 (1H, d, J=9 Hz).

Example 100

(3R)-3-[2-Benzyl-6-(3-ethoxyazetidine-1-yl)-3-pyridyl]ethynyl-3-quinuclidinol

The target compound was synthesized in the same manner as in Example 10 by using (3R)-3-ethynyl-3-quinuclidinol.

¹H-NMR (CDCl₃) δ=1.24 (3H, t, J=7 Hz), 1.34–1.43 (1H, m), 1.51–1.64 (1H, m), 1.80–1.90 (1H, m), 1.97–2.08 (2H, m), 2.66–2.93 (4H, m), 3.00 (1H, d, J=14 Hz), 3.21 (1H, dd, J=2, 14 Hz), 3.49 (2H, q, J=7 Hz), 3.90 (2H, dd, J=4, 10 Hz), 4.16 (2H, s), 4.21 (2H, dd, J=6, 10 Hz), 4.37–4.44 (1H, m), 6.09 (1H, d, J=8 Hz), 7.16 (1H, t, J=7 Hz), 7.24 (2H, t, J=7 Hz), 7.29 (2H, d, J=7 Hz), 7.41 (1H, d, J=8 Hz).

Example 101

(3R)-3-[2-Benzyl-6-(3-methoxymethyloyazetidine-1-yl)-3-pyridyl]ethynyl-3-quinuclidinol The target compound was synthesized in the same manner as in Example 7.

¹H-NMR (CDCl₃) δ=1.35–1.90 (3H, m), 1.97–2.08 (2H, m), 2.68–2.93 (4H, m), 3.00 (1H, d, J=14 Hz), 3.21 (1H, dd, J=2, 14 Hz), 3.41 (3H, s), 3.94 (2H, dd, J=5, 10 Hz), 4.16 (2H, s), 4.26 (2H, dd, J=7, 10 Hz), 4.55–4.61 (1H, m), 4.67 (2H, s), 6.10 (1H, d, J=8 Hz), 7.16 (1H,t,J=7 Hz), 7.22–7.32 (4H, m), 7.42 (1H, d, J=9 Hz).

Example 102

3-[4-Benzyl-2-[(3R,4R)-3-hydroxy-4-ethyloxypyrrolidine-1-yl)-3-pyridyl]ethynyl-3-quinuclidinol The target compound was synthesized in the same manner as in Example 10 except that methyl iodide was altered to ethyl iodide.

¹H-NMR (CDCl₃) δ=1.26 (3H, t, J=7 Hz), 1.38–1.63 (2H, m), 1.84–1.93 (1H, m), 2.00–2.07 (2H, m), 2.74–2.93 (4H, m), 3.00–3.04 (1H, m), 3.21–3.25 (1H, m), 3.48–3.52 (2H, m), 3.61 (2H, q, J=7 Hz), 3.71–3.77 (2H, m), 3.94–3.96 (1H, m), 4.15 (2H, s), 4.37–4.40 (1H, m), 6.15 (1H, d, J=8 Hz), 7.16–7.33 (5H, m), 7.42 (1H, d, J=8 Hz).

Example 103

(3R)-3-[2-Benzyl-6-[(3R,4R)-3,4-dihydroxypyrrolidine-1-yl)-3-pyridyl]ethynyl-3-quinuclidinol The target compound was synthesized in the same manner as in Example 10.

¹H-NMR (DMSO-d₆) δ=1.30–1.32 (1H, m), 1.52 (1H, m), 1.77–1.99 (3H, m), 2.56–2.72 (4H, m), 2.82 (1H, d, J=14 Hz), 3.01 (1H, d, J=14 Hz), 3.50–3.53 (2H, m), 4.01–4.11 (4H, m), 5.10–5.11 (2H, m), 6.26 (1H, d, J=8 Hz), 7.14–7.34 (5H, m), 7.42 (1H, d, J=8 Hz).

Example 104

(3R)-3-[2-Benzyl-6-[(3R,4R)-3,4-dimethoxypyrrolidine-1-yl)-3-pyridyl]ethynyl-3-quinuclidinol a) 2-Benzyl-6-[(3R,4R)-3,4-dimethoxypyrrolidin-1-yl)-3-pyridyl]ethynyl-3-quinuclidinol 700 mg of 60% oily sodium hydride and 1 ml of methyl iodide were added to a mixture of 1.78 g of 2-benzyl-6-[(3R,4R)-3,4-dihydroxypyrrolidine-1-yl]pyridine (Example 10a), 10 ml of tetrahydrofuran and 10 ml of N,N-dimethylformamide. The mixture was extracted with ethyl acetate-water. The organic layer was washed with water and brine, dried over anhydrous magnesium sulfate and evaporated. The residue was subjected to silica gel chromatography and eluted with 15% ethyl acetate/hexane, to give 1.0 g of the target compound.

¹H-NMR (CDCl₃) δ=3.42 (6H, s), 3.55 (2H, dd, J=2, 11 Hz), 3.67 (2H, dd, J=4, 11 Hz), 3.92–3.96 (2H, m), 3.97 (2H, s), 6.16 (1H, d, J=9 Hz), 6.33 (1H, d, J=7 Hz), 7.18 (1H, t, J=7 Hz), 7.24–7.34 (5H, m).

b) (3R)-3-[2-Benzyl-6-(3R,4R)-3,4-dimethoxypyrrolidine-1-yl)-3-pyridyl]ethynyl-3-quinuclidinol The target compound was synthesized in the same manner as in Example 10.

¹H-NMR (CDCl₃) δ=1.34–1.44 (1H, m), 1.52–1.62 (1H, m), 1.82–1.92 (1H, m), 1.97–2.08 (2H, m), 2.70–2.95 (4H, m), 3.01 (1H, d, J=14 Hz), 3.23 (1H, dd, J=2, 14 Hz), 3.41 (6H, s), 3.53–3.67 (4H, m), 3.92–3.96 (2H, m), 4.16 (2H, s), 6.14 (1H, d, J=9 Hz), 7.15 (1H, t, J=7 Hz), 7.24 (2H, t, J=7 Hz), 7.31 (2H, d, J=7 Hz), 7.40 (1H, d, J=9 Hz).

Example 105

(3R)-3-[2-Benzyl-6-[(3R,4R)-3,4-diethoxypyrrolidine-1-yl)-3-pyridyl]ethynyl-3-quinuclidinol The target compound was synthesized in the same manner as in Example 104 by using (3R)-3-ethynyl-3-quinuclidinol.

¹H-NMR (CDCl₃) δ=1.20 (6H, t, J=7 Hz), 1.35–1.95 (3H, m), 1.98–2.09 (2H, m), 2.70–2.95 (4H, m), 3.03 (1H, d, J=14 Hz), 3.24 (1H, dd, J=2, 14 Hz), 3.50–3.56 (2H, m), 3.59 (4H, q, J=7 Hz), 3.67 (2H, dd, J=4, 12 Hz), 4.02 (2H, dd, J=2, 4 Hz), 4.15 (2H, s), 6.14 (1H, d, J=9 Hz), 7.15 (1H, t, J=7 Hz), 7.24 (2H, t, J=7 Hz), 7.32 (2H, d, J=7 Hz), 7.40 (1H, d, J=9 Hz).

Example 106

(3R)-3-[2-Benzyl-6-[(3R,4S)-3-hydroxy-4-methoxypyrrolidine-1-yl)-3-pyridyl]ethynyl-3-quinuclidinol a) 2-Benzyl-3-iodo-6-[(3S,4S)-3-(3-nitrobenzenesulfonyl)oxy-4-methoxypyrrolidine-1-yl)pyridine 300 mg of 4-dimethylaminopyridine, 10 ml of triethylamine and 9.7 g of 3-nitrobenzenesulfonyl chloride were added to a solution of 10.0 g of 2-benzyl-3-iodo-6-[(3S,4S)-3-hydroxy-4-methoxypyrrolidine-1-yl]pyridine obtained in the same manner as in Example 10-c in 150 ml of ethyl acetate, followed by stirring at room temperature for 3 days. The reaction solution was first filtered through 50 g of silica gel, and washed with ethyl acetate. Further, the filtrate was filtered through 50 g of NH-silica gel and washed with ethyl acetate. The filtrate was concentrated, to give 14.6 g of the target compound.

¹H-NMR (CDCl₃) δ=3.38 (3H, s), 3.48 (1H, d, J=12 Hz), 3.58–3.73 (3H, m), 4.08–4.20 (3H, m), 5.10–5.14 (1H, m), 5.92 (1H, d, J=8 Hz), 7.18 (1H, t, J=7 Hz), 7.25 (2H, t, J=7 Hz), 7.32 (2H, d, J=7 Hz), 7.69 (1H, d, J=8 Hz), 7.73 (1H, t, J=8 Hz), 8.21 (1H, d, J=8 Hz), 8.49 (1H, d, J=8 Hz), 8.75 (1H, s).

b) 2-Benzyl-3-iodo-6-[(3S,4S)-3-acetoxy-4-methoxypyrrolidine-1-yl)pyridine 4.2 ml of acetic acid was added to a mixture of 7.9 g of cesium carbonate and 15 ml of dimethyl sulfoxide. After foaming stopped, a mixture of 14.4 g of 2-benzyl-3-iodo-6-[(3S,4S)-3-(3-nitrobenzenesulfonyl)oxy-4-methoxypyrrolidine-1-yl]pyridine and 35 ml of dimethyl sulfoxide was added thereto, followed by heating under stirring for 6 hours in an oil bath kept at 70° C. in a nitrogen atmosphere. The reaction solution was cooled and then subjected to extraction with ethyl acetate-water. The organic phase was washed with water and brine brine, dried over anhydrous magnesium sulfate and then concentrated. The residue was subjected to silica gel column chromatography using 10–15% ethyl acetate/hexane, to give 7.5 g of the target compound.

$^1$H-NMR (CDCl$_3$) δ=2.12 (3H, s), 3.42 (3H, s), 3.37–3.73 (4H, m), 4.04 (1H, dt, J=4, 6 Hz), 4.19 (2H, s), 5.42–5.47 (1H, m), 5.96 (1H, d, J=8 Hz), 7.19 (1H, t, J=7 Hz), 7.27 (2H, t, J=7 Hz), 7.38 (2H, d, J=7 Hz), 7.70 (1H, d, J=8 Hz).

c) 2-Benzyl-3-iodo-6-[(3R,4S)-3-hydroxy-4-methoxypyrrolidine-1-yl)pyridine

A 28% solution of sodium methoxide in 0.33 ml of methanol was added to a mixture of 7.5 g of 2-benzyl-3-iodo-6-[(3R,4S)-3-acetoxy-4-methoxypyrrolidine-1-yl]pyridine and 30 ml of methanol, followed by stirring at room temperature for 30 minutes in a nitrogen atmosphere. Water was added thereto, and the mixture was extracted with ethyl acetate. The organic phase was washed with brine, dried over anhydrous magnesium sulfate and then concentrated. The residue was subjected to silica gel column chromatography using 20–50% ethyl acetate, to give 6.7 g of the target compound.

$^1$H-NMR (CDCl$_3$) δ=2.63 (1H, d, J=5 Hz), 3.38–3.67 (4H, m), 3.47 (3H, s), 3.93 (1H, q, J=5 Hz), 4.18 (2H, s), 4.41 (1H, quint., J=5 Hz), 5.96 (1H, d, J=9 Hz), 7.18 (1H, t, J=7 Hz), 7.26 (2H, t, J=7 Hz), 7.37 (2H, d, J=7 Hz), 7.69 (1H, d, J=9 Hz).

d) (3R)-3-[2-Benzyl-6-[(3R,4S)-3-(3-hydroxy-4-methoxypyrrolidine-1-yl)pyridyl]ethynyl-3-quinuclidinol A mixture of 4.6 g of 2-benzyl-3-iodo-6-[(3R,4S)-3-hydroxy-4-methoxypyrrolidine-1-yl]pyridine, 1.7 g of (3R)-3-ethynyl-3-quinuclidinol, 130 mg of tetrakis (triphenylphosphine)palladium(0), 110 mg of cuprous iodide and 3.1 ml of triethylamine was stirred for 5 hours at room temperature in a nitrogen atmosphere. The reaction solution was extracted with aqueous dilute ammonia-ethyl acetate, and the organic phase was washed with water and brine, dried over anhydrous magnesium sulfate and then concentrated. The residue was subjected to NH-silica gel column chromatography using 0–5% methanol/ethyl acetate, to give 4.0 g of the target compound.

$^1$H-NMR (CDCl$_3$) δ=1.34–1.93 (3H, m), 1.97–2.07 (2H, m), 2.63–2.94 (5H, m), 3.02 (1H, d, J=14 Hz), 3.23 (1H, dd, J=2, 14 Hz), 3.41–3.57 (2H, m), 3.48 (3H, s), 3.60–3.73 (2H, m), 3.94 (1H, q, J=5 Hz), 4.41 (1H, q, J=5 Hz), 6.12 (1H, d, J=9 Hz), 7.16 (1H, t, J=7 Hz), 7.24 (2H, t, J=7 Hz), 7.31 (2H, d, J=7 Hz), 7.41 (1H, d, J=9 Hz).

Example 107

(3R)-3-[2-Benzyl-6-[(3R,4S)-3,4-difluoropyrrolidine-1-yl)-3-pyridyl]ethynyl-3-quinuclidinol a) 2-Benzyl-6-[(3R,4R)-3,4-difluoropyrrolidine-1-yl]pyridine 3.0 ml of a dichloromethane solution containing 481 mg of 2-benzyl-6-[(3S,4S)-3,4-dihydroxypyrrolidine-1-yl]pyridine was slowly added dropwise into 5.0 ml of a dichloromethane solution containing 235 μl of diethylaminosulfur trifluoride at −78° C. After stirring under heating for 30 minutes at room temperature, it was further stirred for one hour at 40° C. After cooling as it was, water was added to the reaction solution and the mixture was then extracted with ethyl acetate. The organic phase was washed with brine and the solvent was removed. The residue was subjected to silica gel column chromatography and eluted with hexane/ethyl acetate (5:1) and then with. hexane/ethyl acetate (2:1), to give 104 mg of the target compound.

$^1$H-NMR (CDCl$_3$) δ=3.71–3.93 (4H, m), 3.99 (2H, s), 5.19–5.34 (2H, m), 6.19 (1H, d, J=8 Hz), 6.42 (1H, d, J=7 Hz), 7.21–7.38 (6H, m).

b) 2-Benzyl-6-[(3R,4R)-3,4-difluoropyrrolidine-1-yl]-3-iodopyridine 94 mg of N-iodosuccinic acid imide was added little by little to 5.0 ml of an N,N-dimethylformamide solution containing 104 mg of 2-benzyl-6-[(3R,4R)-3,4-difluoropyrrolidine-1-yl]pyridine under ice-cooling, followed by stirring overnight as it was. Water was added to the reaction solution and the mixture was extracted with ethyl acetate. The organic phase was washed with an aqueous sodium thiosulfate solution, water and brine, and the solvent was removed. The residue was subjected to NH-silica gel (Fuji Silicia) column chromatography and eluted with hexane/ethyl acetate (10:1), to give 152 mg of the target compound.

$^1$H-NMR (CDCl$_3$) δ=3.66–3.86 (4 H, m), 4.20 (2H, s), 5.18–5.33 (2H, m), 6.01 (1H, d, J=9 Hz), 7.18–7.38 (5H, m), 7.74 (1H, d, J=9 Hz).

c) (3R)-3-[2-Benzyl-6-[(3R,4R)-3,4-difluoropyrrolidine-1-yl]-3-pyridyl]ethynyl-3-quinuclidinol A mixture of 152 mg of 2-benzyl-6-[(3R,4R)-3,4-difluoropyrrolidine-1-yl]-3-iodopyridine, 60 mg of (3R)-3-ethynyl-3-quinuclidinol, 22 mg of tetrakis (triphenylphosphine)palladium(0), 7 mg of cuprous iodide, 106 μl of triethylamine and 1.5 ml of methanol was heated under stirring for 3 hours at 75° C. in a nitrogen atmosphere. The reaction solution was poured into an aqueous dilute ammonia and then extracted with ethyl acetate. The extract was washed with brine and the solvent was removed. The residue was subjected to NH-silica gel (Fuji Silicia) column chromatography, eluted with hexane/ethyl acetate (1:1) and then with ethyl acetate/methanol (15:1) and crystallized from hexane/ethyl acetate, to give 65 mg of the target compound.

$^1$H-NMR (CDCl$_3$) δ=1.37–1.44 (1H, m), 1.58 (1H, m), 1.88–1.89 (1H, m), 2.02–2.05 (2H, m), 2.75–2.88 (4H, m), 3.03 (1H, d, J=14 Hz), 3.24 (1H, dd, J=2, 14 Hz), 3.75–3.93 (4H, m), 4.18 (2H, s), 5.19–5.34 (2H, m), 6.19 (1H, d, J=9 Hz), 7.16–7.33 (5H, m), 7.47 (1H, d, J=9 Hz).

Example 108

(3R)-3-[2-Benzyl-6-[(3R)-3-fluoropyrrolidine-1-yl)-3-pyridyl]ethynyl-3-quinuclidinol The target compound was synthesized from (3S)-1-benzyl-3-pyrrolidinol in the same manner as in Example 107.

$^1$H-NMR (CDCl$_3$) δ=1.37–1.61 (2H, m), 1.86–1.94 (1H, m), 2.00–2.19 (3H, m), 2.33–2.42 (1H, m), 2.75–2.90 (4H, m), 3.03 (1H, d, J=14 Hz), 3.25 (1H, dd, J=2, 14 Hz), 3.52–3.90 (4H, m), 4.17 (2H, s), 5.29–5.43 (1H, m), 6.18 (1H, d, J=8 Hz), 7.15–7.34 (5H, m), 7.44 (1H, d, J=8 Hz).

Example 109

(3R)-3-[2-Benzyl-6-[(3S)-3-fluoropyrrolidine-1-yl)-3-pyridyl]ethynyl-3-quinuclidinol The target compound was synthesized from (3R)-1-benzyl-3-pyrrolidinol in the same manner as in Example 107.

¹H-NMR (CDCl₃) δ=1.37–1.60 (2H, m), 1.86–1.93 (1H, m), 1.99–2.19 (3H, m), 2.32–2.42 (1H, m), 2.75–2.90 (4H, m), 3.03 (1H, d, J=14 Hz), 3.25 (1H, dd, J=2, 14 Hz), 3.52–3.90 (4H, m), 4.17 (2H, s), 5.29–5.43 (1H, m), 6.18 (1H, d, J=8 Hz), 7.15–7.34 (5H, m), 7.44 (1H, d, J=8 Hz).

Example 110

(3R)-3-[2-Benzyl-6-[(3S,4R)-3-fluoropyrrolidine-1-yl)-3-pyridyl]ethynyl-3-quinuclidinol The target compound was synthesized using 2-benzyl-3-iodo-6-[(3R,4R)-3-hydroxy-4-methoxypyrrolidine-1-yl]pyridine (Production Example 10c) in the same manner as in Example 107.

¹H-NMR (CDCl₃) δ=1.39–1.44 (1H, m), 1.57–1.63 (1H, m), 1.87–1.93 (1H, m), 2.02–2.06 (2H, m), 2.75–2.89 (4H, m), 3.03 (1H, d, J=14 Hz), 3.24 (1H, dd, J=2, 14 Hz), 3.43 (3H, s), 3.66–3.80 (4H, m), 4.06–4.09 (1H, m), 4.16 (2H, s), 5.08–5.21 (1H, m), 6.16 (1H, d, J=9 Hz), 7.14–7.32 (5H, m), 7.43 (1H, d, J=9 Hz).

Example 111

(3R)-3-[2-Benzyl-6-[(3S,4R)-3-hydroxy-4-fluoropyrrolidine-1-yl)-3-pyridyl]ethynyl-3-quinuclidinol a) 2-Bromo-6-[(3R,4R-3,4-dihydroxypyrrolidine-1-yl]pyridine A mixture of 12.8 g of 2,6-dibromopyridine, 8.87 g of (3R,4R)-3,4-dihydroxypyrrolidine acetate, 10 ml of 1,8-diazabicyclo[5,4,0]-7-undecene and 20 ml of 1-methyl-2-pyrrolidinone was heated under stirring for 2 hours in a 70° C. oil bath. After cooling, water was added thereto and the mixture was extracted with ethyl acetate five times. The organic layers were combined, washed with water and brine, dried over anhydrous magnesium sulfate and concentrated. The residue was subjected to silica gel column chromatography using 10–100% ethyl acetate/hexane, to give 10.1 g of the target compound. 1H-NMR (CDCl₃) δ=1.86 (2H, br.s), 3.49 (2H, d, J=11Hz), 3.80 (2H, dd,J=4.11 Hz), 4.34 (2H, br.s), 6.26 (1H, d, J=8 Hz), 6.71 (1H, d, J=8 Hz), 7.26 (1H, t, J=8 Hz).

b) 2-Bromo-6-[(3R,4R-3-methoxymethymethyloxy-4-hydroxypyrrolidine-1-yl]pyridine 1.54 g of 60% oily sodium hydride and then 3.0 ml of chloromethyl methyl ether were added to a mixture of 10 g of 2-bromo-6-[(3R,4R)-3,4-dihydroxypyrrolidine-1-yl]pyridine and 100 ml of tetrahydrofuran at room temperature under stirring, followed by stirring at the same temperature for one hour. The reaction solution was extracted with ethyl acetate-water, and the organic phase was washed with brine, dried over anhydrous magnesium sulfate and then concentrated. The residue was subjected to silica gel column chromatography using 10–100% ethyl acetate/hexane, to give 7.6 g of the target compound.

¹H-NMR (CDCl₃) δ=2.95 (1H, d, J=4 Hz), 3.36–3.50 (2H, m), 3.44 (3H, s), 3.78–3.88 (2H, m), 4.06–4.12 (1H, m), 4.32–4.38 (1H, m), 4.72 (1H, d, J=7 Hz), 4.76 (1H, d, J=7 Hz), 6.24 (1H, d, J=8 Hz), 6.70 (1H, d, J=8 Hz), 7.25 (1H, t, J=8 Hz).

c) 2-Benzyl-6-[(3R,4R-3-methoxymethyloxy-4-hydroxypyrrolidine-1-yl]pyridine 46.7 ml of a tetrahydrofuran solution containing 1.07 mol of benzyl magnesium chloride was added dropwise into a solution of 50 ml of tetrahydrofuran containing 5.1 g of 2-bromo-6-[(3R,4R)-3-methoxymethyloxy-4-hydroxypyrrolidine-1-yl]pyridine and 451 mg of 1,3-bis(diphenylphosphino)propanenickel(II) chloride over 10 minutes in an ice bath. After cooling as it was overnight, the reaction solution was poured into aqueous saturated ammonium chloride and extracted with ethyl acetate. The organic phase was washed with brine and the solvent was removed. The residue was subjected to NH-silica gel (Fuji Silicia) column chromatography and eluted with hexane/ethyl acetate (10:1) and then with hexane/ethyl acetate (1:1), to give 5.2 g of the target compound.

¹H-NMR (CDCl₃) δ=3.45 (3H, s), 3.36–3.47 (2H, m), 3.85–3.91 (2H, m), 3.97 (2H, s), 4.05–4.11 (1H, m), 4.32–4.35 (1H, m), 4.73–4.79 (2H, m), 6.16 (1H, d, J=8 Hz), 6.37 (1H, d, J=8 Hz), 7.17–7.38 (6H, m).

d) 2-Benzyl-6-[(3R,4S-3-methoxymethyloxy-4-hydroxypyrrolidine-1-yl]pyridine and 2-Benzyl-6-[(3R,4S-3-(fluoromethoxy)-4-methoxypyrrolidine-1-yl]pyridine 5.0 ml of a dichloromethane solution of 2-benzyl-6-[(3R,4R)-3-methoxymethyloxy-4-hydroxypyrrolidine-1-yl]pyridine was added dropwise into a solution of 10 ml of dichloromethane containing 278 μl of diethylaminosulfur trifluoride at −78° C. over 10 minutes. After stirring at room temperature for one hour, it was heated under stirring at 40° C. for one hour. After cooling as it was, the reaction solution was poured into water. The mixture was extracted with ethyl acetate, and the organic phase was washed with brine and the solvent was removed. Then, the residue was subjected to silica gel column chromatography and eluted with hexane/ethyl acetate (10:1) and then with hexane/ethyl acetate (2:1), to give 56.7 mg of 2-benzyl-6-[(3R,4S)-3-methoxymethyloxy-4-fluoropyrrolidine-1-yl]pyridine (¹H-NMR (CDCl₃) δ=3.38 (3H, s), 3.65–3.82 (4H, m), 3.97 (2H, s), 4.41–4.43 (1H, m), 4.69–4.75 (2H, m), 5.18 (1H, br.d, J=49 Hz), 6.18 (1H, d, J=8 Hz), 6.38 (1H, d, J=7 Hz), 7.01–7.36 (6H, m)) and 294 mg of a crude refined product of 2-benzyl-6-[(3R,4S)-3-(fluoromethoxy)-4-methoxypyrrolidine-1-yl]pyridine. This crude purified product was purified by a thin layer chromatography (developed three timed using hexane/ethyl acetate (5/1) and three times using hexane/ethyl acetate (4/1)), to give 47.8 g of 2-benzyl-6-[(3R,4S)-3-(fluoromethoxy)-4-methoxypyrrolidine-1-yl]pyridine (¹H-NMR (CDCl₃) δ=3.48 (3H, s), 3.54–3.73 (4H, m), 3.97 (2H, s), 4.00–4.04 (1H, m), 4.41–4.46 (1H, m), 5.41 (2H, d, J=56 Hz), 6.15 (1H, d, J=8 Hz), 6.37 (1H, d, J=7 Hz), 7.17–7.35 (6H, m)).

e) 2-Benzyl-6-[(3R,4S-3-methoxymethyloxy-4-fluoropyrrolidine-1-yl]pyridine 44.4 mg of N-iodosuccinic acid imide was added little by little to a solution containing 56.7 mg of 2-benzyl-6-[(3R,4S)-3-methoxymethyloxy-4-fluoropyrrolidine-1-yl]pyridine and 3.0 ml of N,N-dimethylformamide under stirring under ice-cooling, followed by stirring overnight as it was. Water was added to the reaction solution, followed by extracting with ethyl acetate. The organic phase was successively washed with an aqueous sodium thiosulfate solution, water and brine, and the solvent was removed. The residue was eluted with ethyl acetate through NH-silica gel (Fuji Silicia), to give 73.4 mg of the target compound.

¹H-NMR (CDCl₃) δ=3.36 (3H, s), 3.58–3.76 (4H, m), 4.19 (2H, s), 4.37–4.41 (1H, m), 4.70 (2H, s), 5.09–5.22 (1H, m), 6.00 (1H, d, J=9 Hz), 7.16–7.38 (5H, m), 7.70 (1H, d, J=9 Hz).

f) 2-Benzyl-6-[(3R,4R-3-hydroxy-4-fluoropyrrolidine-1-yl]-3-iodopyridine

A mixture of 73.4 mg of 2-benzyl-6-[(3R,4S)-3-methoxymethyloxy-4-fluoropyrrolidine-1-yl]-3-iodopyridine and 5.0 ml of trifluoroacetic acid was heated under stirring for 2 hours at 45° C. After cooling as it was, it was poured into an aqueous potassium carbonate solution and extracted with ethyl acetate. The organic phase was washed with brine and the solvent was removed. Then, the residue was subjected to silica gel column chromatography and eluted with hexane/ethyl acetate (5:1) and then with hexane/ethyl acetate (1:1), to give 50 mg of the target compound.

$^1$H-NMR (CDCl$_3$) δ=3.46–3.82 (4H, m), 4.19 (2H, s), 4.48–4.51 (1H, m), 5.04 (1H, br.d, J=52 Hz), 6.00 (1H, d, J=9 Hz), 7.16–7.38 (5H, m), 7.71 (1H, d, J=9 Hz).

g) (3R)-3-[2-Benzyl-6-[(3R,4S)-3-hydroxy-4-fluoropyrrolidine-1-yl]-3-pyridyl]ethynyl-3-quinuclidinol A mixture of 50 mg of 2-benzyl-6-[(3R,4S)-3-hydroxy-4-fluoropyrrolidine-1-yl]-3-iodopyridine, 21 mg of (3R)-3-ethynyl-3-quinuclidinol, 15 mg of tetrakis(triphenylphosphine)palladium(0), 1 mg of cuprous iodide, 53 μl of triethylamine and 3.0 ml of N,N-dimethylformamide was heated under stirring for 3 hours at 75° C. in a nitrogen atmosphere. The reaction solution was poured into an aqueous dilute ammonia, was then extracted with ethyl acetate. Then, the organic phase was washed with brine and the solvent was removed. The residue was subjected to NH-silica gel (Fuji Silicia) column chromatography and eluted with hexane/ethyl acetate (1:1) and then with ethyl acetate/methanol (15:1), to give 37 mg of the target compound.

$^1$H-NMR (CDCl$_3$) δ=1.35–1.43 (1H, m), 1.56–1.58 (1H, m), 1.85–1.90 (1H, m), 2.01–2.16 (2H, m), 2.73–2.86 (4H, m), 2.97–3.00 (1H, m), 3.15–3.21 (1H, m), 3.57–3.86 (4H, m), 4.15 (2H, s), 4.47–4.49 (1H, m), 5.04 (1H, br.d, J=52 Hz), 6.14 (1H, d, J=9 Hz), 7.15–7.32 (5H, m), 7.42 (1H, d, J=9 Hz).

Example 112

(3R)-3-[2-Benzyl-6-[(3R,4S)-3-(fluoromethoxy)-4-methoxypyrrolidine-1-yl]-3-pyridyl]ethynyl-3-quinuclidinol a) 2-Benzyl-6-[(3R,4S)-3-(fluoromethoxy)-4-methoxypyrrolidine-1-yl]-3-iodopyridine 37.4 mg of N-iodosuccinimide was added little by little to a solution containing 47.8 mg of 2-benzyl-6-[(3R,4S)-3-(fluoromethoxy)-4-methoxypyrrolidine-1-yl]pyridine obtained in Example 111 and 4.0 ml of N,N-dimethylformamide under stirring in an ice-bath, followed by stirring overnight as it was. Water was added to the reaction solution, and the mixture was extracted with ethyl acetate. The organic phase was successively washed with an aqueous sodium thiosulfate solution, water and brine, and the solvent was removed. The residue was subjected to NH-silica gel (Fuji Silicia) chromatography and eluted with hexane/ethyl acetate (5:1) and then with hexane/ethyl acetate (3:1), to give 43.9 mg of the target compound.

$^1$H-NMR (CDCl$_3$) δ=3.47 (3H, s), 3.48–3.64 (4H, m), 3.97–4.03 (1H, m), 4.19 (2H, s), 4.41–4.42 (1H, m), 5.40 (2H, d, J=56 Hz), 5.97 (1H, d, J=9 Hz), 7.17–7.38 (5H, m), 7.70 (1H, d, J=9 Hz).

b) (3R)-3-[2-Benzyl-6-[(3R,4S)-3-(fluoromethoxy)-4-methoxypyrrolidine-1-yl]-3-pyridyl]ethynyl-3-quinuclidinol A mixture of 43.9 mg of 2-benzyl-6-[(3R,4S)-3-(fluoromethoxy)-4-methoxypyrrolidine-1-yl]-3-iodopyridine, 16.5 mg of (3R)-3-ethynyl-3-quinuclidinol, 11.5 mg of tetrakis(triphenylphosphine)palladium(0), 0.9 mg of cuprous iodide, 42 μl of triethylamine and 3.0 ml of N,N-dimethylformamide was heated under stirring for 1 hours at 75° C. in a nitrogen atmosphere. The reaction solution was poured into an aqueous dilute ammonia, and then the mixture was extracted with ethyl acetate. The organic phase was washed with brine and the solvent was removed. The residue was subjected to NH-silica gel (Fuji Silicia) column chromatography and eluted with hexane/ethyl acetate (1:1) and then with ethyl acetate/methanol (15:1), to give 33 mg of the target compound.

$^1$H-NMR (CDCl$_3$) δ=1.34–1.42 (1H, m), 1.54–1.62 (1H, m), 1.85–1.90 (1H, m), 1.99–2.07 (2H, m), 2.73–2.91 (4H, m), 3.01 (1H, d, J=14 Hz), 3.23 (1H, dd, J=2, 14 Hz), 3.48 (3H, s), 3.54–3.58 (1H, m), 3.65–3.69 (3H, m), 3.99–4.03 (1H, m), 4.15 (2H, s), 4.41–4.45 (1H, m), 5.40 (2H, d, J=56 Hz), 6.13 (1H, d, J=9 Hz), 7.13–7.40 (5H, m), 7.42 (1H, d, J=9 Hz).

Example 113

(3R)-3-[2-Benzyl-6-[(3S,4R)-3-chloro-4-methoxypyrrolidine-1-yl]-3-pyridyl]ethynyl-3-quinuclidinol a) 2-Benzyl-6-[(3R,4R)-3-(3-nitribenzenesulfonyl)oxy-4-methoxypyrrolidine-1-yl]-3-iodopyridine A mixture of 1.0 g of 2-benzyl-3-iodo-6-[(3R,4R)-3-hydroxy-4-methoxypyrrolidine-1-yl]pyridine (Example 10c), 1.0 g of 3-nitrobenzenesulfonyl chloride, 0.1 g of 4-dimethylaminopyridine and 5 ml of pyridine was stirred at room temperature overnight. Water was added to the reaction solution, and the mixture was extracted with ethyl acetate. The organic phase was washed with water and brine and the solvent was removed. The residue was subjected to NH-silica gel (Fuji Silicia) column chromatography and eluted with hexane/ethyl acetate (5:1) and then with hexane/ethyl acetate (2:1), to give 1.23 g of the target compound.

$^1$H-NMR (CDCl$_3$) δ=3.38 (3H, s), 3.47–3.51 (1H, m), 3.61–3.73 (3H, m), 4.11–4.16 (3H, m), 5.11–5.12 (1H, m), 5.94 (1H, d, J=9 Hz), 7.18–7.33 (5H, m), 7.68–7.76 (2H, m), 8.20–8.22 (1H, m), 8.48–8.51 (1H, m), 8.75 (1H, s).

b) 2-Benzyl-6-[(3S,4R)-3-chloro-4-methoxypyrrolidine-1-yl]-3-iodopyridine

A mixture of 553 g of 2-benzyl-6-((3R,4R)-3-(3-nitrobenzenesulfonyl)oxy-4-methoxypyrrolidine-1-yl]-3-iodopyridine, 79 mg of lithium chloride and 5.0 ml of N,N-dimethylformamide was heated under stirring at 75° C. for 9 hours. After cooling as it was, water was added to the reaction mixture and the mixture was extracted with ethyl acetate. The organic phase was washed with water and brine, and the solvent was removed. The residue was subjected to NH-silica gel (Fuji Silicia) column chromatography and eluted with hexane/ethyl acetate (10:1) and then with hexane/ethyl acetate (5:1), to give 391 mg of the target compound.

$^1$H-NMR (CDCl$_3$) δ=3.48 (3H, s), 3.48–3.51 (1H, m), 3.65–3.69 (1H, m), 3.83–3.85 (2H, m), 4.05–4.09 (1H, m), 4.19 (2H, s), 4.55–4.58 (1H, m), 5.97 (1H, d, J=9 Hz), 7.18–7.38 (5H, m), 7.72 (1H, d, J=9 Hz).

c) (3R)-3-[2-Benzyl-6-[(3S,4R)-3-chloro-4-methoxypyrrolidine-1-yl]-3-pyridyl]ethynyl-3-quinuclidinol A mixture of 391 mg of 2-benzyl-6-[(3S,4R)-3-chloro-4-methoxypyrrolidine-1-yl]-3-iodopyridine, 152 mg of (3R)-3-ethynyl-3-quinuclidinol, 105 mg of tetrakis(triphenylphosphine)palladium(0), 9 mg of cuprous iodide, 0.38 ml of triethylamine and 5.0 ml of N,N-dimethylformamide was heated under stirring for 4 hours at 75° C. in a nitrogen atmosphere, followed by removing the solvent. The residue was subjected to NH-silica gel (Fuji Silicia) column chromatography and eluted with hexane/ethyl acetate (1:1) and then with ethyl acetate/methanol (20:1) and then crystallized from hexane/ethyl acetate, to give 150 mg of the target compound.

¹H-NMR (CDCl₃) δ=1.46–1.53 (1H, m), 1.64–1.92 (2H, m), 2.04–2.12 (2H, m), 2.82–2.97 (4H, m), 3.11 (1H, d, J=14 Hz), 3.29 (1H, dd, J=2, 14 Hz), 3.49 (3H, s), 3.52–3.56 (1H, m), 3.70–3.75 (1H, m), 3.85–3.91 (2H, m), 4.06–4.11 (1H, m), 4.15 (2H, s), 4.57–4.60 (1H, m), 6.15 (1H, d, J=9 Hz), 7.17–7.30 (5H, m), 7.44 (1H, d, J=9 Hz).

Example 114

(3R)-3-[2-Benzyl-6-[(3R,4R)-3,4-ethylenedioxypyrrolidine-1-yl]-3-pyridyl]ethynyl-3-quinuclidinol a) 2-Bromo-6-[(3R,4R)-3-(3-methoxymethyloxy-4-[2-(tetrahydro-2H-2-pyranyloxy)ethyl]oxypyrrolidine-1-yl]pyridine 3.88 g of 60% oily sodium hydride was added little by little to a solution of 50 ml of N,N-dimethylformamide containing 14.7 g of 2-bromo-6-[(3R,4R)-3-methoxymethyloxy-4-hydroxypyrrolidine-1-yl]pyridine (Example 111b) under stirring in an ice bath. The mixture was stirred for 10 minutes in an ice bath and then for 20 minutes at room temperature. Then, 14.7 ml of 2-(2-bromoethyl)oxytetrahydro-2H-pyran was added dropwise little by little thereinto in an ice bath. The reaction solution was stirred at room temperature for 20 minutes and then at 60° C. for 20 minutes. 7.4 ml of 2-(2-bromoethyl)oxytetrahydro-2H-pyran was further added thereto at room temperature, followed by heating under stirring at 60° C. for 30 minutes. After cooling as it was, the reaction solution was poured into water and the mixture was extracted with ethyl acetate. The organic phase was washed with brine and the solvent was removed. The residue was subjected to silica gel chromatography and eluted with hexane/ethyl acetate (3:1) and then with hexane/ethyl acetate (2:1), to give 17.58 g of the target compound.

¹H-NMR (CDCl₃) δ=1.50–1.59 (4H, m), 1.67–1.83 (2H, m), 3.39 (3H, s), 3.48–3.61 (4H, m), 3.67–3.75 (4H, m), 3.82–3.88 (2H, m), 4.13–4.14 (1H, m), 4.31–4.34 (1H, m), 4.61–4.63 (1H, m), 4.70–4.74 (2H, m), 6.25 (1H, d, J=8 Hz), 6.69 (1H, d, J=7 Hz), 7.22–7.27 (1H, m).

b) 2-Bromo-6-[(3R,4R)-3-methoxymethyloxy-4-(2-hydroxyethyl)oxypyrrolidine-1-yl]pyridine 2.26 g p-toluenesulfonic acid monohydrate was added dropwise little by little into a solution of 60 ml of methanol containing 17.09 g of 2-bromo-6-[(3R,4R)-3-methoxymethyloxy-4-[2-(tetrahydro-2H-2-pyranyloxy)ethyl]oxypyrrolidine-1-yl]pyridine in an ice bath. After stirring for 30 minutes under ice-cooling, it was stirred at room temperature for 2 hours. 377 mg of p-toluenesulfonic acid monohydrate was further added thereto, followed by stirring for 2 hours. Then, the reaction solution was poured into aqueous saturated sodium bicarbonate and extracted twice with ethyl acetate. The organic phase was washed with brine and the solvent was removed. The residue was filtered through silica gel, to give 13.14 g of the target compound.

¹H-NMR (CDCl₃) δ=3.39 (3H, s), 3.53–3.56 (2H, m), 3.66–3.75 (6H, m), 4.10–4.13 (1H, m), 4.30–4.31 (1H, m), 4.70–4.74 (2H, m), 6.25 (1H, d, J=8 Hz), 6.70 (1H, d, J=8 Hz), 7.24–7.28 (1H, m).

c) 2-Bromo-6-[(3R,4R)-3-methoxymethyloxy-4-[2-(methanesulfonyloxy)ethyl]oxypyrrolidine-1-yl]pyridine 7.9 ml of triethylamine was slowly added to a solution of 70 ml of dichloromethane containing 13.14 g of 2-bromo-6-[(3R,4R)-3-methoxymethyloxy-4-(2-hydroxyethyl) oxypyrrolidine-1-yl]pyridine in an ice bath. Then, 3.2 ml of methanesulfonyl chloride was slowly added thereto, followed by stirring for 15 minutes. Then, the reaction solution was poured into water and extracted twice with dichloromethane. The organic phase was washed with brine and the solvent was removed. The residue was filtered through NH-silica gel, to give 15.66 g of the target compound.

¹H-NMR (CDCl₃) δ=3.00 (3H, s), 3.38(3H, s), 3.52–3.59 (2H, m), 3.66–3.72 (2H, m), 3.82–3.84 (2H, m), 4.10–4.15 (1H, m), 4.28–4.30 (1H, m), 4.33–4.35 (2H, m), 4.71 (2H, s), 6.25 (1H, d, J=8 Hz), 6.71 (1H, d, J=8 Hz), 7.24–7.28 (1H, m).

d) 2-Bromo-6-[(3R,4R)-3-hydroxy-4-[2-(methanesulfonyloxyethyl)oxypyrrolidine-1-yl]pyridine 2.0 ml of concentrated sulfuric acid was slowly added dropwise into a solution of 160 ml of methanol containing 15.66 g of 2-bromo-6-[(3R,4R)-3-methoxymethyloxy-4-(2-methanesulfonyloxyethyl)oxypyrrolidine-1-yl]pyridine under stirring in an ice bath. The reaction solution was stirred at room temperature for 10 minutes and then at 50° C. for 45 minutes. Further, after adding dropwise 1.0 ml of concentrated sulfuric acid thereinto, the mixture was stirred at 50° C. for one hour. After cooling as it was, the reaction mixture was poured into an aqueous potassium carbonate solution and extracted twice with ethyl acetate. The organic phase was washed with brine, dried over anhydrous magnesium sulfate and the solvent was removed. The residue was filtered through silica gel, to give 11.82 g of the target compound.

¹H-NMR (CDCl₃) δ=3.01 (3H, s), 3.44–3.56 (2H, m), 3.69–3.87 (4H, m), 4.01–4.04 (1H, m), 4.34–4.37 (2H, m), 4.44–4.45 (1H, m), 6.25 (1H, d, J=8 Hz), 6.72 (1H, d, J=7 Hz), 7.24–7.28 (1H, m).

e) 2-Bromo-6-[(3R,4R)-3,4-ethylenedioxypyrrolidine-1-yl]pyridine 1.49 g of 60% oily sodium hydride was added little by little to a solution of 150 ml of N,N-dimethylformamide containing 11.82 g of 2-bromo-6-[(3R,4R)-3-hydroxy-4-(2-methanesulfonyloxyethyl)oxypyrrolidine-1-yl]pyridine under stirring in an ice bath. Then, after stirring at room temperature for one hour, 372 mg of 60% oily sodium hydride was added thereto. After stirred for further 45 minutes, the reaction mixture was poured into water and extracted twice with ethyl acetate. The organic phase was washed with water and brine, and the solvent was removed. The residue was crystallized from ethyl acetate/hexane, to give 5.35 g of the target compound.

¹H-NMR (CDCl₃) δ=3.20–3.25 (2H, m), 3.73–3.92 (8H, m), 6.23 (1H, d, J=8 Hz), 6.73 (1H, d, J=8 Hz), 7.25–7.29 (1H, m).

f) 2-Benzyl-6-[(3R,4R)-3,4-ethylenedioxypyrrolidine-1-yl]pyridine 26.6 mol of a tetrahydrofuran solution containing 1.06 mol of benzylmagnesium chloride was added dropwise into a solution of 100 ml of tetrahydrofuran containing 5.3 g of 2-bromo-6-[(3R,4R)-3,4-ethylenedioxypyrrolidine-1-yl] pyridine and 509 mg of 1,3-bis(diphenylphosphino) propanenickel(II) chloride over 10 minutes under ice-cooling. After stirring at room temperature overnight, the reaction solution was poured into aqueous saturated ammonium chloride and extracted with ethyl acetate. The organic phase was washed with brine and the solvent was removed. The residue was subjected to silica gel column chromatography and eluted with hexane/ethyl acetate (10:1) and then with hexane/ethyl acetate (1:2). The resulting crude product was crystallized from hexane/ethyl acetate, to give 4.84 g of the target compound.

¹H-NMR (CDCl₃) δ=3.20–3.25 (2H, m), 3.72–3.91 (8H, m), 3.96 (2H, s), 6.13 (1H, d, J=8 Hz), 6.39 (1H, d, J=7Hz), 7.17–7.36 (6H, m).

g) 2-Benzyl-6-[(3R,4R)-3,4-ethylenedioxypyrrolidine-1-yl]-3-iodopyridine 4.04 g of N-iodosuccinimide was added little by little to a solution of 40 ml of N,N-dimethylformamide containing 4.84 g of 2-benzyl-6-[(3R,4R)-3,4-ethylenedioxypyrrolidine-1-yl]pyridine under stirring in an ice bath, followed by stirring overnight as it was. The reaction solution was poured into water, and extracted with ethyl acetate. The organic phase was successively washed with an aqueous sodium sulfite solution, water and brine, dried over anhydrous magnesium sulfate and the solvent was removed. The residue was subjected to filtration using silica gel and crystallized from hexane/ethyl acetate, to give 5.12 g of the target compound.

$^1$H-NMR (CDCl$_3$) δ=3.15–3.18 (2H, m), 3.71–3.91 (8H, m), 4.14–4.22 (2H, m), 5.95 (1H, d, J=9 Hz), 7.18–7.39 (5H, m), 7.70 (1H, d, J=9 Hz).

b) (3R)-3-[2-Benzyl-6-[(3R,4R)-3,4-ethylenedioxypyrrolidine-1-yl]-3-pyridyl]ethynyl-3-quinuclidinol A mixture of 5.12 g of 2-benzyl-6-[(3R,4R)-3,4-ethylenedioxypyrrolidine-1-yl]-3-iodopyridine, 1.83 g of (3R)-3-ethynyl-3-quinuclidinol, 140 mg of tetrakis(triphenylphosphine)palladium(0), 115 mg of cuprous iodide, 3.4 ml of triethylamine and 12 ml of methanol was stirred at room temperature overnight in a nitrogen atmosphere. The reaction solution was poured into aqueous dilute ammonia, and the mixture was extracted with ethyl acetate/tetrahydrofuran (1:1). Then, the organic phase was washed with brine and the solvent was removed. The residue was crystallized from tetrahydrofuran/methanol/ethyl acetate, to give 3.59 g of the target compound.

$^1$H-NMR (CDCl$_3$) δ=1.37–1.44 (1H, m), 1.55–1.64 (1H, m), 1.87–1.91 (1H, m), 2.04–2.05 (2H, m), 2.75–2.89 (4H, m), 3.04 (1H, d, J=14 Hz), 3.18–3.28 (3H, m), 3.73–3.91 (8H, m), 4.11–4.21 (2H, m), 6.12 (1H, d, J=9 Hz), 7.14–7.34 (5H, m), 7.44 (1H, d, J=9 Hz).

Example 115

(3R)-3-[Benzyl-6-[(3R,4R)-3-hydroxy-4-cyclopropyloxypyrrolidine-1-]-3-pyridyl]ethynyl-3-quinuclidinol 145 mg of 60% oily sodium hydride was added to a mixture of 906 mg of 2-benzyl-6-[(3R,4R)-3,4-dihydroxypyrrolidine-1-yl]pyridine (Example 10a) and 10 ml of tetrahydrofuran under ice cooling, followed by stirring for one hour at the same temperature. 0.252 ml of chloromethyl methyl ether was added thereto, followed by stirring at room temperature for 1.5 hours. Water and ethyl acetate were added to the reaction solution, and the organic phase was washed with water and brine, dried over anhydrous magnesium sulfate anhydride and the solvent was removed. To the residue was added 4 ml of ethyl vinyl ether and 238 mg of mercury acetate, followed by stirring two nights at room temperature. To the reaction solution were added an aqueous saturated sodium bicarbonate solution and diethyl ether. The organic phase was washed with water and brine, dried over anhydrous magnesium sulfate and the solvent was removed. The residue was subjected to silica gel column chromatography using 15% ethyl acetate/hexane, to give 229 mg of the target compound.

$^1$H-NMR (CDCl$_3$) δ=3.39 (3H, s), 3.51–3.61 (4H, m), 3.97 (2H, s), 4.12 (1H, dd, J=2, 7 Hz), 4.42–4.46 (2H, m), 4.54–4.55 (1H, m), 4.71–4.76 (2H, m), 6.17 (1H, d, J=8 Hz), 6.34–6.42 (2H, m), 7.16–7.34 (6H, m).

b) 2-Benzyl-6-[(3R,4R)-3-methoxymethyloxy-4-cyclopropyloxypyrrolidine-1-yl]pyridine A mixture of 229 mg of 2-benzyl-6-[(3R,4R)-3-methoxymethyloxy-4-vinyloxypyrrolidine-1-yl]pyridine, 217 μl of diiodomethane, 1.35 ml of hexane solution containing 1.0 mol of diethylzinc and 3 ml of toluene was stirred at 80° C. for 3 hours. Ammonium chloride was added to the reaction solution, and the mixture was washed with brine, dried over anhydrous magnesium sulfate and the solvent was removed. The residue was subjected to silica gel column chromatography using 15% ethyl acetate/hexane, to give 47.8 mg of the target compound.

$^1$H-NMR (CDCl$_3$) δ=0.50–0.63 (4H, m), 3.38–3.42 (4H, m), 3.52–3.60 (2H, m), 3.69–3.75 (2H, m), 3.97 (2H, s), 4.18–4.21 (1H, m), 4.30–4.33 (1H, m), 4.70–4.74 (2H, m), 6.16 (1H, d, J=8 Hz), 6.33 (1H, d, J=8 Hz), 7.17–7.33 (6H, m).

c) (3R)-3-[2-Benzyl-6-[(3R,4R)-3-hydroxy-4-cyclopropyloxypyrrolidine-1-yl]-3pyridyl]ethynyl-3-quinuclidinol A mixture of 47.8 mg of 2-benzyl-6-[(3R,4R)-3-methoxymethyloxy-4-cyclopropyloxypyrrolidine-1-yl]pyridine, 1.5 ml of dichloromethane and 0.156 ml of trifluoroacetic acid was stirred overnight at room temperature. To the reaction solution were added an aqueous saturated sodium bicarbonate solution and ethyl acetate, and the organic phase was washed with water and brine, dried over anhydrous magnesium sulfate and the solvent was removed. The residue was subjected to the same reaction as in Example 10, to synthesize the target compound.

$^1$H-NMR (CDCl$_3$) δ=0.50–0.62 (4H, m), 1.35–1.43 (1H, m), 1.53–1.61 (1H, m), 1.82–1.90 (1H, m), 1.99–2.06 (2H, m), 2.71–2.91 (4H, m), 2.98 (1H, d, J=14 Hz), 3.20 (1H, dd, J=2, 14 Hz), 3.36–3.41 (1H, m), 3.43–3.47 (1H, m), 3.55–3.58 (1H, m ), 3.68 (1H, dd, J=5, 11 Hz), 3.75 (1H, dd, J=5, 12 Hz), 4.06–4.15 (3H, m), 4.39–4.42 (1H, m), 6.12 (1H, d, J=8 Hz), 7.13–7.32 (5H, m), 7.40 (1H, d, J=8 Hz).

Example 116

(3R)-(3R)-3-[2-Benzyl-5-chloro-6[(3R,4R)-3-hydroxy-4-methoxypyrrolidine-1-yl]-3-pyridyl]ethynyl-3-quinuclidinol a) 2-Benzyl-5-chloro-3-iodo-6-[(3R,4R)-3-hydroxy-4-methoxypyrrolidine-1-yl]pyridine 100 mg of N-chlorosuccinimidewas added little by little to a mixture of 256 mg of 2-benzyl-3-iodo-6-[(3R,4R)-3-hydroxy-4-methoxypyrrolidine-1-yl]pyridine (Example 10c) and 3 ml of N,N-dimethylformamide, followed by stirring at 70° C. for 2 hours. After cooling as it was, water and ethyl acetate were added thereto, and the mixture was extracted. The organic phase was washed with water and brine, dried over anhydrous magnesium sulfate and the solvent was removed. The residue was subjected to silica gel column chromatography using 25% ethyl acetate/hexane, to give 132 mg of the target compound.

$^1$H-NMR (CDCl$_3$) δ=3.39 (3H, s), 3.64–3.69 (2H, m), 3.76–3.79 (1H, m), 3.86–3.90 (1H, m), 3.94–3.97 (1H, m), 4.14 (2H, s), 4.30–4.33 (1H, m), 7.18–7.33 (5H, m), 7.74 (1H, s).

b) (3R)-3-[2-Benzyl-5-chloro-6-[(3R,4R)-3-hydroxy-4-methoxypyrrolidine-1-yl]-3pyridyl]ethynyl-3-quinuclidinol A mixture of 132 mg of 2-benzyl-5-chloro-3-iodo-6-[(3R,4R)-3-hydroxy-4-methoxypyrrolidine-1-yl]pyridine, 49.4 mg of (3R)-3-ethynyl-3-quinuclidinol, 17.2 mg of tetrakis(triphenylphosphine)palladium(0), 11.3 mg of cuprous iodide, 124 μl of triethylamine and 1.5 ml of methanol was heated under reflux for one hour in a nitrogen atmosphere.

After cooling as it was, water and ethyl acetate were added to the reaction mixture. The organic phase was washed with water and brine, dried over anhydrous magnesium sulfate and the solvent was removed. The residue was subjected to NH-silica gel column chromatography using 3% methanol/ethyl acetate, to give 125 mg of the target compound.

$^1$H-NMR (CDCl$_3$) δ=1.36–1.44 (1H, m), 1.56–1.63 (1H, m), 1.82–1.89 (1H, m), 1.99–2.05 (2H, m), 2.50–2.88 (4H, m), 3.00 (1H, d, J=14 Hz), 3.20 (1H, dd, J=2, 14 Hz), 3.40 (3H, s), 3.71–3.78 (3H, m), 3.92–3.97 (1H, m), 4.00–4.04 (1H, m), 4.09 (2H, s), 4.30–4.32 (1H, m), 7.17–7.29 (5H, m), 7.45 (1H, s).

Example 117

(3R)-3-[2-Benzyl-5-bromo-6-[(3R,4R)-3-hydroxy-4-methoxypyrrolidine-1-yl]-3-pyridyl]ethynyl-3-quinuclidinol The target compound was synthesized in the same manner as in Example 116 except that N-chlorosuccinimide was altered to N-bromosuccinimide.

$^1$H-NMR (CDCl$_3$) δ=1.36–1.44 (1H, m), 1.58–1.64 (1H, m), 1.82–1.91 (1H, m), 1.99–2.06 (2H, m), 2.72–2.93 (4H, m), 3.02 (1H, d, J=14 Hz), 3.23 (1H, dd, J=2, 14 Hz), 3.40 (3H, s), 3.72–3.80 (3H, m), 3.92–3.97 (1H, m), 4.01–4.06 (1H, m), 4.09 (2H, s), 4.30–4.32 (1H, m), 7.16–7.30 (5H, m), 7.67 (1H, s).

Example 118

(3R)-3-[Benzyl-6-(3,3-ethylenedioxypyrrolidine-1-yl]-3-pyridyl]ethynyl-3-quinuclidinol Next, 4.6 ml of dimethylsulfoxide was added dropwise into a solution of 100 ml of dichloromethane containing 2.8 ml of oxalyl chloride under stirring in a dry ice-acetone bath. Then, a solution of 50 ml of dichloromethane containing 5.9 g of the resulting 2-bromo-6-(3-hydroxypyrrolidine-1-yl) pyridine was added dropwise thereinto. Finally, 17 ml of triethylamine was added dropwise thereinto and the temperature of the mixture was returned to room temperature over one hour. The reaction solution was washed with water and brine, dried over anhydrous magnesium sulfate and then concentrated. To the residue were added 50 ml of toluene, 7 ml of ethylene glycol and a catalytic amount of p-toluenesulfonic acid monohydrate, followed by heating under reflux for 3 hours while draining water. After cooling, the mixture was washed with an aqueous saturated sodium bicarbonate solution and brine, dried over anhydrous magnesium sulfate and then concentrated. The residue was subjected to silica gel column chromatography using 5–7% ethyl acetate/hexane, to give 6.3 g of the target compound.

$^1$H-NMR (CDCl$_3$) δ=2.30 (2H, t, J=7 Hz), 3.54 (2H, s), 3.58 (2H, t, J=7 Hz), 3.96–4.04 (4H, m), 6.22 (1H, d, J=8 Hz), 6.70 (1H, d, J=8 Hz), 7.24 (1H, t, J=8 Hz).

b) 2-Benzyl-6-(3,3-ethylenedioxypyrrolidine-1-yl)pyridine

A mixture of 6.3 g of 2-bromo-6-(3,3-ethylenedioxypyrrolidine-1-yl)pyridine, 240 mg of 1,3-bis(diphenylphosphino)propanenickel (II) chloride and 20 ml of tetrahydrofuran was stirred in an ice bath in a nitrogen atmosphere. Into the mixture were added dropwise a diethyl ether solution of benzyl magnesium bromide prepared from 3.4 ml of benzyl bromide, 0.8 g of magnesium and 15 ml of diethyl ether, followed by stirring at room temperature overnight as it was. The reaction solution was partitioned between an aqueous saturated ammonium chloride solution and ethyl acetate. The organic phase was washed with brine, dried over anhydrous magnesium sulfate and then concentrated. The residue was subjected to silica gel column chromatography using 5–10% ethyl acetate/hexane, to give 6.6 g of the target compound.

$^1$H-NMR (CDCl$_3$) δ=2.19 (2H, t, J=7 Hz), 3.57 (2H, s), 3.59 (2H, t, J=7 Hz), 3.97 (2H, s), 4.01 (4H, s), 6.14 (1H, d, J=8 Hz), 6.34 (1H, d, J=7 Hz), 7.16–7.35 (6H, m)

c) 2-Benzyl-3-iodo-6-(3,3-ethylenedioxypyrrolidine-1-yl)pyridine

A mixture of 6.6 g of 2-benzyl-6-(3,3-ethylenedioxypyrrolidine-1-yl)pyridine and 60 ml of N,N-dimethylformamide was stirred in an ice bath. Into the mixture were added dropwise 5.5 g of N-iodosuccinimide, followed by stirring at room temperature overnight as it was. 10 ml of an aqueous solution containing one mol of sodium thiosulfate was added thereto, and the mixture was partitioned between ethyl acetate and water. The organic phase was washed with water and brine, dried over anhydrous magnesium sulfate and then concentrated. The residue was subjected to silica gel column chromatography using 5–10% ethyl acetate/hexane, to give 6.7 g of the target compound.

$^1$H-NMR (CDCl$_3$) δ=2.17 (2H, t, J=7 Hz), 3.50 (2H, s), 3.54 (2H, t, J=7 Hz), 4.00 (4H, s), 4.18 (2H, s), 5.95 (1H, d, J=8 Hz), 7.18 (1H, t, J=7 Hz), 7.26 (2H, t, J=7 Hz), 7.37 (2H, d, J=7 Hz), 7.68 (1H, d, J=8 Hz).

d) (3R)-3-[2-Benzyl-6-(3,3-ethylenedioxypyrrolidine-1-yl]-3-pyridyl]ethynyl-3-quinuclidinol A mixture of 3.0 g of 2-benzyl-3-iodo-6-(3,3-ethylenedioxypyrrolidine-1-yl)pyridine, 1.07 g of (3R)-3-ethynyl-3-quinuclidinol, 82 mg of tetrakis(triphenylphosphine)palladium (0), 68 mg of cuprous iodide, 2.0 ml of triethylamine and 7 ml of methanol was stirred at room temperature overnight in a nitrogen atmosphere. The reaction solution was partitioned between aqueous dilute ammonia-ethyl acetate, washed with washed with water, dried over anhydrous magnesium sulfate and then concentrated. 10 ml of tetrahydrofuran was added to the residue to dissolve under heating, and to the mixture was added 15 ml of ethyl acetate. The mixture was filtered through 10 g of NH-silica gel, washed with ethyl acetate, and concentrated. The residue was crystallized from ethyl acetate, to give 2.79 g of the target compound.

$^1$H-NMR (CDCl$_3$) δ=1.34–1.94 (3H, m), 1.98–2.06 (2H, m), 2.18 (2H, t, J=8 Hz), 2.70–2.94 (4H, m), 3.02 (1H, d, J=14 Hz), 3.23 (1H, dd, J=2, 14 Hz), 3.55 (2H, s), 3.60 (2H, t, J=8 Hz), 4.01 (4H, s), 4.15 (2H, s), 6.12 (1H, d, J=8 Hz), 7.12–7.34 (5H, m), 7.41 (1H, d, J=8 Hz).

Example 119

(3R)-3-[2-Benzyl-5-chloro-6-(3,3-ethylenedioxypyrrolidine-1-yl)-3-pyridyl]ethynyl-3-quinuclidinol A mixture of 500 mg of 2-benzyl-3-iodo-6-(3,3-ethylenedioxypyrrolidine-1-yl)pyridine obtained in Example 118c, 174 mg of N-chlorosuccinimide and 5 ml of N,N-dimethylformamide was stirred under heating for 5 hours in an oil bath kept at 60° C. 1 ml of aqueous solution containing 1 mol of sodium thiosulfate was added to the reaction solution, the mixture was partitioned between ethyl acetate and water. The organic phase was washed with water and brine, dried over anhydrous magnesium sulfate and then concentrated. The residue was subjected to silica gel column chromatography using 5–10% ethyl acetate/hexane, to give 320 mg of 2-benzyl-3-iodo-5-chloro-6-(3,3-ethylenedioxypyrrolidine-1-yl)pyridine, and then the title compound was obtained in the same procedures as in Example 118d.

¹H-NMR (CDCl₃) δ=1.35–1.92 (3H, m), 1.98–2.05 (2H, m), 2.09 (2H, t, J=7 Hz), 2.70–2.94 (4H, m), 3.03(1H, d, J=14 Hz), 3.23 (1H, dd, J=2, 14 Hz), 3.80 (2H, s), 3.84 (2H, t, J=7 Hz), 4.00 (4H, s), 4.10 (2H, s), 7.14–7.32 (5H, m), 7.44(1H, s).

Example 120

(3R)-3-[2-Benzyl-6-(cis-3,4-dimethoxyprrolidine-1-yl)-3-pyridyl]ethynyl-3-quinuclidinol A mixture of 12.4 g of 2,6-dibromopyridine, 7.2 g of 3-pyrroline (purity: 65%, Aldrich), 14.5 g of potassium carbonate and 100 ml of 1-methyl-2-pyrrolidinone was heated under stirring at 125° C. for 4 hours. After cooling as it was, the reaction mixture was poured into water and extracted with ethyl acetate. The organic phase was washed with water and brine, and the solvent was removed. The residue was subjected to silica gel column chromatography and eluted with hexane and then with hexane/ethyl acetate (10:1), to give 11.6 g of a mixture of the target compound and 2-bromo-6-(pyrrolidine-1-yl)pyridine.

b) 2-Benzyl-6-(3-pyrroline-1-yl)pyridine 72.3 ml of a tetrahydrofuran solution containing 1.07 mol of benzylmagnesium chloride was added dropwise into a mixture of 11.6 g of a mixture of 2-bromo-6-(3-pyrroline-1-yl)pyridine and 2-bromo-6-(pyrrolidine-1-yl)pyridine and 20 ml of tetrahydrofuran containing 1.4 g of 1,3-bis(diphenylphosphino)propanenickel(II) chloride over 10 minutes in an ice bath. After cooling at room temperature overnight, the reaction solution was poured into aqueous saturated ammonium chloride and extracted with ethyl acetate. The organic phase was washed with aqueous saturated sodium chloride and the solvent was removed. The residue was subjected to NH-silica gel (Fuji Silicia) column chromatography and eluted with hexane and then with hexane/ethyl acetate (20:1), to give 11.8 g of the title compound as a mixture with 2-benzyl-6-(pyrrolidine-1-yl)pyridine.

c) 2-Benzyl-6-(cis-3,4-dihydroxypyrrolidine-1-yl)pyridine 2.3 ml of a 2-methyl-2-propanol solution containing 2.5% osmium tetraoxide was added dropwise little by little into a mixture of 11.8 g of a mixture of 2-benzyl-6-(3-pyrroline-1-yl)pyridine and 2-benzyl-6-(pyrrolidine-1-yl)pyridine, 23.5 g of aqueous 50% N-methylmorpholine-N-oxide solution, 50 ml of acetone and 10 ml of water in an ice bath. After stirring for 2 hours in an ice bath, it was further stirred at room temperature overnight. A aqueous sodium thiosulfate solution was added to the reaction solution, followed by stirring at room temperature for 30 minutes. Then, the mixture was extracted with ethyl acetate, and the organic phase was washed with water and brine, and the solvent was removed. Then, the residue was subjected to silica gel column chromatography and eluted with hexane/ethyl acetate (5:1) and then with ethyl acetate, to give 4.2 g of the target compound.

¹H-NMR (CDCl₃) δ=3.47–3.50 (2H, m), 3.71–3.75 (2H, m ), 3.97 (2H, s), 4.37–4.39 (2H, m), 6.15 (1H, d, J=8 Hz), 6.37 (1H, d, J=7 Hz) 7.17–7.35 (6H, m).

d) 2-Benzyl-6-(cis-3,4-dimethoxypyrrolidine-1-yl)pyridine 347 mg of 60% oily sodium hydride was added little by little to a mixture of 781 mg of 2-benzyl-6-(cis-3,4-dihydroxypyrrolidine-1-yl)pyridine, 536 μl of methyl iodide and 6.0 ml of N,N-dimethylformamide in an ice bath. After stirring at room temperature for 2 hours, water was added little by little to the reaction solution and the mixture was extracted with ethyl acetate. The organic phase was washed with water and brine, and the solvent was removed. Then, the residue was subjected to silica gel column chromatography and eluted with hexane/ethyl acetate (5:1) and then with hexane/ethyl acetate (1:1), to give 783 mg of the target compound.

¹H-NMR (CDCl₃) δ=3.47 (6H, s), 3.60–3.65 (4H, m ), 3.97–4.02 (4H, m), 6.16 (1H, d, J=8 Hz), 6.34 (1H, d, J=7 Hz), 7.18–7.34 (6H, m).

e) 2-Benzyl-6-(cis-3,4-dimethoxypyrrolidine-1-yl)-3-iodopyridine 708 mg of N-iodosuccinimide was added little by little to a mixture of 783 mg of 2-benzyl-6-(cis-3,4-dimethoxypyrrolidine-1-yl)pyridine and 7.0 ml of N,N-dimethylformamide under ice-cooling, followed by stirring overnight as it was. The reaction solution was poured into water and extracted with ethyl acetate. The organic phase was washed with sodium thiosulfate, water and brine, and the solvent was removed. Then, the residue was subjected to NH-silica gel (Fuji Silicia) column chromatography and eluted with hexane/ethyl acetate (5:1) and then with hexane/ethyl acetate (3:1), to give 995 mg of the target compound.

¹H-NMR (CDCl₃) δ=3.46 (6H, s), 3.54–3.55 (4H, m ), 3.97–4.01 (2H, m), 4.19 (2H, s), 5.97 (1H, d, J=9 Hz), 7.16–7.38 (5H, m), 7.69 (1H, d, J=9 Hz).

f) (3R)-3-[2-Benzyl-6-(cis-3,4-dimethoxypyrrolidine-1-yl)-3-pyridyl]ethynyl-3-quinuclidinol A mixture of 510 mg of 2-benzyl-6-(cis-3,4-dimethoxypyrrolidine-1-yl)-3-iodopyridine, 200 mg of (3R)-3-ethynyl-3-quinuclidinol, 139 mg of tetrakis(triphenylphosphine) palladium (0), 11 mg of cuprous iodide, 0.50 ml of triethylamine and 5.0 ml of N,N-dimethylformamide was heated under stirring at 75° C. for 2 hours in a nitrogen atmosphere. The reaction solution was poured into aqueous dilute ammonia and extracted with ethyl acetate. The extract was washed with brine and the solvent was removed. The residue was subjected to NH-silica gel (Fuji Silicia) column chromatography and eluted with hexane/ethyl acetate (1:1) and then with ethyl acetate/methanol (15:1), to give 281 mg of the target compound.

¹H-NMR (CDCl₃) δ=1.38–1.40 (1H, m), 1.57–1.68 (1H, m), 1.87–1.92 (1H, m), 2.02–2.04 (2H, m), 2.74–2.87 (4H, m), 3.02 (1H, d, J=14 Hz), 3.23 (1H, d, J=14 Hz), 3.47 (6H, s),3.60 (4H, m), 3.99 (2H, m), 4.16 (2H, s), 6.13–6.15 (1H, m), 7.14–7.33 (5H, m), 7.42 (1H, d, J=9 Hz).

Example 121

(3R)-3-[2-Benzyl-6-(cis-3,4-methylenedioxypyrrolidine-1-yl)-3-pyridyl]ethynyl-3-quinuclidinol a) 2-Benzyl-6-(cis-3,4-methylenedioxypyrrolidine-1-yl)pyridine A mixture of 300 mg of 2-benzyl-6-(cis-3,4-dihydroxypyrrolidine-1-yl)pyridine, 376 mg of paraformaldehyde, 0.7 ml of concentrated sulfuric acid and 5.0 ml of acetic acid was heated under stirring at 90° C. for 2 hours. After cooling as it was, the reaction solution was slowly added to an aqueous potassium carbonate solution. The mixture was extracted with ethyl acetate, and the organic phase was washed with brine and the solvent was removed. The residue was subjected to silica gel column chromatography and eluted with hexane/ethyl acetate (5:1) and then with hexane/ethyl acetate (3:1), to give 221 mg of the target compound.

¹H-NMR (CDCl₃) δ=3.37–3.41 (2H, m), 3.90–3.93 (2H, m), 3.97 (2H, s), 4.81–4.82 (2H, m), 4.97 (1H, s), 5.11 (1H, s), 6.26 (1H, d, J=8 Hz), 6.43 (1H, d, J=7 Hz), 7.17–7.37 (6H, m).

b) 2-Benzyl-6-(cis-3,4-methylenedioxypyrrolidine-1-yl)-3-iodopyridine 143 mg of N-iodosuccinic acid imide was added little by little to a mixture of 150 mg of 2-benzyl-6-(cis-3,4-methylenedioxypyrrolidine-1-yl)pyridine and 5.0 ml of N,N-dimethylformamide under ice-cooling, followed by stirring overnight as it was. The reaction solution was poured into water, and then extracted with ethyl acetate. The organic phase was washed with sodium thiosulfate, water and brine, and the solvent was removed. The residue was subjected to silica gel column chromatography and eluted with hexane and then with hexane/ethyl acetate (4:1), to give 116 mg of the target compound.

$^1$H-NMR (CDCl$_3$) δ=3.34–3.38 (2H, m), 3.82–3.86 (2H, m ), 4.19 (2H, s), 4.79–4.89 (2H, m), 4.95 (1H, s), 5.09(1H, s), 6.06 (1H, d, J=9 Hz), 7.07–7.38 (5H, m), 7.72 (1H, d, J=9 Hz).

c) (3R)-3-[2-Benzyl-6-(cis-3,4-methylenedioxypyrrolidine-1-yl)-3-pyridyl]ethynyl-3-quinuclidinol A mixture of 116 mg of 2-benzyl-6-(cis-3,4-methylenedioxypyrrolidine-1-yl)-3-iodopyridine, 47 mg of (3R)-3-ethynyl-3-quinuclidinol, 33 mg of tetrakis (triphenylphosphine)palladium (0), 3 mg of cuprous iodide, 0.12 ml of triethylamine and 3.0 ml of N,N-dimethylformamide was heated under stirring at 75° C. for 4 hours in a nitrogen atmosphere. The reaction solution was poured into aqueous dilute ammonia, and then extracted with ethyl acetate. The extract was washed with brine and the solvent was removed. The residue was subjected to NH-silica gel (Fuji Silicia) column chromatography and eluted with hexane/ethyl acetate (1:1) and then with ethyl acetate/methanol (20:1), to give 38 mg of the target compound.

$^1$H-NMR (CDCl$_3$) δ=1.40–1.43 (1H, m), 1.63(1H, m), 1.80–1.88 (1H, m), 2.00–2.12 (2H, m), 2.72–2.85 (4H, m), 3.03 (1H, d, J=14 Hz), 3.11–3.23 (1H, m), 3.41–3.44 (2H, m), 3.88–3.91 (2H, m), 4.16 (2H, s), 4.81–4.82 (2H, m), 4.96 (1H, s), 5.10 (1H, s), 6.23 (1H, d, J=9 Hz), 7.17–7.32 (5H, m), 7.45 (1H, d, J=9 Hz).

Example 122

(3R)-3-[2-Benzyl-6-(cis-3-isopropyloxy-4-hydroxypyrrolidine-1-yl)-3-pyridyl]ethynyl-3-quinuclidinol a) 2-Benzyl-6-[cis-3,4-(dimethymethylenedioxy)pyrrolidine-1-yl]pyridine A mixture of 2.5 g of 2-benzyl-6-(cis-3,4-dihydroxypyrrolidine-1-yl)pyridine, 2.3 g of dl-10-camphorsulfonic acid, 20 ml of 2,2-dimethoxypropane and 5.0 ml of N,N-dimethylformamide was stirred at room temperature overnight. Aqueous saturated sodium bicarbonate was added to the reaction solution, and the mixture was extracted with ethyl acetate. The organic phase was washed with water and brine, and the solvent was removed. Then, the residue was subjected to filtration through silica gel and eluted with ethyl acetate, to give 2.87 g of the target compound.

$^1$H-NMR (CDCl$_3$) δ=1.37 (3H, s), 1.48 (3H, s), 3.33–3.40 (2H, m), 3.85–3.88 (2H, m), 3.97 (2H, s), 4.86–4.87 (2H, m), 6.24 (1H, d, J=8 Hz), 6.39 (1H, d, J=7 Hz), 7.17–7.35 (6H, m).

b) 2-Benzyl-6-(cis-3isopropyloxy-4-hydroxypyrrolidine1-yl)pyridine

A hexane solution containing 1.5 mol of diisobutylaluminum hydride was added little by little to a solution of 5.0 ml of diethyl ether containing 460 mg of 2-benzyl-6-[cis-3,4-(dimethylmethylenedioxy)pyrrolidine-1-yl]pyridine at −20° C. After stirring at room temperature overnight, the reaction solution was poured into an aqueous ammonium chloride solution, and the mixture was filtered through Celite and extracted with ethyl acetate. The organic phase was washed with brine and the solvent was removed. Then, the residue was subjected to filtration through silica gel and eluted with ethyl acetate, to give 369 mg of the target compound.

$^1$H-NMR (CDCl$_3$) δ=1.22–1.27 (6H, m), 3.44–3.50 (2H, m), 3.63–3.84 (3H, m), 3.97 (2H, s), 4.09–4.15 (1H, m), 4.33–4.37 (1H, m), 6.13–6.15 (1H, m), 6.34 (1H, d, J=7 Hz), 7.17–7.32 (6H, m).

c) 2-Benzyl-6-(cis-3-isopropyloxy-4-hydroxyprrolidine-1-yl)-3-iodopyridine 342 mg of N-iodosuccinimide was added little by little to a mixture of 396 mg of 2-benzyl-6-(cis-3-isopropyloxy-4-hydroxypyrrolidine-1-yl)pyridine and 5.0 ml of N,N-dimethylformamide under ice-cooling, followed by stirring overnight as it was. The reaction solution was poured into water, and then extracted with ethyl acetate. The organic phase was washed with sodium thiosulfate, water and brine, and the solvent was removed. The residue was subjected to silica gel column chromatography and eluted with hexane and then with hexane/ethyl acetate (3:1), to give 464 mg of the target compound.

$^1$H-NMR (CDCl$_3$) δ=1.21–1.27 (6H, m), 3.40–3.46 (2H, m), 3.56–3.82 (3H, m), 4.09–4.19 (3H, m), 4.31–4.34 (1H, m), 5.96 (1H, d, J=8 Hz), 7.16–7.38 (5H, m), 7.68 (1H, d, J=8 Hz).

d) (3R)-3-[2-Benzyl-6-(cis-3-isopropyloxy-4-hydroxypyrrolidine-1-yl)-3-pyridyl]ethynyl-3-quinuclidinol A mixture of 464 mg of 2-benzyl-6-(cis-3-isopropyloxy-4-hydroxypyrrolidine-1-yl)-3-iodopyridine, 176 mg of (3R)-3-ethynyl-3-quinuclidinol, 122 mg of tetrakis (triphenylphosphine)palladium (0), 10 mg of cuprous iodide, 0.44 ml of triethylamine and 5.0 ml of N,N-dimethylformamide was heated under stirring at 75° C. for 2 hours in a nitrogen atmosphere. The reaction solution was poured into aqueous dilute ammonia, and then extracted with ethyl acetate. The extract was washed with brine and the solvent was removed. The residue was subjected to NH-silica gel (Fuji Silicia) column chromatography and eluted with hexane/ethyl acetate (1:1) and then with ethyl acetate/methanol (20:1), to give 168 mg of the target compound.

$^1$H-NMR (CDCl$_3$) δ=1.21–1.27 (6H, m), 1.50–1.97 (3H, m), 2.04–2.17 (2H, m), 2.75–2.98 (4H, m), 3.12 (1H, d, J=14 Hz), 3.28–3.31 (1H, m), 3.41–3.64 (3H, m), 3.73–3.81 (2H, m), 4.11–4.14 (3H, m), 4.36 (1H, br.s), 6.14 (1H, d, J=9 Hz), 7.16–7.29 (5H, m), 7.41 (1H, d, J=9 Hz).

Example 123

(3R)-3-[2-Benzyl-6-[(3R,4R)-3,4-dimethoxy-2-pyrrolidinone-1-yl]-3-pyridyl]ethynyl-3-quinuclidinol a) 2-Benzyl-3-methoxymethyloxy-6-[(3R,4R)-3,4-dimethylmethylenedioxy-2-pyrrolidinone-1-yl]pyridine 3.6 g of 2-benzyl-3-methoxymethyloxy-6-iodopyridine (Production Example 12), 1.5 g of (3R,4R)-3,4-dimethylmethylenedioxy-2-pyrrolidinone synthesized by a method known in literature (J. Org. Chem., 1969, 34, 675), 1.1 g of cuprous iodide and 3.3 g of potassium carbonate were suspended in 20 ml of 1-methyl-2-pyrrolidinone, followed by heating stirring at 140° C. for 20 minutes in an oil bath in a nitrogen atmosphere. After cooling as it was, ethyl acetate and aqueous ammonia were added thereto, and the mixture was extracted with ethyl acetate. The organic phase was further washed with brine, dried over anhydrous sodium sulfate anhydride and the solvent was removed. The residue was subjected to silica gel column chromatography using 20–50% ethyl acetate/hexane as an eluent for separation and purification, to give 2 g of the target compound.

$^1$H-NMR (CDCl$_3$) δ=1.42 (3H, s), 1.46 (3H, s), 3.37 (3H, s), 4.08–4.13 (3H, m), 4.26 (1H, d, J=13 Hz), 4.80 (2H, s), 5.14 (2H, dd, J=6.8, 10 Hz), 7.17–7.31 (5H, m), 7.42 (1H, d, J=9.0 Hz), 8.22 (1H, d, J=9.0 Hz).

b) 2-Benzyl-6-[(3R,4R)-3,4-dimethylmethylenedioxy-2-pyrrolidinone-1-yl]-3-pyridyl Trifluoromethanesulfonate 5 ml of trifluoroacetic acid was added to 2 g of 2-benzyl-3-methoxymethyloxy-6-[(3R,4R)-3,4-dimethylmethylenedioxy-2-pyrrolidinone-1-yl]pyridine, followed by stirring at room temperature for 6 hours. Then, the mixture was neutralized by an aqueous potassium carbonate solution and extracted with ethyl acetate. Further, the organic phase was washed with brine, dried over anhydrous sodium sulfate and the solvent was removed. After dissolving the resulting residue in 30 ml of dichloromethane, 2.1 g of N-phenyltrifluoromethanesulfonimide, 192 mg of 4-dimethylaminopyridine and 0.8 ml of triethylamine were added thereto. After stirring at room temperature for one hour, the solvent was removed, and the residue was subjected to silica gel column chromatography using 25% ethyl acetate/hexane as an eluent for separation and purification, to give 2.2 g of the target compound.

$^1$H-NMR (CDCl$_3$) δ=1.42 (3H, s), 1.46 (3H, s), 4.03 (1H, dd, J=4.0, 13 Hz), 4.18 (2H, s), 4.23 (1H, d, J=13 Hz), 4.79–4.83 (2H, m), 7.20–7.42 (5H, m), 7.60 (1H, d, J=9.2 Hz), 8.44 (1H, d, J=9.2 Hz).

2-Benzyl-6-[(3R,4R)-3,4-dimethoxy-2-pyrrolidinone-1-yl]-3-pyridyl Trifluoromethanesulfonate (A) and 2-Benzyl-6-[(3R,4R)-4-hydroxy-3-methoxy-2-pyrrolidinone-1-yl]-3-pyridyl Trifluoromethanesulfonate (B)

2.2 g of 2-benzyl-6-[(3R,4R)-3,4-dimethylmethylenedioxy-2-pyrrolidinone-1-yl]-3-pyridyl trifluoromethanesulfonate was dissolved in 20 ml of methanol and 5 ml of 5N hydrochloric acid was added thereto, followed by stirring at room temperature for 1.5 hours and at 50° C. in an oil bath for 2 hours. After cooling as it was, the mixture was neutralized by an aqueous potassium carbonate solution and extracted with ethyl acetate. Further, the organic phase was washed with brine, dried over anhydrous sodium sulfate and the solvent was removed. The resulting residue was dissolved in 20 ml of acetonirile, and 1.5 ml of methyl iodide and 5.6 g of silver (I) oxide were added thereto, followed by heating under stirring at 60° C. in an oil bath for 1.5 hours. Insoluble matters were filtered off through Celite, and the filtrate was evaporated. The residue was subjected to silica gel column chromatography using 33–50% ethyl acetate/hexane as an eluent for separation and purification, to give 685 mg of the target compound (A) and 599 mg of the target compound (B).

Compound (A): $^1$H-NMR (CDCl$_3$) δ=3.47 (3H, s), 3.69 (3H, s), 3.80 (1H, dd, J=3.8, 12 Hz), 4.07–4.21 (5H, m), 7.22–7.29 (5H, m), 7.58 (1H, d, J=9.2 Hz), 8.38 (1H, d, J=9.2 Hz); Compound (B): $^1$H-NMR (CDCl$_3$) δ=3.48 (1H, d, J=4.6 Hz), 3.74 (3H, s), 3.86 (1H, dd, J=13 Hz, 4.0 Hz), 4.06–4.18 (4H, m), 4.54–4.57 (1H, m), 7.24–7.30 (5H, m), 7.59 (1H, d, J=9.0 Hz), 8.37 (1H, d, J=9.0 Hz).

d) (3R)-3-[2-Benzyl-6-[(3R,4R)-dimethoxy-2-pyrrolidinone-1-yl]-3-pyridyl]ethynyl-3-quinuclidinol 5 ml of N,N-dimethylformamide was added to a mixture of 685 mg of 2-benzyl-6-[(3R,4R)-3,4-dimethoxy-2-pyrrolidinone-1-yl]-3-pyridyl trifluoromethanesulfonate, 293 mg of (3R)-3-ethynyl-3-quinuclidinol, 107 mg of tetrakis(triphenylphosphine)palladium(0), 22 mg of cuprous iodide and 0.7 ml of triethylamine, followed by heating under stirring at 60° C. in an oil bath for 1.3 hours in a nitrogen atmosphere. After cooling as it was, ethyl acetate and aqueous ammonia were added thereto, and extracted with ethyl acetate. The organic phase was further washed with brine, dried over anhydrous sodium sulfate and the solvent was removed. The residue was subjected to NH-silica gel column chromatography using 66% ethyl acetate/hexane and 2% methanol/ethyl acetate as eluents for separation and purification, to give 361 mg of the target compound.

$^1$H-NMR (CDCl$_3$) δ=1.38–1.48 (1H, m), 1.57–1.67 (1H, m), 1.68–1.92 (1H, m), 2.00–2.19 (2H, m), 2.70–2.95 (4H, m), 3.03 (1H, d, J=14 Hz), 3.24 (1H, dd, J=1.6, 14 Hz), 3.48 (3H, s), 3.70 (3H, s), 3.84 (1H, dd, J=2.0, 13 Hz), 4.09 (1H, d, J=2.8 Hz), 4.15–4.17 (1H, m), 4.23–4.25 (3H, m), 7.09–7.29 (5H, m), 7.67 (1H, d, J=8.8 Hz), 8.24 (1H, d, J=8.8 Hz).

Example 124

(3R)-3-[2-Benzyl-6-[(3R,4R)-4-hydroxy-3-methoxy-2-pyrrolidinone-1-yl]-3-pyridyl]ethynyl-3-quinuclidinol The target compound was synthesized in the same manner as in Example 123 by using 2-benzyl-6-[(3R,4R)-4-hydroxy-3-methoxy-2-pyrrolidinone-1-yl]-3-pyridyl trifluoromethanesulfonate (Example 123c).

$^1$H-NMR (CDCl$_3$) δ=1.36–1.47 (1H, m), 1.58–1.68 (1H, m), 1.82–1.93 (1H, m), 2.00–2.09 (2H, m), 2.70–2.95 (4H, m), 3.03 (1H, d, J=14 Hz), 3.25 (1H, dd, J=2.0, 14 Hz), 3.74 (3H, s), 3.90 (1H, dd, J=4.0, 13 Hz), 4.07 (1H, d, J=3.6 Hz), 4.21 (1H, d, J=13 Hz), 4.24 (2H, s), 4.55 (1H, dd, J=3.6, 4.0 Hz), 7.08–7.28 (5H, m), 7.66 (1H, d, J=8.4 Hz), 8.21 (1H, d, J=8.4 Hz).

Example 125

(3R)-3-[2-Benzyl-6-[(3R,4R)-3,4-dimethylmethylenedioxy-2-pyrrolidinone-1-yl]-3-pyridyl]ethynyl-3-quinuclidinol The target compound was synthesized in the same manner as in Example 123.

$^1$H-NMR (CDCl$_3$) δ=1.35–1.45 (1H, m), 1.42 (3H, s), 1.47 (3H, s), 1.58–1.72 (1H, m), 1.82–1.92 (1H, m), 2.00–2.08 (2H, m), 2.71–2.95 (4H, m), 3.05 (1H, d, J=14 Hz), 3.26 (1H, dd, J=1.8, 14 Hz), 4.07 (1H, dd, J=4.0, 13 Hz), 4.25 (2H, s), 4.29 (1H, d, J=13 Hz), 4.78–4.83 (2H, m), 7.18–7.28 (5H, m), 7.69 (1H, d, J=8.6 Hz), 8.29 (1H, d, J=8.6 Hz).

Example 126

3-[2-Benzyl-6-(2-oxo-1,3-oxazolidine-3-yl)-3-pyridyl]ethynyl-3-quinuclidinol

The target compound was synthesized in the same manner as in Example 123.

$^1$H-NMR (CDCl$_3$) δ=1.38–1.48 (1H, m), 1.60–1.70 (1H, m), 1.85–1.95 (1H, m), 2.00–2.13 (2H, m), 2.74–2.98 (4H, m), 3.04 (1H, d, J=14 Hz), 3.25 (1H, d, J=14 Hz), 4.23(2H, t, J=8.1 Hz), 4.24 (2H, s), 4.47 (2H, t, J=8.1 Hz), 7.17–7.28 (5H, m), 7.66 (1H, d, J=8.7 Hz), 8.02 (1H, d, J=8.7 Hz)

Example 127

3-[2-Benzyl-6-(2-pyrrolidinone-1-yl)-3-pyridyl]ethynyl-3-quinuclidinol

The target compound was synthesized in the same manner as in Example 123.

$^1$H-NMR (CDCl$_3$) δ=1.38–1.47 (1H, m), 1.58–1.70 (1H, m), 1.85–1.95 (1H, m), 2.03–2.15 (2H, m), 2.09 (2H, tt, J=7.2, 8.1 Hz), 2.65 (2H, t, J=8.1 Hz), 2.73–2.95 (4H, m), 3.03 (1H, d, J=14 Hz), 3.24 (1H, dd, J=2.0, 14 Hz), 4.07 (2H, t, J=7.2 Hz), 4.24 (2H, s), 7.18–7.27 (5H, m), 7.66 (1H, d, J=8.7 Hz), 8.24 (1H, d, J=8.7 Hz).

Example 128

(3R)-3-[2-Benzyl-6-(2-pyrrolidinone-1-yl)-3-pyridyl]ethynyl-3-quinuclidinol

The target compound was synthesized in the same manner as in Example 123.

$^1$H-NMR (CDCl$_3$) δ=1.38–1.47 (1H, m), 1.58–1.70 (1H, m), 1.85–1.95 (1H, m), 2.03–2.15 (2H, m), 2.09(2H, tt, J=7.2, 8.1 Hz), 2.65 (2H, t, J=8.1 Hz), 2.73–2.95 (4H, m), 3.03 (1H, d, J=14 Hz), 3.24 (1H, dd, J=2.0, 14 Hz), 4.07 (2H, t, J=7.2 Hz), 4.24 (2H, s), 7.18–7.27 (5H, m), 7.66 (1H, d, J=8.7 Hz), 8.24 (1H, d, J=8.7 Hz).

Example 129

3-[2-Benzyl-6-(2-piperidinone-1-yl)-3-pyridyl]ethynyl-3-quinuclidinol

The target compound was synthesized in the same manner as in Example 123.

$^1$H-NMR (CDCl$_3$) δ=1.38–1.48 (1H, m), 1.58–1.65 (1H, m), 1.70–1.97 (5H, m), 1.98–2.08 (2H, m), 2.59 (2H, t, J=6.4 Hz), 2.69–2.94 (4H, m), 3.02 (1H, dd, J=1.5, 14 Hz), 3.22 (1H, dd, J=2.0, 14 Hz), 3.93 (2H, t, J=5.7 Hz), 4.25 (2H, s), 7.17–7.27 (5H, m), 7.63 (1H, d, J=8.5 Hz), 7.74 (1H, d, J=8.5 Hz).

Example 130

(3R)-3-[2-Benzyl-6-(2-piperidinone-1-yl)-3-pyridyl]ethynyl-3-quinuclidinol

The target compound was synthesized in the same manner as in Example 123.

$^1$H-NMR (CDCl$_3$) δ=1.38–1.48 (1H, m), 1.58–1.65 (1H, m), 1.70–1.97 (5H, m), 1.98–2.08 (2H, m), 2.59 (2H, t, J=6.4 Hz), 2.69–2.94 (4H, m), 3.02 (1H, dd, J=1.5, 14 Hz), 3.22 (1H, dd, J=2.0, 14 Hz), 3.93 (2H, t, J=5.7 Hz), 4.25 (2H, s), 7.17–7.27 (5H, m), 7.63 (1H, d, J=8.5 Hz), 7.74 (1H, d, J=8.5 Hz).

Example 131

(3R)-3-[2-Benzyl-6-[(4R)-4-hydroxy-2-pyrrolidinone-1-yl)-3-pyridyl]ethynyl-3-quinuclidinol The target compound was synthesized in the same manner as in Example 123.

$^1$H-NMR (CDCl$_3$) δ=1.35–1.47 (1H, m), 1.53–1.63 (1H, m), 1.78–1.89 (1H, m), 2.00–2.09 (2H, m), 2.63 (1H, dd, J=2.0, 18 Hz), 2.68–2.94 (4H, m), 2.93 (1H, dd, J=6.2, 18 Hz), 2.99 (1H, dd, J=1.6, 14 Hz), 3.20 (1H, dd, J=2.0, 14 Hz), 4.09–4.18 (2H, m), 4.20 (2H, s), 4.50–4.56 (1H, m), 7.15–7.28 (5H, m), 7.53 (1H, d, J=8.6 Hz), 8.12 (1H, d, J=8.6 Hz).

Example 132

(3S)-3-[2-Benzyl-6-[(4R)-4-hydroxy-2-pyrrolidinone-1-yl)-3-pyridyl]ethynyl-3-quinuclidinol The target compound was synthesized in the same manner as in Example 123.

$^1$H-NMR (CDCl$_3$) δ=1.35–1.47 (1H, m), 1.53–1.63 (1H, m), 1.78–1.89 (1H, m), 2.00–2.09 (2H, m), 2.63 (1H, dd, J=2.0, 18 Hz), 2.68–2.94 (4H, m), 2.93 (1H, dd, J=6.2, 18 Hz), 2.99 (1H, dd, J=1.6, 14 Hz), 3.20 (1H, dd, J=2.0, 14 Hz), 4.09–4.18 (2H, m), 4.20 (2H, s), 4.50–4.56 (1H, m), 7.15–7.28 (5H, m), 7.53 (1H, d, J=8.6 Hz), 8.12 (1H, d, J=8.6 Hz).

Example 133

3-[2-Benzyl-6-(2-oxo-2,5-dihydropyrrole-1-yl)-3-pyridyl]ethynyl-3-quinuclidinol The target compound was synthesized in the same manner as in Example 123 by using 2-benzyl-6-(2-oxo-2,5-dihydropyrrole-1-yl)-3-pyridiyl trifluoromethanesulfonate which was by-produced when the compound of Example 131 was synthesized.

$^1$H-NMR (CDCl$_3$) δ=1.35–1.47 (1H, m), 1.56–1.67 (1H, m), 1.83–2.10 (3H, m), 2.72–2.95 (4H, m), 3.04 (1H, d, J=14 Hz), 3.25 (1H, dd, J=14 Hz, 2.1 Hz), 4.24 (2H, s), 4.64 (2H, t, J=1.8 Hz), 6.23 (2H, dt, J=6.0 Hz, 1.8 Hz), 7.18–7.29 (6H, m), 7.67 (1H, d, J=8.6 Hz), 8.26 (1H, d, J=8.6 Hz).

Example 134

(3R)-3-[2-Benzyl-6-[(4S)-4-methoxy-2-pyrrolidinone-1-yl)-3-pyridyl]ethynyl-3-quinuclidinol The target compound was synthesized in the same manner as in Example 123.

$^1$H-NMR (CDCl$_3$) δ=1.35–1.49 (1H, m), 1.57–1.68 (1H, m), 1.78–1.92 (1H, m), 1.98–2.10 (2H, m), 2.70–2.98 (5H, m), 3.04 (1H, d, J=14 Hz), 3.25 (1H, d, J=14 Hz), 3.38 (3H, s), 4.07–4.22 (4H, m), 4.25 (2H, s), 7.08–7.29 (5H, m), 7.67 (1H, d, J=8.6 Hz), 8.23 (1H, d, J=8.6 Hz).

Example 135

3-[2-Benzyl-6-(1-imidazolyl)-3-pyridyl]ethynyl-3-quinuclidinol

The target compound was synthesized in the same manner as in Example 123.

$^1$H-NMR (CDCl$_3$) δ=1.39–1.49 (1H, m), 1.58–1.72 (1H, m), 1.82–1.92 (1H, m), 2.00–2.10 (2H, m), 2.75–2.98 (4H, m), 3.07 (1H, d, J=14 Hz), 3.27 (1H, dd, J=1.9, 14 Hz), 4.32 (2H, s), 7.14 (1H, d, J=8.2 Hz), 7.18–7.30 (7H, m), 7.78 (1H, d, J=8.2 Hz), 8.34 (1H, s).

Example 136

3-[2-Benzyl-6-(2-oxo-1,2-dihydropyrrolidine-1-yl)-3-pyridyl]ethynyl-3-quinuclidinol The target compound was synthesized in the same manner as in Example 123.

$^1$H-NMR (CDCl$_3$) δ=1.38–1.48 (1H, m), 1.58–1.68 (1H, m), 1.75–1.90 (1H, m), 2.00–2.09 (2H, m), 2.69–2.95 (4H, m), 3.04 (1H, d, J=14 Hz), 3.25 (1H, dd, J=1.8, 14 Hz), 4.34

(2H, s), 6.29 (1H, dd, J=6.5, 7.2 Hz), 6.63 (1H, d, J=9.2 Hz), 7.16–7.34 (5H, m), 7.37 (1H, ddd, J=2.1, 6.5, 9.2 Hz), 7.79 (1H, d, J=8.4), 7.89 (1H, d, J=8.4 Hz), 7.92 (1H, dd, J=2.1, 7.2 Hz).

Example 137

3-[2-Benzyl-6-(1-pyrazolyl)-3-pyridyl]ethynyl-3-quinuclidinol

The target compound was synthesized in the same manner as in Example 123.

¹H-NMR (CDCl₃) δ=1.38–1.48 (1H, m), 1.58–1.68 (1H, m), 1.79–1.93 (1H, m), 2.00–2.10 (2H, m), 2.70–2.95 (4H, m), 3.04 (1H, d, J=14 Hz), 3.25 (1H, dd, J=2.0, 14 Hz), 4.31 (2H, s), 6.44 (1H, dd, J=1.0, 1.6 Hz), 7.19–7.32 (5H, m), 7.72–7.81 (3H, m), 8.54 (1H, dd, J=1.0, 2.7 Hz).

Example 138

(3R)-3-[2-Benzyl-6-(3,3-ethylenedioxy-2-pyrrolidinone-1-yl)-3-pyridyl]ethynyl-3-quinuclidinol a) 2-Benzyl-3-methoxymethyloxy-6-[(3S)-3-hydroxy-2-pyrrolidinone-1-yl]pyridine 14.3 g of 2-benzyl-3-methoxymethyloxy-6-iodopyridine (Production Example 12) and 4.1 g of (3S)-3-hydroxy-2-pyrrolidinone synthesized according to a method well-known in a literature (Synthesis, 1978, 614), 4.6 g of cuprous iodide and 13.7 g of potassium carbonate were suspended in 30 ml of 1-methyl-2-pyrrolidinone, followed by heating under stirring at 140° C. in an oil bath for 20 minutes in a nitrogen atmosphere. After cooling as it was, ethyl acetate and aqueous ammonia were added thereto. The mixture was extracted with ethyl acetate, and the organic phase was further washed with brine, dried over anhydrous sodium sulfate and the solvent was removed. The residue was subjected to silica gel column chromatography using 50–60% ethyl acetate as an eluent for separation and purification, to give 9.7 g of the target compound.

¹H-NMR (CDCl₃) δ=1.95–2.08 (1H, m), 2.53–2.58 (1H, m), 3.09 (1H, br.s), 3.37 (3H, s), 3.76 (1H, td, J=10 Hz, 6.6 Hz), 4.12 (2H, s), 4.19 (1H, t, J=9.2 Hz), 4.48 (1H, t, J=10 Hz), 5.14 (2H, s), 7.17–7.30 (5H, m), 7.42 (1H, d, J=9.0 Hz), 8.14 (1H, d, J=9.0 Hz).

b) 2-Benzyl-6-(3,3-ethylenedioxy-2-pyrrolidinone-1-yl)-3-hydroxypyridine 1.1 g of 2-benzyl-3-methoxymethyloxy-6-[(3S)-3-hydroxy-2-pyrrolidinone-1-yl]pyridine was dissolved in 20 ml of acetone, and 1 ml of a Jone's reagent was added thereto, followed by stirring at room temperature for 1.5 hours. 2-Propanol and water were added thereto, followed by extracting with ethyl acetate. The organic phase was further washed with brine, dried over anhydrous sodium sulfate and the solvent was removed. The resulting residue was dissolved in 20 ml of toluene. 1 ml of ethylene glycol and 198 mg of p-toluenesulfonic acid were added thereto, followed by heating under reflux for 2 hours while removing water by use of Dean Stark apparatus. After cooling as it was, water was added thereto and the mixture was extracted with ethyl acetate. The organic phase was further washed with brine, dried over anhydrous sodium sulfate and the solvent was removed. The residue was subjected to silica gel column chromatography using 30–40% ethyl acetate/hexane as an eluent for separation and purification, to give 398 mg of the target compound.

¹H-NMR (CDCl₃) δ=2.34 (2H, t, J=6.9 Hz), 4.01 (2H, t, J=6.9 Hz), 4.12 (4H, s), 4.39 (2H, s), 5.28 (1H, br.s), 7.13 (1H, d, J=8.6 Hz), 7.18–7.30 (5H, m), 8.11 (1H, d, J=8.6 Hz).

c) 2-Benzyl-6-(3,3-ethylenedioxy-2-pyrrolidinone-1-yl)-3-pyridyl trifluoromethanesulfonate 505 mg of 2-benzyl-6-(3,3-ethylenedioxy-2-pyrrolidinone-1-yl)-3-hydroxypyridine was dissolved in 10 ml of dichloromethane, and 757 mg of N-phenyltrifluoromethanesulfonimide, 61 mg of 4-dimethylaminopyridine and 0.3 ml of triethylamine were added thereto, followed by stirring at room temperature overnight. Thereafter, the solvent was removed, and the residue was subjected to silica gel column chromatography using 17% ethyl acetate/hexane as an eluent for separation and purification, to give 1.1 g of the target compound.

¹H-NMR (CDCl₃) δ=2.34 (2H, t, J=7.0 Hz), 3.96 (2H, t, J=7.0 Hz), 4.10–4.21 (4H, m), 4.34–4.42 (2H, m), 7.20–7.42 (5H, m), 7.59 (1H, d, J=9.2 Hz), 8.34 (1H, d, J=9.2 Hz).

d) (3R)-3-[2-Benzyl-6-(3,3-ethylenedioxy-2-pyrrolidinone-1-yl)-3-pyridyl]ethynyl-3-quinuclidinol 7 ml of N,N-dimethylformamide was added to a mixture of 1.1 g of 2-benzyl-6-(3,3-ethylenedioxy-2-pyrrolidinone-1-yl)-3-pyridyl trifluoromethanesulfonate, 437 mg of (3R)-3-ethynyl-3-quinuclidinol, 168 mg of tetrakis (triphenylphosphine)palladium(0), 24 mg of cuprous iodide and 1.1 ml of triethylamine, followed by heating under stirring at 60° C. in an oil bath for 1.3 hours in a nitrogen atmosphere. After cooling as it was, ethyl acetate and aqueous ammonia were added thereto and the mixture was extracted with ethyl acetate. The organic phase was further washed with brine, dried over anhydrous sodium sulfate and the solvent was removed. The residue was subjected to NH-silica gel column chromatography using 66% ethyl acetate/hexane and 2% methanol/ethyl acetate as eluents for separation and purification, to give 669 mg of the target compound.

¹H-NMR (CDCl₃) δ=1.35–1.45 (1H, m), 1.58–1.66 (1H, m), 1.82–1.92 (1H, m), 1.95–2.09 (2H, m), 2.34 (2H, t, J=6.8 Hz), 2.71–2.95 (4H, m), 3.03 (1H, d, J=14 Hz), 3.26 (1H, dd, J=2.0, 14 Hz), 4.00 (2H, t, J=6.8 Hz), 4.09–4.18 (2H, m), 4.24 (2H, s), 4.34–4.42 (2H, m), 7.08–7.28 (5H, m), 7.67 (1H, d, J=8.4 Hz), 8.22 (1H, d, J=8.4 Hz).

Example 139

(3R)-3-[2-Benzyl-6-[(3S)-3-fluoro-2-pyrrolidinone-1-yl]-3-pyridyl]ethynyl-3-quinuclidinol a) 2-Benzyl-3-methoxymethyloxy-6-[(3S)-3-(3-nitrobenzenesulfonyloxy)-2-pyrrolidinone-1-yl]pyridine 2.2 g of 2-benzyl-3-methoxymethyloxy-6-[(3S)-3-hydroxy-2-pyrrolidinone-1-yl]pyridine (Example 138a) was dissolved in 20 ml of ethyl acetate, and 2.3 g of 3-nitrobenzenesulfonyl chloride, 183 mg of 4-dimethylaminopyridine and 3 ml of triethylamine were added thereto, followed by stirring at room temperature overnight. Then, water was added thereto, and the mixture was extracted with ethyl acetate. The organic phase was further washed with brine, dried over anhydrous sodium sulfate and the solvent was removed. The residue was subjected to silica gel column chromatography using 25–33% ethyl acetate/hexane as an eluent, to give 3.5 g of the target compound.

¹H-NMR (CDCl₃) δ=2.30–2.42 (1H, m), 2.68–2.76 (1H, m), 3.35 (3H, s), 3.87–3.94 (1H, m), 4.10 (2H, s), 4.21 (1H, ddd, J=2.4, 9.2, 12 Hz), 5.14 (2H, s), 5.32 (1H, t, J=8.2 Hz), 7.15–7.27 (5H, m), 7.38 (1H, d, J=9.0 Hz), 7.81 (1H, t, J=7.9 Hz), 7.97 (1H, d, J=9.0 Hz), 8.38 (1H, d, J=7.9 Hz), 8.53 (1H, d, J=7.9 Hz), 8.88 (1H, s).

b) 2-Benzyl-3-methoxymethyloxy-6-[(3R)-3-acetoxy)-2-pyrrolidinone-1-yl]pyridine 2.7 g of cesium carbonate was suspended in 20 ml of dimethylsulfoxide, followed by adding 1.2 ml of acetic acid thereto. A solution of 20 ml of dimethylsulfoxide containing 3.5 g of 2-benzyl-3-methoxymethyloxy-6-[(3S)-3-(3-nitrobenzenesulfonyloxy)-2-pyrrolidinone-1-yl]pyridine was added thereto under stirring at room temperature, followed by heating under stirring at 70° C. in an oil bath for 3 hours in a nitrogen atmosphere. After cooling as it was, water was added thereto and the mixture was extracted with ethyl acetate. The organic phase was further washed with brine, dried over anhydrous sodium sulfate and the solvent was removed. The residue was subjected to separation and purification using silica gel column chromatography using 33% ethyl acetate/hexane as an eluent, to give 2.2 g of the target compound.

$^1$H-NMR (CDCl$_3$) δ=2.00–2.18 (1H, m), 2.18 (3H, s), 2.60–2.68 (1H, m), 3.37 (3H, s), 3.84–3.91 (1H, m), 4.11 (2H, s), 4.20 (1H, ddd, J=2.4, 9.2, 12 Hz), 5.15 (2H, s), 5.51 (1H, t, J=8.7 Hz), 7.18–7.29 (5H, m), 7.43 (1H, d, J=9.0 Hz), 8.17 (1H, d, J=9.0 Hz).

c) 2-Benzyl-3-methoxymethyloxy-6-[(3R)-3-hydroxy-2-pyrrolidinone-1-yl]pyridine 453 mg of 2-benzyl-3-methoxymethyloxy-6-[(3R)-3-acetoxy-2-pyrrolidinone-1-yl]pyridine was dissolved in 5 ml of methanol, and two droplets of a 28% methanol solution of sodium methoxide was added thereto under stirring at room temperature, followed by stirring for 30 minutes. Then, water was added thereto, and the mixture was extracted with ethyl acetate. The organic phase was further washed with brine, dried over anhydrous sodium sulfate and the solvent was removed. The residue was subjected to separation and purification using silica gel column chromatography using 66% ethyl acetate/hexane as an eluent, to give 371 mg of the target compound.

$^1$H-NMR (CDCl$_3$) δ=1.95–2.08 (1H, m), 2.53–2.58 (1H, m), 3.09 (1H, br.s), 3.37 (3H, s), 3.76 (1H, td, J=10 Hz, 6.6 Hz), 4.12 (2H, s), 4.19 (1H, t, J=9.2 Hz), 4.48 (1H, t, J=10 Hz), 5.14 (2H, s), 7.17–7.30 (5H, m), 7.42 (1H, d, J=9.0 Hz), 8.14 (1H, d, J=9.0 Hz).

d) 2-Benzyl-3-methoxymethyloxy-6-[(3R)-3-fluoro-2-pyrrolidinone-1-yl]pyridine 3 ml of dichloromethane was added to 0.18 ml of diethylaminosulfur trifluoride. Into the mixture was added dropwise a solution of 3 ml of dichloromethane containing 371 mg of 2-benzyl-3-methoxymethyloxy-6-[(3R)-3-hydroxy-2-pyrrolidinone-1-yl]pyridine under cooling in an ethanol/dry ice bath. The mixture was returned to room temperature and stirred for 2 hours. Then, water was added thereto, and the mixture was extracted with ethyl acetate. The organic phase was further washed with brine, dried over anhydrous sodium sulfate and the solvents was removed. The residue was subjected to silica gel column chromatography using 17–20% ethyl acetate/hexane as an eluent for separation and purification, to give 116 mg of the target compound.

$^1$H-NMR (CDCl$_3$) δ=2.20–2.36 (1H, m), 2.52–2.64 (1H, m), 3.37 (3H, s), 3.87–3.95 (1H, m), 4.12 (2H, s), 4.17–4.22 (1H, m), 5.15 (2H, s), 5.23 (1H, dt, J=53, 7.2 Hz), 7.17–7.29 (5H, m), 7.44 (1H, d, J=9.0 Hz), 8.19 (1H, d, J=9.0 Hz).

e) (3R)-3-[2-Benzyl-6-[(3S)-3-fluoro-2-pyrrolidinone-1-yl]-3-pyridyl]ethynyl-3-quinuclidinol The target compound was synthesized in the same manner as in Example 138.

$^1$H-NMR (CDCl$_3$) δ=1.38–1.48 (1H, m), 1.56–1.75 (1H, m), 1.82–1.92 (1H, m), 2.00–2.08 (2H, m), 2.21–2.38 (1H, m), 2.55–2.68 (1H, m), 2.72–2.95 (4H, m), 3.05 (1H, d, J=14 Hz), 3.26 (1H, dd, J=2.0, 14 Hz), 3.85–3.93 (1H, m), 4.19–4.28 (1H, m), 4.26 (2H, s), 5.23 (1H, dt, J=7.9, 7.6 Hz), 7.08–7.28 (5H, m), 7.71 (1H, d, J=8.6 Hz), 8.27 (1H, d, J=8.6 Hz).

Example 140

(3R)-3-[2-Benzyl-6-[(3R)-3-fluoro-2-pyrrolidinone-1-yl]-3-pyridyl]ethynyl-3-quinuclidinol The target compound was synthesized in the same manner as in Example 139c by using 2-benzyl-3-methoxymethyloxy-6-[(3S)-3-hydroxy-2-pyrrolidinone-1-yl]pyridine (Example 138a).

$^1$H-NMR (CDCl$_3$) δ=1.38–1.48 (1H, m), 1.56–1.75 (1H, m), 1.82–1.92 (1H, m), 2.00–2.08 (2H, m), 2.21–2.38 (1H, m), 2.55–2.68 (1H, m), 2.72–2.95 (4H, m), 3.05 (1H, d, J=14 Hz), 3.26 (1H, dd, J=2.0, 14 Hz), 3.85–3.93 (1H, m), 4.19–4.28 (1H, m), 4.26 (2H, s), 5.23 (1H, dt, J=7.9, 7.6 Hz), 7.08–7.28 (5H, m), 7.71 (1H, d, J=8.6 Hz), 8.27 (1H, d, J=8.6 Hz).

Example 141

(3R)-3-[2-Benzyl-6-[(3S)-3-hydroxy-2-pyrrolidinone-1-yl]-3-pyridyl]ethynyl-3-quinuclidinol The target compound was synthesized in the same manner as in Example 123.

$^1$H-NMR (CDCl$_3$) δ=1.39–1.49 (1H, m), 1.50–1.78 (1H, m), 1.82–1.92 (1H, m), 1.98–2.09 (2H, m), 2.52–2.61 (1H, m), 2.73–2.94 (4H, m), 3.05 (1H, d, J=14 Hz), 3.26 (1H, dd, J=2.0, 14 Hz), 3.72–3.79 (1H, m), 4.12 (1H, dd, J=7.2, 14 Hz), 4.20–4.25 (1H, m), 4.25 (2H, s), 4.49 (1H, dd, J=8.0, 10 Hz), 7.08–7.28 (5H, m), 7.69 (1H, d, J=8.8 Hz), 8.22 (1H, d, J=8.8 Hz).

Example 142

(3R)-3-[2-Benzyl-6-[(3R)-3-hydroxy-2-pyrrolidinone-1-yl]-3-pyridyl]ethynyl-3-quinuclidinol The target compound was synthesized in the same manner as in Example 123 except that the hydroxyl group was reversed according to the method of Example 139.

$^1$H-NMR (CDCl$_3$) δ=1.39–1.49 (1H, m), 1.50–1.78 (1H, m), 1.82–1.92 (1H, m), 1.98–2.09 (2H, m), 2.52–2.61 (1H, m), 2.73–2.94 (4H, m), 3.05 (1H, d, J=14 Hz), 3.26 (1H, dd, J=2.0, 14 Hz), 3.72–3.79 (1H, m), 4.12 (1H, dd, J=7.2, 14 Hz), 4.20–4.25 (1H, m), 4.25 (2H, s), 4.49 (1H, dd, J=8.0, 10 Hz), 7.08–7.28 (5H, m), 7.69 (1H, d, J=8.8 Hz), 8.22 (1H, d, J=8.8 Hz).

Example 143

(3R)-3-[2-Benzyl-6-[(3S)-3-methoxy-2-pyrrolidinone-1-yl]-3-pyridyl]ethynyl-3-quinuclidinol The target compound was synthesized in the same manner as in Example 123.

$^1$H-NMR (CDCl$_3$) δ=1.38–1.48 (1H, m), 1.58–1.68 (1H, m), 1.85–2.10 (4H, m), 2.41–2.52 (1H, m), 2.70–2.92 (4H, m), 3.04 (1H, dd, J=2.0, 14 Hz), 3.25 (1H, dd, J=2.0, 14 Hz), 3.61 (3H, s), 3.80–3.87 (1H, m), 4.10–4.18 (2H, m), 4.24 (2H, s), 7.08–7.27 (5H, m), 7.68 (1H, d, J=8.8 Hz), 8.26 (1H, d, J=8.8 Hz).

Example 144

(3R)-3-[2-Benzyl-6-[(3R)-3-methoxy-2-pyrrolidinone-1-yl]-3-pyridyl]ethynyl-3-quinuclidinol The target compound was synthesized in the same manner as in Example 123 except that the hydroxyl group was reversed according to the method of Example 139.

¹H-NMR (CDCl₃) δ=1.38–1.48 (1H, m), 1.58–1.68 (1H, m), 1.85–2.10 (4H, m), 2.41–2.52 (1H, m), 2.70–2.92 (4H, m), 3.04 (1H, dd, J=2.0, 14 Hz), 3.25 (1H, dd, J=2.0, 14 Hz), 3.61 (3H, s), 3.80–3.87 (1H, m), 4.10–4.18 (2H, m), 4.24 (2H, s), 7.08–7.27 (5H, m), 7.68 (1H, d, J=8.8 Hz), 8.26 (1H, d, J=8.8 Hz).

Example 145

(3S)-3-[2-[2-Benzyl-6-[(3R,4R)-3-hydroxy-4-methoxypyrrolidine-1-yl]-pyridyl]ethyl]-3-quinuclidinol 180 mg of the target compound was obtained using 200 mg of (3R)-3-[2-benzyl-6-[(3R,4R)-3-hydroxy-4-methoxypyrrolidine-1-yl]-3-pyridyl]ethynyl-3-quinuclidinol (Example 10) in 2 ml of methanol at normal pressure in a hydrogen atmosphere wherein 10 mg of platinum (IV) oxide was used as a catalyst to carry out catalytic reduction.

¹H-NMR (CDCl₃) δ=1.15–2.03 (7H, m), 2.37–2.91 (8H, m), 3.42 (3H, s), 3.45–3.55 (2H, m), 3.66–3.77 (2H, m), 3.85–3.88 (1H, m), 4.05 (2H, s), 4.35–4.39 (1H, m), 6.22 (1H, d, J=8 Hz), 7.13–7.18 (1H, m), 7.20 (1H, d, J=8 Hz), 7.22–7.28 (4H, m).

Example 146

(3R)-3-[(E)-2-[2-Benzyl-6-[(3R,4R)-3-hydroxy-4-methoxypyrrolidine-1-yl]-pyridyl]ethenyl]-3-quinuclidinol 270 mg of (3R)-3-[2-benzyl-6-[(3R,4R)-3-hydroxy-4-methoxypyrrolidine-1-yl]-3-pyridyl]ethynyl-3-quinuclidinol (Example 10) was dissolved in 10 ml of ethyl ether. 300 mg of lithium aluminum hydride was added thereto, followed by heating under reflux for 6 hours. While stirring in an ice-bath, 0.3 ml of water, 0.3 ml of an aqueous 5N sodium hydroxide solution, 1 ml of water and 10 ml of tetrahydrofuran were added thereto. The mixture was filtered, and the filtrate was concentrated. The residue was then subjected to NH-silica gel column chromatography and eluted with 10% methanol/ethyl acetate, to give 165 mg of the target compound.

¹H-NMR (CDCl₃) δ=1.31–1.55 (3H, m), 1.72–1.77 (1H, m), 2.00–2.10 (1H, m), 2.55–2.65 (1H, m), 2.67–2.83 (3H, m), 2.85–2.97 (2H, m), 3.42 (3H, s), 3.47–3.59 (2H, m), 3.68–3.79 (2H, m), 3.84–3.89 (1H, m), 4.09 (2H, s), 4.37–4.40 (1H, m), 5.97 (1H, J=16 Hz), 6.24 (1H, d, J=9 Hz), 6.65 (1H, d, J=16 Hz), 7.11–7.18 (1H, m), 7.19–7.25 (4H, m), 7.51 (1H, d, J=9 Hz).

Example 147

(3R)-3-[2-Benzyl-6-(2-methoxyethyl)oxy-3-pyridyl]ethynyl-3-quinuclidinol

The target compound was synthesized in the same manner as in Example 12.

¹H-NMR (CDCl₃) δ=1.35–1.45 (1H, m), 1.55–1.65 (1H, m), 1.83–1.93 (1H, m), 1.98–2.08 (2H, m), 2.7–2.93 (4H, m), 3.02 (1H, d, J=14 Hz), 3.23 (1H, dd, J=2, 14 Hz), 3.41 (3H, s), 3.69 (2H, t, J=5 Hz), 4.19 (2H, s), 4.45 (2H, t, J=5 Hz), 6.59 (1H, d, J=8 Hz), 7.14–7.30 (5H, m), 7.53 (1H, d, J=8 Hz).

Example 148

(3R)-3-[2-Benzyl-6-(2-methoxypropyl)oxy-3-pyridyl]ethynyl-3-quinuclidinol

The target compound was synthesized in the same manner as in Example 12.

¹H-NMR (CDCl₃) δ=1.38–1.48 (1H, m), 1.58–1.69 (1H, m), 1.82–1.93 (1H, m), 2.00 (2H, quint, J=6.4 Hz), 2.72–2.94 (6H, m), 3.03 (1H, dd, J=1.2, 14 Hz), 3.24 (1H, dd, J=2.0, 14 Hz), 3.34 (3H, s), 3.51 (2H, t, J=6.4 Hz), 4.20 (2H, s), 4.37 (2H, t, J=6.4 Hz), 6.53 (1H, d, J=8.4 Hz), 7.18–7.31 (5H, m), 7.54 (1H, d, J=8.4 Hz).

Example 149

(3S)-3-[2-Benzyl-6-(2-methoxypropyl)oxy-3-pyridyl]ethynyl-3-quinuclidinol

The target compound was synthesized in the same manner as in Example 12.

¹H-NMR (CDCl₃) δ=1.38–1.48 (1H, m), 1.58–1.69 (1H, m), 1.82–1.93 (1H, m), 2.00 (2H, quint, J=6.4 Hz), 2.72–2.94 (6H, m), 3.03 (1H, dd, J=1.2, 14 Hz), 3.24 (1H, dd, J=2.0, 14 Hz), 3.34 (3H, s), 3.51 (2H, t, J=6.4 Hz), 4.20 (2H, s), 4.37 (2H, t, J=6.4 Hz), 6.53 (1H, d, J=8.4 Hz), 7.18–7.31 (5H, m), 7.54 (1H, d, J=8.4 Hz).

Example 150

(3R)-3-[2-Benzyl-6-(3-fluoropropyl)oxy-3-pyridyl]ethynyl-3-quinuclidinol

The target compound was synthesized in the same manner as in Example 12.

¹H-NMR (CDCl₃) δ=1.36–1.44 (1H, m), 1.58–1.65 (1H, m), 1.85–1.93 (1H, m), 1.99–2.17 (4H, m), 2.74–2.92 (4H, m), 3.04 (1H, d, J=14 Hz), 3.25 (1H, d, J=14 Hz), 4.20 (2H, s), 4.42 (2H, t, J=6 Hz), 4.58 (2H, td, J=6, 47 Hz), 6.53 (1H, d, J=8 Hz), 7.16–7.31 (5H, m), 7.55 (1H, d, J=8 Hz).

Example 151

(3R)-3-[2-Benzyl-6-(4-fluorobutyl)oxy-3-pyridyl]ethynyl-3-quinuclidinol

The target compound was synthesized in the same manner as in Example 12.

¹H-NMR (CDCl₃) δ=1.38–1.46 (1H, m), 1.57–1.93 (6H, m), 2.00–2.09 (2H, m), 2.71–2.94 (4H, m), 3.04 (1H, d, J=14 Hz), 3.25 (1H, dd, J=2, 14 Hz), 4.20 (2H, s), 4.31–4.34 (2H, m), 4.41–4.55 (2H, m), 6.52 (1H, d, J=8 Hz), 7.17–7.31 (5H, m), 7.54 (1H, d, J=8 Hz).

Example 152

(3R)-3-[2-Benzyl-6-(4-chloropropyl)oxy-3-pyridyl]ethynyl-3-quinuclidinol

The target compound was synthesized in the same manner as in Example 12.

¹H-NMR (CDCl₃) δ=1.38–1.46 (1H, m), 1.58–1.94 (6H, m), 2.00–2.09 (2H, m), 2.72–2.94 (4H, m), 3.04 (1H, d, J=14 Hz), 3.25 (1H, dd, J=2, 14 Hz), 4.21 (2H, s), 4.31–4.34 (2H, m), 4.41–4.55 (2H, m), 6.53 (1H, d, J=8 Hz), 7.17–7.34 (5H, m), 7.55 (1H, d, J=8 Hz).

Example 153

(3R)-3-[2-Benzyl-6-(1,3-dioxolan-2-yl)methyloxy-3-pyridyl]ethynyl-3-quinuclidinol The target compound was synthesized in the same manner as in Example 12.

$^1$H-NMR (CDCl$_3$) δ=1.38–1.46 (1H, m), 1.57–1.66 (1H, m), 1.85–1.92 (1H, m), 2.00–2.07 (2H, m), 2.75–2.94 (4H, m), 3.03 (1H, d, J=14 Hz), 3.25 (1H, dd, J=2, 14 Hz), 3.92–4.05 (4H, m), 4.20 (2H, s), 4.38 (2H, d, J=4 Hz), 5.27 (1H, t, J=4 Hz), 6.62 (1H, d, J=8 Hz), 7.17–7.30 (5H, m), 7.56 (1H, d, J=8 Hz).

Example 154

(3R)-3-[2-Benzyl-6-(2-pyridylmethyl)oxy-3-pyridyl]ethynyl-3-quinuclidinol

The target compound was synthesized in the same manner as in Example 12.

$^1$H-NMR (CDCl$_3$) δ=1.38–1.46 (1H, m), 1.58–1.66 (1H, m), 1.86–1.94 (1H, m), 2.00–2.07 (2H, m), 2.75–2.94 (4H, m), 3.05 (1H, d, J=14 Hz), 3.27 (1H, dd, J=2, 14 Hz), 4.17 (2H, s), 5.50 (2H, s), 6.67 (1H, d, J=8 Hz), 7.15–7.22 (6H, m), 7.33 (1H, d, J=8 Hz), 7.58 (1H, d, J=8 Hz), 7.62 (1H, dt, J=2, 8 Hz), 8.59–8.60 (1H, m).

Example 155

(3R)-3-[2-(4-Fluorobenzyl)-6-(3-fluoropropyloxy)-3-pyridyl]ethynyl-3-quinuclidinol The target compound was synthesized in the same manner as in Example 12 except that 2-benzyl-3-bromo-6-hydroxypyridine was altered to 2-(4-fluorobenzyl)-3-bromo-6-hydroxypyridine.

$^1$H-NMR (CDCl$_3$) δ=1.39–1.46 (1H, m), 1.58–1.94 (2H, m), 2.00–2.18 (4H, m), 2.72–2.94 (4H, m), 3.06 (1H, d, J=14 Hz), 3.27 (1H, dd, J=2, 14 Hz), 4.16 (2H, s), 4.41 (2H, t, J=6 Hz), 4.59 (2H, td, J=6, 47 Hz), 6.54 (1H, d, J=8 Hz), 6.93–6.97 (2H, m), 7.24–7.28 (2H, m), 7.56 (1H, d, J=8 Hz).

Example 156

(3R)-3-[2-(3-Fluorobenzyl)-6-(3-fluoropropyloxy)-3-pyridyl]ethynyl-3-quinuclidinol The target compound was synthesized in the same manner as in Example 12 except that 2-benzyl-3-bromo-6-hydroxypyridine was altered to 2-(3-fluorobenzyl)-3-bromo-6-hydroxypyridine in Example 12.

$^1$H-NMR (CDCl$_3$) δ=1.39–1.46 (1H, m), 1.58–1.94 (2H, m), 2.00–2.18 (4H, m), 2.72–2.94 (4H, m), 3.06 (1H, d, J=14 Hz), 3.27 (1H, dd, J=2, 14 Hz), 4.19 (2H, s), 4.40–4.44 (2H, m), 4.52–4.64 (2H, m), 6.56 (1H, d, J=8 Hz), 6.86–6.91 (1H, m), 6.98–7.09 (2H, m), 7.20–7.28 (1H, m), 7.56 (1H, d, J=8 Hz).

Example 157

(3R)-3-[2-(4-Fluorobenzyl)-6-(2-methoxyethyl)oxy-3-pyridyl]ethynyl-3-quinuclidinol The target compound was synthesized in the same manner as in Example 12 except that 2-benzyl-3-bromo-6-hydroxypyridine was altered to 2-(4-fluorobenzyl)-3-bromo-6-hydroxypyridine in Example 12.

$^1$H-NMR (CDCl$_3$) δ=1.37–1.94 (3H, m), 1.98–2.09 (2H, m), 2.70–3.95 (4H, m), 3.06 (1H, d, J=14 Hz), 3.26 (1H, dd, J=2, 14 Hz), 3.42 (3H, s), 3.69 (2H, t, J=5 Hz), 4.16 (2H, s), 4.43 (2H, t, J=5 Hz), 6.61 (d, J=8 Hz), 6.94 (2H, t, J=9Hz), 7.25 (2H, dd, J=6, 9 Hz), 7.55 (1H, d, J=8 Hz).

Example 158

3-[2-Benzyl-6-(2-ethoxyethyl)oxy-3-pyridyl]ethynyl-3-quinuclidinol a) 2-Bromo-6-(2-ethoxyethyl)oxypyridine 1.7 g of 60% oily sodium hydride was suspended in 20 ml of N,N-dimethylformamide, followed by adding a solution of 10 ml of N,N-dimethylformamide containing 4.1 ml of 2-ethoxyethanol thereto with stirring under ice-cooling. After stirring for 20 minutes, a solution of 10 ml of N,N-dimethylformamide containing 5 g of 2,6-dibromopyridine was added thereto and the mixture was further stirred at room temperature for one hour. Then, water was added thereto, and the mixture was extracted with ethyl acetate. The organic phase was further washed with brine, dried over anhydrous sodium sulfate and the solvent was removed. The residue was subjected to silica gel column chromatography using 5% ethyl acetate/hexane as an eluent for separation and purification, to give 4.8 g of the target compound.

$^1$H-NMR (CDCl$_3$) δ=1.24 (3H, t, J=7.0 Hz), 3.59 (2H, q, J=7.0 Hz), 3.78 (2H, t, J=4.8 Hz), 4.47 (2H, t, J=4.8 Hz), 6.75 (1H, dd, J=8.0 Hz, 0.7 Hz), 7.05 (1H, dd, J=7.5 Hz, 0.7 Hz), 7.41 (1H, dd, J=8.0 Hz, 7.5 Hz).

b) 2-Benzyl-6-(2-ethoxyethyl)oxypyridine

A 1.09 mol tetrahydrofuran solution containing benzylmagnesium chloride was slowly added dropwise into a mixture of 1 g of 2-bromo-6-(2-ethoxyethyl)oxypyridine, 145 mg of 1,3-bis(diphenylphosphino)propanenickel(II) chloride and 5 ml of tetrahydrofuran with stirring under ice-cooling in a nitrogen atmosphere. After stirring for 2.5 hours, an aqueous saturated ammonium chloride solution was added thereto and the mixture was extracted with ethyl acetate. The organic phase was further washed with brine, dried over anhydrous sodium sulfate and the solvent was removed. The residue was subjected to silica gel column chromatography using 5% ethyl acetate/hexane as an eluent for separation and purification, to give 1 g of the target compound.

$^1$H-NMR (CDCl$_3$) δ=1.23 (3H, t, J=7.0 Hz), 3.57 (2H, q, J=7.0 Hz), 3.76 (2H, t, J=4.9 Hz), 4.00 (2H, s), 4.47 (2H, t, J=4.9 Hz), 6.59 (1H, d, J=8.2 Hz), 6.65 (1H, d, J=7.2 Hz), 7.19–7.30 (5H, m), 7.44 (1H, dd, J=8.2 Hz, 7.2 Hz).

c) 2-Benzyl-3-bromo-6-(2-ethoxyethyl)oxypyridine

A mixture of 1 g of 2-benzyl-6-(2-ethoxyethyl)oxypyridine, 125 mg of tetraethylammonium chloride and 279 mg of potassium hydroxide was suspended in 5 ml of an aqueous potassium bromide solution (2.5 g of potassium bromide was dissolved in 10 ml of water). Into the suspension was added dropwise a mixture of 0.23 ml of bromine and 5 ml of the aforementioned aqueous potassium bromide solution by using a dropping funnel with stirring under ice-cooling over 10 minutes. The mixture was returned to room temperature and stirred overnight. Then, an aqueous sodium sulfite solution was added thereto, and the mixture was extracted with ethyl acetate. The organic phase was further washed with brine, dried over anhydrous sodium sulfate and the solvent was removed. The residue was subjected to silica gel column chromatography using 5% ethyl acetate/hexane as an eluent for separation and purification, to give 1.2 g of the target compound.

$^1$H-NMR (CDCl$_3$) δ=1.22 (3H, t, J=7.0 Hz), 3.55 (2H, q, J=7.0 Hz), 3.72 (2H, t, J=4.8 Hz), 4.18 (2H, s), 4.41 (2H, t, J=4.8 Hz), 6.53 (1H, d, J=8.6 Hz), 7.19–7.34 (5H, m), 7.30 (1H, d, J=8.6 Hz).

d) 3-[2-Benzyl-6-(2-ethoxyethyl)oxy-3-pyridyl]ethynyl-3-quinuclidinol 7 ml of N,N-dimethylformamide was added to a mixture of 2-benzyl-3-bromo-6-(2-ethoxyethyl)oxypyridine, 601 mg of 3-ethynyl-3-quinuclidinol, 406 mg of tetrakis (triphenylphosphine)palladium(0), 220 mg of cuprous iodide and 1.7 ml of triethylamine, followed by heating under stirring at 80° C. in an oil bath for one hour in a nitrogen atmosphere. After cooling as it was, ethyl acetate was added thereto. The mixture was filtered through Celite, and it was washed with aqueous ammonia. The organic phase was washed with brine, dried over anhydrous sodium sulfate and the solvent was removed. The residue was subjected to NH-silica gel column chromatography using ethyl acetate/hexane as an eluent for separation and purification, to give 247 mg of the target compound.

$^1$H-NMR (CDCl$_3$) δ=1.22 (3H, t, J=7.1 Hz), 1.38–1.48 (1H, m), 1.57–1.67 (1H, m), 1.82–1.92 (1H, m), 1.98–2.08 (2H, m), 2.71–2.95 (4H, m), 3.03 (1H, d, J=14 Hz), 3.24 (1H, dd, J=2.0, 14 Hz), 3.56 (2H, q, J=7.1 Hz), 3.74 (2H, t, J=4.8 Hz), 4.20 (2H, s), 4.46 (2H, t, J=4.8 Hz), 6.60 (1H, d, J=8.5 Hz), 7.18–7.30 (5H, m), 7.54 (1H, d, J=8.5 Hz).

Example 159

3-[2-Benzyl-6-(2-ethoxyethyl)oxy-3-pyridyl]ethynyl-3-quinuclidinol

The target compound was synthesized in the same manner as in Example 158.

$^1$H-NMR (CDCl$_3$) δ=1.20 (3H, t, J=6.9 Hz), 1.37–1.47 (1H, m), 1.57–1.65 (1H, m), 1.83–1.93 (1H, m), 2.01 (2H, quint, J=6.4 Hz), 2.00–2.08 (2H, m), 2.72–2.94 (4H, m), 3.05 (1H, d, J=14 Hz), 3.24 (1H, dd, J=2.0, 14 Hz), 3.48 (2H, q, J=6.9 Hz), 3.55 (2H, t, J=6.4 Hz), 4.20 (2H, s), 4.37 (2H, t, J=6.4 Hz), 6.52 (1H, d, J=8.6 Hz), 7.18–7.31 (5H, m), 7.53 (1H, d, J=8.6 Hz).

Example 160

3-[2-(4-Fluorobenzyl)-6-[(3-tetrahydrofuranyl)methyloxy-3-pyridyl]ethynyl-3-quinclidinol The target compound was synthesized in the same manner as in Example 158.

$^1$H-NMR (CDCl$_3$) δ=1.37–1.47 (1H, m), 1.58–1.92 (3H, m), 1.98–2.12 (2H, m), 2.62–2.95 (4H, m), 3.05 (1H, dd, J=1.6, 14 Hz), 3.25 (1H, dd, J=2.0, 14 Hz), 3.65 (2H, dd, J=5.2, 8.8 Hz), 3.72–3.96 (3H, m), 4.09–4.18 (3H, m), 4.27 (1H, dd, J=6.4, 11 Hz), 6.53 (1H, d, J=8.4 Hz), 6.95 (2H, t, J=8.8 Hz), 7.24 (2H, dd, J=5.5, 8.8 Hz), 7.55 (1H, d, J=8.4 Hz).

Example 161

3-[2-Benzyl-6-[(3-tetrahydrofuranyl)methyloxy-3-pyridyl]ethynyl-3-quinclidinol

The target compound was synthesized in the same manner as in Example 158.

$^1$H-NMR (CDCl$_3$) δ=1.35–1.45 (1H, m), 1.55–1.64 (1H, m), 1.67–1.75 (1H, m), 1.83–1.95 (1H, m), 1.98–2.10 (2H, m), 2.62–2.92 (4H, m), 3.02 (1H, d, J=14 Hz), 3.23 (1H, dd, J=2.0, 14 Hz), 3.65 (2H, dd, J=5.7, 8.8 Hz), 3.73–3.92 (3H, m), 4.10–4.21 (3H, m), 4.28 (1H, dd, J=6.6, 11 Hz), 6.52 (1H, d, J=8.6 Hz), 7.15–7.32 (5H, m), 7.54 (1H, d, J=8.6 Hz).

Example 162

3-[2-(3-Fluorobenzyl)-6-(3-methoxypropyl)oxy-3-pyridyl]ethynyl-3-quinclidinol

The target compound was synthesized in the same manner as in Example 158.

$^1$H-NMR (CDCl$_3$) δ=1.35–1.45 (1H, m), 1.58–1.68 (1H, m), 1.82–1.92 (1H, m), 2.00 (2H, quint, J=6.4 Hz), 2.00–2.10 (2H, m), 2.72–2.95 (4H, m), 3.03 (1H, d, J=14 Hz), 3.23 (1H, dd, J=2.0, 14 Hz), 3.34 (3H, s), 3.51 (2H, t, J=6.4 Hz), 4.17 (2H, s), 4.36 (2H, t, J=6.4 Hz), 6.53 (1H, d, J=8.4 Hz), 6.82–7.25 (4H, m), 7.53 (1H, d, J=8.4 Hz).

Example 163

3-[2-Benzyl-6-(3-tetrahydrofuranyl)methyloxy-3-pyridyl]ethynyl-3-quinclidinol

The target compound was synthesized in the same manner as in Example 158.

$^1$H-NMR (CDCl$_3$) δ=1.38–1.97 (3H, m), 2.00–2.25 (4H, m), 2.70–2.95 (4H, m), 3.05 (1H, d, J=14 Hz), 3.26 (1H, dd, J=2, 14 Hz), 3.80–4.00 (4H, m), 4.19 (2H, s), 5.45–5.52 (1H, m), 6.54 (1H, d, J=8 Hz), 7.14–7.30 (5H, m), 7.55 (1H, d, J=8 Hz).

Example 164

3-[2-Benzyl-6-[2-(2-methoxyethyl)oxyethyl]oxy-3-pyridyl]ethynyl-3-quinclidinol

The target compound was synthesized in the same manner as in Example 158.

$^1$H-NMR (CDCl$_3$) δ=1.35–1.95 (3H, m), 1.98–2.08 (2H, m), 2.70–2.93 (4H, m), 3.04 (1H, d, J=14 Hz), 3.25 (1H, dd, J=2, 14 Hz), 3.38 (3H, s), 3.54–3.57 (2H, m), 3.65–3.69 (2H, m), 3.81 (2H, t, J=5 Hz), 4.19 (2H, s), 4.48 (2H, t, J=5 Hz), 6.59 (1H, d, J=8 Hz), 7.14–7.30 (5H, m), 7.55 (1H, d, J=8 Hz).

Example 165

3-[2-Benzyl-6-(3-hydroxypropyl)oxy-3-pyridyl]ethynyl-3-quinclidinol a) 2-Benzyl-3-bromo-6-(3-hydroxypropyl)oxypyridine A mixture of 1.0 g of 2-benzyl-3-bromo-6-hydroxypyridine obtained in Production Example-3(b), 0.44 ml of 3-bromopropanol, 780 mg of anhydrous potassium carbonate and 10 ml of N,N-dimethylformamide was heated under stirring in an oil bath kept at 80° C. for one hour in a nitrogen atmosphere. The reaction solution was partitioned between ethyl acetate-water, and the organic phase was washed with water and brine, dried over anhydrous magnesium sulfate and then concentrated. The residue was subjected to silica gel chromatography using 10–20% ethyl acetate/hexane, to give 860 mg of the target compound.

$^1$H-NMR (CDCl$_3$) δ=1.94 (2H, quint, J=6 Hz), 2.47 (1H, br.s), 3.69 (2H, br.t, J=6 Hz), 4.20 (2H, s), 4.43 (2H, t, J=6 Hz), 6.49 (1H, d, J=8 Hz), 7.18–7.34 (5H, m), 7.66 (1H, d, J=8 Hz).

b) 3-[2-Benzyl-6-(3-hydroxypropyl)oxy-3-pyridyl]ethynyl-3-quinclidinol

A mixture of 860 mg of 2-benzyl-3-bromo-6-(3-hydroxypropyl)oxypyridine, 400 mg of 3-ethynyl-3-quinuclidinol, 150 mg of tetrakis(triphenylphosphine)palladium(0), 10 mg of cuprous iodide, 1.1 ml of triethylamine and 4 ml of N,N-dimethylformamide was heated under stirring in an oil bath kept at 85° C. for 3 hours in a nitrogen atmosphere. The reaction solution was partitioned between ethyl acetate-aqueous dilute ammonia, and the organic phase was washed with water and brine, dried over anhydrous sodium sulfate and then concentrated. The residue was subjected to column chromatography using NH-silica gel and diluted with 50–100% ethyl acetate/ hexane and then with 2.5–5% methanol/ethyl acetate, to give 470 mg of the target compound.

$^1$H-NMR (CDCl$_3$) δ=1.36–1.46 (1H, m), 1.55–1.66 (1H, m), 1.83–2.08 (5H, m), 2.68–2.96 (4H, m), 3.02 (1H, d, J=14 Hz), 3.24 (1H, dd, J=2, 14 Hz), 3.68 (2H, t, J=6 Hz), 4.00 (2H, s), 4.47 (2H, t, J=6 Hz), 6.55 (1H, d, J=9 Hz), 7.16–7.30 (5H, m), 7.57 (1H, d, J=9 Hz).

Example 166

(3R)-3-[2-Benzyl-6-(3-hydroxypropyl)oxy-3-pyridyl]ethynyl-3-quinclidinol

The target compound was synthesized in the same manner as in Example 165.

$^1$H-NMR (CDCl$_3$) δ=1.36–1.46 (1H, m), 1.55–1.66 (1H, m), 1.83–2.08 (5H, m), 2.68–2.96 (4H, m), 3.02 (1H, d, J=14 Hz), 3.24 (1H, dd, J=2, 14 Hz), 3.68 (2H, t, J=6 Hz), 4.00 (2H, s), 4.47 (2H, t, J=6 Hz), 6.55 (1H, d, J=9 Hz), 7.16–7.30 (5H, m), 7.57 (1H, d, J=9 Hz).

Example 167

3-[2-Benzyl-6-(3-hydroxyethyl)oxy-3-pyridyl]ethynyl-3-quinclidinol

The target compound was synthesized in the same manner as in Example 165.

$^1$H-NMR (CDCl$_3$) δ=1.37–1.93 (3H, m), 1.98–2.08 (2H, m), 2.70–2.95 (4H, m), 3.04 (1H, d, J=14 Hz), 3.26 (1H, dd, J=2, 14 Hz), 3.87–3.92 (2H, m), 4.21 (2H, s), 4.42–4.47 (2H, m), 6.61 (1H, d, J=8 Hz), 7.16–7.32 (5H, m), 7.59 (1H, d, J=8 Hz).

Example 168

3-[2-Benzyl-6-[3-(3-methoxycarbonylpropanoyloxy)propyl]oxy-3-pyridyl]ethynyl-3-quinclidinol a) 2-Benzyl-3-bromo-6-[3-(3-methoxycarbonylpropanoyloxy)propyl]oxypyridine 509 mg of 2-benzyl-3-bromo-6-(3-hydroxypropyl)oxypyridine (Example 165a) was dissolved in 5 ml of dichloromethane. While stirring under ice-cooling, 0.33 ml of triethylamine and 0.29 ml of 3-methoxycarbonylpropionyl chloride were added thereto. After the temperature of the reaction solution was returned to room temperature and the reaction solution was stirred for 30 minutes, water was added to the reaction solution. The mixture was extracted with ethyl acetate, and the organic phase was further washed with brine, dried over anhydrous sodium sulfate and the solvent was removed. The residue was subjected to silica gel column chromatography using 20% ethyl acetate/hexane as an eluent for separation and purification, to give 643 mg of the target compound.

$^1$H-NMR (CDCl$_3$) δ=2.04 (2H, tt, J=6.2, 6.4 Hz), 2.63 (4H, s), 3.68 (3H, s), 4.19 (2H, s), 4.23 (2H, t, J=6.4 Hz), 4.32 (2H, t, J=6.2 Hz), 6.46 (1H, d, J=8.6 Hz), 7.20–7.36 (5H, m), 7.63 (1H, d, J=8.6 Hz).

b) 3-[2-Benzyl-6-[3-(3-methoxycarbonylpropanoyloxy]oxy-3-pyridyl]ethynyl-3-quinclidinol 5 ml of N,N-dimethylformamide was added to a mixture of 643 mg of 2-benzyl-3-bromo-6-[3-(3-methoxycarbonylpropanoyloxy)propyl]oxypyridine, 245 mg of 3-ethynyl-3-quinuclidinol, 84 mg of tetrakis(triphenylphosphine)palladium(0), 10 mg of cuprous iodide and 0.72 ml of triethylamine, followed by heating under stirring at 80° C. in an oil bath for two hours in a nitrogen atmosphere. After cooling as it was, ethyl acetate was added thereto and the mixture was washed with aqueous ammonia. The organic phase was washed with brine, dried over anhydrous sodium sulfate and the solvent was removed. The residue was subjected to NH-silica gel column chromatography using 50% ethyl acetate/hexane and 2% methanol/ethyl acetate as eluents for separation and purification, to give 223 mg of the target compound.

$^1$H-NMR (CDCl$_3$) δ=1.38–1.48 (1H, m), 1.57–1.67 (1H, m), 1.82–1.92 (1H, m), 1.97–2.15 (4H, m), 2.61 (4H, s), 2.70–2.94 (4H, m), 3.04 (1H, d, J=14 Hz), 3.24 (1H, dd, J=2.0, 14 Hz), 3.68 (3H, s), 4.20 (2H, s), 4.23 (2H, t, J=6.4 Hz), 4.36 (2H, t, J=6.2 Hz), 6.53 (1H, d, J=8.4 Hz), 7.18–7.30 (5H, m), 7.54 (1H, d, J=8.4 Hz).

Example 169

3-[2-Benzyl-6-[3-[N-(tert-butoxycarbonyl)aranyloxy]propyl]oxy-3-pyridyl]ethynyl-3-quinuclidinol The target compound was synthesized in the same manner as in Example 168.

$^1$H-NMR (CDCl$_3$) δ=1.27 (3H, d, J=7.1 Hz), 1.38–1.48 (1H, m), 1.44 (9H, s), 1.58–1.68 (1H, m), 1.82–1.94 (1H, m), 2.00–2.10 (2H, m), 2.08 (2H, tt, J=6.2, 6.4 Hz), 2.72–2.95 (4H, m), 3.03 (1H, d, J=14 Hz), 3.25 (1H, dd, J=2.0, 14 Hz), 4.20 (2H, s), 4.22–4.35 (3H, m), 4.36 (2H, t, J=6.2 Hz), 5.04 (1H, br.s), 6.53 (1H, d, J=8.4 Hz), 7.18–7.30 (5H, m), 7.55 (1H, d, J=8.4 Hz).

Example 170

3-[2-Benzyl-6-[3-[N-(benzyloxycarbonyl)glycyloxy]propyl]oxy-3-pyridyl]ethynyl-3-quinuclidinol The target compound was synthesized in the same manner as in Example 168.

$^1$H-NMR (CDCl$_3$) δ=1.35–1.45 (1H, m), 1.55–1.65 (1H, m), 1.82–1.92 (1H, m), 1.98–2.10 (4H, m), 2.70–2.95 (4H, m), 3.03 (1H, d, J=14 Hz), 3.24 (1H, dd, J=2.0, 14 Hz), 3.96 (2H, d, J=5.5 Hz), 4.19 (2H, s), 4.29 (2H, t, J=6.4 Hz), 4.35 (2H, t, J=6.2 Hz), 5.12 (2H, s), 5.28 (1H, br.s), 6.51 (1H, d, J=8.4 Hz), 7.15–7.24 (10H, m), 7.53 (1H, d, J=8.4 Hz).

Example 171

3-[2-Benzyl-6-[3-pivaloyloxy)propyl]oxy-3-pyridyl]ethynyl-3-quinuclidinol

The target compound was synthesized in the same manner as in Example 168.

$^1$H-NMR (CDCl$_3$) δ=1.18 (9H, s), 1.35–1.45 (1H, m), 1.55–1.65 (1H, m), 1.85–2.12 (5H, m), 2.70–2.92 (4H, m), 3.03 (1H, d, J=14 Hz), 3.25 (1H, dd, J=2.0, 14 Hz), 4.19 (2H, t, J=6.2 Hz), 4.20 (2H, s), 4.37 (2H, t, J=6.4 Hz), 6.52 (1H, d, J=8.4 Hz), 7.18–7.30 (5H, m), 7.54 (1H, d, J=8.4 Hz).

Example 172

(3R)-3-[2-Benzyl-6-[(tetrahydro-4H-pyran-2-yl)methyloxy]-3-pyridyl]ethynyl-3-quinuclidinol a) 2-Benzyl-6-[(tetrahydro-4H-pyran-2-yl)methyloxy]3-(methoxymethyloxy)pyridine Sodium hydride was added to a mixture of 456 mg of 2-benzyl-6-iodo-3-(methoxymethyloxy)pyridine, 122 mg of cuprous iodide and 3 ml of tetrahydropyran-2-methanol, followed by stirring at 90° C. for 3 hours. An aqueous ammonium chloride solution and ethyl acetate were added to the reaction solution, followed by stirring at room temperature for one hour. Then, the organic phase was washed with water and brine, dried over anhydrous magnesium sulfate and the solvent was removed. The residue was subjected to silica gel column chromatography using 15% ethyl acetate/hexane, to give 383 mg of the target compound.

$^1$H-NMR (CDCl$_3$) δ=1.36–1.64 (5H, m), 1.84–1.90 (1H, m), 3.40 (3H, s), 3.43–3.49 (1H, m), 3.62–3.68 (1H, m), 4.02–4.07 (3H, m), 4.15–4.29 (2H, m), 5.03 (2H, s), 6.59 (1H, d, J=8 Hz), 7.14–7.34 (6H, m).

b) 2-Benzyl-6-[(tetrahydro-4H-pyran-2-yl)methyloxy]-3-pyridyl Trifluoromethanesulfonate 2 ml of trifluoroacetic acid was added to a mixture of 378 mg of 2-benzyl-6-[(tetrahydro-4H-pyran-2-yl)methyloxy]3-(methoxymethyloxy)pyridine and 3 ml of dichloromethane at room temperature, followed by stirring at the same temperature overnight. An aqueous saturated sodium bicarbonate solution and diethyl ether were added thereto to extract. The organic phase was washed with water and brine, dried over anhydrous magnesium sulfate and the solvent was removed. 424 mg of N-phenyltrifluoromethanesulfonimide, 301 μl of triethylamine and 1.3 mg of 4-dimethylaminopyridine were added to a solution of 5 ml of dichloromethane containing the residue, followed by stirring at room temperature for 2 hours. Silica gel was added to the reaction solution, and the solvent was removed. The residue was subjected to silica gel column chromatography using 10% ethyl acetate/hexane, to give 428 mg of the target compound.

$^1$H-NMR (CDCl$_3$) δ=1.36–1.64 (5H, m), 1.84–1.90 (1H, m), 3.41–3.48 (1H, m), 3.58–3.64 (1H, m), 4.01–4.06 (1H, m), 4.10 (2H, s), 4.18–4.30 (2H, m), 6.70 (1H, d, J=8 Hz), 7.20–7.29 (5H, m), 7.44 (1H, d, J=8 Hz).

c) (3R)-3-[2-Benzyl-6-(tetrahydro-4H-pyran-2-yl)methyloxy-3-pyridyl]ethynyl-3-quinuclidinol A mixture of 428 mg of 2-benzyl-6-[(tetrahydro-4H-pyran-2-yl)methyloxy]-3-pyridyl trifluoromethanesulfonate, 180 mg of (3R)-3-ethynyl-3-quinuclidinol, 57.3 mg of tetrakis(triphenylphosphine)palladium(0), 1.9 mg of cuprous iodide, 415 μl of triethylamine and 5 ml of N,N-dimethylformamide was stirred at 90° C. for 3 hours in a nitrogen atmosphere. NH-silica gel was added to the reaction solution, and the solvent was removed. The residue was subjected to NH-silica gel column chromatography using 3% methanol/ethyl acetate, to give 305 mg of the target compound.

$^1$H-NMR (CDCl$_3$) δ=1.34–1.65 (7H, m), 1.85–1.91 (2H, m), 1.98–2.07 (2H, m), 2.75–2.90 (4H, m), 3.03 (1H, d, J=14 Hz), 3.24 (1H, d, J=14 Hz), 3.42–3.49 (1H, m), 3.61–3.68 (1H, m), 4.02–4.07 (1H, m), 4.18–4.34 (4H, m), 6.62 (1H, d, J=8 Hz), 7.14–7.29 (5H, m), 7.54 (1H, d, J=8 Hz).

Example 173

3-[2-Benzyl-6-(2-hydroxy-3-butenyl)oxy-3-pyridyl]ethynyl-3-quinuclidinol a) 2-Benzyl-6-(2-hydroxyethyl)oxy-3-pyridyl Trifluoromethanesulfonate The target compound was synthesized in the same manner as in Example 172a and b except that tetrahydropyran-2-methanol was altered to ethylene glycol.

$^1$H-NMR (CDCl$_3$) δ=3.87–3.89 (2H, m), 4.12 (2H, s), 4.39–4.42 (2H, m), 6.68 (1H, d, J=8 Hz), 7.21–7.32 (5H, m), 7.49 (1H, d, J=8 Hz).

b) 2-Benzyl-6-(2-hydroxy-3-butenyl)oxy-3-pyridyl Trifluoromethanesulfonate 473 mg of pyridinium dichromate was added to a mixture of 395 mg of 2-benzyl-6-(2-hydroxyethyl)oxy-3-pyridyl trifluoromethanesulfonate, 1.4 g of molecular sieves 4A and 5 ml of dichloromethane at room temperature, followed by stirring for 3 hours. The mixture was filtered through Celite, and the solvent was removed. 236 μl of a tetrahydrofuran solution containing 1.1 mol of vinylmagnesium bromide was added to a solution of 5 ml of diethyl ether containing the residue at 0° C., followed by stirring at the same temperature for 40 minutes. An aqueous saturated ammonium chloride solution and diethyl ether were added to the reaction solution, and the organic phase was washed with water and brine, dried over anhydrous magnesium sulfate and the solvent was removed. The residue was subjected to silica gel column chromatography using 30% ethyl acetate/hexane, to give 46.5 mg of the target compound.

$^1$H-NMR (CDCl$_3$) δ=2.67–2.68 (1H, m), 4.13 (2H, s), 4.19–4.24 (1H, m), 4.37–4.41 (1H, m), 4.46 (1H, br s), 5.23–5.27 (1H, m), 5.36–5.41 (1H, m), 5.84–5.93 (1H, m), 6.70 (1H, d, J=8 Hz), 7.21–7.32 (5H, m), 7.49 (1H, d, J=8 Hz).

c) 3-[2-Benzyl-6-(2-hydroxy-3-butenyl)oxy-3-pyridyl]ethynyl-3-quinuclidinol

A mixture of 46.5 mg of 2-benzyl-6-(2-hydroxy-3-butenyl)oxy-3-pyridyl trifluoromethane sulfonate, 22.7 mg of 3-ethynyl-3-quinuclidinol, 6.6 mg of tetrakis(triphenylphosphine)palladium(0), 0.1 mg of cuprous iodide, 60.1 μl of diisopropylethylamine and 1 ml of N,N-dimethylformamide was stirred at 80° C. for 3 hours in a nitrogen atmosphere. NH-silica gel was added to the reaction solution and the solvent was removed. The residue was subjected to NH-silica gel column chromatography using 5% methanol/ethyl acetate, to give 10.7 mg of the target compound.

$^1$H-NMR (CDCl$_3$) δ=1.38–1.46 (1H, m), 1.58–1.66 (1H, m), 1.84–1.93 (1H, m), 1.99–2.08 (2H, m), 2.75–2.91 (4H, m), 3.04 (1H, d, J=14 Hz), 3.25 (1H, dd, J=2, 14 Hz), 4.21 (2H, s), 4.24–4.28 (1H, m), 4.39–4.48 (2H, m), 5.21–5.24 (1H, m), 5.36–5.41 (1H, m), 5.85–5.94 (1H, m), 6.60 (1H, d, J=8 Hz), 7.27–7.31 (5H, m), 7.58 (1H, d, J=8 Hz).

Example 174

3-[2-Benzyl-6-(3-methoxypropyl)thio-3-pyridyl]ethynyl-3-quinuclidinol a) 2-Benzyl-3-bromo-6-mercaptopyridine A mixture of 5.0 g of 2-benzyl-3-bromo-6-hydroxypyridine obtained in Production Example-3(b), 5.7 g of a Lawesson's reagent and 50 ml of toluene was heated under stirring for 6 hours in an oil bath kept at 100° C. Chloroform and silica gel were added to the reaction solution, and the mixture was concentrated to dryness. The residue was subjected silica gel column chromatography using 10% ethyl acetate/toluene, to give 3.5 g of the target compound.

$^1$H-NMR (CDCl$_3$) δ=4.15 (2H, s), 7.21–7.27 (3H, m), 7.30–7.42 (4H, m).

b) 2-Benzyl-3-bromo-6-(3-methoxypropyl)thiopyridine

A mixture of 500 mg of 2-benzyl-3-bromo-6-mercaptopyridine, 360 mg of 3-methoxypropylmethane sulfonate, 370 mg of anhydrous potassium carbonate and 10 ml of N,N-dimethylformamide was stirred at room temperature for one hour in a nitrogen atmosphere. The reaction solution was partitioned between ethyl acetate-water, and the organic phase was washed with water and brine, dried over anhydrous magnesium sulfate and then concentrated. The residue was subjected to silica gel column chromatography using 1–2% ethyl acetate/hexane, to give 425 mg of the target compound.

$^1$H-NMR (CDCl$_3$) δ=1.85 (2H, quint, J=7 Hz), 3.13 (2H, t, J=7 Hz), 3.32 (3H, s), 3.41 (2H, t, J=7 Hz), 4.25 (2H, s), 6.88 (1H, d, J=8 Hz), 7.17–7.34 (5H, m), 7.56 (1H, d, J=8 Hz).

c) 3-[2-Benzyl-6-(3-methoxypropyl)thio-3-pyridyl]ethynyl-3-quinuclidinol

A mixture of 425 mg of 2-benzyl-3-bromo-6-(3-methoxypropyl)thiopyridine, 200 mg of 3-ethynyl-3-quinuclidinol, 70 mg of tetrakis(triphenylphosphine) palladium(0), 4.6 mg of cuprous iodide, 0.5 ml of triethylamine and 2 ml of N,N-dimethylformamide was heated under stirring in an oil bath kept at 85° C. for 4 hours in a nitrogen atmosphere. The reaction solution was partitioned between ethyl acetate-aqueous dilute ammonia, and the organic phase was washed with water and brine, dried over anhydrous magnesium sulfate and then concentrated. The residue was subjected to column chromatography using NH-silica gel and eluted with 20–100% ethyl acetate/hexane and then with 2.5% methanol/ethyl acetate, to give 300 mg of the target compound.

$^1$H-NMR (CDCl$_3$) δ=1.36–1.93 (5H, m), 1.98–2.08 (2H, m), 2.70–2.94 (4H, m), 3.03 (1H, d, J=14 Hz), 3.18 (2H, t, J=7 Hz), 3.24 (1H, dd, J=2, 14 Hz), 3.32 (3H, s), 3.42 (2H, t, J=7 Hz), 4.26 (2H, s), 6.97 (1H, d, J=8 Hz), 7.16–7.31 (5H, m), 7.43 (1H, d, J=8 Hz). Example 175 3-[2-Benzyl-6-(3-hydroxypropyl)thio-3-pyridyl]ethynyl-3-quinuclidinol The target compound was synthesized in the same manner as in Example 174.

$^1$H-NMR (CDCl$_3$) δ=1.36–1.90 (5H, m), 1.98–2.06 (2H, m), 2.68–2.94 (4H, m), 3.02 (1H, d, J=14 Hz), 3.22 (1H, dd, J=2, 14 Hz), 3.28 (2H, t, J=6 Hz), 3.67 (2H, t, J=6 Hz), 4.27 (2H, s), 7.04 (1H, d, J=8 Hz), 7.16–7.31 (5H, m), 7.47 (1H, d, J=8 Hz).

Example 176

(3R)-3-[4-Benzyl-2-(3-pyridyl)-5-pyridyl]ethynyl-3-quinuclidinol

The target compound was synthesized in the same manner as in Example 1.

$^1$H-NMR (CDCl$_3$) δ=1.38–1.92 (3H, m), 2.00–2.11 (2H, m), 2.70–3.00 (4H, m), 3.06 (1H, d, J=14 Hz), 3.25 (1H, dd, J=2, 14 Hz), 4.18 (2H, s), 7.20 (2H, d, J=7 Hz), 7.22–7.29 (1H, m), 7.32 (2H, t, J=7 Hz), 7.39 (1H, dd, J=5, 7 Hz), 7.49 (1H, s), 8.22–8.27 (1H, m), 8.63 (1H, dd, J=2, 5 Hz), 8.74 (1H, s), 9.13 (1H, dd, J=l, 2 Hz).

Example 177

3-[4-Benzyl-2-(1-methyl-2-oxo-1,2-dihydropyridine-5-pyridyl]ethynyl-3-quinuclidinol The target compound was synthesized in the same manner as in Example 1.

$^1$H-NMR (CDCl$_3$) δ=1.36–1.46 (1H, m), 1.56–1.89 (2H, m), 1.99–2.10 (2H, m), 2.68–2.96 (4H, m), 3.05 (1H, dd, J=2, 14 Hz), 3.23 (1H, dd, J=2, 14 Hz), 3.63 (3H, s), 4.12 (2H, s), 6.61 (1H, d, J=10 Hz), 7.15–7.22 (3H, m), 7.26 (1H, t, J=7 Hz), 7.32 (2H, t, J=7 Hz), 7.76 (1H, dd, J=2, 10 Hz), 8.15 (1H, d, J=2 Hz), 8.54 (1H, s).

Example 178

3-[4-Benzyl-2-(2-cyano-5-pyridyl)-5-pyridyl]ethynyl-3-quinuclidinol

The target compound was synthesized in the same manner as in Example 1.

$^1$H-NMR (CDCl$_3$) δ=1.38–1.92 (3H, m), 2.00–2.17 (2H, m), 2.70–3.00 (4H, m), 3.06 (1H, dd, J=2, 14 Hz), 3.26 (1H, dd, J=2, 14 Hz), 4.21 (2H, s), 7.20 (2H, d, J=7 Hz), 7.28 (1H, t, J=7 Hz), 7.34 (2H, t, J=7 Hz), 7.53 (1H, s), 7.77 (1H, dd, J=1, 8 Hz), 8.41 (1H, dd, J=2, 8 Hz), 8.74 (1H, s), 9.22 (1H, dd, J=1, 2 Hz).

Example 179

(3R)-3-[4-Benzyl-2-(2-pyridyl)-5-pyridyl]ethynyl-3-quinuclidinol

The target compound was synthesized in the same manner as in Example 1.

$^1$H-NMR (CDCl$_3$) δ=1.35–1.90 (3H, m), 2.00–2.15 (2H, m), 2.70–2.95 (4H, m), 3.03 (1H, d, J=14 Hz), 3.23 (1H, dd, J=2, 14 Hz), 4.21 (2H, s), 7.20–7.32 (6H, m), 7.81 (1H, dt, J=2, 8 Hz), 8.29 (1H, s), 8.38 (1H, d, J=8 Hz), 8.64–8.67 (1H, m), 8.68 (1H, s).

Example 180

(3R)-3-[4-Benzyl-2-(3,4-methylenedioxyphenyl)-5-pyridyl]ethynyl-3-quinuclidinol

The target compound was synthesized in the same manner as in Example 1.

$^1$H-NMR (CDCl$_3$) δ=1.30–1.95 (3H, m), 2.00–2.15 (2H, m), 2.65–2 95 (4H, m), 3.03 (1H, d, J=14 Hz), 3.23 (1H, d, J=14 Hz), 4.15 (2H, s), 6.01 (2H, s), 6.87 (1H, d, J=8 Hz), 7.19 (2H, d, J=8 Hz), 7.22–7.28 (1H, m), 7.32 (2H, t, J=7 Hz), 7.40 (1H, s), 7.42–7.46 (2H, m), 8.65 (1H, s).

Example 181

3-[4-Benzyl-2-(2-pyrimidyl)-5-pyridyl]ethynyl-3-quinuclidinol

The target compound was synthesized in the same manner as in Example 1.

$^1$H-NMR (CDCl$_3$) δ=1.32–1.44 (1H, m), 1.61–1.63 (1H, m), 1.84–1.99 (1H, m), 2.05–2.09 (2H, m), 2.75–2.92 (4H, m), 3.08 (1H, d, J=14 Hz), 3.24 (1H, dd, J=2, 14 Hz), 4.23 (2H, s), 7.19–7.32 (6H, m), 8.38 (1H, s), 8.84 (1H, s), 8.90 (2H, d, J=5 Hz).

Example 182

3-[4-Benzyl-2-(5-pyrimidyl)-5-pyridyl]ethynyl-3-quinuclidinol

The target compound was synthesized in the same manner as in Example 1.

$^1$H-NMR (CDCl$_3$) δ=1.42–1.46 (1H, m), 1.64–1.88 (2H, m), 2.05–2.08 (2H, m), 2.75–2.89 (4H, m), 3.06 (1H, d, J=14 Hz), 3.26 (1H, dd, J=2, 14 Hz), 4.12 (2H, s), 7.18–7.36 (5H, m), 7.48 (1H, s), 8.74 (1H, s), 9.23 (1H, s), 9.26 (2H, s).

Example 183

3-[4-Benzyl-2-(4-pyrimidyl)-5-pyridyl]ethynyl-3-quinuclidinol

The title compound was synthesized in the same manner as in Example 1.

$^1$H-NMR (CDCl$_3$) δ=1.42–1.47 (1H, m), 1.62–1.86 (2H, m), 2.05–2.06 (2H, m), 2.74–2.91 (4H, m), 3.05 (1H, dd, J=2, 14 Hz), 3.25 (1H, dd, J=2, 14 Hz), 4.23 (2H, s), 7.21–7.33 (5H, m), 8.33–8.35 (2H, m), 8.71 (1H, s), 8.85 (1H, d, J=5 Hz), 9.25 (1H, d, J=1 Hz).

Example 184

3-[4-Benzyl-2-(3-pyridazyl)-5-pyridyl]ethynyl-3-quinuclidinol

The title compound was synthesized in the same manner as in Example 1.

$^1$H-NMR (CDCl$_3$) δ=1.42–1.47 (1H, m), 1.64–1.87 (2H, m), 2.00–2.07 (2H, m), 2.77–2.88 (4H, m), 3.06 (1H, d, J=14 Hz), 3.26 (1H, dd, J=2, 14 Hz), 4.23 (2H, s), 7.22–7.32 (5H, m), 7.57–7.61 (1H, m), 8.53 (1H, dd, J=1.6, 8.6 Hz), 8.58 (1H, s), 8.70 (1H, s), 9.18 (1H, dd, J=1.6, 4.9 Hz).

Example 185

3-[4-Benzyl-2-(4-pyridazyl)-5-pyridyl]ethynyl-3-quinuclidinol

The title compound was synthesized in the same manner as in Example 1.

$^1$H-NMR (CDCl$_3$) δ=1.40–1.47 (1H, m), 1.62–1.88 (2H, m), 2.05–2.09 (2H, m), 2.75–2.92 (4H, m), 3.07 (1H, dd, J=2, 14 Hz), 3.26 (1H, dd, J=2, 14 Hz), 4.20 (2H, s), 7.18–7.36 (5H, m), 7.57 (1H, s), 7.98 (1H, dd, J=2, 5 Hz), 8.76 (1H, s), 9.26 (1H, dd, J=1, 5 Hz), 9.71 (1H, dd, J=1, 2 Hz).

Example 186

(3R)-3-[4-Benzyl-2-(1,4-dioxene-2-yl)-5-pyridyl]ethynyl-3-quinuclidinol

The title compound was synthesized in the same manner as in Example 1.

$^1$H-NMR (CDCl$_3$) δ=1.31–1.49 (1H, m), 1.57–1.90 (2H, m), 2.02–2.08 (2H, m), 2.73–2.87 (4H, m), 3.01 (1H, d, J=14 Hz), 3.20 (1H, dd, J=2, 14 Hz), 4.09 (2H, s), 4.15–4.24 (4H, m), 7.15–7.31 (7H, m), 8.47 (1H, s).

Example 187

3-[4-Benzyl-2-(3-oxo-1-cyclohexenyl)-5-pyridyl]ethynyl-3-quinuclidinol

The title compound was synthesized in the same manner as in Example 1 by using (3-oxo-1-cyclohexenyl)tributyltin synthesized according to a method described in literature (Tetrahedron Letters, Vol. 31, No. 13, 1837 (1990)).

$^1$H-NMR (CDCl$_3$) δ=1.42–1.44 (1H, m), 1.62–1.89 (2H, m), 2.02–2.16 (4H, m), 2.47–2.50 (2H, m), 2.76–2.87 (6H, m), 3.05 (1H, d, J=14 Hz), 3.24 (1H, d, J=14 Hz), 4.14 (2H, s), 6.63 (1H, s), 7.15–7.43 (6H, m), 8.66 (1H, s).

Example 188

3-[4-Benzyl-2-(3,4-dihydro-2H-6-pyranyl)-5-pyridyl]ethynyl-3-quinuclidinol

The title compound was synthesized in the same manner as in Example 1 by using (3,4-dihydro-2H-6-pyranyl)tributyltin synthesized with reference to a method described in literature (Synlett 152 (1994)).

$^1$H-NMR (CDCl$_3$) δ=1.37–1.40 (1H, m), 1.52–1.89 (2H, m), 1.89–1.96 (2H, m), 2.01–2.05 (2H, m), 2.24–2.28 (2H, m), 2.51–2.94 (4H, m), 3.01 (1H, m), 3.19 (1H, d, J=14 Hz), 4.10 (2H, s), 4.13–4.18 (2H, m) 6.04–6.06 (1H, m), 7.14–7.30 (5H, m), 7.38 (1H, s), 8.55 (1H, s).

Example 189

3-[4-Benzyl-2-(3-hydroxy-1-butynyl)-5-pyridyl]ethynyl-3-quinuclidinol a) 4-Benzyl-5-bromo-2-(3-hydroxy-1-butynyl)pyridine 650 mg of 4-benzyl-5-bromo-2-pyridyl trifluoromethanesulfonate (Production Example 1), 115 mg of 1-butyne-3-ol, 100 mg of tetrakis(triphenylphosphine)palladium(0), 30 mg of cuprous iodide and 1 ml of triethylamine were mixed with 5 ml of N,N-dimethylformamide, followed by stirring for one hour in an oil bath kept at 60° C. After cooling as it was, aqueous ammonia was added thereto and the mixture was extracted with ethyl acetate. The extract was washed with brine and then evaporated. The residue was subjected to silica gel column chromatography and eluted with 30% ethyl acetate/hexane, to give 410 mg of the target compound.

$^1$H-NMR (CDCl$_3$) δ=1.54 (3H, d, J=7 Hz), 2.01 (1H, d, J=5 Hz), 4.05 (2H, s), 4.67–4.77 (1H, m), 7.12 (1H, s), 7.18 (2H, d, J=7 Hz), 7.29 (1H, t, J=7 Hz), 7.35 (2H, t, J=7 Hz), 8.63 (1H, s).

b) 3-[4-Benzyl-2-(3-hydroxy-1-butynyl)-5-pyridyl]ethynyl-3-quinuclidinol 110 mg of 4-benzyl-5-bromo-2-(3-hydroxy-1-butynyl)pyridine, 53 mg of 3-ethynyl-3-quinuclidinol, 50 mg of tetrakis(triphenylphosphine)palladium(0), 7 mg of cuprous iodide and 0.5 ml of triethylamine were added to 2 ml of 1-methyl-2-pyrrolidinone, followed by stirring for one hour in an oil bath kept at 100° C. After cooling as it was, it was evaporated. The residue was subjected to NH-silica gel column chromatography and eluted with 5% methanol/ethyl acetate, to synthesize 32 mg of the target compound.

$^1$H-NMR (CDCl$_3$) δ=1.35–1.88 (6H, m), 2.01–2.12 (2H, m), 2.69–2.94 (4H, m), 3.09 (1H, d, J=14 Hz), 3.24 (1H, dd, J=2, 14 Hz), 4.04 (2H, s), 4.72 (1H, q, J=7 Hz), 7.12–7.16 (3H, m), 7.22–7.33 (3H, m), 8.55 (1H, d, J=2 Hz).

Example 190

3-[4-Benzyl-2-(3-hydroyxbutyl)-5-pyridyl]ethynyl-3-quinuclidinol a) 4-Benzyl-5-bromo-2-(3-hydroxybutyl)pyridine 200 mg of 4-benzyl-5-bromo-2-(3-hydroxy-1-butynyl)pyridine (Example 189a) and 10 mg of platinum (IV) oxide were added to 10 ml of methanol, 10 ml of tetrahydrofuran and 10 ml of ethyl acetate, followed by stirring at room temperature at normal pressure in a hydrogen atmosphere overnight. The catalyst was filtered off and the filtrate was evaporated, to give 50 mg of the target compound.

$^1$H-NMR (CDCl$_3$) δ=1.20 (3H, d, J=6 Hz), 1.70–1.89 (2H, m), 2.77–2.89 (2H, m), 3.25–3.38 (1H, brs), 3.76–3.85 (1H, m), 4.05 (2H, s), 6.90 (1H, s), 7.18 (2H, d, J=7 Hz), 7.27 (1H, t, J=7 Hz), 7.33 (2H, t, J=7 Hz), 8.56 (1H, s).

b) 3-[4-Benzyl-2-(3-hydroxybutyl)-5-pyridyl]ethynyl-3-quinuclidinol 50 mg of 4-benzyl-5-bromo-2-(3-hydroxybutyl)pyridine, 20 mg of 3-ethynyl-3-quinuclidinol, 20 mg of tetrakis(triphenylphosphine)palladium(0), 5 mg of cuprous iodide and 0.5 ml of triethylamine were added to 2 ml of 1-methyl-2-pyrrolidinone, followed by stirring for one hour in an oil bath kept at 110° C. After cooling as it was, it was evaporated. The residue was subjected to NH-silica gel column chromatography and eluted with 5% methanol/ethyl acetate, to give 30 mg of the target compound.

$^1$H-NMR (CDCl$_3$) δ=1.20 (3H, d, J=6 Hz), 1.35–1.90 (5H, m), 1.99–2.09 (2H, m), 2.68–2.95 (6H, m), 3.04 (1H, dd, J=2, 14 Hz), 3.22 (1H, dd, J=2, 14 Hz), 3.76–3.85 (1H, m), 4.09 (2H, s), 6.94 (1H, s), 7.15 (2H, d, J=7 Hz), 7.24 (1H, t, J=7 Hz), 7.31 (2H, t, J=7 Hz), 8.56 (1H, s).

Example 191

3-[4-Benzyl-2-(4-hydroxypiperidino)-5-pyridyl]ethynyl-3-quinuclidinol a) 4-Benzyl-5-bromo-2-(4-hydroxypiperidino)pyridine A mixture of 550 mg of 4-benzyl-5-bromo-2-pyridyl trifluoromethanesulfonate (Production Example 1), 600 mg of 4-hydroxypiperidine hydrochloride, 1 ml of triethylamine and 2 ml of N,N-dimethylformamide was heated under stirring for 3 hours in an oil bath kept at 100° C. in a nitrogen atmosphere. After cooling as it was, the reaction mixture was extracted with ethyl acetate/water. The organic phase was washed with water and brine, dried over anhydrous magnesium sulfate and evaporated. The residue was subjected to silica gel column chromatography and eluted with 50% ethyl acetate/hexane, to give 270 mg of the target compound.

$^1$H-NMR (CDCl$_3$) δ=1.44–1.60 (2H, m), 1.88–1.97 (2H, m), 3.03–3.12 (2H, m), 3.75–3.96 (3H, m), 3.99 (2H, s), 6.41 (1H, s), 7.19 (2H, d, J=7 Hz), 7.25 (1H, t, J=7 Hz), 7.32 (2H, t, J=7 Hz), 8.20 (1H, s).

b) 3-[4-Benzyl-2-(4-hydroxypiperidino)-5-pyridyl]ethynyl-3-quinuclidinol

A mixture of 270 mg of 4-benzyl-5-bromo-2-(4-hydroxypiperidino)pyridine, 130 mg of 3-ethynyl-3-quinuclidinol, 50 mg of tetrakis(triphenylphosphine)palladium(0), 2 mg of cuprous iodide, 0.35 ml of triethylamine and 2 ml of N,N-dimethylformamide was stirred at 100° C. for 3 hours in a nitrogen atmosphere. After cooling as it was, the reaction solution was extracted with ethyl acetate-aqueous dilute ammonia. The organic phase was washed with water and brine, dried over anhydrous magnesium sulfate and evaporated. The residue was subjected to NH-silica gel column chromatography and eluted with 20–100% ethyl acetate/hexane and then with 5% methanol/ethyl acetate, to give 120 mg of the target compound.

$^1$H-NMR (CDCl$_3$) δ=1.33–1.87 (5H, m), 1.90–2.05 (4H, m), 2.65–2.94 (4H, m), 2.98 (1H, dd, J=2, 14Hz), 3.12–3.20 (3H, m), 3.88–3.96 (1H, m), 3.98–4.07 (4H, m), 6.41 (1H, s), 7.14–7.32 (5H, m), 8.22 (1H, s).

Example 192

3-[4-Benzyl-2-(morpholino)-5-pyridyl]ethynyl-3-quinuclidinol

The title compound was synthesized in the same manner as in Example 191.

$^1$H-NMR (CDCl$_3$) δ=1.34–1.87 (3H, m), 1.95–2.07 (2H, m), 2.64–2.92 (4H, m), 3.04 (1H, d, J=14 Hz), 3.18 (1H, dd, J=2, 14 Hz), 3.48 (4H, t, J=5 Hz), 3.78 (4H, t, J=5 Hz), 4.03 (2H, s), 6.36 (1H, s), 7.17 (2H, d, J=8 Hz), 7.22 (1H, t, J=8 Hz), 7.30 (2H, t, J=8 Hz), 8.24 (1H, s).

Example 193

3-[4-Benzyl-2-(3-methoxypropylamino)-5-pyridyl]ethynyl-3-quinuclidinol

The title compound was synthesized in the same manner as in Example 191.

$^1$H-NMR (CDCl$_3$) δ=1.33–1.89 (5H, m), 1.97–2.07 (2H, m), 2.65–2.93 (4H, m), 2.99 (1H, dd, J=2, 14 Hz), 3.18 (1H, dd, J=2, 14 Hz), 3.32 (3H, s), 3.35 (2H, q, J=6 Hz), 3.47 (2H, t, J=6 Hz), 3.99 (2H, s), 4.92 (1H, t, J=6 Hz), 6.11 (1H, s), 7.14–7.32 (5H, m), 8.16 (1H, s).

Example 194

3-[4-Benzyl-2-(thiomorpholino)-5-pyridyl]ethynyl-3-quinuclidinol

The title compound was synthesized in the same manner as in Example 191.

$^1$H-NMR (CDCl$_3$) δ=1.34–1.86 (3H, m), 1.95–2.06 (2H, m), 2.58–2.94 (8H, m), 2.99 (1H, dd, J=2, 14 Hz), 3.17 (1H, dd, J=2, 14 Hz), 3.89–3.94 (4H, m), 4.02 (2H, s), 6.35 (1H, s), 7.14–7.32 (5H, m), 8.22 (1H, s).

Example 195

(3R)-3-[4-Benzyl-2-[(3R,4R)-3-hydroxy-4-methoxypyrrolidine-1-yl]-5-pyridyl]ethynyl-3-quinuclidinol a) 4-Benzyl-5-bromo-2-[(3R,4R)-3,4-dihydroxypyrrolidine-1-yl]pyridine A mixture of 4.0 g of 4-benzyl-5-bromo-2-pyridyl trifluoromethanesulfonate, 1.8 g of (3R,4R)-3,4-dihydroxypyrrolidine acetate, 3 ml of 1,8-diazabicyclo[5.4.0]-7-undecene and 5 ml of tetrahydrofuran was heated under stirring for 3 hours in an oil bath kept at 70° C. in a nitrogen atmosphere. After cooling as it was, the reaction mixture was extracted with ethyl acetate-water. The organic phase was washed with water and brine, dried over anhydrous magnesium sulfate and evaporated. The residue was subjected to silica gel column chromatography and eluted with 10% methanol/ethyl acetate, to give 1.67 g of the target compound.

$^1$H-NMR (CDCl$_3$) δ=3.27–3.33 (2H, m), 3.61–3.67 (2H, m), 3.99 (2H, s), 4.17–4.21 (2H, m), 6.14 (1H, s), 7.20 (2H, d, J=7 Hz), 7.24 (1H, t, J=7 Hz), 7.31 (2H, t, J=7 Hz), 8.09 (1H, s).

b) 4-Benzyl-5-bromo-2-[(3R,4R)-3-hydroxy-4-methoxypyrrolidine-1-yl]pyridine 190 mg of 60% oily sodium hydride and 0.3 ml of methyl iodide were added to a solution of 1.67 g of 4-benzyl-5-bromo-2-[(3R,4R)-3,4-dihydroxypyrrolidine-1-yl]pyridine in tetrahydrofuran, followed by stirring for 6 hours. Then, the reaction solution was extracted with ethyl acetate-water, and the organic phase was washed with water and brine, dried over anhydrous magnesium sulfate and evaporated. The residue was subjected to silica gel column chromatography and eluted with 50% ethyl acetate, to give 560 mg of the target compound.

$^1$H-NMR (CDCl$_3$) δ=3.34–3.47 (2H, m), 3.40 (3H, s), 3.58–3.67 (2H, m), 3.82–3.86 (1H, m), 3.99 (2H, s), 4.37–4.41 (1H, m), 6.08 (1H, s), 7.19 (2H, d, J=7 Hz), 7.24 (1H, t, J=7 Hz), 7.31 (2H, t, J=7 Hz), 8.18 (1H, s).

c) (3R)-3-[4-Benzyl-2-[(3R,4R)-3-hydroxy-4-methoxypyrrolidine-1-yl]-5-pyridyl]ethynyl-3-quinuclidinol The target compound was synthesized in the same manner as in Example 191 by using (3R)-3-ethynyl-3-quinuclidinol.

$^1$H-NMR (CDCl$_3$+CD$_3$OD) δ=1.35–1.45 (1H, m), 1.52–1.62 (1H, m), 1.78–1.88 (1H, m), 1.97–2.08 (2H, m), 2.60–2.90 (4H, m), 2.95 (1H, d, J=14 Hz), 3.13 (1H, dd, J=2, 14 Hz), 3.40 (3H, s), 3.40–3.50 (2H, m), 3.58–3.68 (2H, m), 3.82–3.86 (1H, m), 4.02 (2H, s), 4.32–4.36 (1H, m), 6.13 (1H, s), 7.17 (2H, d, J=7 Hz), 7.21 (1H, t, J=7 Hz), 7.29 (2H, d, J=7 Hz), 8.13 (1H, s).

Example 196

(3R)-3-[4-Benzyl-2-[(3R,4R)-3,4-dimethoxypyrrolidine-1-yl]-5-pyridyl]ethynyl-3-quinuclidinol The target compound was synthesized in the same manner as in Example 195 by using two equivalents of methyl iodide and sodium hydride to 4-benzyl-5-bromo-2-[(3R,4R)-3,4-dihydroxypyrrolidine-1-yl]pyridine (Example 195a).

¹H-NMR (CDCl₃) δ=1.30–1.88 (3H, m), 1.95–2.08 (2H, m), 2.60–2.90 (4H, m), 2.99 (1H, d, J=14 Hz), 3.17 (1H, d, J=14 Hz), 3.40 (6H, s), 3.50–3.65 (4H, m), 3.92 (2H, brs), 4.02 (2H, s), 6.10 (1H, s), 7.15–7.32 (5H, m), 8.22 (1H, s).

Example 197

3-[4-Benzyl-2-(2-thiazolyl)-5-pyrimidyl]ethynyl-3-quinuclidinol

The target compound was synthesized in the same manner as in Example 18.

¹H-NMR (CDCl₃) δ=1.40–1.48 (1H, m), 1.61–1.69 (1H, m), 1.79–1.87 (1H, m), 2.00–2.09 (2H, m), 2.75–2.94 (4H, m), 3.05 (1H, dd, J=1, 14 Hz), 3.23 (1H, dd, J=2, 14 Hz), 4.37 (2H, s), 7.21–7.34 (5H, m), 7.56 (1H, d, J=3 Hz), 8.06 (1H, d, J=3 Hz), 8.75 (1H, s).

Example 198

3-[4-Benzyl-2-(2-thienyl)-5-pyrimidyl]ethynyl-3-quinuclidinol

The target compound was synthesized in the same manner as in Example 18.

¹H-NMR (CDCl₃) δ=1.40–1.48 (1H, m), 1.61–1.68 (1H, m), 1.81–1.89 (1H, m), 2.01–2.08 (2H, m), 2.73–2.95 (4H, m), 3.06 (1H, d, J=14 Hz), 3.25 (1H, dd, J=2, 14 Hz), 4.27 (2H, s), 7.15 (1H, dd, J=4, 5 Hz), 7.20–7.34 (5H, m), 7.50 (1H, dd, J=1, 5 Hz), 8.01 (1H, dd, J=1, 4 Hz), 8.61 (1H, s).

Example 199

3-[4-Benzyl-2-(2-furyl)-5-pyrimidyl]ethynyl-3-quinuclidinol

The target compound was synthesized in the same manner as in Example 18.

¹H-NMR (CDCl₃) δ=1.39–1.47 (1H, m), 1.60–1.68 (1H, m), 1.78–1.86 (1H, m), 2.01–2.08 (2H, m), 2.70–2.94 (4H, m), 3.04 (1H, dd, J=1, 14 Hz), 3.22 (1H, dd, J=2, 14 Hz), 4.30 (2H, s), 6.58 (1H, dd, J=2, 3 Hz), 7.20–7.31 (5H, m), 7.36 (1H, d, J=3 Hz), 7.65 (1H, d, J=2 Hz), 8.67 (1H, s).

Example 200

3-[4-Benzyl-2-(2-methoxypyridine-5-yl)-5-pyrimidyl]ethynyl-3-quinuclidinol

The target compound was synthesized in the same manner as in Example 18 except that (3-pyridyl)tributyltin was altered to (2-methoxypyridine-5-yl)tributyltin.

¹H-NMR (CDCl₃) δ=1.40–1.48 (1H, m), 1.61–1.68 (1H, m), 1.83–1.92 (1H, m), 2.01–2.10 (2H, m), 2.78–2.94 (4H, m), 3.07 (1H, d, J=14 Hz), 3.28 (1H, dd, J=2, 14 Hz), 4.02 (3H, s), 4.29 (2H, s), 6.82 (1H, d, J=9 Hz), 7.20–7.36 (5H, m), 8.57 (1H, dd, J=2, 9 Hz), 8.68 (1H, s), 9.25 (1H, d, J=2 Hz).

Example 201

(3R)-3-[4-Benzyl-2-[(3R,4R)-3-hydroxy-4-methoxypyrrolidine-1-yl]-3-pyrimidyl]ethynyl-3-quinuclidinol a) 4-Benzyl-5-bromo-2-[(3R,4R)-3,4-dihydroxypyrrolidine-1-yl]-3-pyrimidine 644 µl of 1,8-diazabicyclo[5.4.0]-7-undecene was added to a mixture of 509 mg of 4-benzyl-5-bromo-2-chloropyrimidine (Production Example 15), 351 mg of (3R,4R)-3,4-dihydroxypyrrolidine acetate and 5 ml of 1-methyl-2-pyrrolidinone at room temperature, followed by stirring at 70° C. for one hour. Water and ethyl acetate were added thereto, and the organic phase was washed with water and brine, dried over anhydrous magnesium sulfate and the solvent was removed. The residue was subjected to silica gel column chromatography using 20% hexane/ethyl acetate, to give 766 mg of the target compound.

¹H-NMR (CDCl₃) δ=3.60 (2H, d, J=12 Hz), 3.85 (2H, dd, J=4, 12 Hz), 4.08 (2H, s), 4.31 (2H, br.s), 7.20–7.37 (5H, m), 8.26 (1H, s).

b) (3R)-3-[4-Benzyl-2-[(3R,4R)-3-hydroxy-4-methoxypyrrolidine-1-yl]-3-pyrimidyl]ethynyl-3-quinuclidinol 70.0 mg of 60% oily sodium hydride was added to a mixture of 766 mg of 4-benzyl-5-bromo-2-[(3R,4R)-3,4-dihydroxypyrrolidine-1-yl]-3-pyrimidine and 10 ml of tetrahydrofuran under ice-cooling, followed by adding 99.6 µl of methyl iodide thereto. After stirring at room temperature for 6 hours, water and ethyl acetate were added to the reaction solution. The organic phase was washed with water and brine, dried over anhydrous magnesium sulfate and the solvent was evaporated. A mixture of the residue, 4.5 mg of tetrakis(triphenylphosphine)palladium(0), 0.1 mg of cuprous iodide, 32.6 µl of triethylamine and 1 ml of N,N-dimethylformamide was stirred at 90° C. for 3 hours in a nitrogen atmosphere. NH-silica gel was added to the reaction solution and the solvent was removed. The residue was subjected to NH-silica gel column chromatography using 5% methanol/ethyl acetate, to give 22.0 mg of the target compound. ¹H-NMR (CDCl₃) δ=1.36–1.43 (1H, m), 1.55–1.62 (1H, m), 1.78–1.85 (1H, m), 2.01–2.08 (2H, m), 2.67–2.90 (4H, m), 2.95–3.00 (1H, m), 3.13–3.18 (1H, m), 3.41 (3H, s), 3.64–3.84 (5H, m), 4.06 (2H, s), 4.37 (1H, br.s), 7.18–7.30 (5H, m), 8.29 (1H, s).

Example 202

(3R)-3-[4-Benzyl-2-(2-furylmethoxy)-5-pyrimidyl]ethynyl-3-quinuclidinol a) 4-Benzyl-2-(2-furylmethoxy)-5-bromopyrimidine 14.1 mg of 60% oily sodium hydride was added to a mixture of 73.3 mg of 4-benzyl-5-bromo-2-chloropyrimidine (Production Example 15), 1 ml of furfuryl alcohol and 14.8 mg of cuprous iodide at room temperature, followed by stirring at 90° C. for 2 hours. Water and diethyl ether were added to the reaction solution, and the organic phase was washed with water and brine, dried over anhydrous magnesium sulfate and the solvent was removed. The residue was subjected to silica gel column chromatography using 10% ethyl acetate/hexane, to give 50.9 mg of the target compound.

¹H-NMR (CDCl₃) δ=4.19 (2H, s), 5.33 (2H, s), 6.32–6.37 (2H, m), 7.22–7.41 (6H, m), 8.48 (1H, s).

b) (3R)-3-[4-Benzyl-2-(2-furylmethoxy)-5-pyrimidyl]ethynyl-3-quinuclidinol

A mixture of 50.9 mg of 4-benzyl-2-(2-furylmethoxy)-5-bromopyrimidine, 26.8 mg of (3R)-3-ethynyl-3-quinuclidinol, 8.5 mg of tetrakis(triphenylphosphine)palladium(0), 0.3 mg of cuprous iodide, 61.5 µl of triethylamine and 1 ml of N,N-dimethylformamide was stirred at 90° C. for 4 hours in a nitrogen atmosphere. NH-silica gel was added to the reaction solution and the solvent was removed. The residue was subjected to NH-silica gel column chromatography using 3% methanol/ethyl acetate, to give 29.0 mg of the target compound.

¹H-NMR (CDCl₃) δ=1.38–1.46 (1H, m), 1.60–1.89 (2H, m), 2.00–2.07 (2H, m), 2.73–2.93 (4H, m), 3.05 (1H, d, J=14 Hz), 3.25 (1H, dd, J=2, 14 Hz), 4.19 (2H, s), 5.38 (2H, s), 6.32–6.39 (2H, m), 7.21–7.30 (5H, m), 7.40–7.41 (1H, m), 8.48 (1H, s).

Example 203

(3R)-3-[4-Benzyl-2-(3-hydroxypropyloxy)-5-pyrimidyl]ethynyl-3-quinuclidinol

The target compound was synthesized in the same manner as in Example 202 except that furfuryl alcohol was altered to 1,3-propanediol.

¹H-NMR (CDCl₃) δ=1.38–1.46 (1H, m), 1.58–1.67 (1H, m), 1.79–1.89 (1H, m), 1.99–2.07 (4H, m), 2.71–2.93 (4H, m), 3.04 (1H, d, J=14 Hz), 3.22 (1H, d, J=14 Hz), 3.77 (2H, t, J=6 Hz), 4.17 (2H, s), 4.52 (2H, t, J=6 Hz), 7.20–7.29 (5H, m), 8.45 (1H, s).

Example 204

3-(3-Phenyl-5benzyl-6-pyridazyl)ethynyl-3-quinuclidinol a) 3-Phenyl-6-methoxypyridazine A mixture of 3.0 g of 3-chloro-6-methoxypyridazine, 3.8 g of phenylboric acid, 2.4 g of tetrakis(triphenylphosphine) palladium(0), 160 ml of toluene, 40 ml of methanol, 80 ml of an aqueous 2 mol sodium carbonate solution and 30 ml of tetrahydrofuran was stirred under heating at 85° C. for one hour. After cooling as it was, the reaction solution was extracted with ethyl acetate. The organic phase was washed with brine and eluted with ethyl acetate through NH-silica gel (Fuji Silicia). After removing the solvent, the residue was crystallized, to give 1.8 g of the target compound.

¹H-NMR (CDCl₃) δ=4.20 (3H, s), 7.06 (1H, d, J=9 Hz), 7.44–7.52 (3H, m), 7.79 (1H, d, J=9 Hz), 7.99–8.03 (2H, m).

b) 5-(α-Hydroxybenzyl)3-phenyl-6-methoxypyridazine 7,7 ml of a hexane solution containing 1.52 mol of normal butyllithium was slowly added dropwise into a solution of 50 ml of tetrahydrofuran containing 2.0 ml of 2,2,6,6-tetramethylpiperidine under ice-cooling. After stirring for one hour under ice-cooling, it was cooled to −78° C. and 10 ml of a tetrahydrofuran solution containing 1.68 g of 3-phenyl-6-methoxypyridazine was slowly added dropwise thereinto. After stirirng at −78° C. for 2 hours, benzaldehyde was slowly added dropwise thereinto. After stirring at −78° C. for further 30 minutes, it was stirred at room temperature overnight. Water was added to the reaction solution, extracted with ethyl acetate and the organic phase was washed with brine. After removing the solvent, the residue was subjected to NH-silica gel (Fuji Silicia) chromatography and eluted with hexane/ethyl acetate (3:1) and then with hexane/ethyl acetate (1:1), to give 1.39 g of the target compound.

¹H-NMR (CDCl₃) δ=4.15 (3H, s), 5.99 (1H, s), 7.17–7.69 (9H, m), 7.99–8.04 (2H, m).

c) 5-(α-Acetoxybenzyl)3-phenyl-6-methoxypyridazine 5.0 ml of acetic acid anhydride was slowly added dropwise into a solution of 1.39 g of 5-(α-hydroxybenzyl)-3-phenyl-6-methoxypyridazine, 174 mg of 4-dimethylaminopyridine and 1.0 ml of triethylamine in 10 ml of dichloromethane under ice-cooling. After stirring at room temperature for one hour, water was added to the reaction solution. After extracting with dichloromethane, the organic phase was washed with brine. After removing the solvent, the residue was subjected to NH-silica gel (Fuji Silicia) and eluted with ethyl acetate, to give 1.58 g of the target compound.

¹H-NMR (CDCl₃) δ=2.20 (3H, s), 4.16 (3H, s), 7.02 (1H, s), 7.34–7.54 (9H, m), 8.00–8.02 (2H, m).

d) 3-Phenyl-5-benzyl-6-methoxypyridazine 600 mg of 10% palladium carbon was added to a mixture of 1.58 g of 5-(α-acetoxybenzyl)-3-phenyl-6-methoxypyridazine, 2.0 ml of triethylamine and 10 ml of ethanol, and the mixture was subjected to hydrocracking in a hydrogen atmosphere. The catalyst was filtered off, and the solvent was removed. Then, the residue was subjected to NH-silica gel (Fuji Silicia) and eluted with ethyl acetate, to give 1.31 g of the target compound.

¹H-NMR (CDCl₃) δ=3.98 (2H, s), 4.22 (3H, s), 7.23–7.73 (9H, m), 7.89–7.93 (2H, m).

e) 3-Phenyl-5-benzyl-6-pyridazyl Trifluoromethanesulfonate 10 ml of 47% hydrobromic acid was added to 1.31 g of 3-phenyl-5-benzyl-6-methoxypyridazine, followed by heating under stirring in an oil bath kept at 90° C. for 3 hours. After cooling as it was, the reaction solution was added little by little to an aqueous potassium carbonate solution to neutralize. After extracting with ethyl acetate, the organic phase was washed with brine and the solvent was removed, to give 1.18 g of a crude product. A mixture of 1.18 g of the crude product, 1.93 g of N-phenyltrifluoromethanesulfonimide, 165 mg of 4-dimethylaminopyridine, 943 µl of triethylamine and 10 ml of dichloromethane was stirred at room temperature overnight. After the reaction solution was concentrated, the residue was subjected to silica gel chromatography to elute with hexane/ethyl acetate (10:1) and then with hexane/ethyl acetate (7:1), to give 484 mg of the target compound.

¹H-NMR (CDCl₃) δ=4.12 (2H, s), 7.23–7.64 (9H, m), 7.94–7.96 (2H, m).

f) 3-(3-Phenyl-5-benzyl-6pyridazyl)ethynyl-3-quinuclidinol

A mixture of 484 mg of 3-phenyl-5-benzyl-6-pyridazyl trifluoromethane sulfonate, 223 mg of 3-ethynyl-3-quinuclidinol, 284 mg of tetrakis (triphenylphosphine) palladium(0), 47 mg of cuprous iodide, 513 µl of triethylamine and 5.0 ml of N,N-dimethylformamide was heated under stirring at 80° C. for 2 hours in a nitrogen atmosphere. The reaction solution was poured into aqueous dilute ammonia and the mixture was extracted with ethyl acetate. The organic phase was washed with brine and the solvent was removed. The residue was subjected to NH-silica gel (Fuji Silicia) column chromatography and eluted with hexane/ethyl acetate (1:1) and then with ethyl acetate/methanol (20:1) and then crystallized from hexane/ethyl acetate, to give 413 mg of the target compound.

¹H-NMR (CDCl₃) δ=1.25–1.99 (3H, m), 2.02–2.15 (2H, m), 2.78–2.95 (4H, m), 3.08 (1H, d, J=14 Hz), 3.30 (1H, d, J=14 Hz), 4.18 (2H, s), 7.07–7.38 (5H, m), 7.48–7.52 (4H, m), 7.99–8.02 (2H, m).

Example 205

3-[3-(3-Pyridyl)-5-benzyl-6-pyridazyl]ethynyl-3-quinuclidinol

The target compound was synthesized in the same manner as in Example 204.

¹H-NMR (CDCl₃) δ=1.38–1.96 (3H, m), 2.03–2.17 (2H, m), 2.81–2.98 (4H, m), 3.11 (1H, d, J=14 Hz), 3.32 (1H, dd, J=2, 14 Hz), 4.19 (2H, s), 7.19–7.38 (5H, m), 7.43–7.46 (1H, m), 7.53 (1H, s), 8.39–8.42 (1H, m), 8.70–8.71 (1H, m), 9.14 (1H, d, J=2 Hz).

Example 206

3-(2-Benzyl-3-thienyl)ethynyl-3-quinuclidinol a) 2-Methoxycarbonyl-3-thienyl Trifluoromethanesulfonate A mixture of 4.12 g of 3-hydroxy-2-methoxycarbonylthiophene, 9.76 g of N-phenyltrifluoromethanesulfonimide, 5.44 ml of triethylamine, 318 mg of 4-dimethylaminopyridine and 70 ml of dichloromethane was stirred at room temperature overnight. Silica gel was added to the reaction solution, and the solvent was removed. The residue was subjected to silica gel column chromatography using 10% ethyl acetate/hexane, to give 6.21 g of the target compound.

$^1$H-NMR (CDCl$_3$) δ=3.92 (3H, s), 7.01 (1H, d, J=5 Hz), 7.55 (1H, d, J=5 Hz).

b) 2-Methoxycarbonyl-3-(trimethylsilylethynyl)thiophene

A mixture of 2.07 g of 2-methoxycarbonyl-3-thienyl trifluoromethane sulfonate, 2.02 ml of trimethylsilylacetylene, 1.57 g of tetrakis(triphenylphosphine)palladium(0), 272 mg of cuprous iodide, 2.98 ml of triethylamine and 30 ml of N,N-dimethylformamide was stirred at 65° C. for 3 hours in a nitrogen atmosphere. Silica gel was added to the reaction solution, and the solvent was removed. The residue was subjected to silica gel column chromatography using 6% ethyl acetate/hexane, to give 1.78 g of the target compound.

$^1$HH-NMR (CDCl$_3$) δ=0.29 (9H, s), 3.90 (3H, s), 7.14 (1H, d, J=5 Hz), 7.41 (1H, d, J=5 Hz).

c) 3-Ethynyl-2-(α-hydroxybenzyl)thiophene 131 mg of lithium aluminum hydride was added to a mixture of 821 mg of 2-methoxycarbonyl-3-(trimethylsilylethynyl)thiophene and 10 ml of tetrahydrofuran, followed by heating under reflux for 1.5 hours. After cooling as it was, 131 μl of water, 131 μl of an aqueous 1N sodium hydroxide solution and 393 μl of water were successively added thereto, followed by filtering through Celite. After removing the solvent, 5.25 g of manganese dioxide was added to a solution of 10 ml of dichloromethane containing the residue, followed by stirring at room temperature overnight. The mixture was filtered through Celite, and the solvent was removed. 3.5 ml of a cyclohexane-diethyl ether solution containing 1.8 mol of phenyl lithium was added dropwise to a mixture of the residue and 5 ml of diethyl ether at −78° C., followed by stirring at the same temperature for 20 minutes. Aqueous ammonium chloride was added to the reaction solution and the temperature of the system was raised to room temperature. Ethyl acetate was added thereto, and the organic phase was washed with water and brine, dried over anhydrous magnesium sulfate and the solvent was removed. The residue was subjected to silica gel column chromatography using 10% ethyl acetate/hexane, to give 85.7 mg of the target compound.

$^1$H-NMR (CDCl$_3$) δ=2.59 (1H, d, J=3 Hz), 3.26 (1H, s), 6.34 (1H, d, J=3 Hz), 7.02 (1H, d, J=5 Hz), 7.17 (1H, d, J=5 Hz), 7.22–7.38 (3H, m), 7.49–7.51 (2H, m).

d) 2-Benzyl-3-ethynylthiophene 201 mg of sodium cyanotrihydroborate was added to a mixture of 85.7 mg of 3-ethynyl-2-(α-hydroxybenzyl)thiophene, 192 mg of zinc iodide and 1.5 ml of 1,2-dichloroethane at room temperature, followed by stirring at the same temperature overnight. 5 ml of diethyl ether was added to the reaction solution, followed by filtering through Celite. After the solvent was removed, the residue was subjected to silica gel column chromatography using 2% ethyl acetate/hexane, to give 45.2 mg of the target compound.

$^1$H-NMR (CDCl$_3$) δ=3.21 (1H, s), 4.25 (2H, s), 7.02 (1H, d, J=5 Hz), 7.05 (1H, d, J=5 Hz), 7.21–7.32 (5H, m).

e) 3-(2-Benzyl-3-thienyl)ethynyl-3-quinuclidinol 0.200 ml of a hexane solution containing 1.8 mol of butyl lithium was added dropwise to a mixture of 45.2 mg of 2-benzyl-3-ethynyl-thiophene and 1 ml of tetrahydrofuran at −78° C., followed by stirring at the same temperature for 20 hours. A solution of 0.5 ml of tetrahydrofuran containing 39.9 mg of 3-quinuclidinone was added dropwise to the reaction solution at the same temperature, followed by stirring and then at room temperature for 4 hours. 0.5 ml of water and NH-silica gel were added to the reaction solution, and the solvent was removed. The residue was subjected to NH-silica gel column chromatography using ethyl acetate, to give 39.5 mg of the target compound.

$^1$H-NMR (CDCl$_3$) δ=1.36–1.44 (1H, m), 1.56–1.64 (1H, m), 1.86–1.95 (1H, m), 1.98–2.07 (2H, m), 2.72–2.92 (4H, m), 3.02 (1H, d, J=14 Hz), 3.24 (1H, dd, J=2, 14 Hz), 4.21 (2H, s), 6.98 (1H, d, J=5 Hz), 7.06 (1H, d, J=5 Hz), 7.20 (5H, m).

Example 207

3-(3-Benzyl-5-pyrazyl-2-thienyl)ethynyl-3quinuclidinol a) 1-Phenyl-1-(3-thienyl)methanol 10 ml of 3-thiophenecarboxyaldehyde was dissolved in 50 ml of tetrahydrofuran. To the mixture was added dropwise 64 ml of a hexane/cyclohexane solution containing 1.8 mol of phenyl lithium in a dry ice/acetone bath. After an aqueous ammonium chloride solution was added to the mixture, it was extracted with ethyl acetate. The extract was washed with brine, dried over anhydrous magnesium sulfate and evaporated. The residue was subjected to silica gel column chromatography and eluted with 10% ethyl acetate/hexane, to give the target compound.

$^1$H-NMR (CDCl$_3$) δ=2.20 (1H, d, J=4 Hz), 5.90 (1H, d, J=4 Hz), 7.00 (1H, dd, J=1, 5 Hz), 7.17–7.21 (1H, m), 7.26–7.42 (6H, m).

b) 3-Benzoylthiophene 6.2 g of 1-phenyl-1-(3-thienyl)methanol was dissolved in 50 ml of chloroform. To the mixture was added 30 g of manganese dioxide, followed by stirring overnight. Manganese dioxide was filtered off, and the filtrate was evaporated, to give 6.08 g of the target compound.

$^1$H-NMR (CDCl$_3$) δ=7.39 (1H, dd, J=3, 5 Hz), 7.49 (2H, t, J=7 Hz), 7.56–7.62 (2H, m), 7.84–7.87 (2H, m), 7.94 (1H, dd, J=1, 3 Hz).

c) 3-Benzoyl-5-bromothiophene 3.0 g of 3-benzoylthiophene was dissolved in 10 ml of N,N-dimethylacetamide and 1 ml of acetic acid, and 2.83 g of N-bromosuccinimide was added thereto, followed by stirring overnight. Water was added to the reaction solution, followed by extracting with diethyl ether. The extract was washed with an aqueous saturated sodium bicarbonate solution, dried over anhydrous magnesium and then evaporated. The residue was subjected to silica gel column chromatography and eluted with 10% ethyl acetate/hexan, to give 2.7 g of the target compound.

$^1$H-NMR (CDCl$_3$) δ=7.50 (2H, t, J=8 Hz), 7.55 (1H, d, J=2 Hz), 7.60 (1H, t, J=8 Hz), 7.79–7.84 (3H, m).

d) 3-(3-Benzyl-5-pyrazyl-2-thienyl)ethynyl-3-quinoclidinol 2.7 g of 3-benzoyl-5-bromothiophene, 3.0 g of pyrazyl-tributyltin and 1.0 g of tetrakis(triphenylphosphine)palladium(0) were mixed with 30 ml of xylene, followed by heating under reflux in a nitrogen stream. The reaction solution was subjected to NH-silica gel chromatography and eluted with 10% ethyl acetate/hexane, to give 1.23 g of a product. 500 mg of the product was dissolved in 5 ml of tetrahydrofuran and 20 ml of methanol. 60 mg of sodium borohydride was added thereto, followed by stirring at room temperature. Water was added to the reaction solution and the mixture was extracted with ethyl acetate. The extract was dried over anhydrous magnesium sulfate and then evaporated. To the residue were added 1 ml of triethylsilane and 10 ml of trifluoroacetic acid, followed by stirring in an ice bath. After the mixture was neutralized by adding an aqueous saturated sodium carbonate solution, it was extracted with ethyl acetate and evaporated. To the residue was added 10 ml of N,N-dimethylformamide, and to the mixture was further added 40 mg of N-bromosuccinimide in an ice bath, followed by stirring for one hour. Water was added thereto, followed by extracting with ethyl acetate. The extract was washed with brine, dried over anhydrous magnesium sulfate and then evaporated. To the residue were added 300 mg of 3-ethynyl-3-quinuclidinol, 100 mg of tetrakis (triphenylphosphine)palladium(0), 50 mg of cuprous iodide, 1 ml of triethylamine and 10 ml of N,N-dimethylformamide, followed by heating under stirring in an oil bath kept at 100° C. The reaction solution was evaporated, and the residue was subjected to NH-silica gel chromatography, to give 225 mg of the target compound.

$^1$H-NMR (CDCl$_3$) δ=1.37–1.68 (2H, m), 1.86–1.96 (1H, m), 1.98–2.10 (2H, m), 2.76–2.96 (4H, m), 3.06 (1H, d, J=14 Hz), 3.29 (1H, dd, J=2, 14 Hz), 4.05 (2H, s), 7.21–7.34 (5H, m), 7.36 (1H, s), 8.39 (1H, d, J=3 Hz), 8.47 (1H, dd, J=1,3 Hz), 8.83 (1H, d, J=1 Hz).

Example 208

3-[3-Benzyl-6-(hydroxymethyl)-4,5,6,7-tetrahedrobenzo[b]thiophene-2-yl]ethynyl)-3-quinuclidinol a) Ethyl-4-oxo-1-cyclohexane Carboxylate 120 ml of a Jone's reagent was added dropwise into a solution of 800 ml of acetone containing 81.1 g of ethyl 4-hydroxycyclohexane carboxylate over 30 minutes in an ice bath. After stirring at the same temperature for 20 minutes, 2-propanol was added thereto. The reaction solution was poured into water, followed by extracting with ethyl acetate. The organic phase was washed with brine, dried over anhydrous magnesium sulfate and the solvent was removed, to give 80.0 g of the target compound.

$^1$H-NMR (CDCl$_3$) δ=1.28 (3H, t, J=7 Hz), 1.98–2.10 (2H, m), 2.18–2.25 (2H, m), 2.31–2.39 (2H, m), 2.45–2.51 (2H, m), 2.71–2.77 (1H, m), 4.18 (2H, q, J=7 Hz).

b) 2-Amino-3-benzoyl-6ethoxycarbonyl-4,5,6,7-tetrahydrobenzo[b]thiophene

A mixture of 25.2 g of ethyl-4-oxo-1-cyclohexane carboxylate, 21.4 g of benzoylacetonitrile, 25.2 ml of diethylamine and 250 ml of ethanol was heated under reflux for 45 minutes. 4.7 g of sulfur was added to the mixture all at once while heating under reflux, followed by heating under reflux for further 2 hours. After cooling as it was, the solvent was removed, and the residue was crystallized from methanol, to give 13.4 g of the target compound.

$^1$H-NMR (CDCl$_3$) δ=1.24 (3H, t, J=7 Hz), 1.52–1.61 (1H, m), 1.82–1.99 (3H, m), 2.05–2.79 (3H, m), 4.10–4.18 (2H, m), 6.66 (2H, br.s), 7.37–7.48 (5H, m).

c) 3-(α-Hydroxybenzyl)-6-ethoxycarbonyl-4,5,6,7-tetrahydrobenzo[b]thiophene

A mixture of 21.5 g of 2-amino-3-benzoyl-6-ethoxycarbonyl-4,5,6,7-tetrahydrobenzo[b]thiophene, 12.5 g of cuprous iodide, 26.3 ml of diiodomethane, 26.3 ml of isopentyl nitrite and 250 ml of tetrahydrofuran was heated under reflux for 1.5 hours. After cooling as it was, 500 ml of ethyl acetate was added to the reaction solution. The insoluble matters were filtered off, the mixture was subjected to silica gel column chromatography, and eluted with hexane and then with hexane/ethyl acetate (10:1), to give 17.4 g of a crude product. 1.5 g of sodium borohydride was added little by little to a solution of 200 ml of ethanol containing 17.4 g of this crude product under ice-cooling. After stirring at room temperature for one hour, the solvent was removed. Ethyl acetate and water were added to the residue, followed by extracting with ethyl acetate. The organic phase was washed with brine and the solvent was removed. The residue was subjected to silica gel column chromatography, and eluted with hexane and then with hexane/ethyl acetate (4:1), to give 11.2 g of the target compound.

$^1$H-NMR (CDCl$_3$) δ=1.23–1.28 (3H, m), 1.72–1.85 (1H, m), 2.09–2.28 (2H, m), 2.47–2.76 (2H, m), 2.93–3.06 (2H, m), 4.13–4.18 (2H, m), 5.75–5.76 (1H, m), 7.27–7.38 (6H, m).

d) 3-Benzyl-6-ethoxycarbonyl-4,5,6,7-tetrahydrobenzo[b]thiophene

A mixture of 8.3 g of 3-(α-hydroxybenzyl)-6-ethoxycarbonyl-4,5,6,7-tetrahydrobenzo[b]thiophene, 12.5 g of zinc iodide, 2.0 g of sodium cyanoborohydride and 150 ml of dichloromethane was stirred at room temperature for 3 hours. After adding methanol to the reaction solution, insoluble matters were filtered off. The solvent was removed, and the residue was subjected to silica gel column chromatography and eluted with hexane and then with hexane/ethyl acetate (10:1), to give 5.9 g of the target compound.

$^1$H-NMR (CDCl$_3$) δ=1.26 (3H, t, J=7 Hz), 1.77–1.87 (1H, m), 2.16–2.22 (1H, m), 2.33–2.42 (1H, m), 2.54–2.75 (2H, m), 2.93–3.06 (2H, m), 3.75–3.86 (2H, m), 4.16 (2H, q, J=7 Hz), 6.64 (1H, s), 7.16–7.30 (5H, m).

e) 3-Benzyl-6-(hydroxymethyl)-4,5,6,7,-tetrahydrobenzo[b]thiophene

A solution of 10 ml of diethyl ether containing 2.8 g of 3-benzyl-6-ethoxycarbonyl-4,5,6,7-tetrahydrobenzo[b]thiophene was slowly added dropwise into a suspension of 100 ml of diethyl ether containing 421 mg of lithium aluminum hydride under ice-cooling. After stirring as it was for 30 minutes, 0.4 ml of water, 0.4 ml of an aqueous 1N sodium hydroxide solution and 0.4 ml of water were successively added to the reaction solution and the mixture was dried over anhydrous magnesium sulfate. After filtering, the solvent was removed, to give 2.5 g of the target compound.

$^1$H-NMR (CDCl$_3$) δ=1.39–1.50 (1H, m), 1.94–2.09 (2H, m), 2.32–2.59 (3H, m), 2.88–2.94 (1H, m), 3.63–3.64 (2H, m), 3.77–3.86 (2H, m), 6.62 (1H, s), 7.16–7.31 (5H, m).

f) 2-Bromo-3-benzyl-6-hydroxymethyl-4,5,6,7,-tetrahydrobenzo[b]thiophene 103 mg of N-bromosuccinimide was added little by little to a solution of 5.0 ml of N,N-dimethylformamide containing 136 mg of 3-benzyl-6-(hydroxymethyl)-4,5,6,7-tetrahydrobenzo[b]thiophene under ice-cooling. After stirring for one hour, water was added to the reaction solution and the mixture was extracted with ethyl acetate. The organic phase was washed with water and brine, and the solvent was removed. Then, the residue was subjected to silica gel column chromatography and eluted with hexane and then with hexane/ethyl acetate (2:1), to give 164 mg of the target compound.

$^1$H-NMR (CDCl$_3$) δ=1.34–1.44 (1H, m), 1.87–1.99 (2H, m), 2.23–2.8 (3H, m), 2.78–2.83 (1H, m), 3.59–3.60 (2H, m), 3.81–3.92 (2H, m), 7.13–7.28 (5H, m).

g) 3-[3-Benzyl-6-(hydroxymethyl)-4,5,6,7,-tetrahedrobenzo[b]thiophene-2-yl]ethynyl-3-quinuclidinol A mixture of 164 mg of 2-bromo-3-benzyl-6-hydroxymethyl-4,5,6,7-tetrahydrobenzo[b]thiophene, 88 mg of 3-ethynyl-3-quinuclidinol, 112 mg of tetrakis (triphenylphosphine)palladium(0), 19 mg of cuprous iodide, 203 µl of triethylamine and 5.0 ml of N,N-dimethylformamide was heated under stirring at 80° C. for one hour in a nitrogen atmosphere. After cooling as it was, the solvent was removed and the residue was subjected to NH-silica gel (Fuji Silicia) column chromatography and eluted with hexane/ethyl acetate (1:1) and then with ethyl acetate/methanol (20:1), to give 113 mg of the target compound.

$^1$H-NMR (CDCl$_3$) δ=1.33–1.44 (2H, m), 1.52–1.60 (1H, m), 1.84–2.01 (5H, m), 2.23–2.31 (1H, m), 2.39–2.45 (2H, m), 2.71–2.90 (5H, m), 2.99 (1H, d, J=14 Hz), 3.23 (1H, dd, J=2, 14 Hz), 3.57–3.59 (2H, m), 3.86–3.98 (2H, m), 7.14–7.34 (5H, m).

Example 209

3-(2-Benzyl-7-pyrazyl-3-quinolyl)ethyl-3-quinuclidinol a) 1-Methoxy-3-phenyl-2-propanol 35 ml of a 28% sodium methoxide methanol solution was added to a solution of 100 ml of methanol containing 14.0 g of benzyloxirane, followed by heating under stirring for 2 hours in an oil bath kept at 80° C. After cooling as it was, the solvent was removed. Water was added thereto, followed by extracting with ethyl acetate. The organic phase was washed with brine and the solvent was removed, to give 17.3 g of the target compound.

$^1$H-NMR (CDCl$_3$) δ=2.75–2.84 (2H, m), 3.28–3.32 (1H, m), 3.38 (3H, s), 3.39–3.43 (1H, m), 4.01–4.03 (1H, m), 7.22–7.33 (5H, m).

b) 1-Methoxy-3-phenylacetone 20.4 ml of a Jone's reagent was slowly added dropwise into 200 ml of an acetone solution containing 5.1 g of 1-methoxy-3-phenyl-2-propanol. After stirring for 30 minutes at room temperature, 30 ml of 2-propanol was slowly added to the reaction solution. After removing the solvent, water was added thereto and the mixture was extracted with ethyl acetate. The organic phase was washed with brine and the solvent was removed. The residue was subjected to silica gel column chromatography and elute with hexane/ethyl acetate (6:1), to give 3.7 g of the target compound.

$^1$H-NMR (CDCl$_3$) δ=3.39 (3H, s), 3.76 (2H, s), 4.06 (2H, s), 7.22–7.36 (5H, m).

c) 2-Amino-4-bromobenzaldehyde 16.1 ml of an aqueous 29% ammonia solution was added to a mixture of 5.0 g of 2-nitro-4-bromobenzaldehyde, 60.4 g of iron (II) sulfate heptahydrate, 200 ml of methanol, 100 ml of water and 335 µl of concentrated hydrochloric acid in an oil bath kept at 90° C., followed by heating under stirring for 10 minutes. After cooling as it was, insoluble matters were filtered through Celite and the filtrate was extracted with ethyl acetate. The organic phase was washed with brine and the solvent was removed, to give 3.9 g of the target compound.

$^1$H-NMR (CDCl$_3$) δ=6.17 (2H, br.s), 6.84–6.89 (2H, m), 7.33 (1H, d, J=8 Hz), 9.82 (1H, s).

d) 2-Benzyl-7-bromo-3-methoxyquinoline

A mixture of 3.3 g of 2-amino-4-bromobenzaldehyde, 3.3 g of 1-methoxy-3-phenylacetone, an aqueous potassium hydroxide solution (10 g of potassium hydroxide was dissolved in 10 ml of water) and 20 ml of ethanol was heated under stirring at 100° C. for 4 hours in a sealed tube. After cooling as it was, the reaction solution was poured into water and the mixture was extracted with diethyl ether. The organic phase was washed with brine and the solvent was removed. The residue was crystallized from hexane/ethyl acetate, to give 3.7 g of the target compound.

$^1$H-NMR (CDCl$_3$) δ=3.90 (3H, s), 4.34 (2H, s), 7.15–7.27 (4H, m), 7.32–7.35 (2H, m), 7.51–7.56 (2H, m), 8.20–8.21 (1H, m).

e) 2-Benzyl-7-pyrazyl-3-methoxyquinoline

A mixture of 200 mg of 2-benzyl-7-bromo-3-methoxyquinoline, 337 mg of pyrazyltributyltin, 141 mg of tetrakis(triphenylphosphine)palladium(0) and 10 ml of xylene was heated under stirring for 3 hours in an oil bath kept at 150° C. in a nitrogen atmosphere. After cooling as it was, the solvent was removed. The residue was subjected to silica gel column chromatography and eluted with hexane/ethyl acetate (5:1) and then with hexane/ethyl acetate (1:1), to give 126 mg of the target compound.

$^1$H-NMR (CDCl$_3$) δ=3.95 (3H, s), 4.39 (2H, s), 7.16–7.28 (3H, s), 7.35–7.39 (3H, m), 7.83 (1H, d, J=8 Hz), 8.20–8.23 (1H, m), 8.53 (1H, d, J=3 Hz), 8.66–8.68 (2H, m), 9.22 (1H, m).

f) 2-Benzyl-7-pyrazyl-3-quinolyl Trifluoromethane-sulfonate

A mixture of 127 mg of 2-benzyl-7-pyrazyl-3-methoxyquinoline, 40 mg of n-hexadecyl-tri-n-butylphosphonium bromide and 10 ml of 47% hydrobromic acid was heated under stirring for 48 hours in an oil bath kept at 120° C. The reaction solution was slowly poured into an aqueous potassium carbonate solution, the mixture was extracted with diethyl ether and the solvent was removed. To the residue were added 274 mg of N-phenyltrifluoromethanesulfonimide, 133 µl of triethylamine, 23 mg of 4-dimethylaminopyridine, 10 ml of dichloromethane and 3.0 ml of N,N-dimethylformamide, followed by stirring at room temperature overnight. After removing the solvent, the residue was subjected to silica gel column chromatography and eluted with hexane/ethyl acetate (4:1) and then with hexane/ethyl acetate (2:1), to give 134 mg of the target compound.

$^1$H-NMR (CDCl$_3$) δ=4.46 (2H, s), 7.25–7.40 (5H, m), 7.77 (1H, d, J=8 Hz), 8.09 (1H, s), 8.34–8.37 (1H, m), 8.61 (1H, d, J=2 Hz), 8.72–8.76 (2H, m), 9.25 (1H, m).

g) 3-(2-Benzyl-7-pyrazyl-3-quinolyl)ethynyl-3-quinuclidinol

A mixture of 134 mg of 2-benzyl-7-pyrazyl-3-quinolyl trifluoromethanesulfonate, 55 mg of 3-ethynyl-3-quinuclidinol, 70 mg of tetrakis(triphenylphosphine) palladium(0), 11 mg of cuprous iodide, 126 µl of triethylamine and 5.0 ml of N,N-dimethylformamide was heated under stirring at 85° C. for 30 minutes in a nitrogen atmosphere. The reaction solution was poured into aqueous dilute ammonia, and the mixture was extracted with ethyl acetate. Then, the organic phase was washed with brine and the solvent was removed, to give 76 mg of the target compound.

$^1$H-NMR (CDCl$_3$) δ=1.41–1.46 (1H, m), 1.60–1.93 (2H, m), 2.05–2.06 (2H, m), 2.77–2.89 (4H, m), 3.04 (1H, d, J=14 Hz), 3.21–3.25 (1H, m), 4.55 (2H, s), 7.20–7.36 (5H, m), 7.89 (1H, d, J=9 Hz), 8.25 (1H, s), 8.27–8.29 (1H, m), 8.58 (1H, d, J=3 Hz), 8.69–8.71 (2H, m), 9.24 (1H, d, J=1 Hz).

Example 210

3-(2-Benzyl-7-ethoxycarbonyl-3-quinolyl)ethynyl-3-quinuclidinol a) 2-Benzyl-7-bromo-3-hydroxyquinoline A mixture of 1.28 g of 2-benzyl-7-bromo-3-methoxyquinoline obtained in Example 209d, 990 mg of n-hexadecyl-tri-n-butylphosphonium bromide, 12 ml of 47% hydrobromic acid and 10 ml of acetic acid was heated under reflux for 12 hours. After cooling as it was, the reaction solution was slowly poured into an aqueous potassium carbonate solution and the mixture was extracted with diethyl ether. The organic phase was washed with brine and the solvent was removed, to give 1.8 g of the target compound (including n-hexadecyl-tri-n-butylphosphonium bromide) as a crude product.

b) 2-Benzyl-7-cyano-3-hydroxyquinoline

A mixture of 370 mg of 2-benzyl-7-bromo-3-hydroxyquinoline (including n-hexadecyl-tri-n-butylphosphonium bromide), 208 mg of zinc cyanide, 272 mg of tetrakis(triphenylphosphine) palladium(0) and 10 ml of N,N-dimethylformamide was heated under stirring for 7 hours in an oil bath kept at 90° C. After cooling as it was, insoluble matters were filtered through Celite and an aqueous potassium carbonate solution was added to the filtrate. The mixture was extracted with ethyl acetate, and the organic phase was washed with brine and the solvent was removed. The residue was subjected to silica gel column chromatography and eluted with hexane/ethyl acetate (3:1) and then with hexane/ethyl acetate (2:1), to give 203 mg of the target compound.

$^1$H-NMR (CDCl$_3$) δ=4.28 (2H, s), 7.15–7.30(5H, m), 7.54 (1H, s), 7.71–7.74 (1H, m), 7.95 (1H, d, J=9 Hz), 8.37 (1H, s).

c) 2-Benzyl-7-ethoxycarbonyl-3-hydroxyquinoline

A mixture of 203 mg of 2-benzyl-7-cyano-3-hydroxyquinoline, 2.6 g of potassium hydroxide, 5.5 ml of water and 20 ml of ethanol was heated under reflux for 2 hours. After cooling as it was, dilute hydrochloric acid was added thereto. The mixture was extracted with diethyl ether and the solvent was removed. To the residue were added 30 ml of ethanol and 3.0 ml of concentrated sulfuric acid, followed by heating under reflux for one hour. After cooling as it was, the solvent was removed. Diethyl ether and an aqueous potassium carbonate solution were added thereto, followed by extracting with diethyl ether. The organic phase was washed with brine and the solvent was removed, to give 204 mg of the target compound.

$^1$H-NMR (CDCl$_3$) δ=1.43 (3H, t), 4.40–4.45 (4H, m), 7.20–7.38 (6H, m), 7.67 (1H, d, J=8 Hz), 8.05–8.08 (1H, m), 8.79 (1H, s).

d) 2-Benzyl-7-ethoxycarbonyl-3-quinolyl Trifluoromethanesulfonate 204 mg of 2-benzyl-7-ethoxycarbonyl-3-hydroxyquinoline, 285 mg of N-phenyltrifluoromethanesulfonimide, 134 μl of triethylamine, 24 mg of 4-dimethylaminopyridine and 20 ml of dichloromethane were mixed, followed by stirring at room temperature for 2 hours. After removing the solvent, the residue was subjected to silica gel chromatography and eluted with hexane/ethyl acetate (10:1) and then with hexane/ethyl acetate (5:1), to give 220 mg of the target compound.

$^1$H-NMR (CDCl$_3$) δ=1.46 (3H, t), 4.44–4.50 (4H, m), 7.21–7.34 (5H, m), 7.87 (1H, d, J=8 Hz), 8.08 (1H, s), 8.19–8.22 (1H, m), 8.84 (1H, d, J=1 Hz).

e) 3-(Benzyl-7-ethoxycarbonyl-3-quinolyl)ethynyl-3-quinuclidinol

A mixture of 220 mg of 2-benzyl-7-ethoxycarbonyl-3-quinolyl Trifluoromethane sulfonate, 83 mg of 3-ethynyl-3-quinuclidinol, 116 mg of tetrakis(triphenylphosphine) palladium(0), 19 mg of cuprous iodide, 209 μl of triethylamine and 5.0 ml of N,N-dimethylformamide was stirred at room temperature for 45 minutes in a nitrogen atmosphere. The reaction solution was poured into aqueous dilute ammonia, followed by extracting with ethyl acetate. Then, the organic phase was washed with brine and the solvent was removed. The residue was subjected to NH-silica gel (Fuji Silicia) chromatography and eluted with hexane/ethyl acetate (1:1) and then with ethyl acetate/methanol (15:1), to give 220 mg of the target compound.

$^1$H-NMR (CDCl$_3$) δ=1.41–1.68 (5H, t), 1.81–1.88 (1H, m), 2.01–2.09 (2H, m), 2.73–2.92 (4H, m), 3.02–3.06 (1H, m), 3.19–3.24 (1H, m), 4.46 (2H, q), 4.54 (2H, s), 7.20–7.58 (5H, m), 7.80 (1H, d, J=8 Hz), 8.21–8.49 (1H, m), 8.23 (1H, s), 8.79–8.81 (1H, m).

Example 211

3-[4-Benzyl-2-(3,4,-methylenedioxyphenyl)-5-thiazolyl]ethynyl-3-quinuclidinol a) Benzyl Chloromethyl Ketone 100 ml of anhydrous diethyl ether was added to 12.4 g of magnesium (used for the synthesis of a Grignard's reagent), to which were then added dropwise a mixture of 45 ml of benzyl bromide and 50 ml of an ether anhydride by using a dropping funnel over 30 minutes in a nitrogen atmosphere in a manner that the solution was mildly refluxed. This diethyl ether solution of benzylmagnesium bromide was added dropwise to a mixture of 40 ml of chloroacetyl chloride, 778 mg of cuprous iodide and 100 ml of tetrahydrofuran by using a dropping funnel over 2 hours in a nitrogen atmosphere such that the system temperature was kept at −60° C. After the addition was completed, the mixture was further stirred for 2.5 hours. Then, an aqueous saturated ammonium chloride solution was added thereto, and the mixture was extracted with ethyl acetate. The organic phase was further washed with brine, dried over anhydrous sodium sulfate and the solvent was removed. The residue was subjected to silica gel column chromatography using 1–3% ethyl acetate/hexane as an eluent for separation and purification, to give 20.4 g of the target compound.

$^1$H-NMR (CDCl$_3$) δ=3.89 (2H, s), 4.12 (2H, s), 7.22–7.38 (5H, m).

b) 3,4-Methylenedioxythiobenzamide 882 mg of 3,4-methylenedioxybenzoyl chloride was dissolved in 20 ml of acetone, to which was then added 1 ml of aqueous 36% ammonia and the mixture was stirred at room temperature for 20 minutes. Then, water was added thereto, and the mixture was extracted with ethyl acetate. The organic phase was washed with brine, dried over anhydrous sodium sulfate and the solvent was removed. The resulting residue was dissolved in 20 ml of tetrahydrofuran, to which was then added 1.9 g of a Lawesson's reagent and the mixture was refluxed under heating for 3 hours. After cooling as it was, the solvent was removed and the residue was subjected to silica gel column chromatography using 25% ethyl acetate/hexane as an eluent for separation and purification, to give 637 mg of the target compound.

c) 4-Benzyl-5-bromo-2-(3,4-methylenedioxyphenyl)thiazole

A mixture of 372 mg of 3,4-methylenedioxythiobenzamide and 343 mg of benzyl chloromethyl ketone was dissolved in 20 ml of ethanol, followed by heating under reflux for 3 hours. After cooling as it was, the solvent was removed, and the resulting crystals were collected by filtration, to give 367 mg of the target compound.

$^1$H-NMR (CDCl$_3$) δ=4.53 (2H, s), 6.11 (2H, s), 6.73 (1H, s), 6.99 (1H, d, J=8.2 Hz), 7.27–7.40 (5H, m), 7.80 (1H, d, J=1.9 Hz), 8.03 (1H, dd, J=1.9,8.2 Hz).

d) 4-Benzyl-5-bromo-2-(3,4-methylenedioxyphenyl)thiazole 367 mg of 4-benzyl-2-(3,4-methylenedioxyphenyl)thiazole was dissolved in 2 ml of N,N-dimethylformamide 244 mg of N-bromosuccinimide was added thereto under ice-cooling, followed by stirring overnight. Then, ethyl acetate was added to the reaction solution, followed by washing with water. The organic phase was further washed with brine, dried over anhydrous sodium sulfate and the solvent was removed. The residue was subjected to silica gel column chromatography using 3% ethyl acetate/hexane as an eluent for separation and purification, to give 377 mg of the target compound.

$^1$H-NMR (CDCl$_3$) δ=4.12 (2H, s), 6.01 (2H, s), 6.82 (1H, d, J=8.1 Hz), 7.19–7.37 (7H, m).

e) 3-[4-Benzyl-2-(3,4-methylenedioxyphenyl)-5-thiazolyl]ethynyl-3-quinuclidinol 5 ml of N,N-dimethylformamide was added to a mixture of 377 mg of 4-benzyl-5-bromo-2-(3,4-methylenedioxyphenyl)thiazole, 178 mg of 3-ethynyl-3-quinuclidinol, 68 mg of tetrakis (triphenylphosphine) palladium(0), 18 mg of cuprous iodide and 0.5 ml of triethylamine, followed by heating under stirring at 100° C. in an oil bath for 15 minutes in a nitrogen atmosphere. After cooling as it was, ethyl acetate and aqueous ammonia were added thereto, and the mixture was extracted with ethyl acetate. The organic phase was further washed with brine, dried over anhydrous sodium sulfate and the solvent was removed. The resulting crystals were collected by filtration, to give 253 mg of the target compound.

$^1$H-NMR (CDCl$_3$) δ=1.38–1.48 (1H, m), 1.59–1.69 (1H, m), 1.85–1.98 (1H, m), 2.00–2.12 (2H, m), 2.77–2.98 (4H, m), 3.03 (1H, d, J=14 Hz), 3.25 (1H, dd, J=1.9, 14 Hz), 4.18 (2H, s), 6.01 (2H, s), 6.81 (1H, d, J=8.0 Hz), 7.19–7.40 (7H, m).

Example 212

3-[4-Benzyl-2-(2-pyridyl)-5-thiazolyl]ethynyl-3-quinuclidinol a) 4-Benzyl-2-(2-pyridyl)thiazole 532 mg of 2-cyanopyridine was dissolved in 2 ml of 1,3-dimethyl-2-imidazolidinone. A mixture of 474 mg of sodium methoxide, 2.2 ml of bis(trimethylsilyl) sulfide and 4 ml of 1,3-dimethyl-2-imidazolidinone was added thereto, followed by heating under stirring at 40° C. in an oil bath overnight. After cooling as it was, water was added thereto and the mixture was extracted with ether. The organic phase was further washed with brine, dried over anhydrous sodium sulfate and the solvent was removed. To the resulting residue were added 560 mg of benzyl chloromethyl ketone (Example 211a) and 20 ml of ethanol, followed by heating under reflux for 5 hours. After cooling as it was, the solvent was removed and the residue was subjected to silica gel column chromatography using 11% ethyl acetate/hexane as an eluent for separation and purification, to give 302 mg of the target compound.

$^1$H-NMR (CDCl$_3$) δ=4.21 (2H, s), 6.89 (1H, s), 7.21–7.38 (6H, m), 7.78 (1H, dd, J=7.7, 9.3 Hz), 8.18 (1H, d, J=7.7 Hz), 8.60 (1H, d, J=4.9 Hz).

b)-[4-Benzyl-2-(2-pyridyl)-5-thiazolyl]ethynyl-3-quinuclidinol

The target compound was synthesized in the same manner as in Example 211.

$^1$H-NMR (CDCl$_3$) δ=1.40–1.50 (1H, m), 1.62–1.72 (1H, m), 1.85–1.95 (1H, m), 2.02–2.10 (2H, m), 2.78–2.95 (4H, m), 3.04 (1H, d, J=14 Hz), 3.26 (1H, dd, J=2.0, 14 Hz), 4.24 (2H, s), 7.20–7.35 (6H, m), 7.76 (1H, dd, 7.7, 9.3 Hz), 8.14 (1H, d, 7.7 Hz), 8.57 (1H, d, J=4.0 Hz).

Example 213

3-[4-Benzyl-2-(4-pyridyl)-5-thiazolyl]ethynyl-3-quinuclidinol a) 4-Benzyl-2-(4-pyridyl)thiazole 1 g of 4-cyanopyridine and 2 ml of triethylamine were dissolved in 20 ml of pyridine. Hydrogen sulfide gas was introduced into the reaction solution for 30 minutes while the reaction solution was stirred under heating at 50° C. in an oil bath. After cooling as it was, hydrogen sulfide gas in the system was replaced by nitrogen gas and the solvent was removed. To the resulting residue were added 619 mg of benzyl chloromethyl ketone (Example 211a) and 20 ml of ethanol, followed by heating under reflux for 3 hours. After cooling as it was, the solvent was removed and the residue was subjected to silica gel column chromatography using 20% ethyl acetate/hexane as an eluent for separation and purification, to give 215 mg of the target compound.

$^1$H-NMR (CDCl$_3$) δ=4.21 (2H, s), 6.91 (1H, s), 7.22–7.40 (5H, m), 7.80 (2H, dd, J=4.6 Hz, 1.6 Hz), 8.69 (2H, dd, J=4.6 Hz, 1.6 Hz).

b) 3-[4-Benzyl-2-(4-pyridyl)-5-thiazolyl]ethynyl-3-quinuclidinol

The target compound was synthesized in the same manner as in Example 211.

$^1$H-NMR (CDCl$_3$) δ=1.40–1.50 (1H, m), 1.62–1.72 (1H, m), 1.82–1.92 (1H, m), 2.00–2.10 (2H, m), 2.78–2.95 (4H, m), 3.06 (1H, d, J=14 Hz), 3.26 (1H, dd, J=14 Hz, 2.0 Hz), 4.23 (2H, s), 7.20–7.35 (5H, m), 7.71 (2H, dd, J=1.6, 4.4 Hz), 8.66 (2H, dd, J=1.6, 4.4 Hz).

Example 214

3-[4-Benzyl-2-(3-pyridyl)-5-thiazolyl]ethynyl-3-quinuclidinol a) 2-Amino-4-benzylthiazole 5.0 g of benzyl chloromethyl ketone (Example 211a) was dissolved in 20 ml of ethanol and 2.3 g of thiourea was added thereto, followed by heating under reflux for 3 hours. After cooling as it was, the solvent was removed and the residue was subjected to NH-silica gel column chromatography using 50% ethyl acetate/hexane and ethyl acetate as an eluent for separation and purification, to give 1.7 g of the target compound.

$^1$H-NMR (CDCl$_3$) δ=3.86 (2H, s), 5.06 (2H, br.s), 6.01 (1H, s), 7.21–7.32 (5H, m).

b) 4-Benzyl-2-idothiazole

A mixture of 504 mg of 2-amino-4-benzylthiazole, 520 mg of cuprous iodide, 1.1 ml of diiodomethane and 1.1 ml of isoamyl nitrite was suspended in 10 ml of tetrahydrofuran, followed by heating under stirring in an oil bath at 80° C. for one hour in a nitrogen atmosphere. After cooling as it was, insoluble matters were filtered off through Celite. The filtrate was washed with tetrahydrofuran and the solvent was removed. The resulting residue was subjected to silica gel column chromatography using 2–4% ethyl acetate/hexane as an eluent for separation and purification, to give 468 mg of the target compound.

$^1$H-NMR (CDCl$_3$) δ=4.15 (2H, s), 6.73 (1H, s), 7.24–7.35 (5H, m).

c) 4-Benzyl-2-(3-pyridyl)thiazole 5 ml of xylene was added to a mixture of 468 mg of 4-benzyl-2-iodothiazole, 580 mg of (3-pyridyl)tributyltin and 90 mg of tetrakis(triphenylphosphine)palladium(0), followed by heating under stirring at 150° C. in an oil bath for 2.5 hours. After cooling as it was, insoluble matters were filtered off through Celite and the solvent was removed. The residue was subjected to silica gel column chromatography using 20–25% ethyl acetate/hexane as an eluent for separation and purification, to give 101 mg of the target compound.

¹H-NMR (CDCl₃) δ=4.21 (2H, s), 6.84 (1H, s), 7.33–7.40 (6H, m), 8.24 (1H, dd, J=1.7, 8.1 Hz), 8.64 (1H, dd, J=1.7, 4.9 Hz), 9.15 (1H, s).

d) 3-[4-Benzyl-2-(3-pyridyl)-5-thiazolyl]ethynyl-3-quinuclidinol

The title compound was synthesized in the same manner as in Example 211.

¹H-NMR (CDCl₃) δ=1.48–1.58 (1H, m), 1.60–1.70 (1H, m), 1.85–1.95 (1H, m), 2.03–2.12 (2H, m), 2.75–2.98 (4H, m), 3.06 (1H, d, J=14 Hz), 3.27 (1H, dd, J=2.0, 14 Hz), 4.20 (2H, s), 7.19–7.38 (6H, m), 8.12 (1H, dd, J=1.7, 8.0 Hz), 8.61 (1H, dd, J=1.7, 4.8 Hz), 9.06 (1H, s).

TABLE 5

Example 1

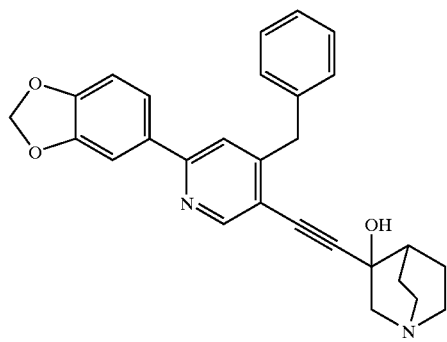

Example 2

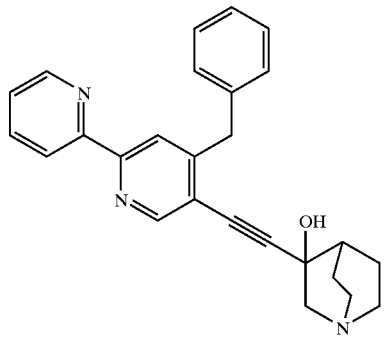

Example 3

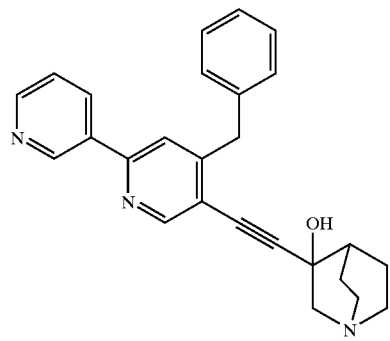

Example 4

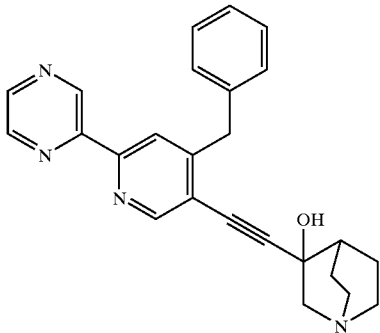

Example 5

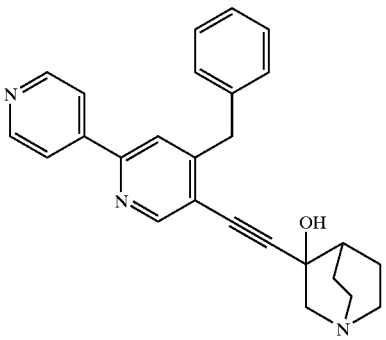

Example 6

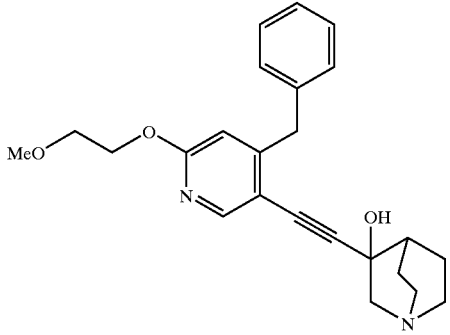

Example 7
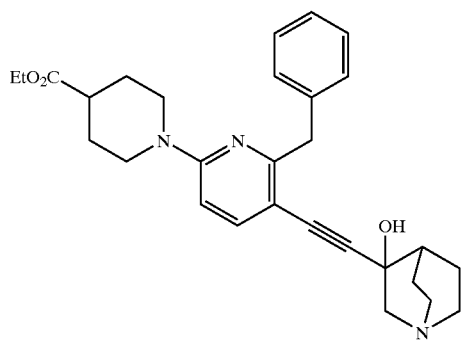
Example 8
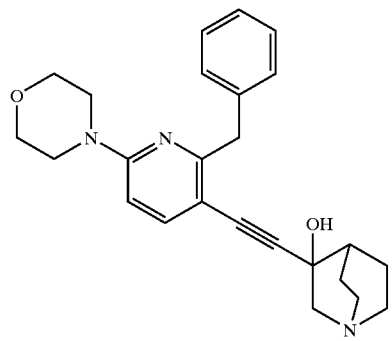
Example 9
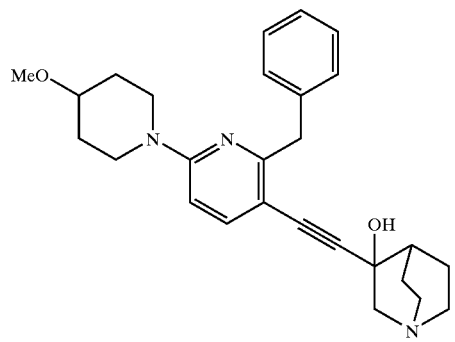
Example 10
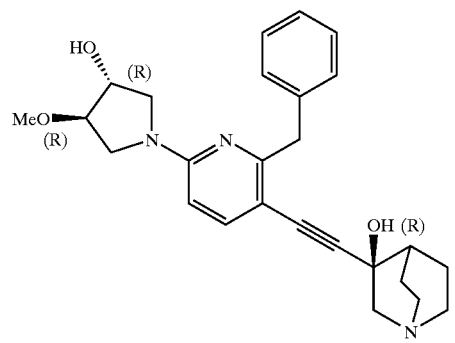
Example 11
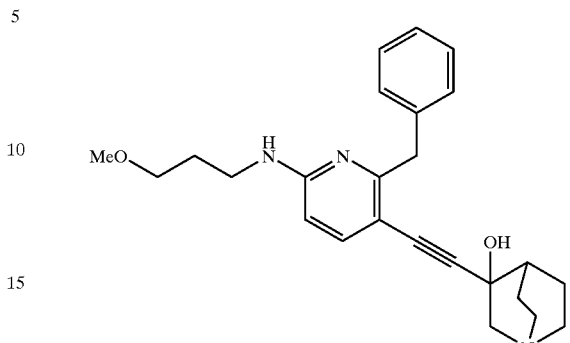
Example 12
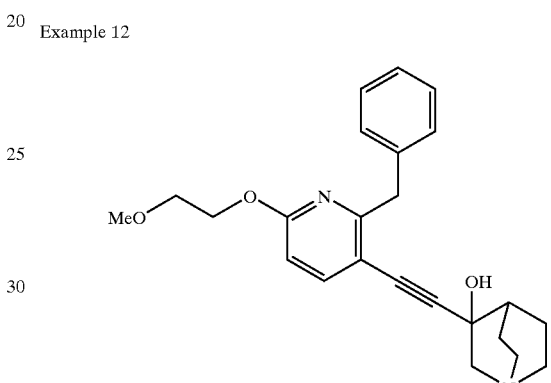
Example 14
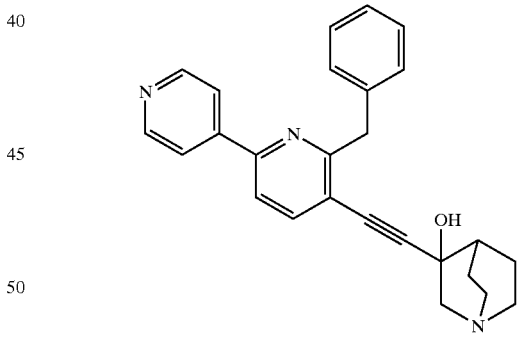
Example 15
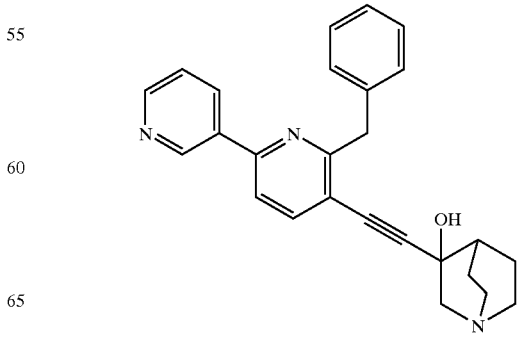

Example 16
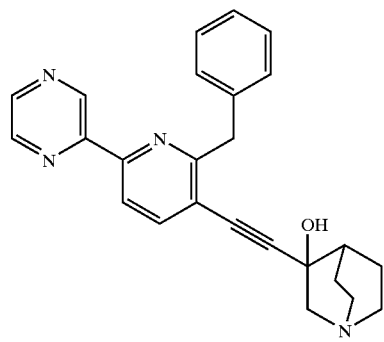
Example 17
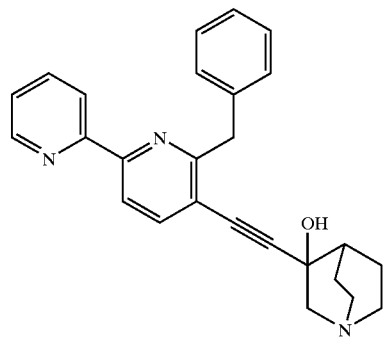
Example 18
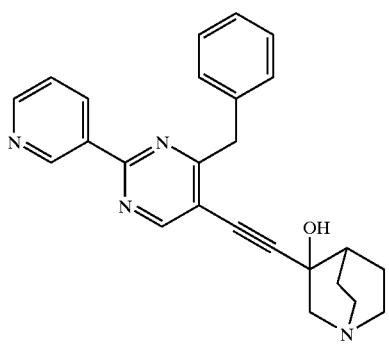
Example 19
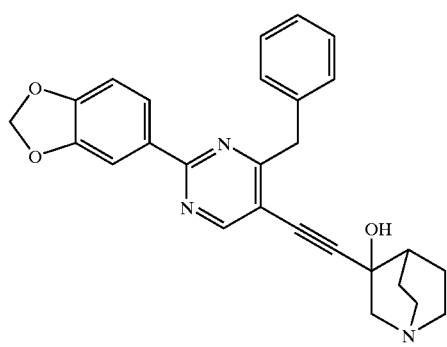
Example 20
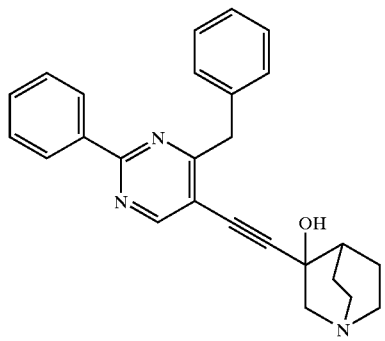
Example 21
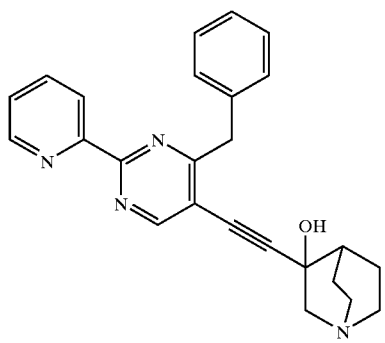
Example 22
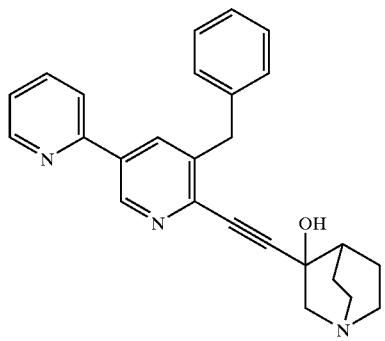

Example 23
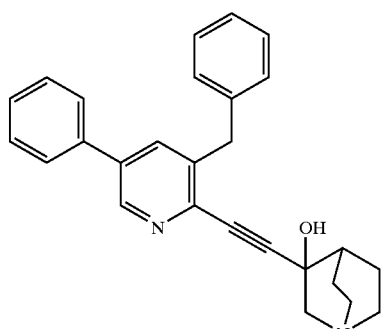
Example 24
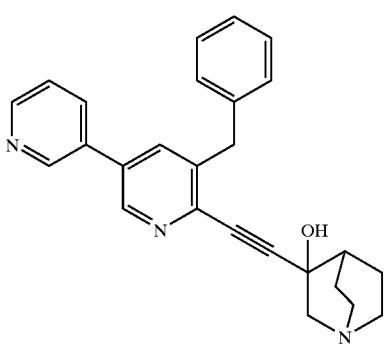
Example 25
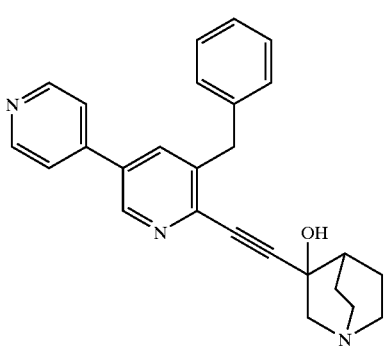
Example 26
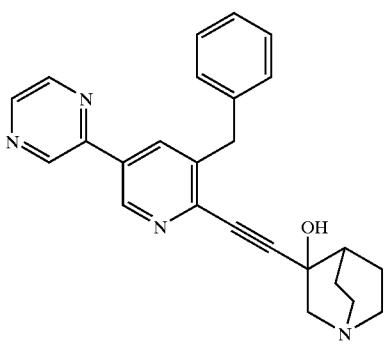
Example 27
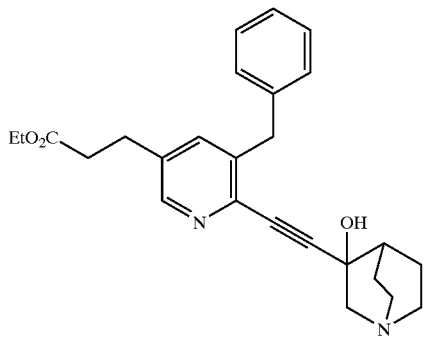
Example 28
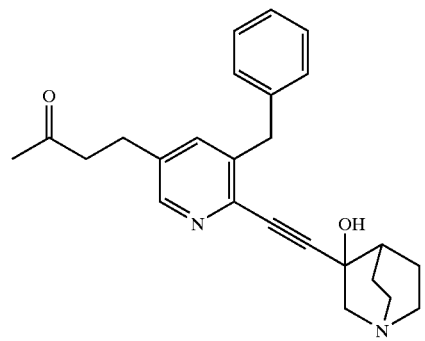
Example 29
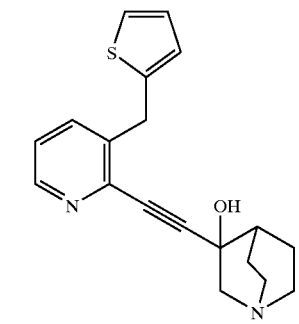
Example 30

Example 31
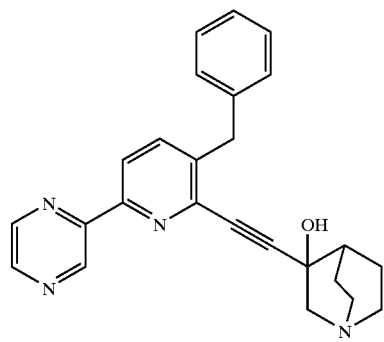
Example 32
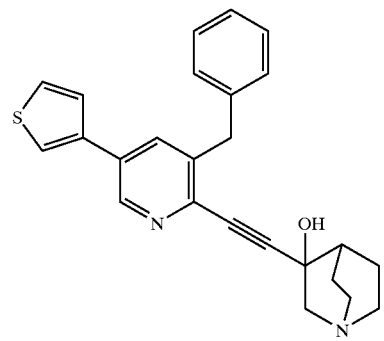
Example 33
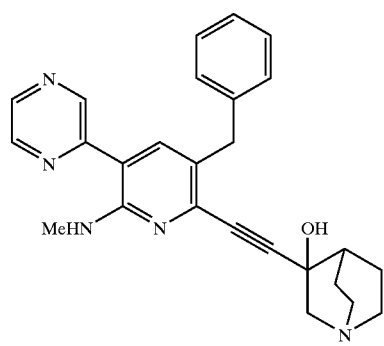
Example 34
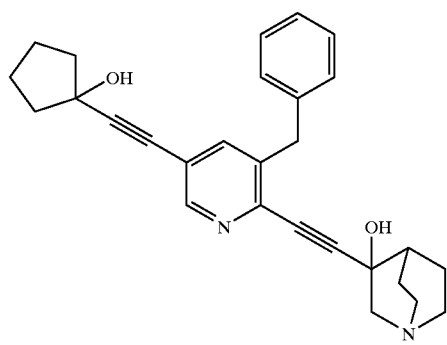
Example 35
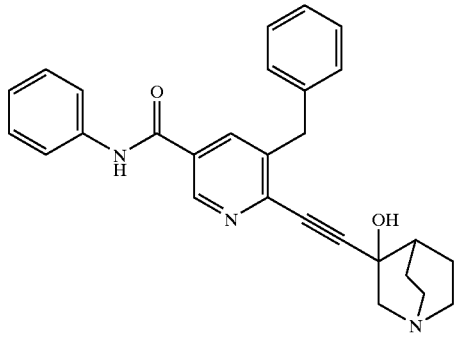
Example 36
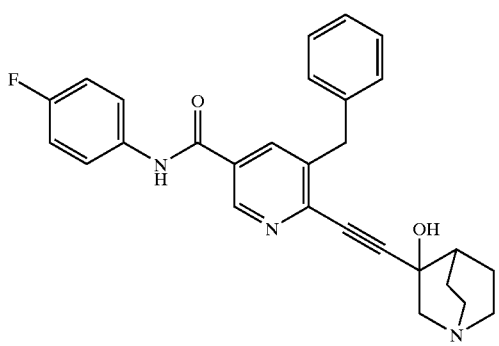
Example 37
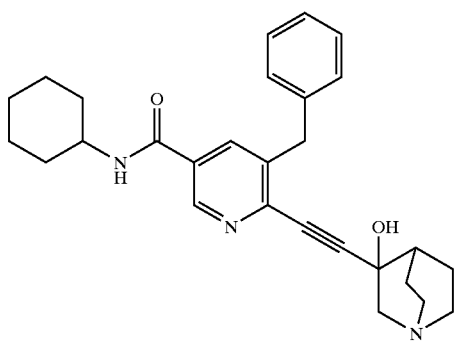
Example 38
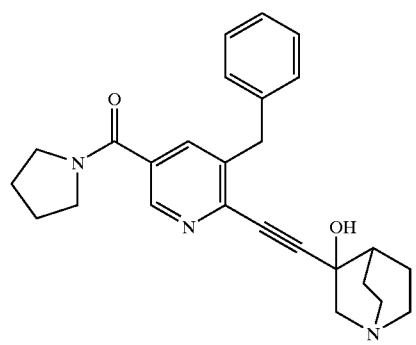

Example 39
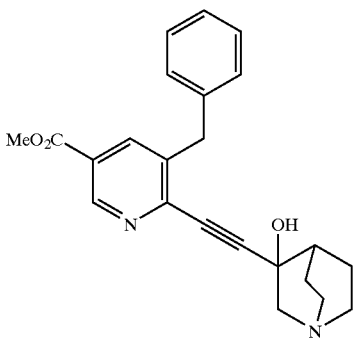
Example 40
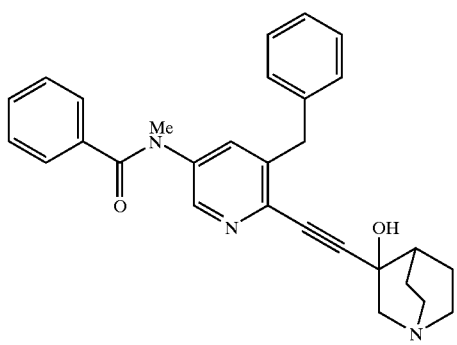
TABLE 6
Example 41
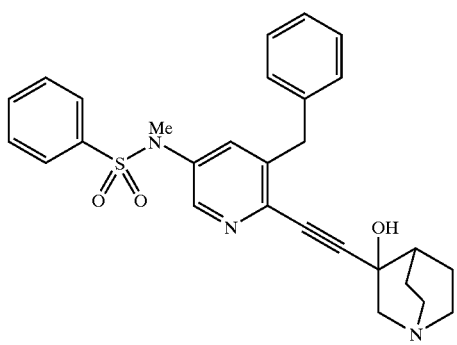
Example 42
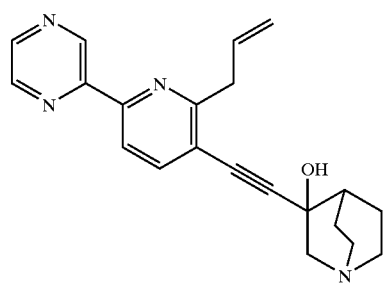
Example 43
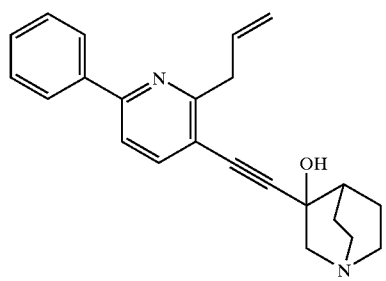
Example 44
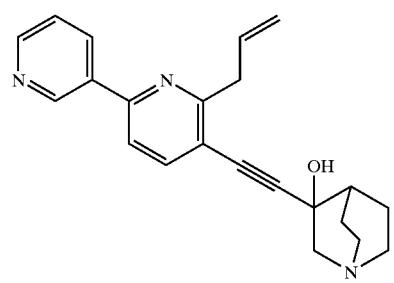
Example 45
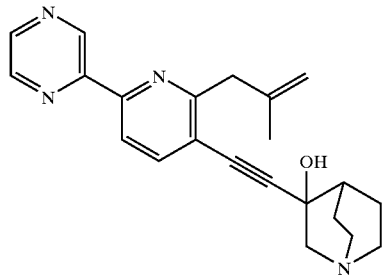
Example 46
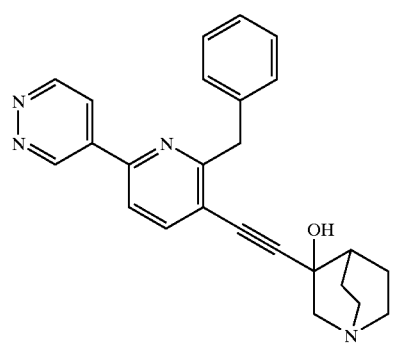
Example 47
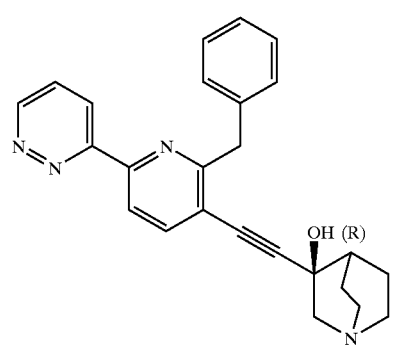

Example 48
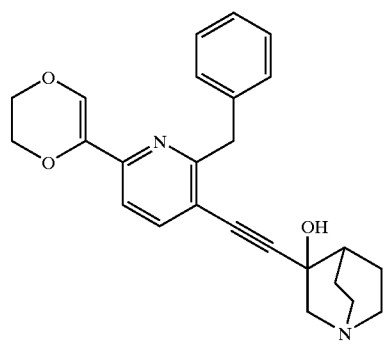
Example 49
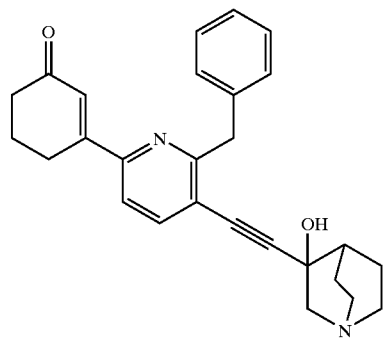
Example 50
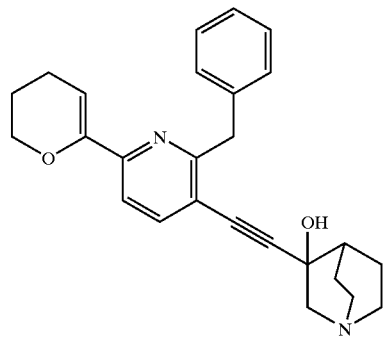
Example 51
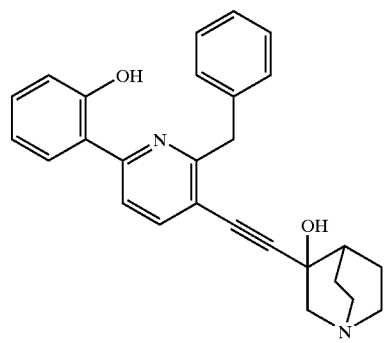
Example 52
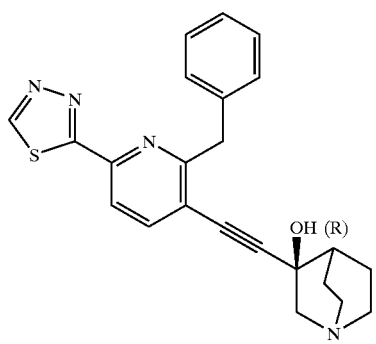
Example 53
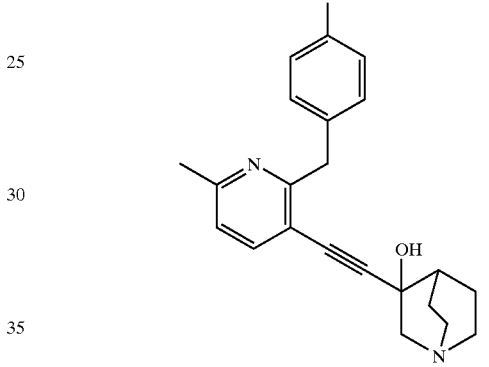
Example 54
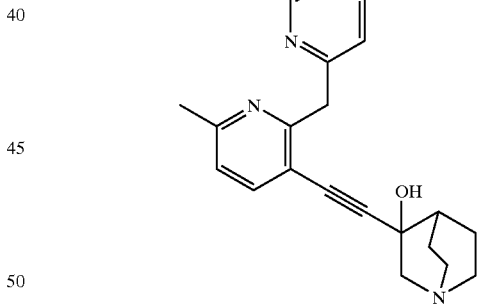
Example 55
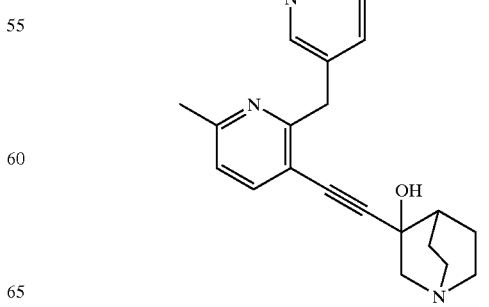

-continued
Example 56
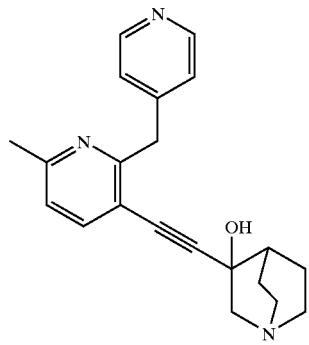
Example 57
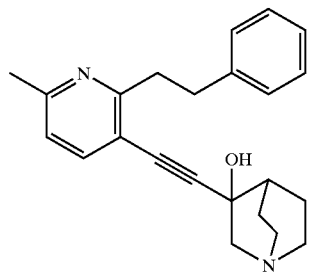
Example 58
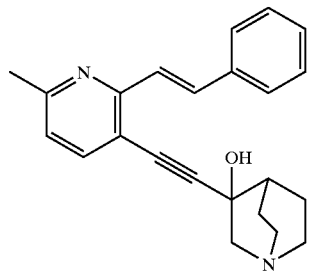
Example 59
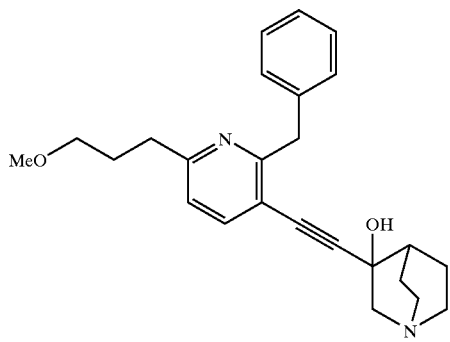
-continued
Example 60
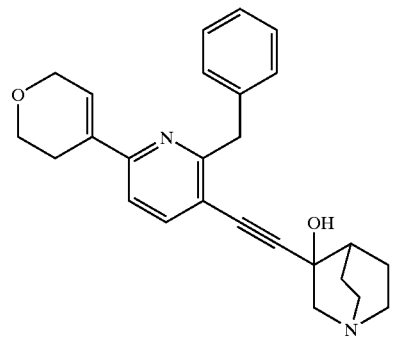
Example 61
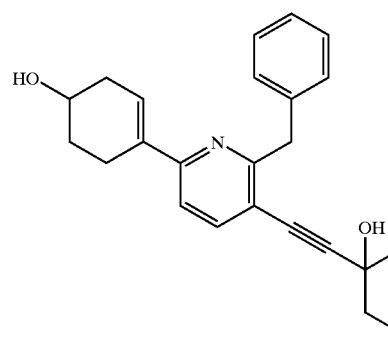
Example 62
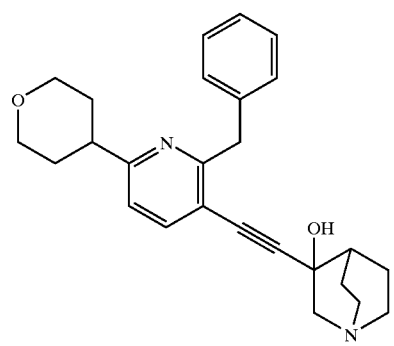
Example 63
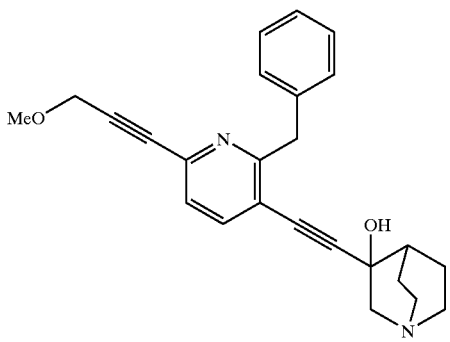

Example 64
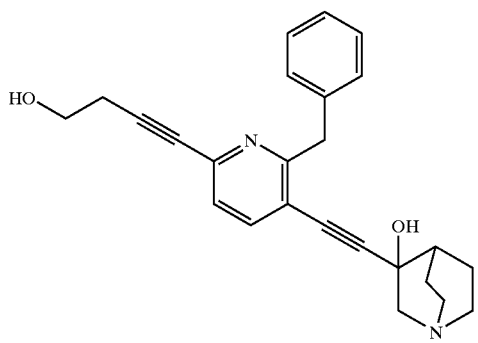
Example 65
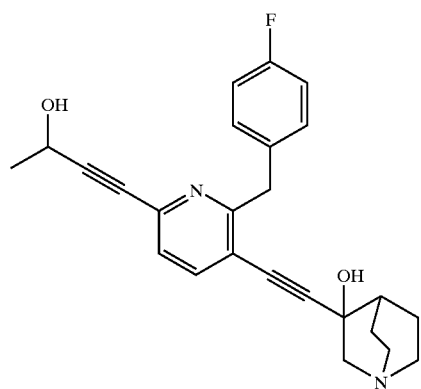
Example 66
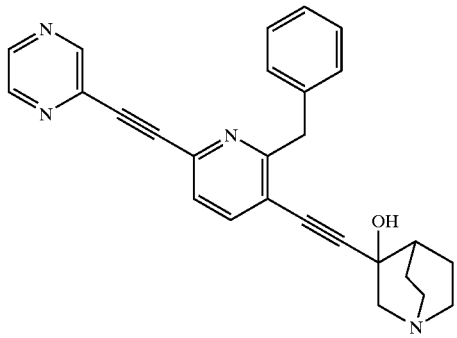
Example 67
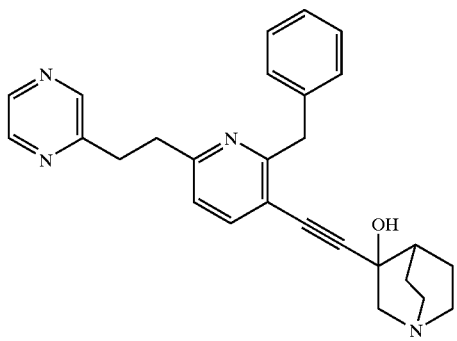
Example 68
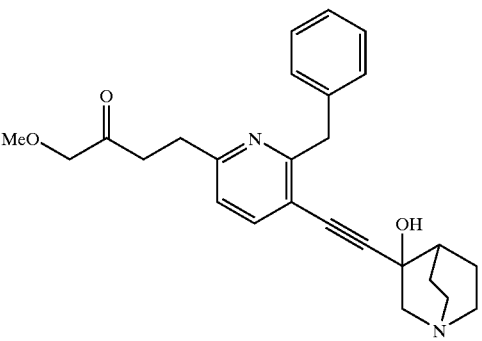
Example 69
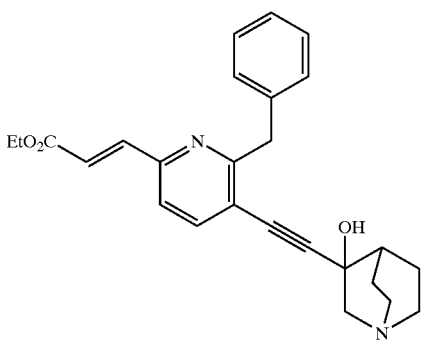
Example 70
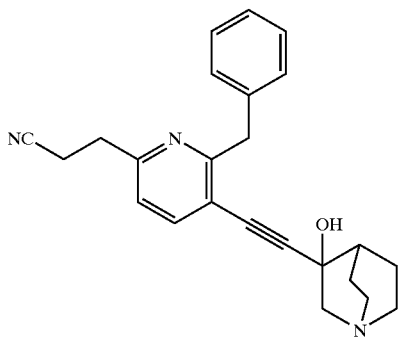
Example 71
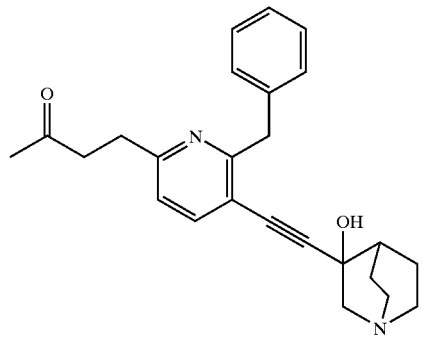

Example 72
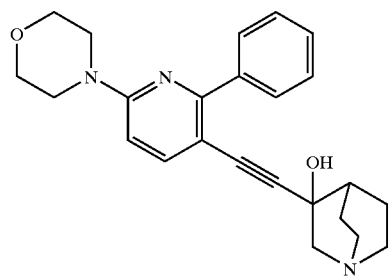
Example 73
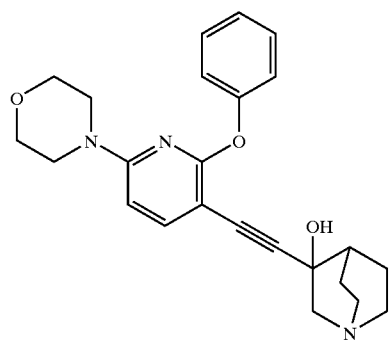
Example 74
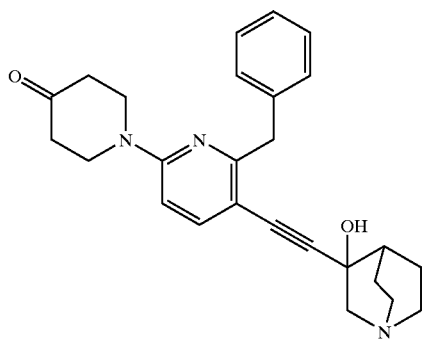
Example 75
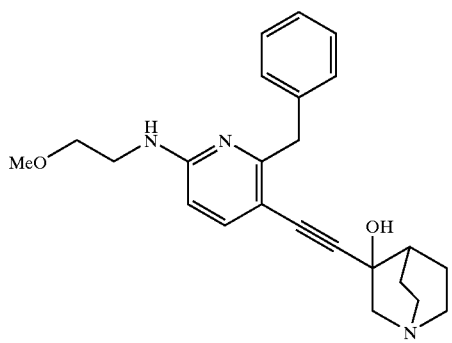
Example 76
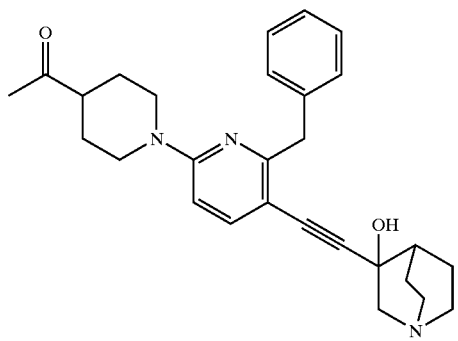
Example 77
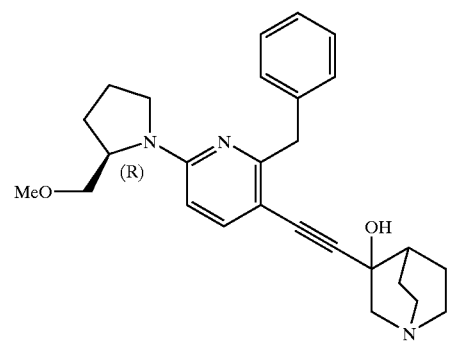
Example 78
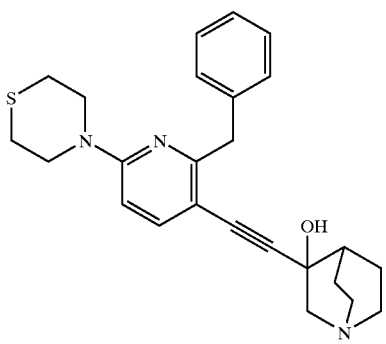
Example 79
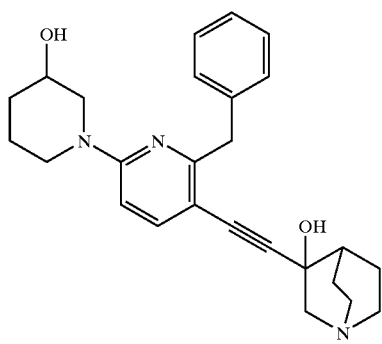

Example 80
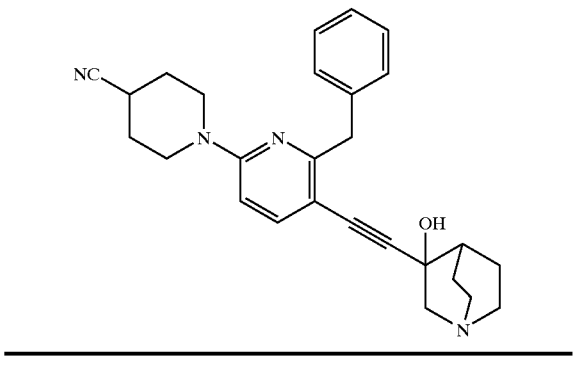
TABLE 7
Example 81
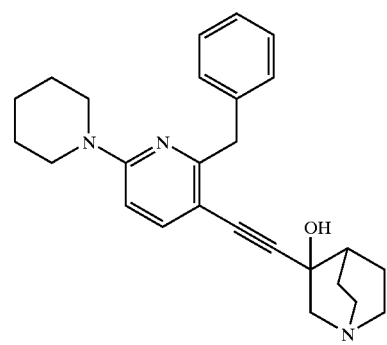
Example 82
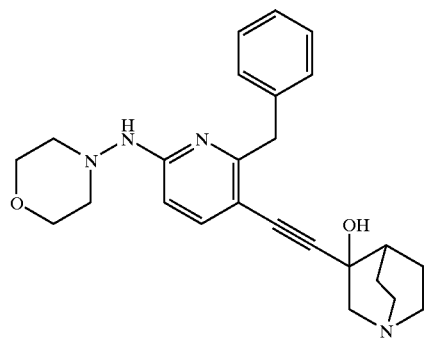
Example 83
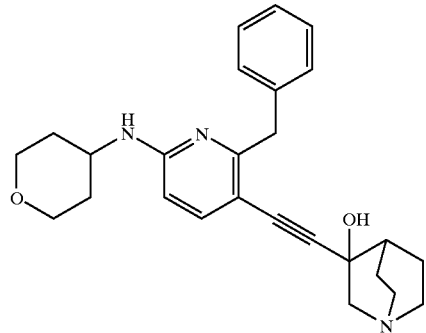
Example 84
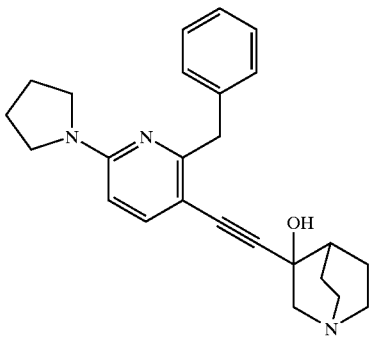
Example 85
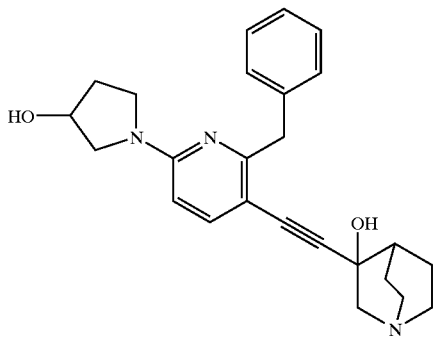
Example 86
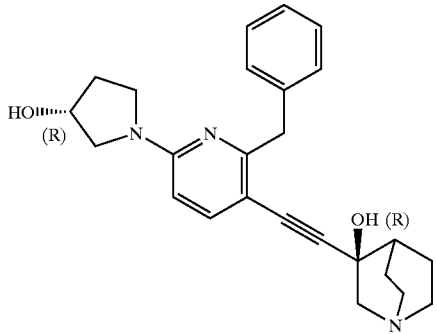
Example 87
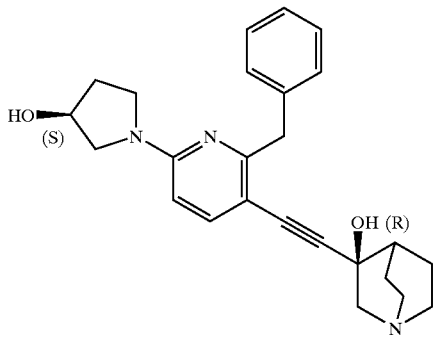

Example 88
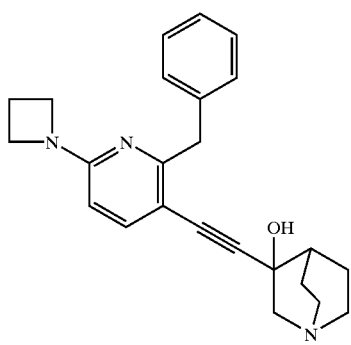
Example 89
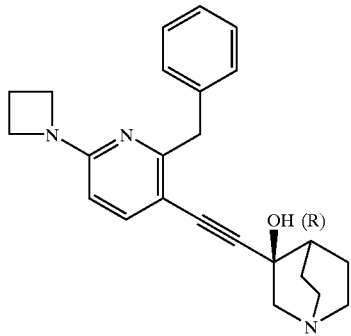
Example 90
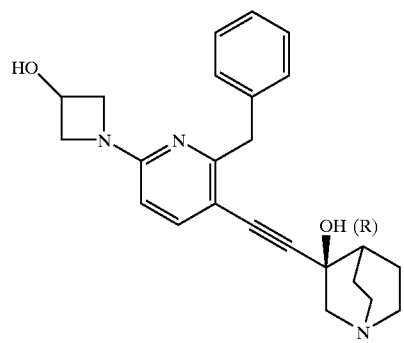
Example 91
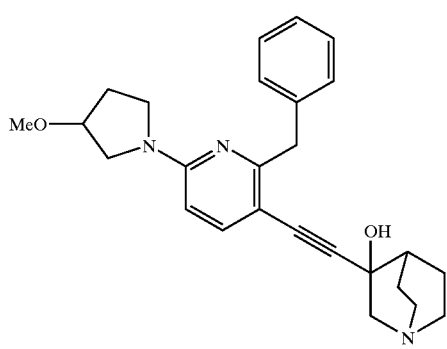
Example 92
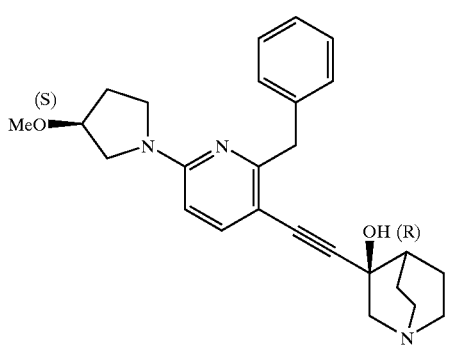
Example 93
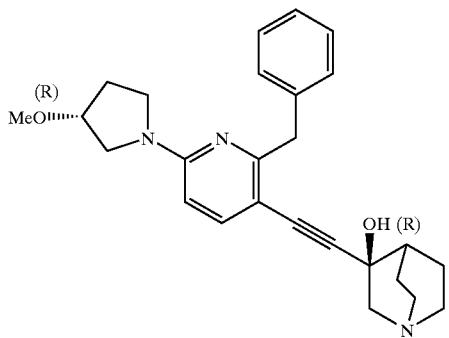
Example 94
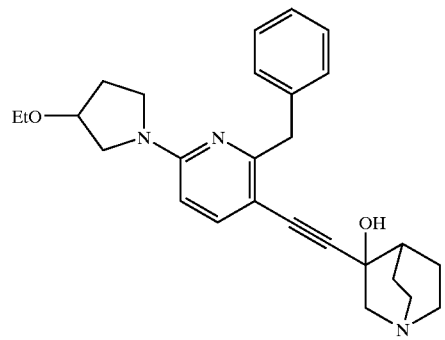
Example 95
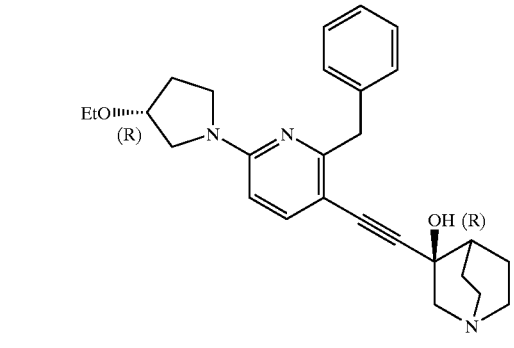

Example 96
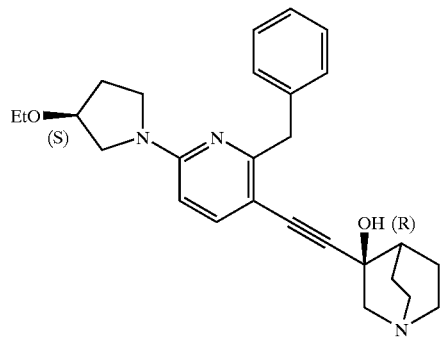
Example 97
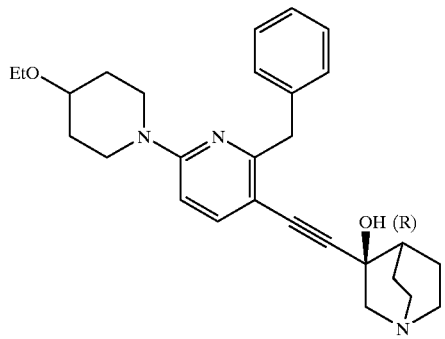
Example 98
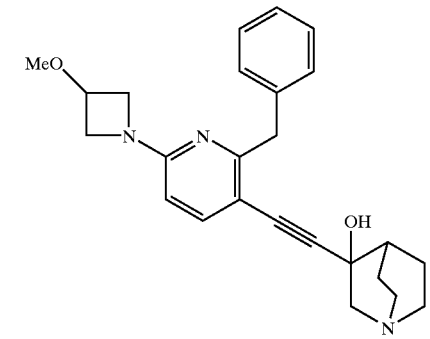
Example 99
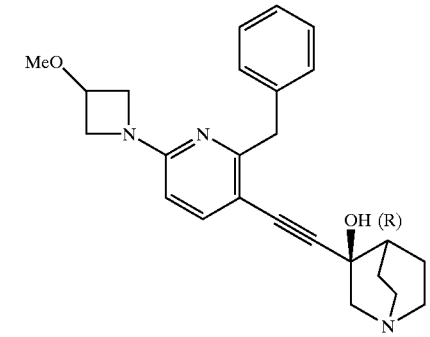
Example 100
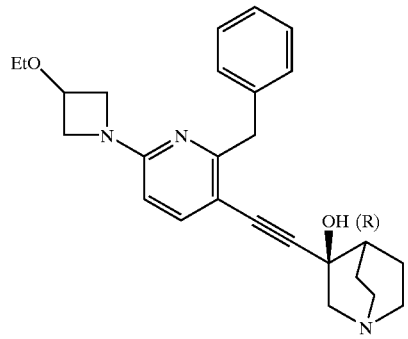
Example 101
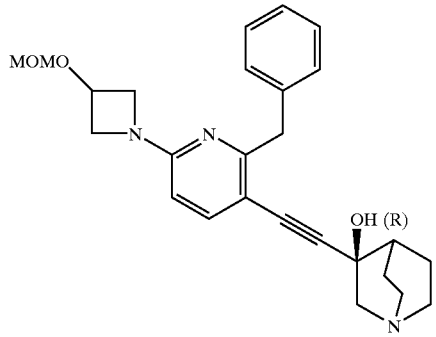
Example 102
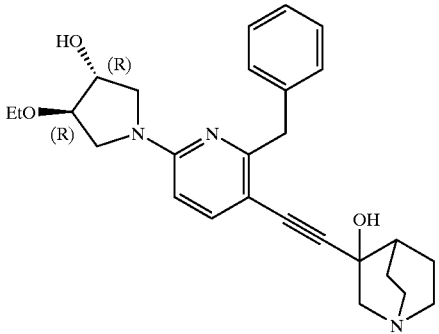
Example 103
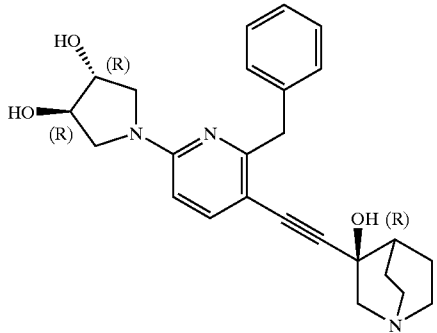

Example 104
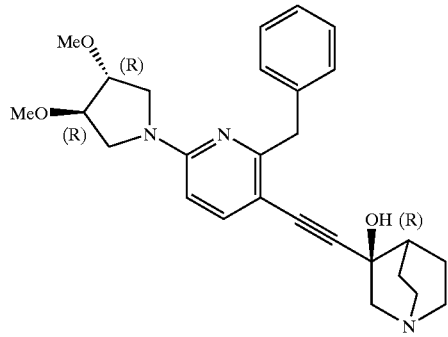
Example 105
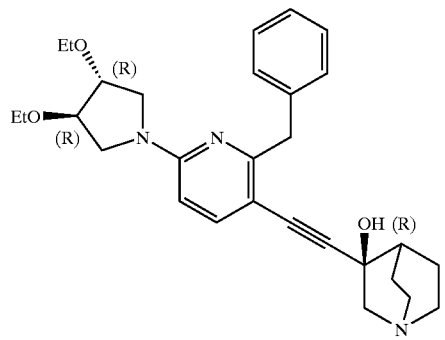
Example 106
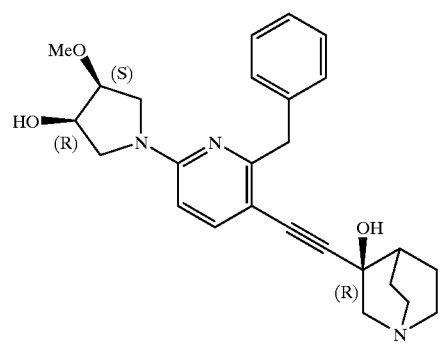
Example 107
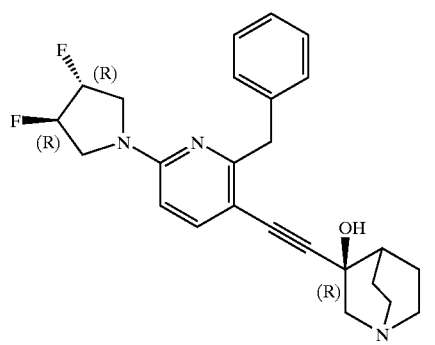
Example 108
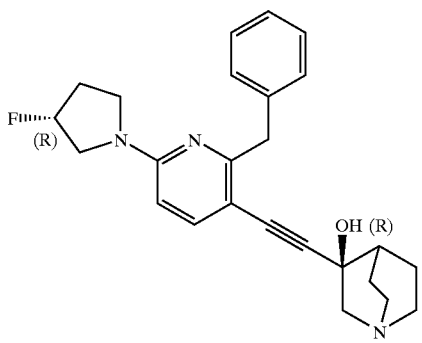
Example 109
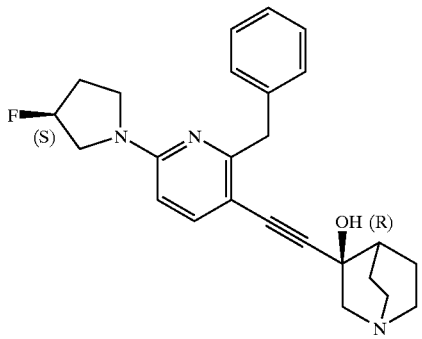
Example 110
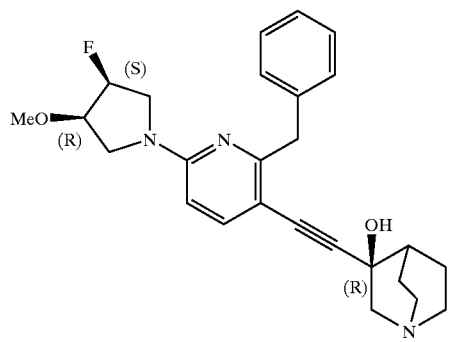
Example 111
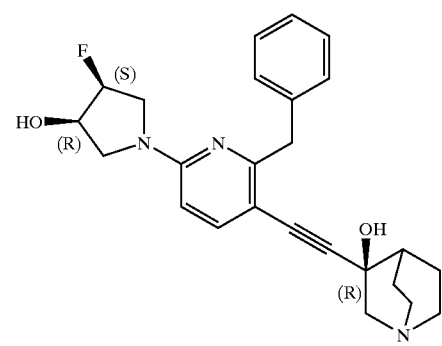

-continued
Example 112
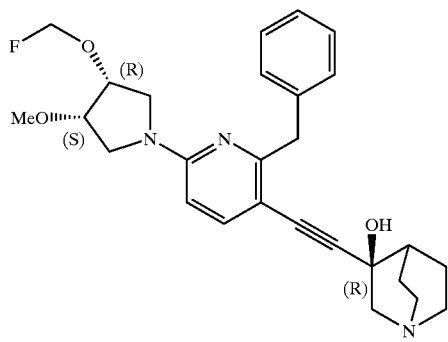
Example 113
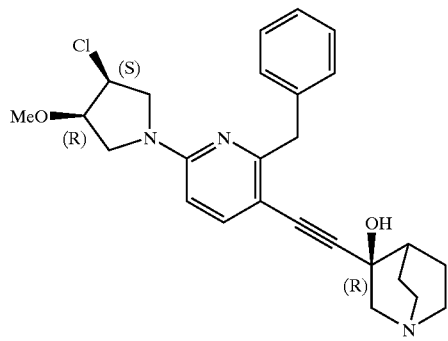
Example 114
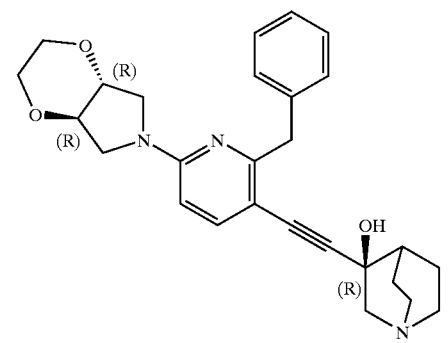
Example 115
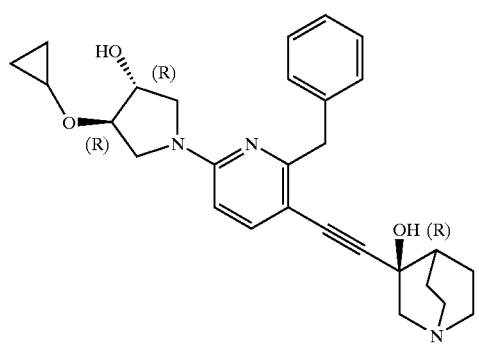
-continued
Example 116
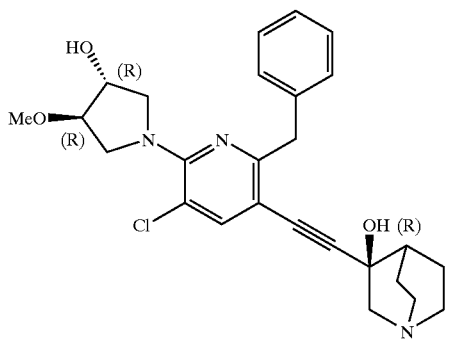
Example 117
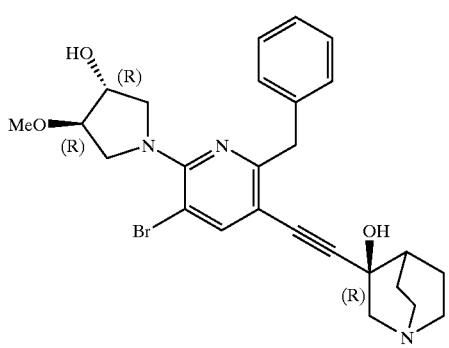
Example 118
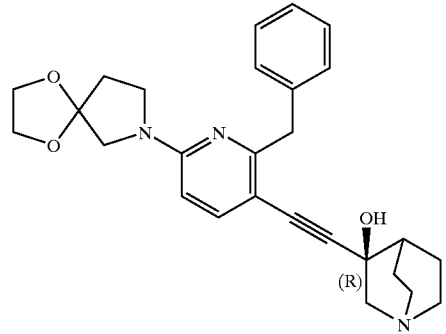
Example 119
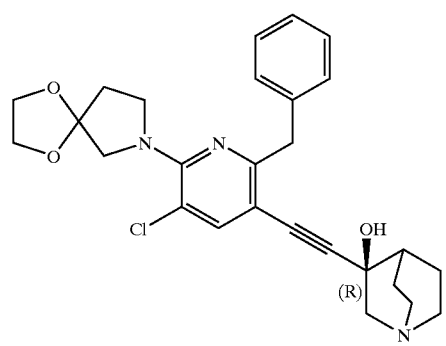

Example 120
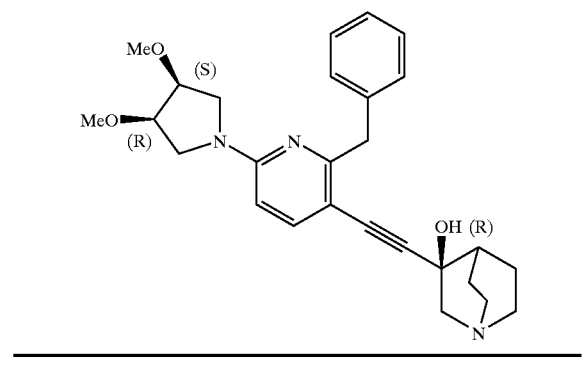
TABLE 8
Example 121
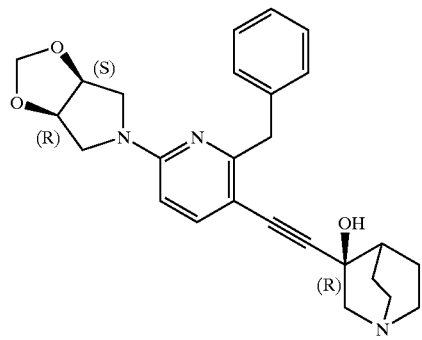
Example 122
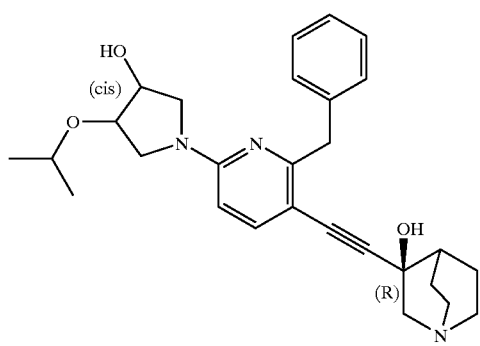
Example 123
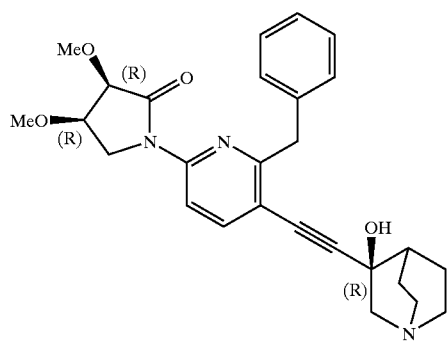
Example 124
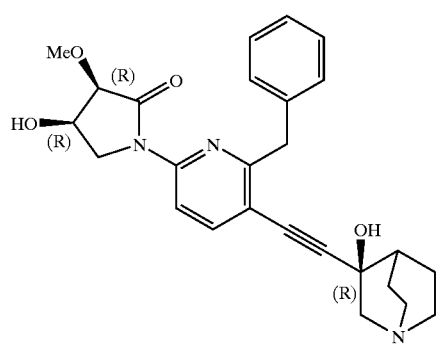
Example 125
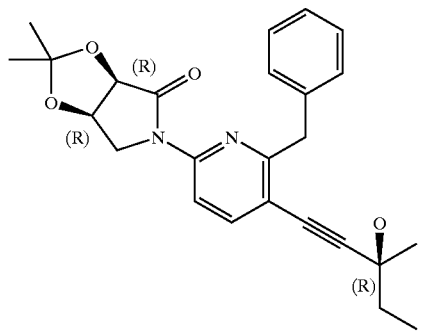
Example 126
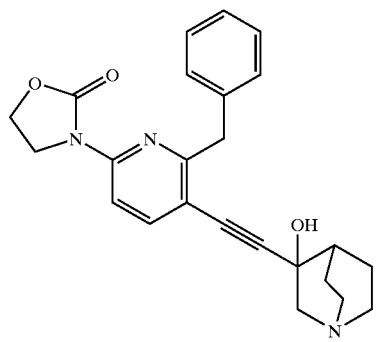
Example 127
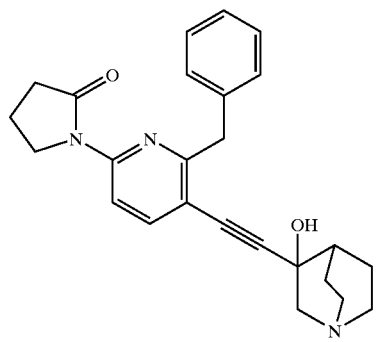

Example 128
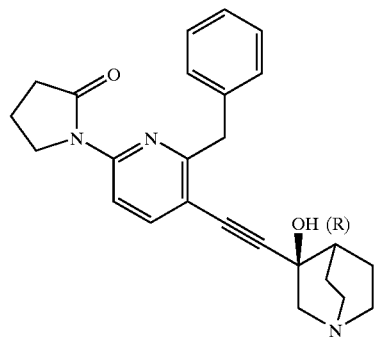
Example 129
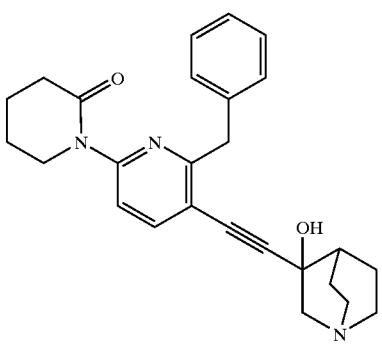
Example 130
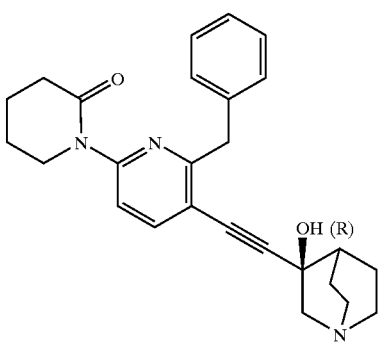
Example 131
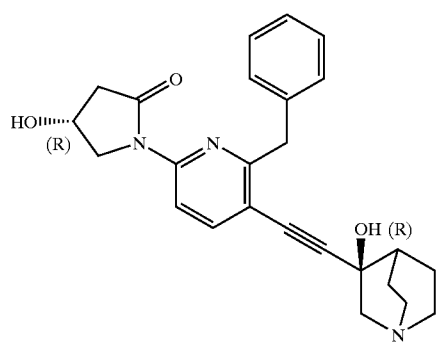
Example 132
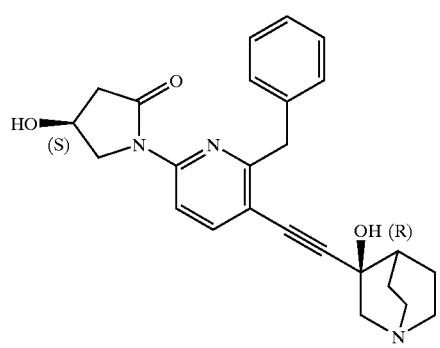
Example 133
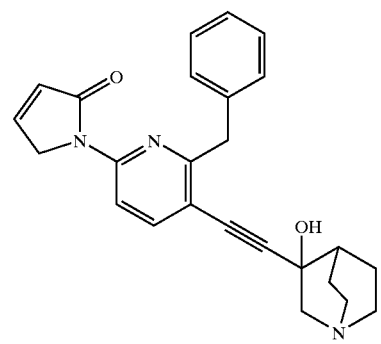
Example 134
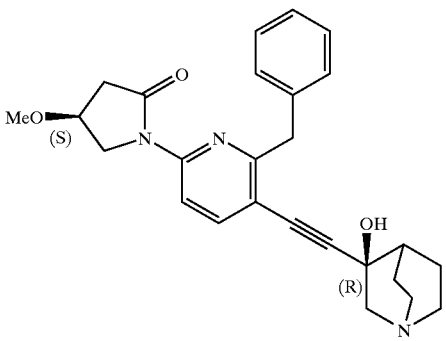
Example 135
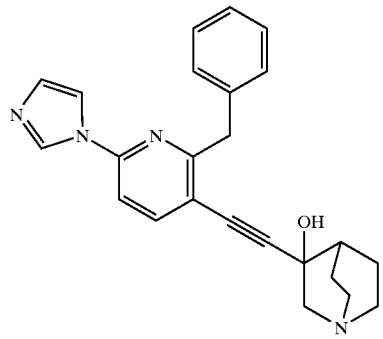

-continued
Example 136
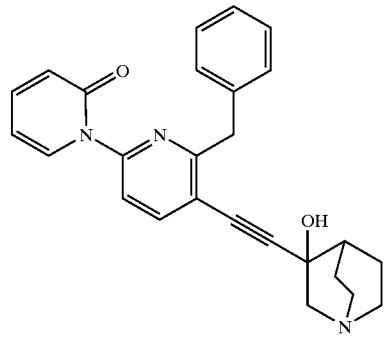
Example 137
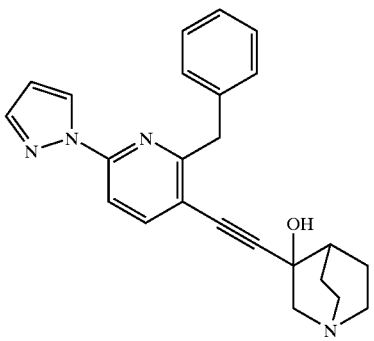
Example 138
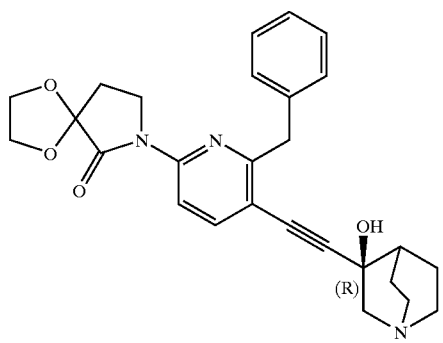
Example 139
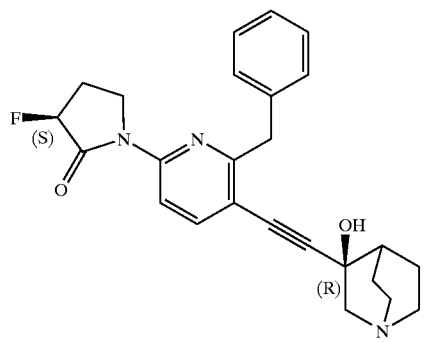
-continued
Example 140
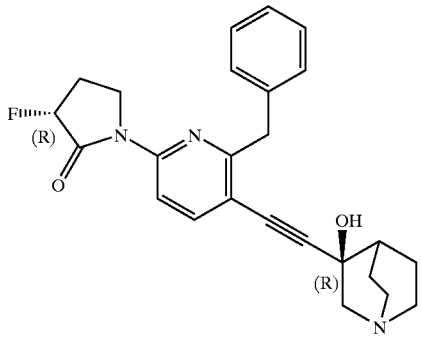
Example 141
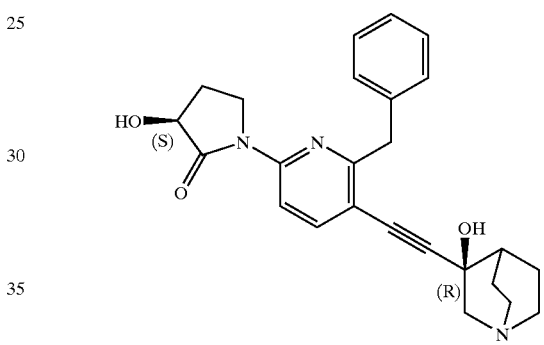
Example 142
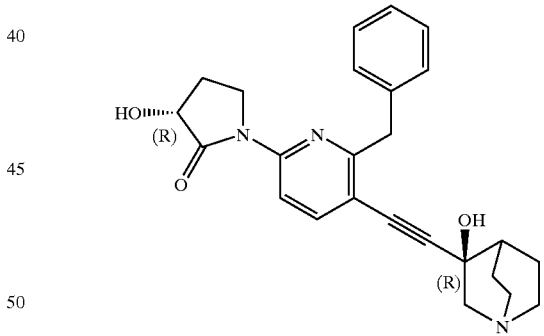
Example 143
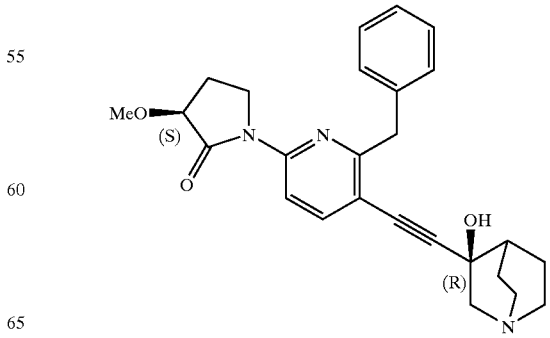

Example 144
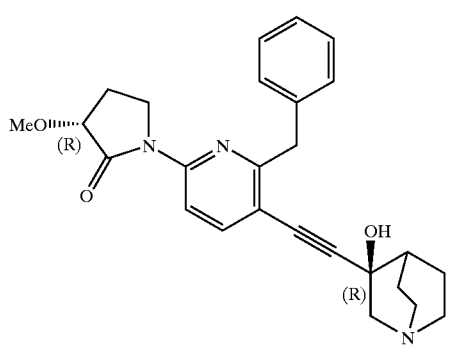
Example 145
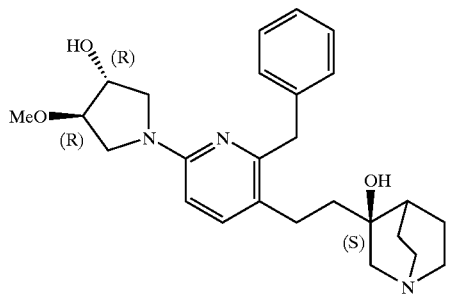
Example 146
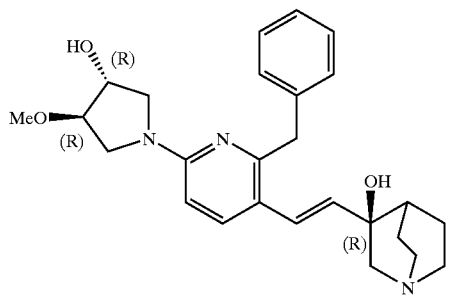
Example 147
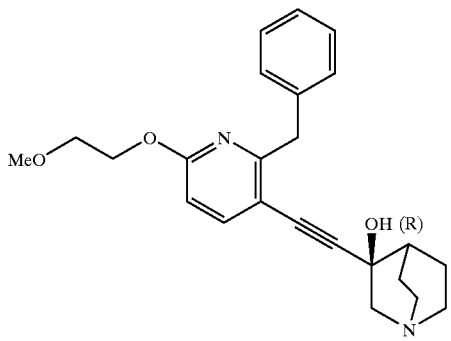
Example 148
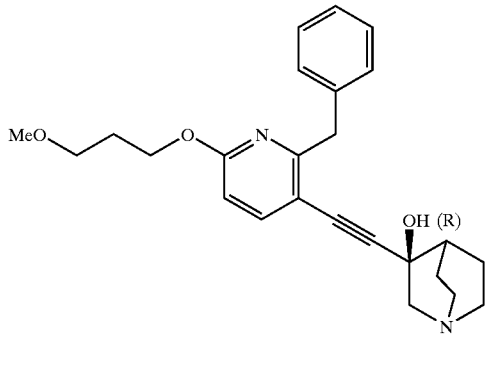
Example 149
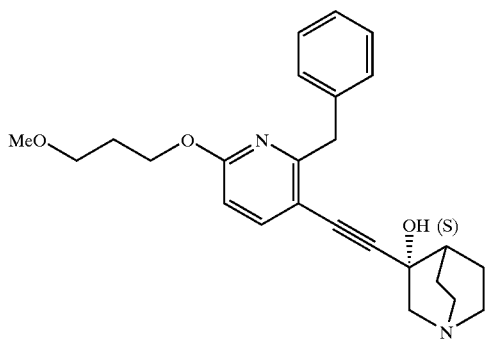
Example 150
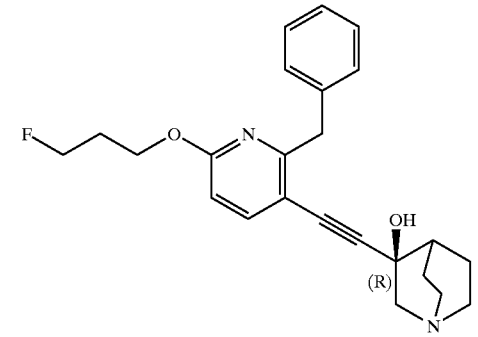
Example 151
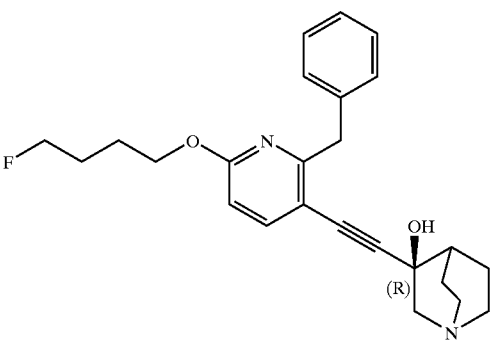

Example 152
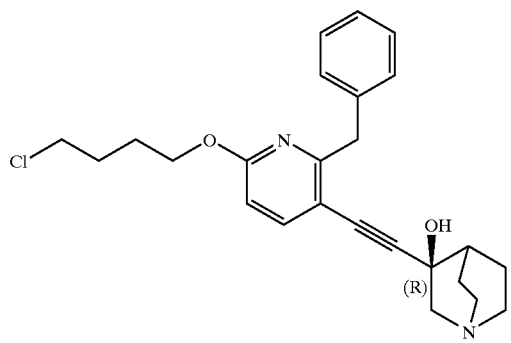
Example 153
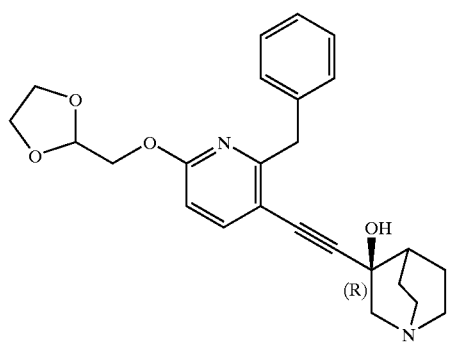
Example 154
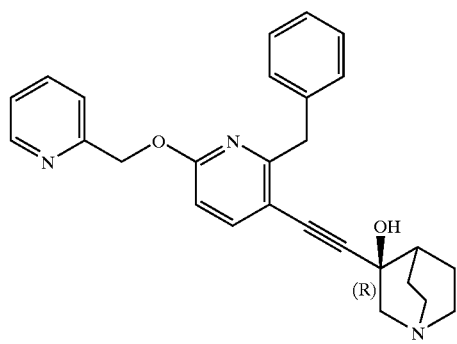
Example 155
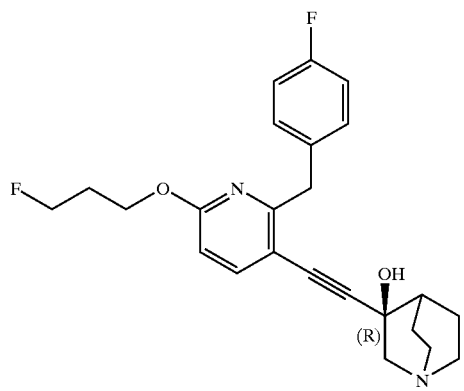
Example 156
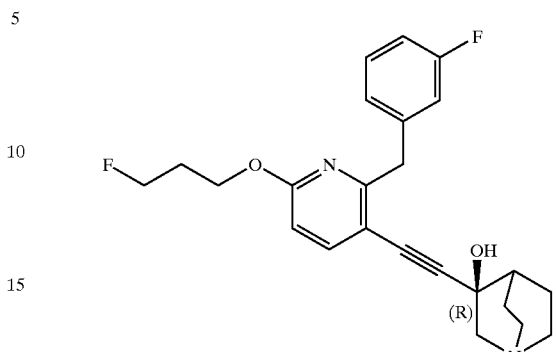
Example 157
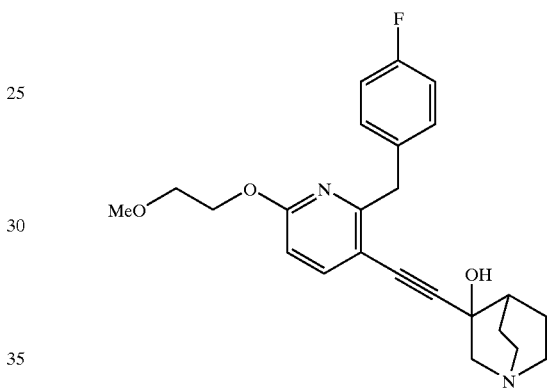
Example 158
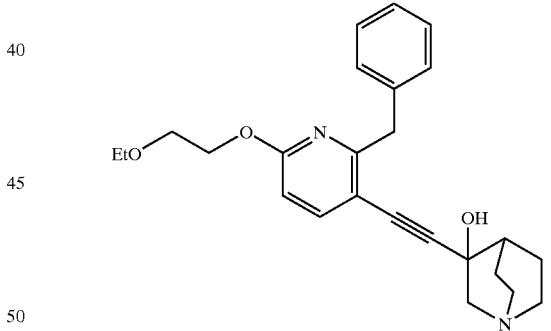
Example 159
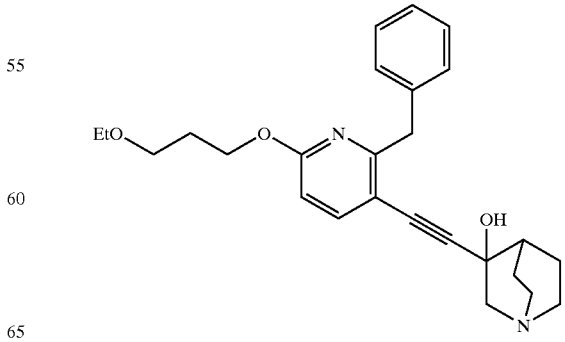

Example 160
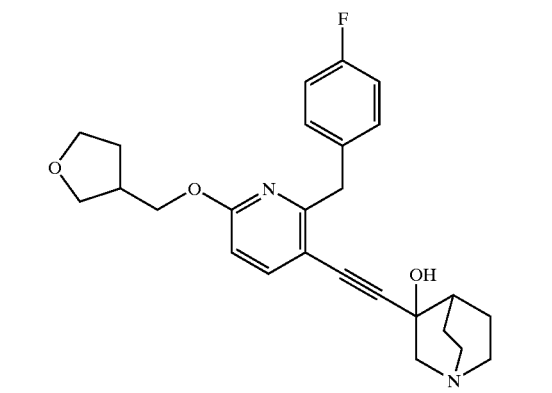
TABLE 9
Example 161
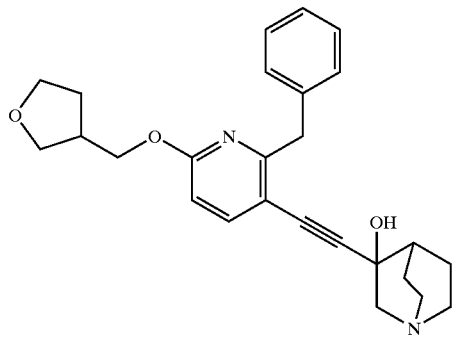
Example 162
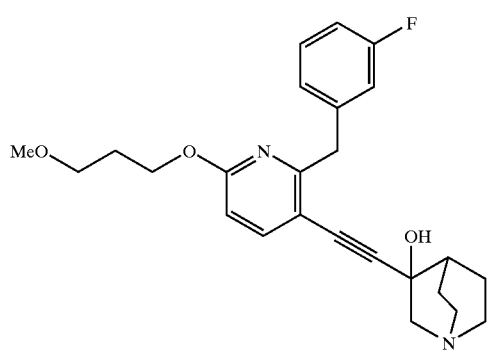
Example 163
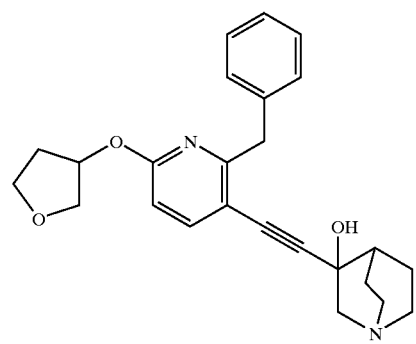
Example 164
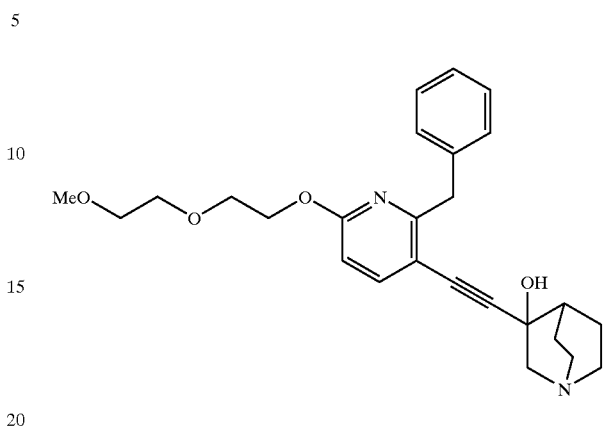
Example 165
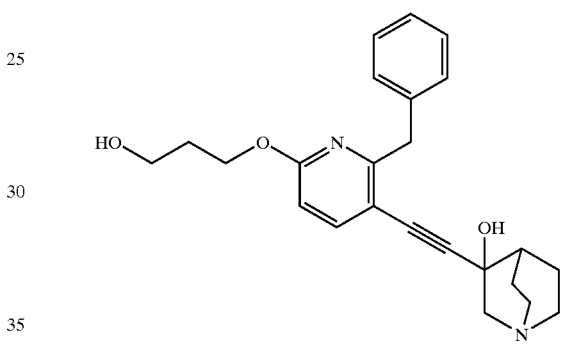
Example 166
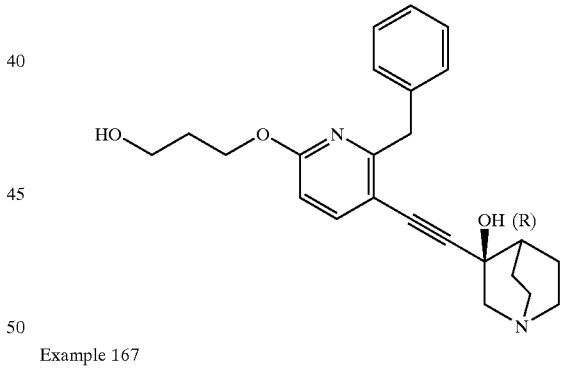
Example 167
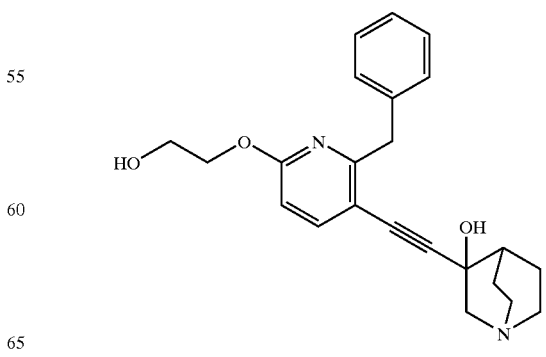

Example 171
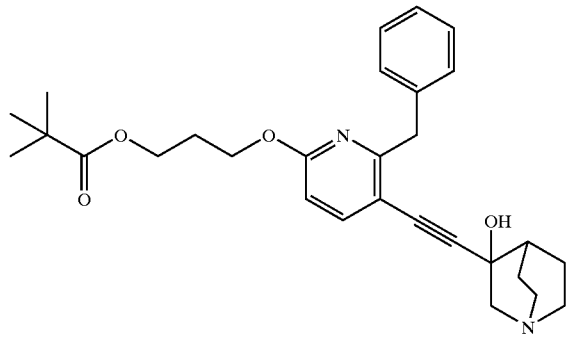
Example 175
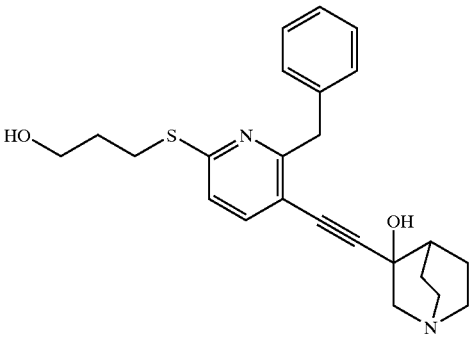
Example 172
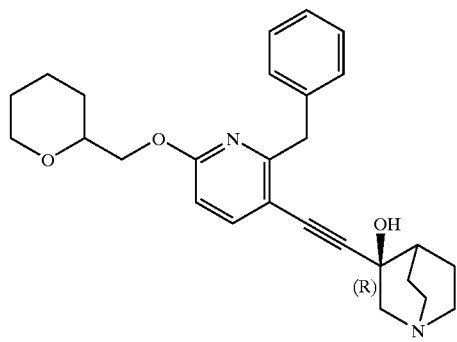
Example 176
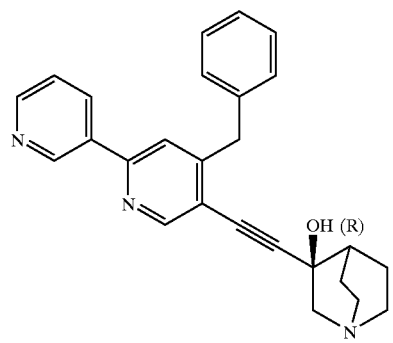
Example 173
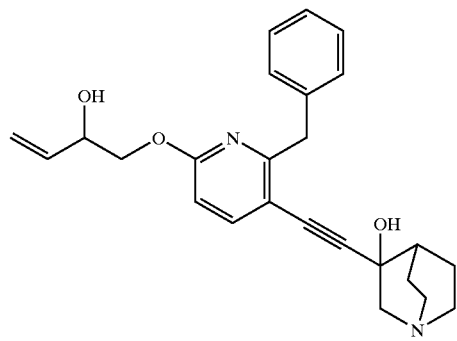
Example 177
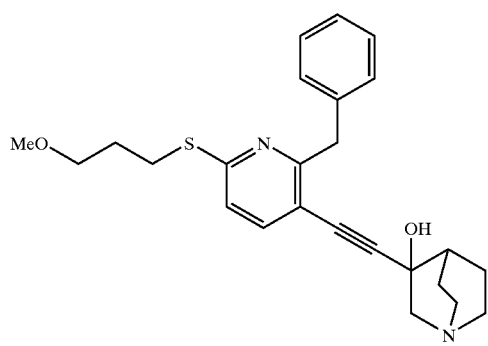
Example 174
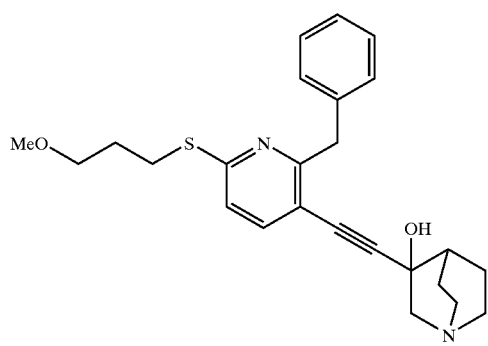
Example 178
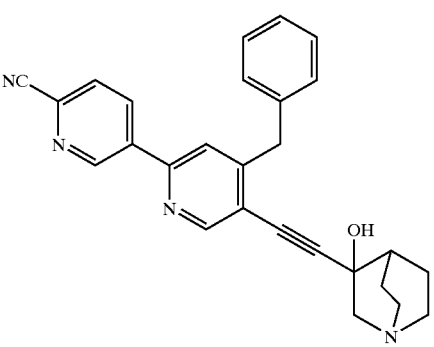

Example 179
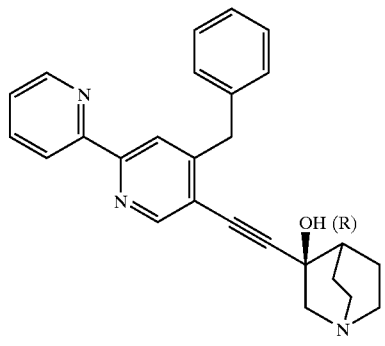
Example 180
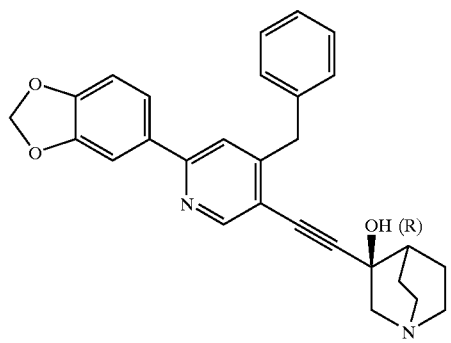
Example 181
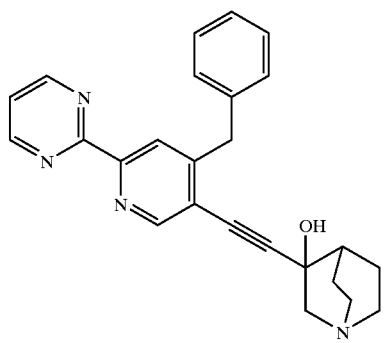
Example 182
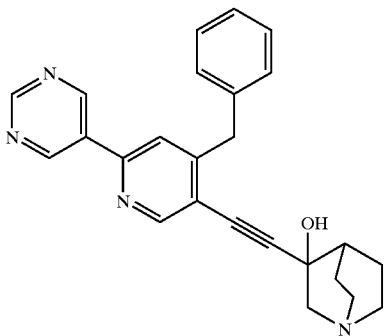
Example 183
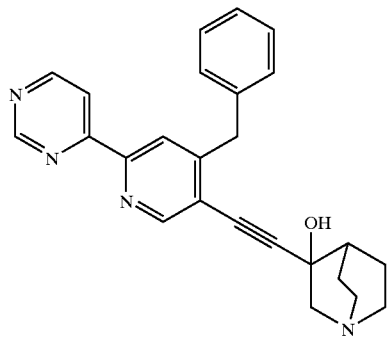
Example 184
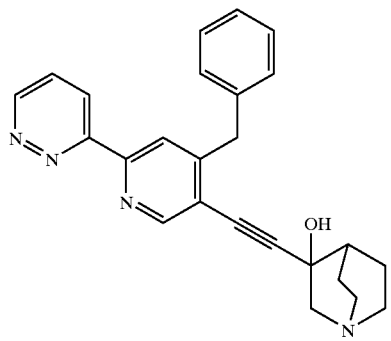
Example 185
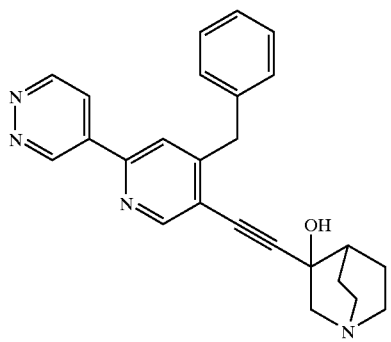
Example 186
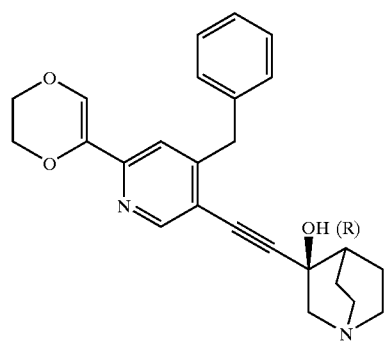

Example 187
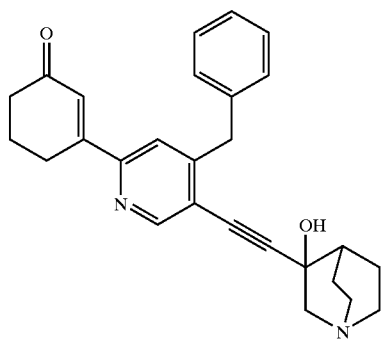
Example 188
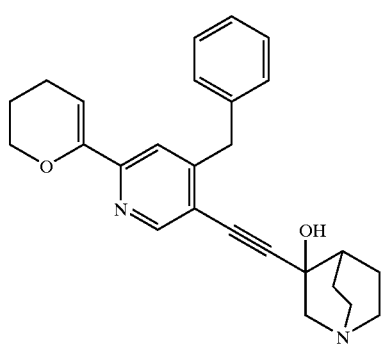
Example 189
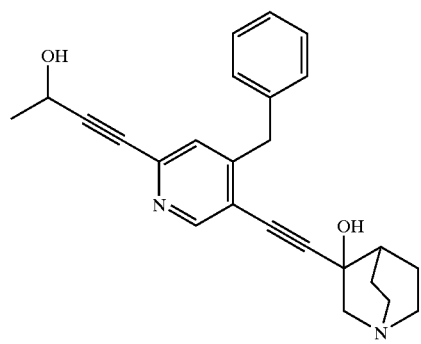
Example 190
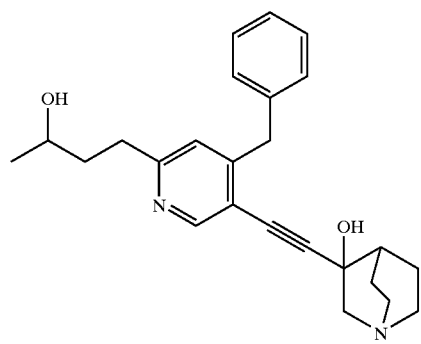
Example 191
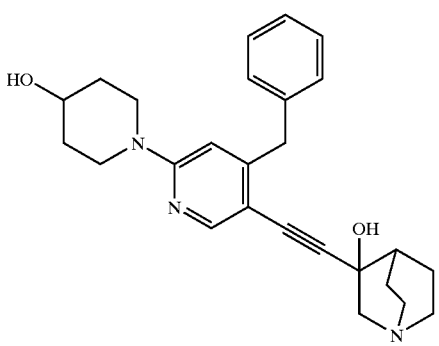
Example 192
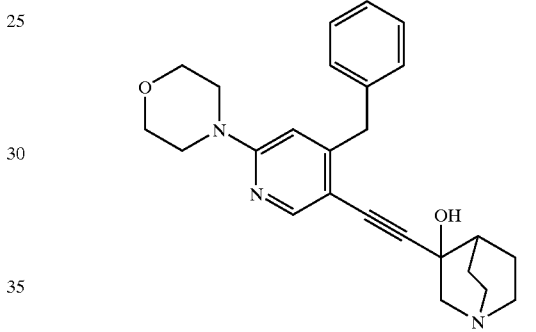
Example 193
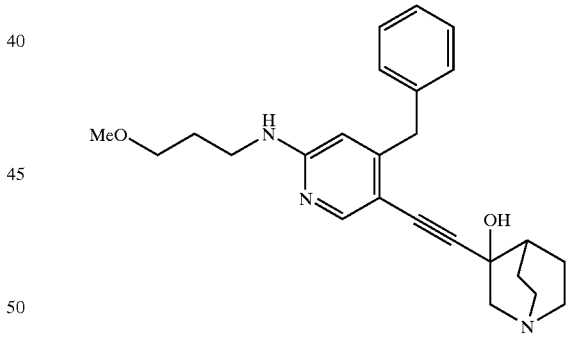
Example 194
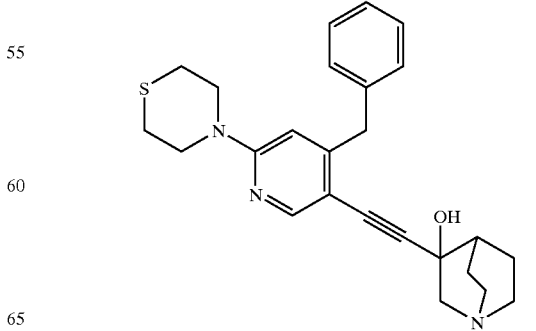

Example 195
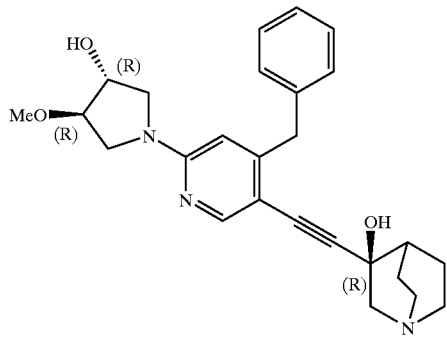
Example 196
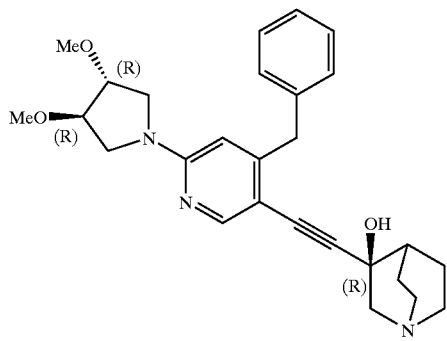
Example 197
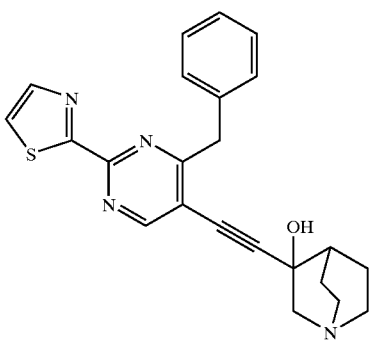
Example 198
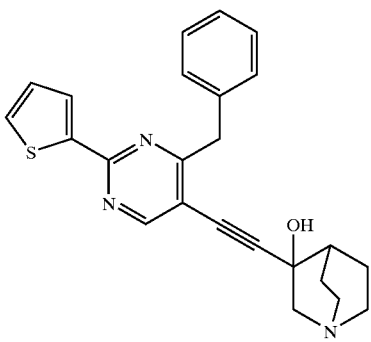
Example 199
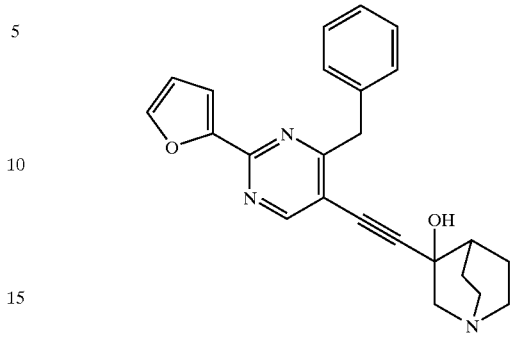
Example 200
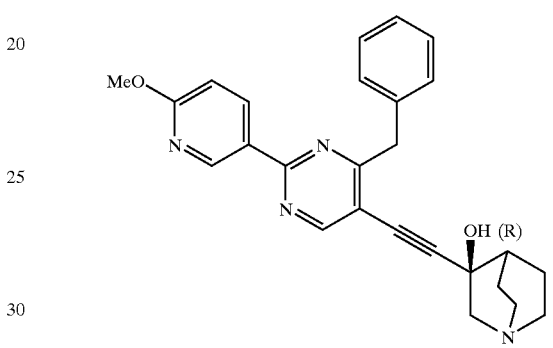
TABLE 10
Example 201
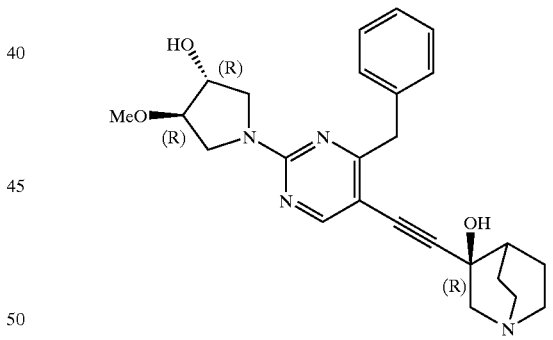
Example 202
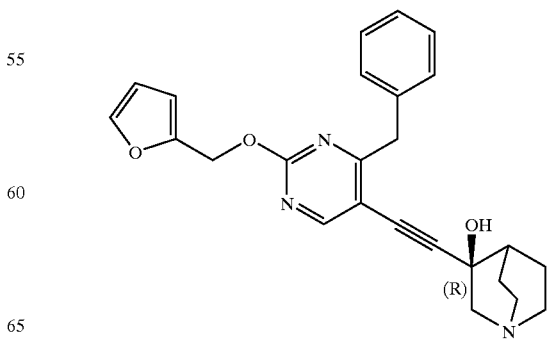

Example 203
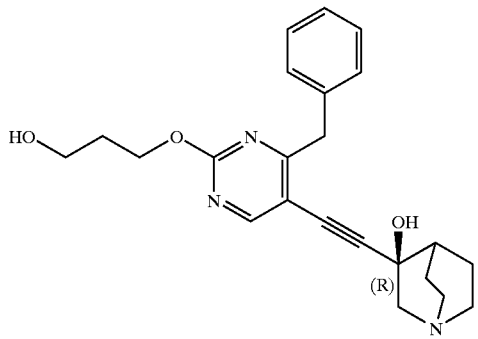
Example 204
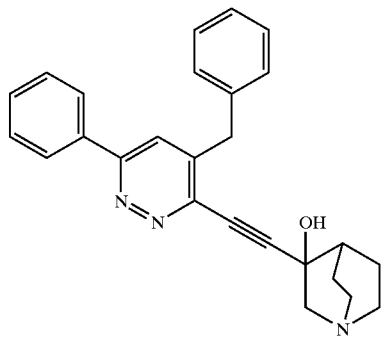
Example 205
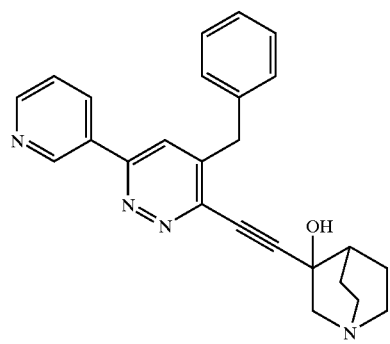
Example 206
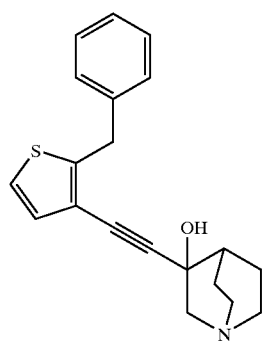
Example 207
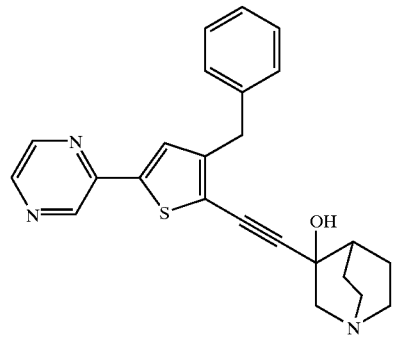
Example 208
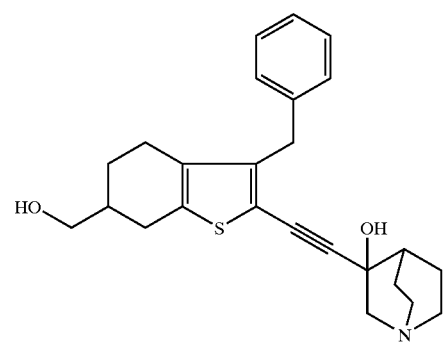
Example 209
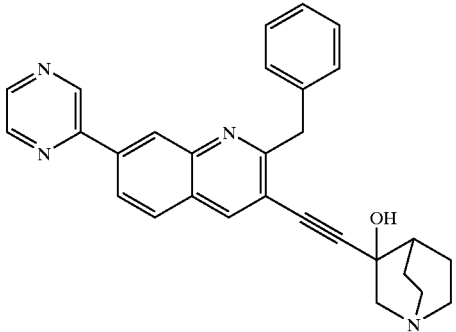
Example 210
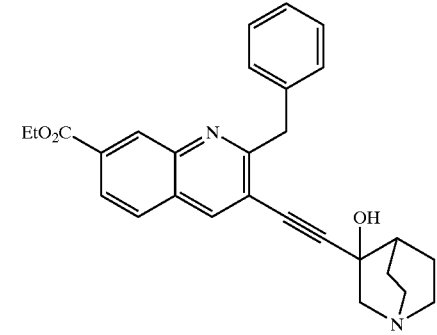

-continued

Example 211

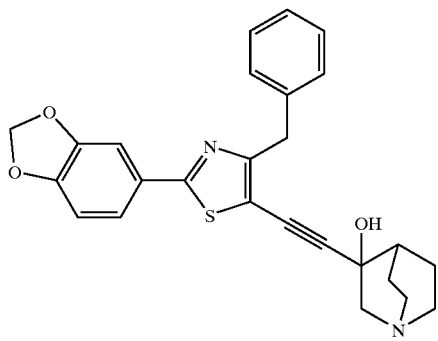

Example 212

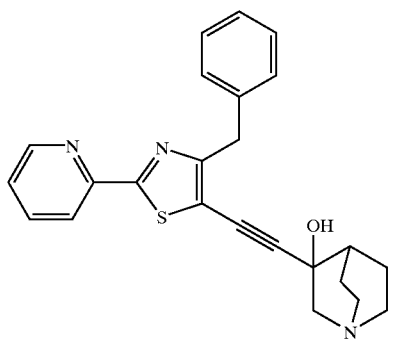

Example 213

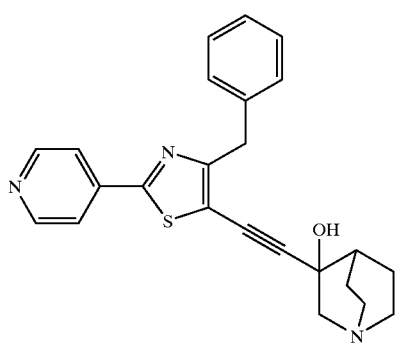

Example 214

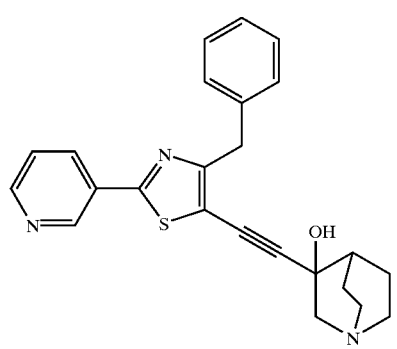

What is claimed is:

1. A compound (I) represented by the following formula, a salt thereof or a hydrate of them:

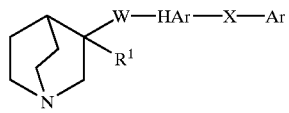

wherein $R^1$ represents (1) hydrogen atom or (2) hydroxyl group; HAr represents an aromatic heterocycle which may be substituted with 1 to 3 groups;
Ar represents an optionally substituted aromatic ring;
W represents a chain represented by (1) —CH$_2$—CH$_2$— which may be substituted, (2) —CH=CH— which may be substituted, (3) —C≡C—, (4) —CO—NH—, (5) —NH—CH$_2$—, (6) —CH$_2$—NH—, (7) —CH$_2$—CO—, (8) —CO—CH$_2$—, (9) —NH—S(O)$_l$—, (10) —S(O)$_l$—NH—, (11) —CH$_2$—S(O)$_l$— or (12) —S(O)$_l$—CH$_2$—, wherein l denotes 0, 1 or 2; and
X represents a chain represented by (1) a single bond, (2) an optionally substituted $C_{1-6}$ alkylene chain, (3) an optionally substituted $C_{2-6}$ alkenylene chain, (4) an optionally substituted $C_{2-6}$ alkynylene chain, (5) a formula —Q—, wherein Q represents oxygen atom, sulfur atom, CO or N(R$^2$), wherein R$^2$ represents a $C_{1-6}$ alkyl group or a $C_{1-6}$ alkoxy group, (6) —NH—CO—, (7) —CO—NH—, (8) —NH—CH$_2$—, (9) —CH$_2$—NH—, (10) —CH$_2$—CO—, (11) —CO—CH$_2$—, (12) —NH—S(O)$_m$—, (13) —S(O)$_m$—NH—, (14) —CH$_2$—S(O)$_m$—, (15) —S(O)$_m$—CH$_2$—, wherein m denotes 0, 1 or 2, or (16) —(CH$_2$)$_n$—O—, wherein n denotes an integer from 1 to 6.

2. The compound as claimed in claim 1, a salt thereof or a hydrate of them, wherein $R^1$ represents (1) hydrogen atom or (2) hydroxyl group; HAr is a 5- to 14-membered aromatic heterocycle which contains 1 to 4 atoms selected from nitrogen atom, sulfur atom and oxygen atom and may be substituted with 1 to 3 groups selected from (1) a halogen atom, (2) hydroxyl group, (3) thiol group, (4) nitro group, (5) nitrile group, (6) a $C_{1-6}$ chain hydrocarbon group which may be substituted, (7) a $C_{3-8}$ cyclic hydrocarbon group which may be substituted, (8) a $C_{1-4}$ aromatic cyclic hydrocarbon group which may be substituted, (9) a 5- to 14-membered aromatic heterocyclic group which may be substituted, (10) a 4- to 10-membered non-aromatic heterocyclic group which may be substituted, (11) a $C_{1-6}$ alkoxy group which may be substituted, (12) a $C_{1-8}$ cycloalkyloxy group which may be substituted, (13) a $C_{1-6}$ chain hydrocarbon-thio group which may be substituted, (14) a $C_{3-8}$ cyclic hydrocarbon-thio group which may be substituted, (15) a $C_{6-14}$ aromatic hydrocarbon-oxy group which may be substituted, (16) a 5- to 14-membered heterocycle-oxy group which may be substituted, (17) a $C_{6-14}$ aromatic hydrocarbon-thio group which may be substituted, (18) a 5- to 14-membered heterocycle-thio group which may be substituted, (19) an amino group which may be substituted, (20) azide group, (21) guanidino group, (22) carbamide group, (23) formyl group, (24) a $C_{1-6}$ imidoyl group which may be substituted, (25) a substituted carbonyl group, (26) a substituted carbonyl-oxy group, (27) a carboxyl group which may form a salt, (28) a carbamoyl group which may be substituted, (29) a $C_{1-4}$ alkylenedioxy group which may be substituted, (30) a sulfinyl group which may be substituted and (31) a sulfonyl group which may be substituted; Ar is a $C_{6-14}$ aromatic hydrocarbon ring or a 5- to 14-membered aromatic heterocycle which may be substituted with one or more groups selected from (1) hydroxyl group, (2) a halogen atom, (3) a $C_{1-6}$ chain hydrocarbon group which may be substituted, (4) a $C_{3-8}$ cyclic hydrocarbon group which may be substituted, (5) a $C_{1-6}$ alkoxy group which may be substituted, (6) a $C_{3-8}$ cycloalkyloxy group which may be substituted, (7) a $C_{1-6}$ chain hydrocarbon-thio group which may be substituted, (8) a $C_{3-8}$ cyclic hydrocarbon-thio group, (9) a $C_{1-4}$ aromatic hydrocarbon cyclic group which may be substituted, (10) a 5- to 14-membered heterocyclic group which may be substituted, (11) an amino group which may be substituted with a $C_{1-6}$ alkyl group and (12) a $C_{1-4}$ alkylenedioxy group; W is a chain represented by (1) —$CH_2$—$CH_2$— which may be substituted, (2) —CH=CH— which may be substituted, (3) —C≡C—, (4) —CO—NH—, (5) —NH—$CH_2$—, (6) —$CH_2$—NH—, (7) —$CH_2$—CO—, (8) —CO—$CH_2$—, (9) —NH—S(O)$_l$—, (10) —S(O)$_l$—NH—, (11) —$CH_2$—S(O)— or (12) —S(O)—$CH_2$—(l denotes 0, 1 or 2); and X represents a chain represented by (1) a single bond, (2) a $C_{1-6}$ alkylene chain which may be substituted, (3) a $C_{2-6}$ alkenylene chain which may be substituted, (4) a $C_{2-6}$ alkynylene chain which may be substituted, (5) the formula —Q— (wherein Q represents oxygen atom, sulfur atom, CO or $N(R^2)$ (wherein $R^2$ represents a $C_{1-6}$ alkyl group or a $C_{1-6}$ alkoxy group)), (6) —NH—CO—, (7) —CO—NH—, (8) —NH—$CH_2$—, (9) —$CH_2$—NH—, (10) —$CH_2$—CO—, (11) —CO—$CH_2$—, (12) —NH—S(O)$_m$—, (13) —S(O)$_m$—NH—, (14) —$CH_2$—S(O)$_m$—, (15) —S(O)$_m$—$CH_2$— (wherein m denotes 0, 1 or 2) or (16) —$(CH_2)_n$—O—

3. The compound as claimed in claim 1 or 2, a salt thereof or a hydrate of them, in which $R^1$ is hydroxyl group.

4. The compound as claimed in claim 1 or 2, a salt thereof or a hydrate of them, in which W is —$CH_2$—$CH_2$—, —CH=CH— or —C≡C—.

5. The compound as claimed in claim 1 or 2, a salt thereof or a hydrate of them, in which X is a single bond, —$CH_2$—, —$CH_2$—$CH_2$—, —CH=CH— or —CO—.

6. The compound as claimed in claim 1 or 2, a salt thereof or a hydrate of them, wherein HAr is a 5- to 14-membered aromatic heterocycle containing 1 to 4 atoms selected from nitrogen atom, sulfur atom and oxygen atom and may be substituted with 1 to 3 groups selected from (1) hydroxyl group, (2) a halogen atom, (3) thiol group, (4) nitro group, (5) nitrile group, (6) a $C_{1-6}$ alkyl group, $C_{2-6}$ alkenyl group or $C_{2-6}$ alkynyl group, which may be substituted with one or two groups selected from (a) a hydroxyl group which may be protected, (b) a halogen atom, (c) nitrile group, (d) carboxyl group, (e) a $C_{3-8}$ cycloalkyl group, $C_{3-8}$ cycloalkenyl group or $C_{3-8}$ cycloalkynyl group, which may be hydroxylated or halogenated, (f) a $C_{1-6}$ alkoxy group which may be substituted with a group selected from a halogen atom, hydroxyl group, a $C_{6-14}$ aryl group, a 5- to 14-membered heteroaryl group and a $C_{6-14}$ aryl-$C_{1-6}$ alkoxy group, (g) a $C_{3-8}$ cycloalkyloxy group which may be halogenated or hydroxylated, (h) a $C_{3-8}$ cycloalkenyloxy group which may be halogenated or hydroxylated, (i) a 5- to 14 membered aryl-oxy group which may be halogenated or hydroxylated, (j) a 5- to 14 membered non-aromatic cycleoxy group which may be halogenated or hydroxylated, (k) a $C_{1-6}$ alkoxy-carbonyl group, (l) a $C_{1-4}$ alkylenedioxy group which may be halogenated, (m) a $C_{1-6}$ alkanoyl group which may be substituted with a group selected from hydroxyl group, a $C_{1-6}$ alkoxy group and a $C_{1-6}$ alkanoyloxy group, (n) a $C_{6-14}$ aryl group which may be substituted with a group selected from a halogen atom, a $C_{1-6}$ alkyl group and a $C_{1-6}$ alkoxy group, (o) a 5- to 14-membered aromatic heterocyclic group which may be substituted with a group selected from a halogen atom, a $C_{1-6}$ alkyl group, a $C_{3-8}$ alkenyl group, a $C_{3-8}$ alkynyl group and a $C_{1-6}$ alkoxy group, (p) a 5- to 10-membered non-aromatic heterocyclic group which may be substituted with a group selected from a halogen atom, a $C_{1-6}$ alkyl group, a $C_{3-8}$ alkenyl group, a $C_{3-8}$ alkynyl group and a $C_{1-6}$ alkoxy group, (q) a group $(EtO)_2PO$—, (r) acetyl group, (s) a sulfonyl group which may be substituted with a group selected from a $C_{1-6}$ hydrocarbon group, a mono-($C_{1-6}$ hydrocarbon)-amino group and a di-($C_{1-6}$ hydrocarbon)-amino group, (t) an amino group which may be substituted with a $C_{1-6}$ hydrocarbon group, (u) a $C_{1-6}$ hydrocarbon group-thio group which may be hydroxylated or halogenated and (v) a carbamoyl group which may be substituted with a $C_{1-6}$ hydrocarbon group, (7) a $C_{3-8}$ cycloalkyl group or $C_{3-8}$ cycloalkenyl group which may be substituted with one or two groups selected from (a) hydroxyl group, (b) a halogen atom, (c) nitrile group, (d) carboxyl group, (e) a $C_{1-6}$ alkyl group which may be substituted with a group selected from a $C_{1-6}$ alkoxy group which may be hydroxylated or halogenated, a $C_{1-6}$ hydrocarbon-thio group which may be halogenated, an amino group which may be substituted with a $C_{1-6}$ hydrocarbon group and a $C_{1-6}$ alkanoyl group, (f) a $C_{1-6}$ alkenyl group which may be substituted with a group selected from a $C_{1-6}$ alkoxy group which may be hydroxylated or halogenated, a $C_{1-6}$ hydrocarbon-thio group which maybe halogenated, an amino group which may be substituted with a $C_{1-6}$ hydrocarbon group and a $C_{1-6}$ alkanoyl group, (g) a $C_{1-6}$ alkynyl group which may be substituted with a group selected from a $C_{1-6}$ alkoxy group which may be hydroxylated or halogenated, a $C_{1-6}$ hydrocarbon-thio group which may be halogenated, an amino group which may be substituted with a $C_{1-6}$ hydrocarbon group and a $C_{1-6}$ alkanoyl group, (h) an amino group which may be substituted with a group selected from a $C_{1-6}$ alkoxy group which may be hydroxylated or halogenated, a $C_{1-6}$ hydrocarbon-thio group which may be halogenated, a $C_{1-6}$ alkanoyl group and a $C_{1-6}$ hydrocarbon group, (i) a $C_{1-6}$ alkoxy group which may be substituted with a group selected from a $C_{1-6}$ alkyl group which may be hydroxylated or halogenated, a $C_{1-6}$ alkoxy group which may be hydroxylated or halogenated, a $C_{1-6}$ hydrocarbon-thio group which may be halogenated, an amino group which may be substituted with a $C_{1-6}$ hydrocarbon group and a $C_{1-6}$ alkanoyl group, (j) a $C_{1-6}$ hydrocarbon-thio group which may be substituted with a group selected from a $C_{1-6}$ alkyl group which may be hydroxylated or halogenated, a $C_{1-6}$ alkenyl group which may be halogenated, a $C_{1-6}$ alkynyl group which may be halogenated, a $C_{1-6}$ alkoxy group which may be hydroxylated or halogenated, a $C_{1-6}$ hydrocarbon-thio group which may be halogenated, an amino group which may be substituted with a $C_{1-6}$ hydrocarbon group and a $C_{1-6}$ alkanoyl group, (k) a $C_{1-6}$ alkanoyl group which may be substituted with a group selected from hydroxyl group, a $C_{1-6}$ alkoxy group and a $C_{1-6}$ alkanoyloxy group, (l) a $C_{6-14}$ aryl group which may be substituted with a group selected from a halogen atom, a $C_{1-6}$ alkyl group and a $C_{1-6}$ alkoxy group, (m) a 5- to 14-membered aromatic heterocyclic group which may be substituted with a group selected from a halogen atom, a $C_{1-6}$ alkyl group, a $C_{3-8}$ alkenyl group, a $C_{3-8}$ alkynyl group and a $C_{1-6}$ alkoxy group, (n) a non-aromatic heterocyclic group which may be substituted with a group selected from a halogen atom, a $C_{1-6}$ alkyl group, a $C_{3-8}$ alkenyl group, a $C_{3-8}$ alkynyl group and a $C_{1-6}$ alkoxy group, (o) a $C_{1-6}$ alkoxy-carbonyl group, (p) a $C_{1-4}$ alkylenedioxy group which may be halogenated, (q) a group $(EtO)_2PO$— and (r) acetyl group, (8) a $C_{6-14}$ aromatic hydrocarbon group which may be substituted with one or more groups selected from (a) hydroxyl group, (b) a halogen atom, (c) a $C_{1-6}$ alkyl-sulfonyl group, $C_{1-6}$ alkenyl-sulfonyl group and $C_{1-6}$ alkynyl-sulfonyl group, which may be halogenated, (d) a $C_{1-4}$ alkylenedioxy group which may be halogenated, (e) a $C_{1-6}$ alkoxy group which may be halogenated, (f) a $C_{1-6}$ hydrocarbon-thio group which may be halogenated, (g) a $C_{1-6}$ alkoxy-carbonyl group, (h) a $C_{6-14}$ aryl-$C_{1-6}$ alkoxy group, (i) a $C_{1-7}$ alkanoylamino group, (j) a $C_{1-6}$ alkyl-carbamoyl group, (k) a $C_{1-6}$ alkenyl-carbamoyl group, (l) a $C_{1-6}$ alkynyl-carbamoyl group and (m) an amino group which may be substituted with a $C_{1-6}$ hydrocarbon group, (9) a 5- to 14-membered aromatic-heterocyclic group which may be substituted with one or more groups selected from (a) hydroxyl group, (b) a halogen atom, (c) nitrile group, (d) a $C_{1-6}$ alkyl group, $C_{1-6}$ alkenyl group or $C_{1-6}$ alkynyl group, which may be halogenated, (e) a $C_{1-6}$ alkoxy group which may be halogenated, (f) a $C_{1-6}$ alkylthio group, $C_{1-6}$ alkenylthio group or $C_{1-6}$ alkynylthio group which may be halogenated, (g) a $C_{1-6}$ alkoxy-$C_{1-6}$ alkyl group, (h) acetyl group, (i) an $C_{1-6}$ alkanoyl group, (j) a mono-($C_{1-6}$ hydrocarbon)-amino group, (k) a di-($C_{1-6}$ hydrocarbon)-amino group and (l) a tri-($C_{1-6}$ hydrocarbon)-amino group, (10) a 4- to 10-membered non-aromatic heterocyclic group which may be substituted with one or more groups selected from (a) hydroxyl group, (b) a halogen atom, (c) nitrile group, (d) a $C_{1-6}$ alkyl group, $C_{1-6}$ alkenyl group or $C_{1-6}$ alkynyl group, which may be halogenated, (e) a $C_{1-6}$ alkoxy group which may be halogenated, (f) a $C_{1-6}$ alkylthio group, $C_{1-6}$ alkenylthio group or $C_{1-6}$ alkynylthio group, which may be halogenated, (g) a $C_{1-6}$ alkoxy-$C_{1-6}$ alkyl group, (h) acetyl group, (i) a $C_{1-6}$ alkanoyl group, (j) a mono-($C_{1-6}$ hydrocarbon)-amino group, (k) a di-($C_{1-6}$ hydrocarbon)-amino group and (l) a tri-($C_{1-6}$ hydrocarbon)-amino group, (m) a $C_{1-4}$ alkylenedioxy group and (n) an oxo group, (11) a $C_{1-6}$ alkoxy group which may be substituted with one or more groups selected from (a) hydroxyl group, (b) a halogen atom, (c) a $C_{1-6}$ alkyl group, $C_{1-6}$ alkenyl group or $C_{1-6}$ alkynyl group, which may be substituted with a group selected from hydroxyl group, a halogen atom, a 5- to 14-membered aromatic heterocyclic group and a 4 to 10-membered non-aromatic heterocyclic group, (d) a $C_{3-8}$ cycloalkyl group or $C_{3-8}$ cycloalkenyl group which may be hydroxylated or halogenated, (e) a $C_{1-6}$ alkoxy group which may be hydroxylated or halogenated, (f) a $C_{1-6}$ alkylthio group, $C_{1-6}$ alkenylthio group or $C_{1-6}$ alkynylthio group, which may be halogenated, (g) a $C_{3-8}$ cycloalkyloxy group or $C_{3-8}$ cycloalkenyloxy group which may be halogenated, (h) a $C_{3-8}$ cycloalkylthio group or $C_{3-8}$ cycloalkenylthio group which may be halogenated, (i) a $C_{6-14}$ aryl group, (j) a $C_{1-6}$ alkanoyl group which may be halogenated, (k) a 5- to 14-membered aromatic heterocyclic group and (l) a 4- to 10-membered non-aromatic heterocyclic group, (12) a $C_{3-8}$ cycloalkyloxy group which may be substituted with one or two groups selected from (a) hydroxyl group, (b) a halogen atom, (c) a $C_{1-6}$ a hydrocarbon group which may be substituted with a group selected from hydroxyl group, a halogen atom, a $C_{1-6}$ alkoxy group and a $C_{1-6}$ alkanoyl group, (d) a $C_{1-6}$ alkoxy group which may be substituted with a group selected from a halogen atom, a $C_{1-6}$ alkoxy group and a $C_{1-6}$ alkanoyl group and (e) a $C_{1-6}$ hydrocarbon-thio group which may be substituted with a group selected from a halogen atom, a $C_{1-6}$ alkoxy group and a $C_{1-6}$ alkanoyl group, (13) a $C_{1-6}$ alkylthio group, $C_{1-6}$ alkenylthio group or $C_{1-6}$ alkynylthio group, which may be substituted with one or two groups selected from (a) hydroxyl group, (b) a halogen atom, (c) a $C_{1-6}$ alkyl group, $C_{1-6}$ alkenyl group or $C_{1-6}$ alkynyl group which may be substituted with a group selected from hydroxyl group, a halogen atom, a 5- to 14-membered aromatic heterocyclic group and 4- to 10-membered non-aromatic heterocyclic group, (d) a $C_{3-8}$ cycloalkyl group, $C_{3-8}$ cycloalkenyl group or $C_{3-8}$ cycloalkynyl group, which may be hydroxylated or halogenated, (e) a $C_{1-6}$ alkoxy group which may be hydroxylated or halogenated, (f) a $C_{1-6}$ alkylthio group, $C_{1-6}$ alkenylthio group or $C_{1-6}$ alkynylthio group, which may be halogenated, (g) a $C_{3-8}$ cycloalkyloxy group or $C_{3-8}$ cycloalkenyloxy group which may be halogenated, (h) a $C_{3-8}$ cycloalkylthio group or $C_{3-8}$ cycloalkenylthio group which may be halogenated, (i) a $C_{6-14}$ aryl group, (j) a $C_{1-6}$ alkanoyl group which may be halogenated, (k) a 5- to 14-membered aromatic heterocyclic group and (l) a 4- to 10-membered non-aromatic heterocycle, (14) a $C_{3-8}$ cycloalkylthio group or a $C_{3-8}$ cycloalkenylthio group which may be substituted with one or two groups selected from (a) hydroxyl group, (b) a halogen atom, (c) a $C_{3-8}$ alkyl group, $C_{3-8}$ alkenyl group or $C_{3-8}$ alkynyl group, which may be halogenated, (d) a $C_{1-6}$ alkoxy group which may be halogenated, (e) a $C_{1-6}$ hydrocarbon-thio group which may be halogenated and (f) a $C_{1-6}$ alkanoyl group which may be halogenated, (15) an amino group represented by the formula —N(R$^3$)R$^4$ (wherein R$^3$ and R$^4$ are the same as or different from each other and each represents a group selected from (a) an aromatic heterocyclic group, (b) a non-aromatic heterocyclic group, (c) a $C_{1-6}$ alkyl group, $C_{1-6}$ alkenyl group or $C_{1-6}$ alkynyl group, which may be substituted with a halogen atom or a $C_{1-6}$ alkoxy group, (d) a $C_{3-8}$ cycloalkyl group or a $C_{3-8}$ cycloalkenyl group which may be halogenated, (e) a carbonyl group which is substituted with a $C_{1-6}$ alkyl group, $C_{1-6}$ alkenyl group or $C_{1-6}$ alkynyl group, which may be halogenated, a $C_{3-8}$ cycloalkyl group or $C_{3-8}$ cycloalkenyl group, which may be halogenated, a $C_{1-6}$ alkoxy group which may be halogenated, a $C_{6-14}$ aryl group or an aromatic heterocyclic group, (f) a $C_{1-6}$ alkanoyl group which may be substituted with a group selected from a $C_{6-14}$ aryl group and an aromatic heterocyclic group, (g) a carbamoyl group which may be substituted with a $C_{1-6}$ alkyl group, a $C_{1-6}$ alkenyl group, a $C_{1-6}$ alkynyl group, a $C_{6-14}$ aryl group or an aromatic heterocyclic group and (h) a sulfonyl group which is substituted with a $C_{1-6}$ alkyl group, a $C_{1-6}$ alkenyl group or a $C_{1-6}$ alkynyl group, and also, (i) R$^3$ and R$^4$ may be combined and united to form a 3- to 10-membered ring and the cyclic amino group may be substituted with one or more groups selected from hydroxyl group, a halogen atom, a $C_{1-6}$ alkyl group, a $C_{1-6}$ alkenyl group, a $C_{1-6}$ alkynyl group, a $C_{1-6}$ alkoxy group, a $C_{1-6}$ hydrocarbon-thio group and a $C_{1-4}$ alkylenedioxy group), (16) a $C_{6-14}$ aryl-oxy group which may be substituted with one or more groups selected from (a) hydroxyl group, (b) a halogen atom, (c) a $C_{1-6}$ alkyl-sulfonyl group, $C_{1-6}$ alkenyl-sulfonyl group or $C_{1-6}$ alkynyl-sulfonyl group which may be halogenated, (d) a $C_{1-4}$ alkylenedioxy group which may be halogenated, (e) a $C_{1-6}$ alkoxy group which may be halogenated, (f) a $C_{1-6}$ hydrocarbon-thio group which may be halogenated, (g) a $C_{1-6}$ alkoxy-carbonyl group, (h) a $C_{6-14}$ aryl-$C_{1-6}$ alkoxy group, (i) a $C_{1-7}$ alkanoylamino group, (j) a $C_{1-6}$ alkyl-carbamoyl group, (k) a $C_{1-6}$ alkenyl-carbamoyl group, (l) a $C_{1-6}$ alkynyl-carbamoyl group and (m) an amino group which may be substituted with a $C_{1-6}$ hydrocarbon group, (17) a $C_{6-14}$ aryl-thio group which may be substituted with one or more groups selected from (a) hydroxyl group, (b) a halogen atom, (c) a $C_{1-6}$ alkyl-sulfonyl group, $C_{1-6}$ alkenyl-sulfonyl group or $C_{1-6}$ alkynyl-sulfonyl group, which may be halogenated, (d) a $C_{1-4}$ alkylenedioxy group which may be halogenated, (e) a $C_{1-6}$ alkoxy group which may be halogenated, (f) a $C_{1-6}$ hydrocarbon-thio group which may be halogenated, (g) a C$_{1-6}$ alkoxy-carbonyl group, (h) a C$_{6-14}$ aryl-C$_{1-6}$ alkoxy group, (i) a C$_{1-7}$ alkanoylamino group (j) a C$_{1-6}$ alkyl-carbamoyl group, (k) a C$_{1-6}$ alkenyl-carbamoyl group, (l) a C$_{1-6}$ alkynyl-carbamoyl group and (m) an amino group which may be substituted with a C$_{1-6}$ hydrocarbon group, (18) a 5- to 15-membered aromatic heterocycle-oxy group which may be substituted one or more groups selected from (a) hydroxyl group, (b) a halogen atom, (c) nitrile group, (d) a C$_{1-6}$ alkyl group, C$_{1-6}$ alkenyl group or C$_{1-6}$ alkynyl group, which may be halogenated, (e) a C$_{1-6}$ alkoxy group which may be halogenated, (f) a C$_{1-6}$ alkylthio group, C$_{1-6}$ alkenylthio group or C$_{1-6}$ alkynylthio group, which may be halogenated, (g) a C$_{1-6}$ alkoxy-C$_{1-6}$ alkyl group, (h) acetyl group, (i) a C$_{1-6}$ alkanoyl group, (j) a mono-(C$_{1-6}$ hydrocarbon)-amino group, (k) a di-(C$_{1-6}$ hydrocarbon)-amino group and (l) a tri-(C$_{1-6}$ hydrocarbon)-amino group, (19) a 5- to 15-membered aromatic heterocycle-thio group which may be substituted one or more groups selected from (a) hydroxyl group, (b) a halogen atom, (c) nitrile group, (d) a C$_{1-6}$ alkyl group, C$_{1-6}$ alkenyl group or C$_{1-6}$ alkynyl group, which may be halogenated, (e) a C$_{1-6}$ alkoxy group which may be halogenated, (f) a C$_{1-6}$ alkylthio group, C$_{1-6}$ alkenylthio group or C$_{1-6}$ alkynylthio group, which may be halogenated, (g) a C$_{1-6}$ alkoxy-C$_{1-6}$ alkyl group, (h) acetyl group, (i) a C$_{1-6}$ alkanoyl group, (j) a mono-(C$_{1-6}$ hydrocarbon)-amino group, (k) a di-(C$_{1-6}$ hydrocarbon)-amino group and (l) a tri-(C$_{1-6}$ hydrocarbon)-amino group, (20) a 4- to 10-membered non-aromatic heterocycle-oxy group which may be substituted one or more groups selected from (a) hydroxyl group, (b) a halogen atom, (c) nitrile group, (d) a C$_{1-6}$ alkyl group, C$_{1-6}$ alkenyl group or C$_{1-6}$ alkynyl group, which may be halogenated, (e) a C$_{1-6}$ alkoxy group which may be halogenated, (f) a C$_{1-6}$ alkylthio group, C$_{1-6}$ alkenylthio group or C$_{1-6}$ alkynylthio group which may be halogenated, (g) a C$_{1-6}$ alkoxy-C$_{1-6}$ alkyl group, (h) acetyl group, (i) a C$_{1-6}$ alkanoyl group, (j) a mono-(C$_{1-6}$ hydrocarbon)-amino group, (k) a di-(C$_{1-6}$ hydrocarbon)-amino group and (l) a tri-(C$_{1-6}$ hydrocarbon)-amino group, (21) a 4- to 10-membered non-aromatic heterocycle-thio group which may be substituted one or more groups selected from (a) hydroxyl group, (b) a halogen atom, (c) nitrile group, (d) a C$_{1-6}$ alkyl group, C$_{1-6}$ alkenyl group or C$_{1-6}$ alkynyl group, which may be halogenated, (e) a C$_{1-6}$ alkoxy group which may be halogenated, (f) a C$_{1-6}$ alkylthio group, C$_{1-6}$ alkenylthio group or C$_{1-6}$ alkynylthio group which may be halogenated, (g) a C$_{1-6}$ alkoxy-C$_{1-6}$ alkyl group, (h) acetyl group, (i) a C$_{1-6}$ alkanoyl group, (j) a mono-(C$_{1-6}$ hydrocarbon)-amino group, (k) a di-(C$_{1-6}$ hydrocarbon)-amino group and (l) a tri-(C$_{1-6}$ hydrocarbon)-amino group, (22) azide group, (23) guanidino group, (24) carbamide group, (25) formyl group, (26) a C$_{1-6}$ imidoyl group which may be substituted, (27) a C$_{1-6}$ alkanoyl group which may be substituted with a C$_{1-6}$ alkoxy group, (28) a C$_{1-6}$ alkanoyloxy group which may be substituted with a C$_{1-6}$ alkoxy group, (29) a carboxyl group which may form a salt, (30) a carbonyl group which is substituted with a group selected from (a) a C$_{1-6}$ alkoxy group, (b) a C$_{6-14}$ aryl group and (c) a 5- to 14-membered aromatic heterocyclic group, (31) a carbamoyl group represented by the formula —CO—N(R$^5$)R$^6$ (wherein R$^5$ and R$^6$ are the same as or different from each other and each represents a group selected from (a) hydrogen atom, (b) a C$_{1-6}$ alkyl group, (c) a C$_{1-6}$ alkenyl group, (d) a C$_{1-6}$ alkynyl group, (e) a C$_{3-8}$ cycloalkyl group, (f) a C$_{3-8}$ cycloalkenyl group, (g) a C$_{6-14}$ aryl group and (h) an aromatic heterocyclic group or (i) R$^5$ and R$^6$ may be combined and united to form a 3- to 8-membered ring), (32) a C$_{1-4}$ alkylenedioxy group which may be substituted with (a) hydroxyl group or (b) a halogen atom, (33) a sulfinyl group which may be substituted with a group selected from (a) a C$_{1-6}$ hydrocarbon group which may be halogenated and (b) an amino group which may be mono-substituted or di-substituted with a C$_{1-6}$ hydrocarbon group which may be halogenated and (34) a sulfonyl group which may be substituted with (a) a C$_{1-6}$ hydrocarbon group which may be halogenated or (b) an amino group which may be mono-substituted or di-substituted with a C$_{1-6}$ hydrocarbon group which may be halogenated.

7. The compound as claimed in claim 1 or 2, a salt thereof or a hydrate of them, wherein HAr is a 5- to 14-membered aromatic heterocycle which may be substituted with, in addition to a substituent —X—Ar, 1 to 3 groups selected from (1) a 5- or 6-membered aromatic heterocycle which may be substituted with a C$_{1-6}$ alkyl group, (2) a 5- to 6-membered non-aromatic heterocycle which may be substituted with one or more groups selected from (a) hydroxyl group, (b) a C$_{1-6}$ alkyl group and (c) a C$_{1-6}$ alkoxy group, (3) a C$_{6-10}$ aromatic hydrocarbon ring which may be substituted with one or more groups selected from (a) a halogen atom, (b) a C$_{1-6}$ alkoxy group, (c) a C$_{1-4}$ alkylenedioxy group and (d) a sulfonyl group which may be substituted with a C$_{1-6}$ alkyl group, (4) a C$_{1-6}$ alkyl group which may be substituted with one or more groups selected from (a) hydroxyl group, (b) a halogen atom, (c) a 5- or 6-membered aromatic heterocycle and (d) a C$_{1-6}$ alkoxy group and (5) a C$_{1-6}$ alkoxy group which may be substituted with (a) a halogen atom or (b) a C$_{1-6}$ alkoxy group.

8. The compound as claimed in claim 1 or 2, a salt thereof or a hydrate of them, wherein HAr is a 5- to 10-membered aromatic heterocycle which may be substituted with, in addition to a substituent —X—Ar, 1 to 3 groups selected from (1) a benzene ring which may be substituted with a C$_{1-4}$ alkylenedioxy group, (2) pyridine ring, (3) pyrimidine ring, (4) pyridazine ring, (5) pyrazine ring, (6) thiophene ring, (7) a piperidine ring which may be substituted with a C$_{1-6}$ alkoxy group, (8) a piperazine ring which may be substituted with a C$_{1-6}$ alkoxy group, (9) a pyrrolidine ring which may be substituted with a C$_{1-6}$ alkoxy group, (10) a piperidine ring which is substituted with hydroxyl group and a C$_{1-6}$ alkoxy group, (11) a piperazine ring which is substituted with hydroxyl group and a C$_{1-6}$ alkoxy group, (12) a pyrrolidine ring which is substituted with hydroxyl group and a C$_{1-6}$ alkoxy group, (13) morpholine ring, (14) a C$_{1-6}$ alkyl group which may be substituted with a C$_{1-6}$ alkoxy group and (15) a C$_{1-6}$ alkoxy group which may be substituted with hydroxyl group or a C$_{1-6}$ alkoxy group.

9. The compound as claimed in claim 1 or 2, a salt thereof or a hydrate of them, in which HAr is a pyridine ring, pyrimidine ring, pyridazine ring, pyrazine ring, indole ring, quinoline ring, thiophene ring or benzothiophene ring which may be substituted with 1 to 3 groups.

10. The compound as claimed in claim 1 or 2, a salt thereof or a hydrate of them, wherein HAr is a pyridine ring, pyrimidine ring, pyridazine ring, pyrazine ring, indole ring, quinoline ring, thiophene ring or benzothiophene ring, which may be substituted with, in addition to a substituent —X—Ar, 1 to 3 groups selected from (1) a 5- or 6-membered aromatic heterocycle which may be substituted with a C$_{1-6}$ alkyl group, (2) a 5- or 6-membered aromatic heterocycle which may be substituted with one or more groups selected from (a) hydroxyl group, (b) a C$_{1-6}$ alkyl group and (c) a C$_{1-6}$ alkoxy group, (3) a C$_{6-10}$ aromatic hydrocarbon ring which may be substituted with one or more groups selected from (a) a halogen atom, (b) a C$_{1-6}$ alkoxy group, (c) a $C_{1-4}$ alkylenedioxy group and (d) a sulfonyl group which may be substituted with a $C_{1-6}$ alkyl group, (4) a $C_{1-6}$ alkyl group which may be substituted with one or more groups selected from (a) hydroxyl group, (b) a halogen atom, (c) a 5- or 6-membered heterocycle and (d) a $C_{1-6}$ alkoxy group and (5) a $C_{1-6}$ alkoxy group which may be substituted with (a) a halogen atom and (b) a $C_{1-6}$ alkoxy group.

11. The compound as claimed in claim 1 or 2, a salt thereof or a hydrate of them, wherein Ar is a $C_{6-14}$ aromatic hydrocarbon ring or 5- to 14-membered aromatic heterocycle, which may have 1 to 3 substituents selected from (1) a halogen atom, (2) a $C_{1-6}$ alkyl group, $C_{2-6}$ alkenyl group or $C_{2-6}$ alkynyl group, which may be substituted with one or more groups selected from (a) a halogen atom, (b) a $C_{1-6}$ alkoxy group and (c) a sulfonyl group which may be substituted, (3) a $C_{1-6}$ alkoxy group which may be halogenated, (4) a mono-($C_{1-6}$ alkyl)-amino group, (5) a di-($C_{1-6}$ alkyl)-amino group and (6) a $C_{1-4}$ alkylenedioxy group which may be halogenated.

12. The compound as claimed in claim 1 or 2, a salt thereof or a hydrate of them, in which Ar is an optionally substituted benzene ring or pyridine ring.

13. The compound as claimed in claim 1 or 2, a salt thereof or a hydrate of them, in which X is —$CH_2$—; and Ar is benzene ring.

14. The compound as claimed in claim 1 or 2, a salt thereof or a hydrate of them, in which the compound is represented by the following formula.

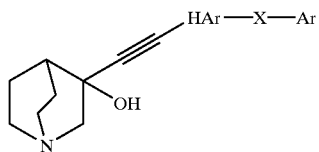

In the formula, HAr represents a 5- to 10-membered aromatic heterocycle containing 1 to 4 atoms selected from nitrogen atom, sulfur atom and oxygen atom and may be substituted with 1 to 3 groups selected from (1) a halogen atom, (2) hydroxyl group, (3) thiol group, (4) nitro group, (5) nitrile group, (6) a $C_{1-6}$ chain hydrocarbon group which may be substituted, (7) a $C_{3-8}$ cyclic hydrocarbon group which may be substituted, (8) a $C_{6-14}$ aromatic cyclic hydrocarbon group which may be substituted, (9) a 5- to 14-membered aromatic heterocyclic group which may be substituted, (10) a 4- to 10-membered non-aromatic heterocyclic group which may be substituted, (11) a $C_{1-6}$ alkoxy group which may be substituted, (12) a $C_{3-8}$ cycloalkyloxy group which may be substituted, (13) a $C_{1-6}$ chain hydrocarbon-thio group which may be substituted, (14) a $C_{3-8}$ cyclic hydrocarbon-thio group which may be substituted, (15) a $C_{6-14}$ aromatic hydrocarbon-oxy group which may be substituted, (16) a 5- to 14-membered heterocycle-oxy group which may be substituted, (17) a $C_{6-14}$ aromatic hydrocarbon-thio group which may be substituted, (18) a 5- to 14-membered heterocycle-thio group which may be substituted, (19) an amino group which may be substituted, (20) azide group, (21) guanidino group, (22) carbamide group, (23) a formyl group, (24) a $C_{1-6}$ imidoyl group which may be substituted, (25) a substituted carbonyl group, (26) a substituted carbonyl-oxy group, (27) a carboxyl group which may form a salt, (28) a carbamoyl group which may be substituted, (29) a $C_{1-4}$ alkylenedioxy group which may be substituted, (30) a sulfinyl group which may be substituted and (31) a sulfonyl group which may be substituted;

Ar is a $C_{6-14}$ aromatic hydrocarbon ring or 5- to 14-membered aromatic heterocycle, which may be substituted with a group selected from (1) hydroxyl group, (2) a halogen atom, (3) a $C_{1-6}$ chain hydrocarbon group which may be substituted, (4) a $C_{3-8}$ cyclic hydrocarbon group which may be substituted, (5) a $C_{1-6}$ alkoxy group which may be substituted, (6) a $C_{3-8}$ cycloalkyloxy group which may be substituted, (7) a $C_{1-6}$ chain hydrocarbon-thio group which may be substituted, (8) a $C_{3-8}$ cyclic hydrocarbon-thio group, (9) a $C_{6-14}$ aromatic hydrocarbon cyclic group which may be substituted, (10) a 5- to 14-membered heterocyclic group which may be substituted, (11) an amino group which may be substituted with a $C_{1-6}$ alkyl group and (12) a $C_{1-4}$ alkylenedioxy group; and X represents a chain represented by (1) a single bond, (2) a $C_{1-6}$ alkylene chain which may be substituted, (3) a $C_{2-6}$ alkenylene chain which may be substituted, (4) a $C_{2-6}$ alkynylene chain which may be substituted, (5) the formula —Q— (wherein Q represents oxygen atom, sulfur atom, CO or N($R^2$) (wherein $R^2$ represents a $C_{1-6}$ alkyl group or a $C_{1-6}$ alkoxy group)), (6) —NH—CO—, (7) —CO—NH—, (8) —NH—$CH_2$—, (9) —$CH_2$—NH—, (10) —$CH_2$—CO—, (11) —CO—$CH_2$—, (12) —NH—S(O)$_m$—, (13) —S(O)$_m$—NH—, (14) —$CH_2$—S(O)$_m$—, (15) —S(O)$_m$—$CH_2$— (wherein m is 0, 1 or 2) or (16) —$(CH_2)_n$—O— (wherein n denotes an integer from 1 to 6).

15. The compound as claimed in claim 14, a salt thereof or a hydrate of them, in which HAr is a pyridine ring, pyrazine ring, pyrimidine ring or pyridazine ring, which may be substituted with, in addition to a substituent —X—Ar, one or more groups selected from (1) a 5- or 6-membered aromatic heterocycle, (2) a 5- or 6-membered non-aromatic heterocycle which may be substituted with a $C_{1-6}$ alkoxy group and (3) a $C_{6-10}$ aromatic hydrocarbon ring; Ar is a benzene ring or pyridine ring which may be halogenated; and X is —$CH_2$—.

16. The compound as claimed in claim 14, a salt thereof or a hydrate of them, in which HAr is a pyridine ring, pyrazine ring, pyrimidine ring or pyridazine ring, which may be substituted with, in addition to a substituent —X—Ar, a group selected from (1) a $C_{1-6}$ alkoxy group which may be substituted with hydroxyl group, (2) a $C_{1-6}$ alkoxy-$C_{1-6}$ alkoxy group and (3) a $C_{1-6}$ alkoxy-$C_{1-6}$ alkyl-amino group; Ar is an optionally halogenated benzene or pyridine ring; and X is —$CH_2$—.

17. The compound as claimed in claim 14, a salt thereof or a hydrate of them, wherein HAr is a pyridine ring, pyrazine ring, pyrimidine ring or pyridazine ring, which may be substituted with, in addition to a substituent —X—Ar, 1 to 3 groups selected from (1) a benzene ring which may be substituted with a $C_{1-4}$ alkylenedioxy group, (2) pyridine ring, (3) pyrimidine ring, (4) pyridazine ring, (5) pyrazine ring, (6) thiophene ring, (7) a piperidine ring which may be substituted with a $C_{1-6}$ alkoxy group, (8) a piperazine ring which may be substituted with a $C_{1-6}$ alkoxy group, (9) a pyrrolidine ring which may be substituted with a $C_{1-6}$ alkoxy group, (10) a piperidine ring which is substituted with hydroxyl group and a $C_{1-6}$ alkoxy group, (11) a piperazine ring which is substituted with hydroxyl group and a $C_{1-6}$ alkoxy group, (12) a pyrrolidine ring which is substituted with hydroxyl group and a $C_{1-6}$ alkoxy group, (13) morpholine ring, (14) a $C_{1-6}$ alkyl group which may be substituted with a $C_{1-6}$ alkoxy group and (15) a $C_{1-6}$ alkoxy group which may be substituted with hydroxyl group or a $C_{1-6}$ alkoxy group; Ar is a benzene ring or pyridine ring, which may be halogenated; and X is —$CH_2$—.

18. The compound as claimed in claim 1, a salt thereof or a hydrate of them, in which the compound is any one selected from:

3-(4-benzyl-2-phenyl-5-pyrimidyl)ethynyl-3-quinuclidinol;
3-[4-benzyl-2-(2-pyridyl)-5-pyrimidyl]ethynyl-3-quinuclidinol;
3-[3-benzyl-5-(2-pyridyl)-2-pyridyl]ethynyl-3-quinuclidinol;
3-(3-benzyl-5-phenyl-2-pyridyl)ethynyl-3-quinuclidinol;
3-[3-benzyl-5-(3-pyridyl)-2-pyridyl]ethynyl-3-quinuclidinol;
3-[3-benzyl-5-(4-pyridyl)-2-pyridyl]ethynyl-3-quinuclidinol;
3-(3-benzyl-5-pyrazyl-2-pyridyl)ethynyl-3-quinuclidinol;
3-[3-benzyl-5-(2-ethoxycarbonylethyl)-2-pyridyl]ethynyl-3-quinuclidinol;
3-[3-benzyl-5-(3-oxobutyl)-2-pyridyl]ethynyl-3-quinuclidinol;
3-[3-benzyl-5-(3-hydroxybutyl)-2-pyridyl]ethynyl-3-quinuclidinol;
3-[2-benzyl-6-(3-methoxypropylamino)-3-pyridyl]ethynyl-3-quinuclidinol;
3-[2-benzyl-6-(2-methoxyethyloxy)-3-pyridyl]ethynyl-3-quinuclidinol;
3-[2-benzyl-6-(3-methoxypropyloxy)-3-pyridyl]ethynyl-3-quinuclidinol;
3-[2-benzyl-6-(4-pyridyl)-3-pyridyl]ethynyl-3-quinuclidinol;
3-[2-benzyl-6-(3-pyridyl)-3-pyridyl]ethynyl-3-quinuclidinol;
3-(2-benzyl-6-pyrazyl-3-pyridyl)ethynyl-3-quinuclidinol;
3-[2-benzyl-6-(2-pyridyl)-3-pyridyl]ethynyl-3-quinuclidinol;
3-[4-benzyl-2-(3-pyridyl)-5-pyrimidyl]ethynyl-3-quinuclidinol;
3-[4-benzyl-2-(3,4-methylenedioxyphenyl)-5-pyrimidyl]ethynyl-3-quinuclidinol;
3-[4-benzyl-2-(3,4-methylenedioxyphenyl)-5-pyridyl]ethynyl-3-quinuclidinol;
3-[4-benzyl-2-(2-pyridyl)-5-pyridyl]ethynyl-3-quinuclidinol;
3-[4-benzyl-2-(3-pyridyl)-5-pyridyl]ethynyl-3-quinuclidinol;
3-(4-benzyl-2-pyrazyl-5-pyridyl)ethynyl-3-quinuclidinol;
3-[4-benzyl-2-(4-pyridyl)-5-pyridyl]ethynyl-3-quinuclidinol;
3-[4-benzyl-2-(2-methoxyethoxy)-5-pyridyl]ethynyl-3-quinuclidinol;
3-[2-benzyl-6-(4-ethoxycarbonylpiperidino)-3-pyridyl]ethynyl-3-quinuclidinol;
3-(2-benzyl-6-morpholino-3-pyridyl)ethynyl-3-quinuclidinol;
3-[2-benzyl-6-(4-methoxypiperidino)-3-pyridyl]ethynyl-3-quinuclidinol;
(3R)-3-[2-benzyl-6-(2-methoxyethyl)oxy-3-pyridyl]ethynyl-3-quinuclidinol;
(3R)-3-[2-benzyl-6-(3-methoxypropyl)oxy-3-pyridyl]ethynyl-3-quinuclidinol;
(3S)-3-[2-benzyl-6-(3-methoxypropyl)oxy-3-pyridyl]ethynyl-3-quinuclidinol;
(3R)-3-[2-benzyl-6-(3-fluoropropyl)oxy-3-pyridyl]ethynyl-3-quinuclidinol;
(3R)-3-[2-benzyl-6-(1,3-dioxolan-2-yl)methyloxy-3-pyridyl]ethynyl-3-quinuclidinol;
(3R)-3-[2-benzyl-6-(3-hydroxypropyl)oxy-3-pyridyl]ethynyl-3-quinuclidinol;
3-[2-benzyl-6-[3-(3-methoxycarbonylpropanoyloxy)propyl]oxy-3-pyridyl]ethynyl-3-quinuclidinol;
3-[2-benzyl-6-[3-[N-(tert-butoxycarbonyl)alanyloxy]propyl]oxy-3-pyridyl]ethynyl-3-quinuclidinol;
(3R)-3-[4-benzyl-2-(3-pyridyl)-5-pyridyl]ethynyl-3-quinuclidinol;
(3R)-3-[4-benzyl-2-(2-pyridyl)-5-pyridyl]ethynyl-3-quinuclidinol;
(3R)-3-[4-benzyl-2-(3,4-methylenedioxyphenyl)-5-pyridyl]ethynyl-3-quinuclidinol;
(3R)-3-[2-benzyl-6-[(3R,4S)-3-hydroxy-4-methoxypyrrolidine-1-yl]-3-pyridyl]ethynyl-3-quinuclidinol;
(3R)-3-[2-benzyl-6-[(3S,4R)-3-fluoro-4-methoxypyrrolidine-1-yl]-3-pyridyl]ethynyl-3-quinuclidinol;
(3R)-3-[2-benzyl-6-[(3R,4R)-3-hydroxy-4-methoxypyrrolidine-1-yl]-3-pyridyl]ethynyl-3-quinuclidinol;
(3R)-3-[2-benzyl-6-[(3R,4R)-3,4-dimethoxypyrrolidine-1-yl]-3-pyridyl]ethynyl-3-quinuclidinol;
(3R)-3-[2-benzyl-5-chloro-6-[(3R,4R)-3-hydroxy-4-methoxypyrrolidine-1-yl]-3-pyridyl]ethynyl-3-quinuclidinol;
(3R)-3-[2-benzyl-5-bromo-6-[(3R,4R)-3-hydroxy-4-methoxypyrrolidine-1-yl]-3-pyridyl]ethynyl-3-quinuclidinol;
(3R)-3-[2-benzyl-6-(3,3-ethylenedioxypyrrolidine-1-yl)-3-pyridyl]ethynyl-3-quinuclidinol;
(3R)-3-[2-benzyl-5-chloro-6-(3,3-ethylenedioxypyrrolidine-1-yl)-3-pyridyl]ethynyl-3-quinuclidinol;
(3R)-3-[2-benzyl-6-(cis-3,4-dimethoxypyrrolidine-1-yl)-3-pyridyl]ethynyl-3-quinuclidinol;
(3R)-3-[2-benzyl-6-[(3R,4R)-3,4-dimethoxy-2-pyrrolidinone-1-yl]-3-pyridyl]ethynyl-3-quinuclidinol;
(3R)-3-[2-benzyl-6-[(3R,4R)-4-hydroxy-3-methoxy-2-pyrrolidinone-1-yl]-3-pyridyl]ethynyl-3-quinuclidinol;
(3R)-3-[2-benzyl-6-(3,3-ethylenedioxy-2-pyrrolidinone-1-yl)-3-pyridyl]ethynyl-3-quinuclidinol;
(3R)-3-[2-benzyl-6-[(3R)-3-hydroxy-2-pyrrolidinone-1-yl]-3-pyridyl]ethynyl-3-quinuclidinol;
(3R)-3-[2-benzyl-6-[(3R)-3-methoxy-2-pyrrolidinone-1-yl]-3-pyridyl]ethynyl-3-quinuclidinol;
(3R)-3-[4-benzyl-2-(1,4-dioxene-2-yl)-5-pyridyl]ethynyl-3-quinuclidinol; and
(3R)-3-[4-benzyl-2-[(3R,4R)-3-hydroxy-4-methoxypyrrolidine-1-yl]-3-pyrimidyl]ethynyl-3-quinuclidinol.

19. A method of inhibiting squalene synthesizing enzyme in a mammal comprising administering to said mammal an effective amount of the compound as claimed in claim 1 or 2, a salt thereof or a hydrate of them.

20. A pharmaceutical composition comprising a compound (I) represented by the following formula, a salt thereof or a hydrate of them:

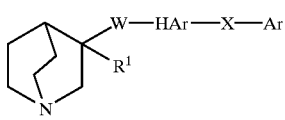

(I)

wherein $R^1$ represents (1) hydrogen atom or (2) hydroxyl group;

HAr represents an aromatic heterocycle which may be substituted with 1 to 3 groups;

Ar represents an optionally substituted aromatic ring;

W represents a chain represented by (1) —$CH_2$—$CH_2$— which may be substituted, (2) —CH=CH— which may be substituted, (3) —C≡C—, (4) —CO—NH—, (5) —NH—$CH_2$—, (6) —$CH_2$—NH—, (7) —$CH_2$—CO—, (8) —CO—$CH_2$—, (9) —NH—S(O)$_l$—, (10) —S(O)$_l$—NH—, (11) —$CH_2$—S(O)$_l$— or (12) —S(O)$_l$—$CH_2$—, wherein l denotes 0, 1 or 2; and X represents a chain represented by (1) a single bond, (2) an optionally substituted $C_{1-6}$ alkylene chain, (3) an optionally substituted $C_{2-6}$ alkenylene chain, (4) an optionally substituted $C_{2-6}$ alkynylene chain, (5) a formula —Q—, wherein Q represents oxygen atom, sulfur atom, CO or N($R^2$), wherein $R^2$ represents a $C_{1-6}$ alkyl group or a $C_{1-6}$ alkoxy group, (6) —NH—CO—, (7) —CO—NH—, (8) —NH—$CH_2$—, (9) —$CH_2$—NH—, (10) —$CH_2$—CO—, (11) —CO—$CH_2$—, (12) —NH—S(O)$_m$—, (13) S(O)$_m$—NH, (14) —$CH_2$—S(O)$_m$—, (15) —S(O)$_m$—$CH_2$—, wherein m denotes 0, 1 or 2, or (16) —($CH_2$)$_n$—O—, wherein n denotes an integer from 1 to 6.

21. The pharmaceutical composition according to claim 20, which is a preventative or curative agent for a disease against which squalene synthesizing enzyme inhibition is efficacious.

22. The pharmaceutical composition according to claim 20, which is a cholesterol biosynthesis inhibitor.

23. The pharmaceutical composition according to claim 20, which is a triglyceride biosynthesis inhibitor.

24. The pharmaceutical composition according to claim 20, which is an agent for preventing or curing hyper lipidemia by inhibiting the squalene synthesizing enzyme.

25. The pharmaceutical composition according to claim 20, which is an agent for preventing or curing arterial sclerosis diseases or ischaemic heart diseases by inhibiting the squalene synthesizing enzyme.

26. The pharmaceutical composition according to claim 20, which is an agent for preventing or curing hypertension, coronary diseases, cerebrovascular diseases, aortic diseases, peripheral arterial diseases, angina pectoris, acute coronary syndromes or cardiac infarction by inhibiting the squalene synthesizing enzyme.

27. A method of preparing a quinuclidine compound (IV) represented by the following formula:

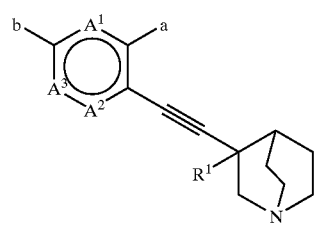

(IV)

wherein $A^1$, $A^2$, $A^3$, a, b and $R^1$ have the same meanings as defined above, a salt thereof or a hydrate of them, which comprises the step of reacting an aromatic heterocyclic compound (II) represented by the following formula:

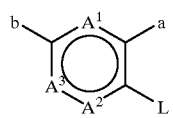

(II)

wherein $A^1$ and $A^3$ are the same as or different from each other and each means 1) an optionally substituted carbon atom or 2) a hetero atom; $A^2$ means 1) an optionally substituted carbon atom, 2) a hetero atom or 3) a single bond; L means a leaving group; and a and b are different from each other and each means 1) a group —X—Ar wherein X represents a chain represented by (1) a single bond; (2) an optionally substituted $C_{1-6}$ alkylene chain; (3) an optionally substituted $C_{2-6}$ alkenylene chain; (4) an optionally substituted $C_{2-6}$ alkynylene chain; (5) a formula —Q— wherein Q represents oxygen atom, sulfur atom, CO or N($R^2$) wherein $R^2$ represents a $C_{1-6}$ alkyl group or a $C_{1-6}$ alkoxy group; (6) —NH—CO—; (7) —CO—NH—; (8) —NH—$CH_2$—; (9) —$CH_2$—NH—; (10) —$CH_2$—CO—; (11) —CO—$CH_2$—; (12) —NH—S(O)$_m$—; (13) —S(O)$_m$—NH—; (14) —$CH_2$—S(O)$_m$—; (15) —S(O)$_m$—$CH_2$— wherein m denotes 0, 1 or 2; or (16) —($CH_2$)$_n$—O— wherein n denotes an integer from 1 to 6; and Ar represents an optionally substituted aromatic ring, respectively, or 2) any one group selected from:

(1) a halogen atom; (2) hydroxyl group; (3) thiol group; (4) nitro group; (5) nitrile group; (6) an optionally substituted linear $C_{1-6}$ hydrocarbon group; (7) an optionally substituted $C_{3-8}$ cyclic hydrocarbon group; (8) an optionally substituted $C_{6-14}$ aromatic hydrocarbon cyclic group; (9) an optionally substituted 5- to 14-membered aromatic heterocyclic group; (10) an optionally substituted 4- to 10-membered non-aromatic heterocyclic group; (11) an optionally substituted $C_{1-6}$ alkoxy group; (12) an optionally substituted $C_{3-8}$ cycloalkyloxy group; (13) an optionally substituted linear $C_{1-6}$ hydrocarbon-thio group; (14) an optionally substituted $C_{3-8}$ cyclic hydrocarbon-thio group; (15) an optionally substituted $C_{6-14}$ aromatic hydrocarbon-oxy group; (16) an optionally substituted 5- to 14-membered heterocyclic-oxy group; (17) an optionally substituted $C_{6-14}$ aromatic hydrocarbon-thio group; (18) an optionally substituted 5- to 14-membered heterocyclic-thio group; (19) an optionally substituted amino group; (20) an azide group; (21) guanidino group; (22) carbamide group; (23) formyl group; (24) an optionally substituted $C_{1-6}$ imidoyl group; (25) a substituted carbonyl group; (26) a substituted carbonyloxy group; (27) a carboxyl group which may form a salt; (28) an optionally substituted carbamoyl group; (29) an optionally substituted $C_{1-4}$ alkylenedioxy group; (30) an optionally substituted sulfinyl group; and (31) an optionally substituted sulfonyl group, respectively) and a quinuclidine compound (III) represented by the following formula:

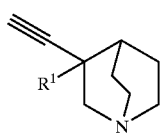
(III)

wherein $R^1$ means hydrogen atom or hydroxyl group in the presence of a Pd catalyst, a copper salt and a base.

28. A method of preparing a quinuclidine compound (VI) represented by the following formula:

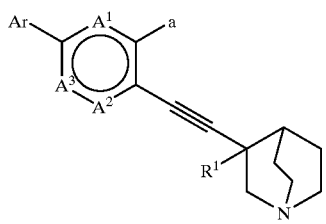
(VI)

wherein $A^1$, $A^2$, $A^3$, a, Ar and $R^1$ have the same meanings as defined above, a salt thereof or a hydrate of them, which comprises the step of reacting a quinuclidine compound (V) represented by the following formula:

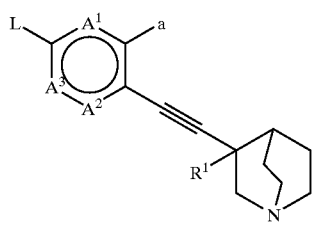
(V)

wherein $A^1$ and $A^3$ are the same as or different from each other and each means 1) an optionally substituted carbon atom or 2) a hetero atom; A represent 1) an optionally substituted carbon atom, 2) a hetero atom or 3) a single bond; L means a leaving group; a means a group —X—Ar wherein X and Ar have the same meanings as defined above; and $R^1$ means hydrogen atom or hydroxyl group, respectively, and an aromatic cyclic compound represented by the following formula:

Ar—M wherein Ar means an optionally substituted aromatic ring; and M means an optionally substituted metal atom, respectively, in the presence of a Pd catalyst.

29. method of preparing a quinuclidine compound (VIII) represented by the following formula:

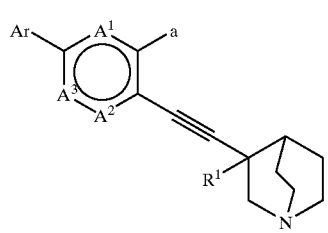
(VIII)

wherein $A^1$, $A^2$, $A^3$, a, Ar and $R^1$ have the same meanings as defined above, a salt thereof or a hydrate of them, which comprises the step of reacting a quinuclidine compound (VII) represented by the following formula:

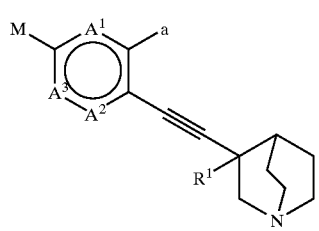
(VII)

wherein $A^1$ and $A^3$ are the same as or different from each other and each means 1) an optionally substituted carbon atom or 2) a hetero atom; $A^2$ means 1) an optionally substituted carbon atom, 2) a hetero atom or 3) a single bond; M means an optionally substituted metal atom; a means 1) a group —X—Ar wherein X and Ar have the same meanings as defined above; and $R^1$ means hydrogen atom or hydroxyl group, respectively, and an aromatic cyclic compound represented by the following formula:

Ar—L wherein Ar means an optionally substituted aromatic ring; and L means a leaving group, respectively, in the presence of a Pd catalyst.

30. A method of preventing or curing a disease against which squalene synthesizing enzyme inhibition is efficacious, by administering a pharmacologically effective amount of the compound as claimed in claim 1, a salt thereof or a hydrate of them to a patient.

* * * * *